US012667613B2

(12) United States Patent
Pardi et al.

(10) Patent No.: US 12,667,613 B2
(45) Date of Patent: Jun. 30, 2026

(54) NUCLEOSIDE-MODIFIED RNA FOR INDUCING AN IMMUNE RESPONSE AGAINST SARS-CoV-2

(71) Applicant: The Trustees of the University of Pennsylvania, Philadelphia, PA (US)

(72) Inventors: Norbert Pardi, Philadelphia, PA (US); Drew Weissman, Wynnewood, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 694 days.

(21) Appl. No.: 18/004,494

(22) PCT Filed: Jul. 8, 2021

(86) PCT No.: PCT/US2021/040811
§ 371 (c)(1),
(2) Date: Jan. 6, 2023

(87) PCT Pub. No.: WO2022/011092
PCT Pub. Date: Jan. 13, 2022

(65) Prior Publication Data
US 2023/0248818 A1      Aug. 10, 2023

Related U.S. Application Data

(60) Provisional application No. 63/049,295, filed on Jul. 8, 2020.

(51) Int. Cl.
| *A61P 31/14* | (2006.01) |
| *A61K 9/00* | (2006.01) |
| *A61K 39/215* | (2006.01) |
| *A61K 39/00* | (2006.01) |

(52) U.S. Cl.
CPC .......... *A61K 39/215* (2013.01); *A61K 9/0019* (2013.01); *A61P 31/14* (2018.01); *A61K 2039/53* (2013.01); *A61K 2039/6018* (2013.01)

(58) Field of Classification Search
None
See application file for complete search history.

(56) References Cited

U.S. PATENT DOCUMENTS

| 2,856,420 | A | 10/1958 | Crawford, Jr. |
| 3,340,299 | A | 9/1967 | Weintraub |
| 3,931,430 | A | 1/1976 | Tada |
| 6,034,137 | A | 3/2000 | Belloni |
| 6,333,433 | B1 | 12/2001 | Banerjee |
| 6,458,381 | B1 | 10/2002 | Sourovoi |
| 8,278,036 | B2 | 10/2012 | Kariko |
| 8,748,089 | B2 | 6/2014 | Kariko |
| 8,835,108 | B2 | 9/2014 | Kariko |
| 9,352,042 | B2 | 5/2016 | Heyes |
| 9,737,619 | B2 | 8/2017 | Ansell |
| 9,738,593 | B2 | 8/2017 | Ansell |
| 9,750,824 | B2 | 9/2017 | Kariko |

| 9,795,566 | B2 | 10/2017 | Oya |
| 10,106,490 | B2 | 10/2018 | Du |
| 10,144,725 | B2 | 12/2018 | Brown |
| 10,166,298 | B2 | 1/2019 | Ansell |
| 10,221,127 | B2 | 3/2019 | Du |
| 10,723,692 | B2 | 7/2020 | Ansell |
| 10,973,909 | B1 * | 4/2021 | Csiszovszki ......... C07K 14/005 |
| 2003/0153081 | A1 | 8/2003 | Tagawa |
| 2004/0253271 | A1 | 12/2004 | Platteborze |
| 2005/0032730 | A1 | 2/2005 | Von |
| 2005/0059624 | A1 | 3/2005 | Hoerr |
| 2005/0250723 | A1 | 11/2005 | Hoerr |
| 2006/0100177 | A1 | 5/2006 | Nishimura |
| 2006/0188490 | A1 | 8/2006 | Hoerr |
| 2008/0025944 | A1 | 1/2008 | Hoerr |
| 2009/0324584 | A1 | 12/2009 | Hoerr |
| 2010/0189729 | A1 | 7/2010 | Hoerr |
| 2010/0203076 | A1 | 8/2010 | Fotin-Mleczek |
| 2010/0291156 | A1 | 11/2010 | Barner |
| 2010/0305196 | A1 | 12/2010 | Probst |
| 2011/0250225 | A1 | 10/2011 | Fotin-Mleczek |
| 2011/0256175 | A1 | 10/2011 | Hope |

(Continued)

FOREIGN PATENT DOCUMENTS

| CN | 110951756 | 4/2020 |
| CN | 111088283 | 5/2020 |

(Continued)

OTHER PUBLICATIONS

Akinc et al., "A combinatorial library of lipid-like materials for delivery of RNAi therapeutics," Nature Biotechnology 26(5):561-569, May 2008.
Akinc et al., 2010, "Targeted delivery of RNAi therapeutics with endogenous and exogenous ligand-based mechanisms." Mol Ther., 18(7): 1357-1364.
Alabi C.A, et al., "Multiparametric approach for the evaluation of lipid nanoparticles for siRNA delivery," PNAS, vol. 110, No. 32, , ISSN 0027-8424, pp. 12881-12886, Aug. 6, 2013.
Anderson et al., 2010, "Incorporation of pseudouridine into mRNA enhances translation by diminishing PKR activation." Nucleic Acids Res 38:5884-5892.
Anderson et al., 2011. "Nucleoside modifications in RNA limit activation of 2'-5'-oligoadenylate synthetase and increase resistance to cleavage by RNase L. Nucleic Acids Research," 39:9329-9338.

(Continued)

*Primary Examiner* — Nicole Kinsey White
(74) *Attorney, Agent, or Firm* — Riverside Law LLP

(57) ABSTRACT

The present invention relates to compositions and methods for inducing an adaptive immune response against severe acute respiratory syndrome coronavirus 2 (SARS-CoV-2) in a subject. In certain embodiments, the present invention provides a composition comprising a nucleoside-modified nucleic acid molecule encoding a SARS-CoV-2 antigen, adjuvant, or a combination thereof. For example, in certain embodiments, the composition comprises a vaccine comprising a nucleoside-modified nucleic acid molecule encoding a SARS-CoV-2 antigen, adjuvant, or a combination thereof.

12 Claims, 44 Drawing Sheets
Specification includes a Sequence Listing.

(56) References Cited

U.S. PATENT DOCUMENTS

| | | | |
|---|---|---|---|
| 2011/0300205 A1 | 12/2011 | Geall | |
| 2011/0305770 A1 | 12/2011 | Zhao | |
| 2012/0021043 A1 | 1/2012 | Kramps | |
| 2012/0276209 A1 | 11/2012 | Cullis | |
| 2013/0129754 A1 | 5/2013 | Thess | |
| 2013/0259879 A1 | 10/2013 | Baumhof | |
| 2013/0261172 A1 | 10/2013 | Kariko | |
| 2013/0266640 A1 | 10/2013 | De Fougerolles | |
| 2013/0280283 A1 | 10/2013 | Lorenz | |
| 2013/0280305 A1 | 10/2013 | Kuboyama | |
| 2013/0295043 A1 | 11/2013 | Kallen | |
| 2013/0336998 A1 | 12/2013 | Kallen | |
| 2014/0323548 A1 | 10/2014 | Budzik | |
| 2015/0037326 A1 | 2/2015 | Butler-Ransohoff | |
| 2015/0050302 A1 | 2/2015 | Thess | |
| 2015/0057340 A1 | 2/2015 | Thess | |
| 2015/0093413 A1 | 4/2015 | Thess | |
| 2015/0118183 A1 | 4/2015 | Baumhof | |
| 2015/0118264 A1 | 4/2015 | Baumhof | |
| 2015/0165006 A1 | 6/2015 | Thess | |
| 2015/0184195 A1 | 7/2015 | Thess | |
| 2015/0203446 A1 | 7/2015 | Manoharan | |
| 2015/0218554 A1 | 8/2015 | Thess | |
| 2015/0306249 A1 | 10/2015 | Baumhof | |
| 2015/0376115 A1 | 12/2015 | Ansell | |
| 2016/0038612 A1 | 2/2016 | Hoge | |
| 2016/0130345 A1 | 5/2016 | Fotin-Mleczek | |
| 2016/0166668 A1 | 6/2016 | Kallen | |
| 2016/0166678 A1 | 6/2016 | Kallen | |
| 2016/0166710 A1 | 6/2016 | Baumhof | |
| 2016/0166711 A1 | 6/2016 | Schnee | |
| 2016/0168207 A1 | 6/2016 | Kramps | |
| 2016/0168227 A1 | 6/2016 | Kallen | |
| 2016/0235864 A1 | 8/2016 | Schlake | |
| 2016/0304883 A1 | 10/2016 | Grund | |
| 2016/0361411 A1 | 12/2016 | Gindy | |
| 2016/0376224 A1 | 12/2016 | Du | |
| 2017/0029847 A1 | 2/2017 | Thess | |
| 2017/0119904 A1 | 5/2017 | Ansell | |
| 2017/0157268 A1 | 6/2017 | Ansell | |
| 2017/0252430 A1 | 9/2017 | Fotin-Mleczek | |
| 2017/0283367 A1 | 10/2017 | Ansell | |
| 2017/0326225 A1 | 11/2017 | Rauch | |
| 2018/0044687 A1 | 2/2018 | Thess | |
| 2018/0125952 A1 | 5/2018 | Fotin-Mleczek | |
| 2018/0126003 A1 | 5/2018 | Hoerr | |
| 2018/0148727 A1 | 5/2018 | Grund | |
| 2018/0214537 A1 | 8/2018 | Mutzke | |
| 2018/0237786 A1 | 8/2018 | Schlake | |
| 2018/0296663 A1 | 10/2018 | Hipp | |
| 2018/0303925 A1 | 10/2018 | Weissman | |
| 2018/0312545 A1 | 11/2018 | Baumhof | |
| 2019/0022247 A1 | 1/2019 | Ansell | |
| 2019/0024096 A1 | 1/2019 | Schmid | |
| 2019/0160164 A1 | 5/2019 | Rauch | |
| 2019/0270697 A1 | 9/2019 | Ansell | |
| 2019/0274968 A1 | 9/2019 | Weissman | |
| 2019/0314524 A1 | 10/2019 | Ansell | |
| 2019/0359556 A1 | 11/2019 | Du | |
| 2020/0030432 A1 | 1/2020 | Ciaramella | |
| 2020/0046838 A1 | 2/2020 | Ansell | |
| 2020/0121809 A1 | 4/2020 | Hope | |
| 2020/0163878 A1 | 5/2020 | Baumhof | |
| 2020/0172472 A1 | 6/2020 | Du | |
| 2020/0283372 A1 | 9/2020 | Du | |
| 2021/0107861 A1 | 4/2021 | Ansell | |
| 2021/0228707 A1* | 7/2021 | Metkar | A61K 39/12 |

FOREIGN PATENT DOCUMENTS

| | | | |
|---|---|---|---|
| EP | 1083232 A1 | 3/2001 | |
| EP | 2567951 | 3/2013 | |
| EP | 3289083 | 3/2018 | |
| JP | 5331118 | 10/2013 | |
| WO | 1987007183 | 12/1987 | |
| WO | 1997003939 | 2/1997 | |
| WO | 1999005094 | 2/1999 | |
| WO | 2000030444 | 6/2000 | |
| WO | 2003053409 | 7/2003 | |
| WO | 2005060934 | 7/2005 | |
| WO | 2006138380 A2 | 12/2006 | |
| WO | 2007024708 | 3/2007 | |
| WO | 2011143230 | 11/2011 | |
| WO | 2011153493 | 12/2011 | |
| WO | 2012016184 | 2/2012 | |
| WO | 2012068176 | 5/2012 | |
| WO | 2013016058 | 1/2013 | |
| WO | 2013086373 | 6/2013 | |
| WO | 2013143555 | 10/2013 | |
| WO | 2014028487 | 2/2014 | |
| WO | 2014160243 | 10/2014 | |
| WO | 2014160284 | 10/2014 | |
| WO | 2015164674 A1 | 10/2015 | |
| WO | 2015177752 A1 | 11/2015 | |
| WO | 2015199952 | 12/2015 | |
| WO | 2016145149 | 9/2016 | |
| WO | 2016176330 | 11/2016 | |
| WO | 2016210127 | 12/2016 | |
| WO | 2017015463 | 1/2017 | |
| WO | 2017021546 | 2/2017 | |
| WO | 2017048770 | 3/2017 | |
| WO | 2017049245 | 3/2017 | |
| WO | 2017070624 A1 | 4/2017 | |
| WO | 2017070626 | 4/2017 | |
| WO | 2017075531 A1 | 5/2017 | |
| WO | 2017140905 | 8/2017 | |
| WO | 2017173054 | 10/2017 | |
| WO | 2017182634 | 10/2017 | |
| WO | 2018132537 | 7/2018 | |
| WO | 2018191657 | 10/2018 | |
| WO | 2021178623 | 9/2021 | |
| WO | WO-2021178623 A1 * | 9/2021 | C07K 14/005 |

OTHER PUBLICATIONS

Andries et al., "N1-methylpseudouridine-incorporated mRNA out-performs pseudouridine-incorporated mRNA by providing enhanced protein expression and reduced immunogenicity in mammalian cell lines and mice," Journal of Controlled Release, vol. 217, Nov. 10, 2015, pp. 337-344.

Basha et al., 2011, "Influence of cationic lipid composition on gene silencing properties of lipid nanoparticle formulations of siRNA in antigen-presenting cells." Mol Ther, 19(12): 2186-2200.

Belliveau et al., 2012, "Microfluidic Synthesis of Highly Potent Limit-size Lipid Nanoparticles for In Vivo Delivery of siRNA." Mol Ther Nucleic Acids, 1: e37, 9 pages.

Brito et al: "A Cationic Nanoemulsion for the Delivery of Next-generation RNA Vaccines", Molecular Therapy, vol. 22, No. 12, Jul. 16, 2014 (Jul. 16, 2014) pp. 2118-2129.

D.N. Nguyen et al: "Lipid-derived nanoparticles for immunostimulatory RNA adjuvant delivery", Proceedings of the National Academy of Sciences of the United States of America, vol. 109, No. 14, Apr. 3, 2012 (Apr. 3, 2012), pp. E797-E803.

Database EMBL [Online] EBI; Jan. 15, 2020 (Jan. 15, 2020), Zhang Y.-Z. et al: "Wuhan seafood market pneumonia virus isolate Wuhan-Hu-1, complete genome.", XP055796635, Database accession No. MN908947.

Freyn et al., 2020, "A Multi-Targeting, Nucleoside-Modified mRNA Influenza Virus Vaccine Provides Broad Protection in Mice," Mol Ther. Jul. 8, 2020;28(7):1569-1584.

Gao et al., 2020, "Rapid development of an inactivated vaccine candidate for SARS-CoV-2." Science. Jul. 3, 2020;369(6499):77-81.

Huang Chaolin et al: "Clinical features of patients infected with 2019 novel coronavirus in Wuhan, China", The Lancet, Elsevier, Amsterdam, NL, vol. 395, No. 10223, Jan. 24, 2020 (Jan. 24, 2020), pp. 497-506, XP086050317, ISSN: 0140-6736, DOI: 10.1016/S0140-6736(20)30183-5 [retrieved on Jan. 24, 2020].

Jayaraman, M et al., "Maximizing the Potency of siRNA Lipid Nanoparticles for Hepatic Gene Silencing In Vivo.", Angewandte Chemie, (Jul. 10, 2012), vol. 51, No. 34, pp. 8529-8533, XP055063645.

(56) References Cited

OTHER PUBLICATIONS

Karikó et al., "Incorporation of Pseudouridine Into mRNA Yields Superior Nonimmunogenic Vector With Increased Translational Capacity and Biological Stability," Mol Ther, vol. 16, Issue 11, Nov. 2008, pp. 1833-1840.

Karikó et al., "Suppression of RNA Recognition by Toll-like Receptors: The Impact of Nucleoside Modification and the Evolutionary Origin of RNA," Immunity, Aug. 2005, vol. 23, 165-175.

Kariko et al., 2011. "Generating the optimal mRNA for therapy: HPLC purification eliminates immune activation and improves translation of nucleosidemodified, protein-encoding mRNA." Nucleic Acids Research 39(21):e142, pp. 1-10.

Kariko et al., 2012, "Increased Erythropoiesis in Mice Injected with Submicrogram Quantities of Pseudouridine-containing mRNA Encoding Erythropoietin." Mol Ther 20:948-953.

Kirchdoerfer et al., 2016, "Pre-fusion structure of a human coronavirus spike protein," Nature. Mar. 3, 2016;531(7592):118-21.

Laczko et al., "A Single Immunization with Nucleoside-Modified mRNA Vaccines Elicits Strong Cellular and Humoral Immune Responses against SARS-CoV-2 in Mice", Cell Press, (Oct. 13, 2020), vol. 53, pp. 724-732, XP086292180.

Lee et al., 2012, "Lipid nanoparticle siRNA systems for silencing the androgen receptor in human prostate cancer in vivo." Int J Cancer., 131(5): E781-90.

Leung et al., 2012, "Lipid Nanoparticles Containing siRNA Synthesized by Microfluidic Mixing Exhibit an Electron-Dense Nanostructured Core." J Phys Chem C Nanomater Interfaces, 116(34): 18440-18450.

Maier et al., 2013, "Biodegradable lipids enabling rapidly eliminated lipid nanoparticles for systemic delivery of RNAi therapeutics." Mol Ther., 21(8): 1570-1578, XP055551712, ISSN: 1525-0016.

Minor, 2015, "Live attenuated vaccines: Historical successes and current challenges," Virology, 479-480: 379-392.

Mui et al., 2013, "Influence of Polyethylene Glycol Lipid Desorption Rates on Pharmacokinetics and Pharmacodynamics of siRNA Lipid Nanoparticles." Mol Ther Nucleic Acids. 2, e139, 8 pages.

Muthumani et al. "In vivo protection against ZIKV infection and pathogenesis through passive antibody transfer and active immunisation with a prMEnv DNA vaccine," Npj Vaccines (2016) 1, 16021, 11 pages.

Pardi et al. (2018a). "Nucleoside-modified mRNA vaccines induce potent T follicular helper and germinal center B cell responses." J Exp Med. Jun. 4, 2018;215(6):1571-1588.

Pardi et al. (2018b). Nucleoside-modified mRNA immunization elicits influenza virus hemagglutinin stalk-specific antibodies. Nat Commun. Aug. 22, 2018;9(1):3361.

Pardi et al. (2017). "Zika virus protection by a single low-dose nucleoside-modified mRNA vaccination." Nature. Mar. 9, 2017;543(7644):248-251.

Pardi et al., "Expression kinetics of nucleoside-modified mRNA delivered in lipid nanoparticles to mice by various routes," Journal of Controlled Release vol. 217, Nov. 10, 2015, pp. 345-351.

Petsch et al., "Protective efficacy of in vitro synthesized, specific mRNA vaccines against influenza A virus infection," Nature Biotechnology 30:1210-1216, 2012.

Sahin et al., "mRNA-based therapeutics—developing a new class of drugs," Nature Reviews Drug Discovery vol. 13, pp. 759-780(2014).

Semple et al., 2010, "Rational design of cationic lipids for siRNA delivery." Nat Biotechnol., 28(2):172-176.

Smatti et al., 2018, "Viral-Induced Enhanced Disease Illness," Front Microbiol. Dec. 5, 2018:9:2991.

Smith et al., (2020). "Immunogenicity of a DNA vaccine candidate for COVID-19." Nat Commun. May 20, 2020;11(1):2601.

Tam et al., "Advances in Lipid Nanoparticles for siRNA Delivery," Pharmaceutics 5:498-507, 2013.

Tam et al., 2013, "Small molecule ligands for enhanced intracellular delivery of lipid nanoparticle formulations of siRNA." Nanomedicine, 9(5): 665-74.

Torrecilla, J et al., "Lipid Nanoparticles as Carriers for RNAi against Viral infections: Current Status and Future Perspectives.", BioMed Research International., (Aug. 12, 2014), vol. 2014, No. 2014, pp. 1-18, XP055326069.

Wang et al., 2009, "Efficient Assembly and Secretion of Recombinant Subviral Particles of the Four Dengue Serotypes Using Native prM and E Proteins," PLoS One 4: e8325, 13 pages.

Weissman et al., 2000, "HIV Gag mRNA Transfection of Dendritic Cells (DC) Delivers Encoded Antigen to MHC Class I and II Molecules, Causes DC Maturation, and Induces a Potent Human In Vitro Primary Immune Response," J Immunol, 165: 4710-4717.

Weissman et al., 2013, "HPLC purification of in vitro transcribed long RNA," Methods Mol Biol, 969: 43-54.

Weissman, 2015, "mRNA transcript therapy," Expert Rev Vaccines, 14: 265-281.

Whitehead et al: "Synergistic Silencing: Combinations of Lipid-like Materials for Efficacious siRNA Delivery", Molecular Therapy, vol. 19, No. 9, Sep. 1, 2011 (Sep. 1, 2011), pp. 1688-1694.

Yu et al., (2020). DNA vaccine protection against SARS-CoV-2 in rhesus macaques. Science. Aug. 14, 2020;369(6505):806-811.

Zhao et al., 2016, "Airway Memory CD4(+) T Cells Mediate Protective Immunity against Emerging Respiratory Coronaviruses," Immunity. Jun. 21, 2016;44(6):1379-91.

* cited by examiner

C

*P* values of vaccine groups vs Naïve

| Reciprocal dilution | Luc | Full length Δfurin | RBD | ZIKV |
|---|---|---|---|---|
| $3 \times 10^1$ | <0.0001 | <0.0001 | <0.0001 | >0.9999 |
| $1 \times 10^2$ | 0.0018 | <0.0001 | <0.0001 | >0.9999 |
| $3 \times 10^2$ | 0.1648 | <0.0001 | <0.0001 | >0.9999 |
| $1 \times 10^3$ | 0.0526 | <0.0001 | <0.0001 | 0.9962 |
| $3 \times 10^3$ | 0.3007 | 0.3497 | 0.0022 | 0.0068 |
| $1 \times 10^4$ | 0.9156 | >0.9999 | 0.9781 | <0.0001 |
| $3 \times 10^4$ | 0.9436 | 0.9969 | 0.7579 | <0.0001 |
| $1 \times 10^5$ | 0.9817 | 0.9924 | 0.9944 | <0.0001 |

INGUINAL LYMPH NODES
GATED on DUMP- CD19+ CELLS

GATED on DUMP- CD19+Fas+GL7+ RBD-PE+ RBD AF647+ CELLS

Day 7 INGUINAL LYMPH NODES

NUCLEOSIDE-MODIFIED RNA FOR INDUCING AN IMMUNE RESPONSE AGAINST SARS-CoV-2

CROSS REFERENCE TO RELATED APPLICATIONS

This application claims priority to International Patent Application No. PCT/US21/40811, filed Jul. 8, 2021, claiming priority U.S. Provisional Application No. 63/049,295, filed Jul. 8, 2020, each of which is hereby incorporated by reference herein in its entirety.

STATEMENT REGARDING FEDERALLY SPONSORED RESEARCH OR DEVELOPMENT

This invention was made with government support under AI146101 awarded by National Institutes of Health. The government has certain rights in the invention.

REFERENCE TO A "SEQUENCE LISTING," A TABLE, OR A COMPUTER PROGRAM LISTING APPENDIX SUBMITTED AS AN ASCII TEXT FILE

The Sequence Listing written in the ASCII text file: "046483-6209-00US_SequenceListing.txt"; created on Jan. 4, 2023, and 49,977 bytes in size, is hereby incorporated by reference.

BACKGROUND OF THE INVENTION

Severe acute respiratory syndrome coronavirus 2 (SARS-CoV-2), the causative agent of COVID-19, causes significant mortality and morbidity worldwide and was declared a pandemic by the World Health Organization in March, 2020 (Cucinotta and Vanelli, 2020, Acta Biomed, 91:157-160). The rapid spread of the virus has caused not only a significant health care burden but also an economic crisis. Governments around the world have introduced strict social distancing measures to keep transmission under control. However, a vaccine will ultimately be required to fully suppress the SARS-CoV-2 pandemic.

Thus, there is a need in the art for compositions and methods to treat and prevent SARS-CoV-2 infection. The present invention satisfies this unmet need.

SUMMARY OF THE INVENTION

In one aspect, the present invention provides a composition for inducing an immune response against severe acute respiratory syndrome coronavirus 2 (SARS-CoV-2) in a subject, the composition comprising at least one isolated nucleoside-modified RNA encoding at least one SARS-CoV-2 antigen.

In one embodiment, the at least one isolated nucleoside-modified RNA comprises pseudouridine. In one embodiment, the at least one isolated nucleoside-modified RNA comprises 1-methyl-pseudouridine. In one embodiment, the at least one isolated nucleoside-modified RNA is a purified nucleoside-modified RNA.

In one embodiment, the SARS-CoV-2 antigen is a SARS-CoV-2 spike antigen, a fragment thereof, or a variant thereof. In one embodiment, the SARS-CoV-2 antigen comprises at least one of a full length SARS-CoV-2 spike antigen, a fragment of the full length SARS-CoV-2 spike antigen comprising the receptor binding domain, and a variant of the full length SARS-CoV-2 spike antigen comprising a mutation of the furin cleavage site.

In one embodiment, the at least one SARS-CoV-2 antigen comprises an amino acid sequence of SEQ ID NO: 3, SEQ ID NO:6 or SEQ ID NO:9. In one embodiment, the at least one nucleoside-modified RNA comprises a nucleotide sequence transcribed from a nucleotide sequence of SEQ ID NO: 1, SEQ ID NO:2, SEQ ID NO:4, SEQ ID NO:5, SEQ ID NO:7 or SEQ ID NO:8.

In one embodiment, the composition is a vaccine. In one embodiment, the composition further comprises an adjuvant. In one embodiment, the at least one nucleoside-modified RNA further encodes at least one adjuvant.

In one embodiment, the composition comprises a lipid nanoparticle (LNP). In one embodiment, the at least one nucleoside-modified RNA is encapsulated within the LNP. In one embodiment, the LNP comprises a compound having a structure of Formula (I):

(I)

or a pharmaceutically acceptable salt, tautomer, prodrug or stereoisomer thereof, wherein:

$L^1$ and $L^2$ are each independently —O(C=O)—, —(C=O)O— or a carbon-carbon double bond;

$R^{1a}$ and $R^{1b}$ are, at each occurrence, independently either (a) H or $C_1$-$C_{12}$ alkyl, or (b) $R^{1a}$ is H or $C_1$-$C_{12}$ alkyl, and $R^{1b}$ together with the carbon atom to which it is bound is taken together with an adjacent $R^{1b}$ and the carbon atom to which it is bound to form a carbon-carbon double bond;

$R^{2a}$ and $R^{2b}$ are, at each occurrence, independently either (a) H or $C_1$-$C_{12}$ alkyl, or (b) $R^{2a}$ is H or $C_1$-$C_{12}$ alkyl, and $R^{2b}$ together with the carbon atom to which it is bound is taken together with an adjacent $R^{2b}$ and the carbon atom to which it is bound to form a carbon-carbon double bond;

$R^{3a}$ and $R^{3b}$ are, at each occurrence, independently either (a) H or $C_1$-$C_{12}$ alkyl, or (b) $R^{3a}$ is H or $C_1$-$C_{12}$ alkyl, and $R^{3b}$ together with the carbon atom to which it is bound is taken together with an adjacent $R^{3b}$ and the carbon atom to which it is bound to form a carbon-carbon double bond;

$R^{4a}$ and $R^{4b}$ are, at each occurrence, independently either (a) H or $C_1$-$C_{12}$ alkyl, or (b) $R^{4a}$ is H or $C_1$-$C_{12}$ alkyl, and $R^{4b}$ together with the carbon atom to which it is bound is taken together with an adjacent $R^{4b}$ and the carbon atom to which it is bound to form a carbon-carbon double bond;

$R^5$ and $R^6$ are each independently methyl or cycloalkyl;

$R^7$ is, at each occurrence, independently H or $C_1$-$C_{12}$ alkyl;

$R^8$ and $R^9$ are each independently unsubstituted $C_1$-$C_{12}$ alkyl; or $R^8$ and $R^9$, together with the nitrogen atom to which they are attached, form a 5, 6 or 7-membered heterocyclic ring comprising one nitrogen atom;

a and d are each independently an integer from 0 to 24;

b and c are each independently an integer from 1 to 24; and e is 1 or 2.

In one embodiment, the LNP comprises a compound having a structure of Formula (II):

(II)

or a pharmaceutically acceptable salt, tautomer, prodrug or stereoisomer thereof, wherein:

$L^1$ and $L^2$ are each independently —O(C=O)—, —(C=O)O—, —C(=O)—, —O—, —S(O)$_x$—, —S—S—, —C(=O)S—, —SC(=O)—, —NR$^a$C(=O)—, —C(=O)NR$^a$—, —NR$^a$C(=O)NR$^a$, —OC(=O)NR$^a$—, —NR$^a$C(=O)O—, or a direct bond;

$G^1$ is $C_1$-$C_2$ alkylene, —(C=O)—, —O(C=O)—, —SC(=O)—, —NR$^a$C(=O)— or a direct bond;

$G^2$ is —C(=O)—, —(C=O)O—, —C(=O)S—, —C(=O)NR$^a$ or a direct bond;

$G^3$ is $C_1$-$C_6$ alkylene;

$R^a$ is H or $C_1$-$C_{12}$ alkyl;

$R^{1a}$ and $R^{1b}$ are, at each occurrence, independently either:
   (a) H or $C_1$-$C_{12}$ alkyl; or (b) $R^{1a}$ is H or $C_1$-$C_{12}$ alkyl, and $R^{1b}$ together with the carbon atom to which it is bound is taken together with an adjacent $R^{1b}$ and the carbon atom to which it is bound to form a carbon-carbon double bond;

$R^{2a}$ and $R^{2b}$ are, at each occurrence, independently either:
   (a) H or $C_1$-$C_{12}$ alkyl; or (b) $R^{2a}$ is H or $C_1$-$C_{12}$ alkyl, and $R^{2b}$ together with the carbon atom to which it is bound is taken together with an adjacent $R^{2b}$ and the carbon atom to which it is bound to form a carbon-carbon double bond;

$R^{3a}$ and $R^{3b}$ are, at each occurrence, independently either:
   (a) H or $C_1$-$C_{12}$ alkyl; or (b) $R^{3a}$ is H or $C_1$-$C_{12}$ alkyl, and $R^{3b}$ together with the carbon atom to which it is bound is taken together with an adjacent $R^{3b}$ and the carbon atom to which it is bound to form a carbon-carbon double bond;

$R^{4a}$ and $R^{4b}$ are, at each occurrence, independently either:
   (a) H or $C_1$-$C_{12}$ alkyl; or (b) $R^{4a}$ is H or $C_1$-$C_{12}$ alkyl, and $R^{4b}$ together with the carbon atom to which it is bound is taken together with an adjacent $R^{4b}$ and the carbon atom to which it is bound to form a carbon-carbon double bond;

$R^5$ and $R^6$ are each independently H or methyl;

$R^7$ is $C_4$-$C_{20}$ alkyl;

$R^8$ and $R^9$ are each independently $C_1$-$C_{12}$ alkyl; or $R^8$ and $R^9$, together with the nitrogen atom to which they are attached, form a 5, 6 or 7-membered heterocyclic ring;

a, b, c and d are each independently an integer from 1 to 24; and x is 0, 1 or 2.

In one embodiment, the LNP comprises a compound having a structure of (III)

or a pharmaceutically acceptable salt, tautomer, prodrug or stereoisomer thereof, wherein:

one of $L^1$ or $L^2$ is —O(C=O)—, —(C=O)O—, —C(=O)—, —O—, —S(O)$_x$—, —S—S—, —C(=O)S—, SC(=O)—, —NR$^a$C(=O)—, —C(=O)NR$^a$—, NR$^a$C(=O)NR$^a$, —OC(=O)NR$^a$— or —NR$^a$C(=O)O—, and the other of $L^1$ or $L^2$ is —O(C=O)—, —(C=O)O—, —C(=O)—, —O—, —S(O)$_x$—, —S—S—, —C(=O)S—, SC(=O)—, —NR$^a$C(=O)—, —C(=O)NR$^a$—, NR$^a$C(=O)NR$^a$, —OC(=O)NR$^a$— or —NR$^a$C(=O)O— or a direct bond;

$G^1$ and $G^2$ are each independently unsubstituted $C_1$-$C_{12}$ alkylene or $C_1$-$C_{12}$ alkenylene;

$G^3$ is $C_1$-$C_{24}$ alkylene, $C_1$-$C_{24}$ alkenylene, $C_3$-$C_8$ cycloalkylene, $C_3$-$C_8$ cycloalkenylene;

$R^a$ is H or $C_1$-$C_{12}$ alkyl;

$R^1$ and $R^2$ are each independently $C_6$-$C_{24}$ alkyl or $C_6$-$C_{24}$ alkenyl;

$R^3$ is H, OR$^5$, CN, —C(=O)OR$^4$, —OC(=O)R$^4$ or —NR$^5$C(=O)R$^4$;

$R^4$ is $C_1$-$C_{12}$ alkyl;

$R^5$ is H or $C_1$-$C_6$ alkyl; and x is 0, 1 or 2.

In one embodiment, the LNP comprises a compound having one of the following s

-continued

-continued

In one embodiment, the LNP comprises a pegylated lipid having the following structure (IV):

(IV)

or a pharmaceutically acceptable salt, tautomer or stereoisomer thereof, wherein:

R$^{10}$ and R$^{11}$ are each independently a straight or branched, saturated or unsaturated alkyl chain containing from 10 to 30 carbon atoms, wherein the alkyl chain is optionally interrupted by one or more ester bonds; and z has a mean value ranging from 30 to 60.

In one embodiment, the pegylated lipid has the following structure (IVa):

(IVa)

wherein n is an integer selected such that the average molecular weight of the pegylated lipid is about 2500 g/mol.

In one aspect, the present invention provides a method of inducing an adaptive immune response against SARS-CoV-2 in a subject. The method comprises administering to the subject an effective amount of a composition comprising at least one nucleoside-modified RNA encoding at least one SARS-CoV-2 antigen.

In one embodiment, the composition is administered by a delivery route selected from the group consisting of intradermal, subcutaneous, inhalation, intranasal, and intramuscular.

In one embodiment, the method comprises a single administration of the composition. In one embodiment, the method comprises more than one administration (i.e., at least two, at least three, at least four, at least five, at least six, at least seven, at least eight, at least nine, at least ten, or more) of the composition.

In one embodiment, the method treats or prevents an infection, disease, or disorder associated with SARS-CoV-2 in the subject. In one embodiment, the method treats or prevents COVID-19.

BRIEF DESCRIPTION OF THE DRAWINGS

The following detailed description of embodiments of the invention will be better understood when read in conjunction with the appended drawings. It should be understood that the invention is not limited to the precise arrangements and instrumentalities of the embodiments shown in the drawings.

FIG. 1A depicts exemplary results demonstrating that supernatant from 293F cells transfected with RBD-encoding mRNA or mock was tested for binding reactivity to D001 and hACE2-Fc by ELISA. Data shown are area under curve of the log-transformed concentrations (log AUC). Symbols represent independent experiments. All samples were run in triplicate. FIG. 1B depicts exemplary results demonstrating that 293F cells were transfected with mRNA encoding SARS-CoV-2 full-length WT and Δfurin S protein. Binding reactivity of full-length WT and Δfurin S proteins to D001, hACE2-Fc and negative control CH65 (an anti-influenza neutralizing antibody) was measured by flow cytometry.

Binding capacity was expressed in mean fluorescence intensity (MFI). Each dot represents an independent experiment. P value indicates a paired t-test; *P<0.05. Data represent mean plus SEM.

Figures 2A, 2B:
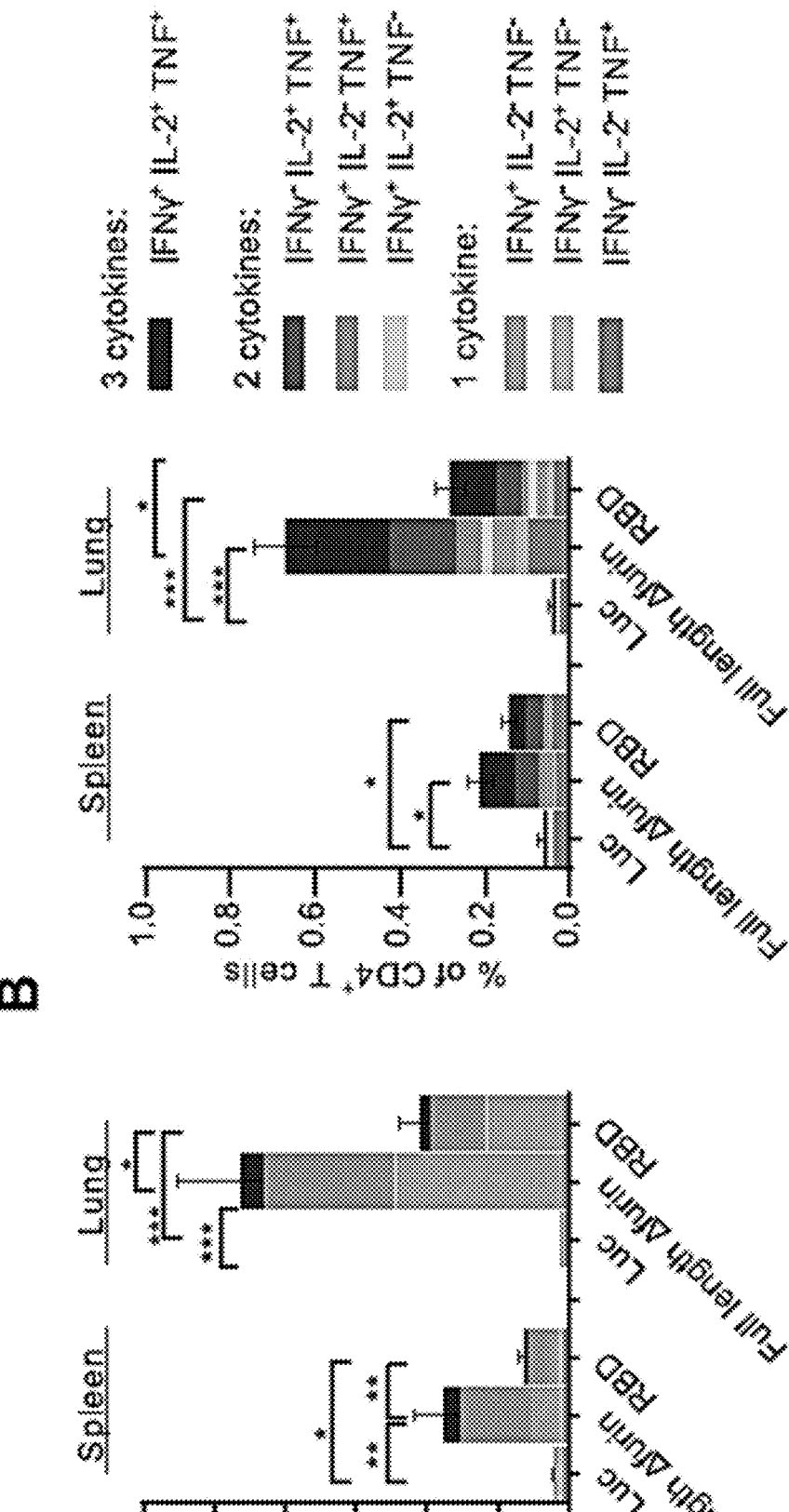
Figure 2C:
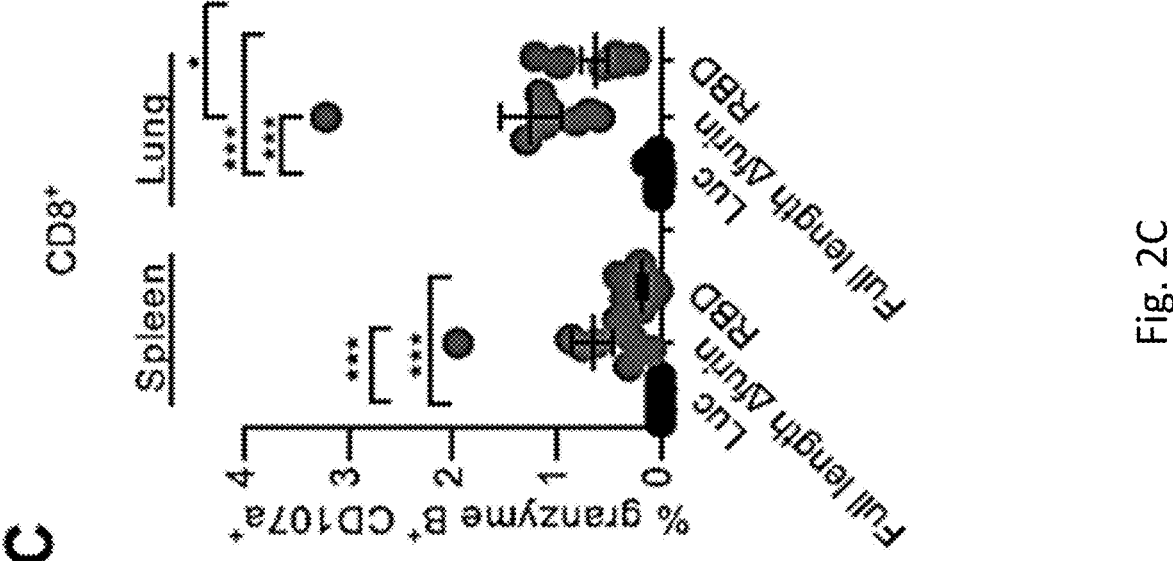
Figures 2D, 2E:
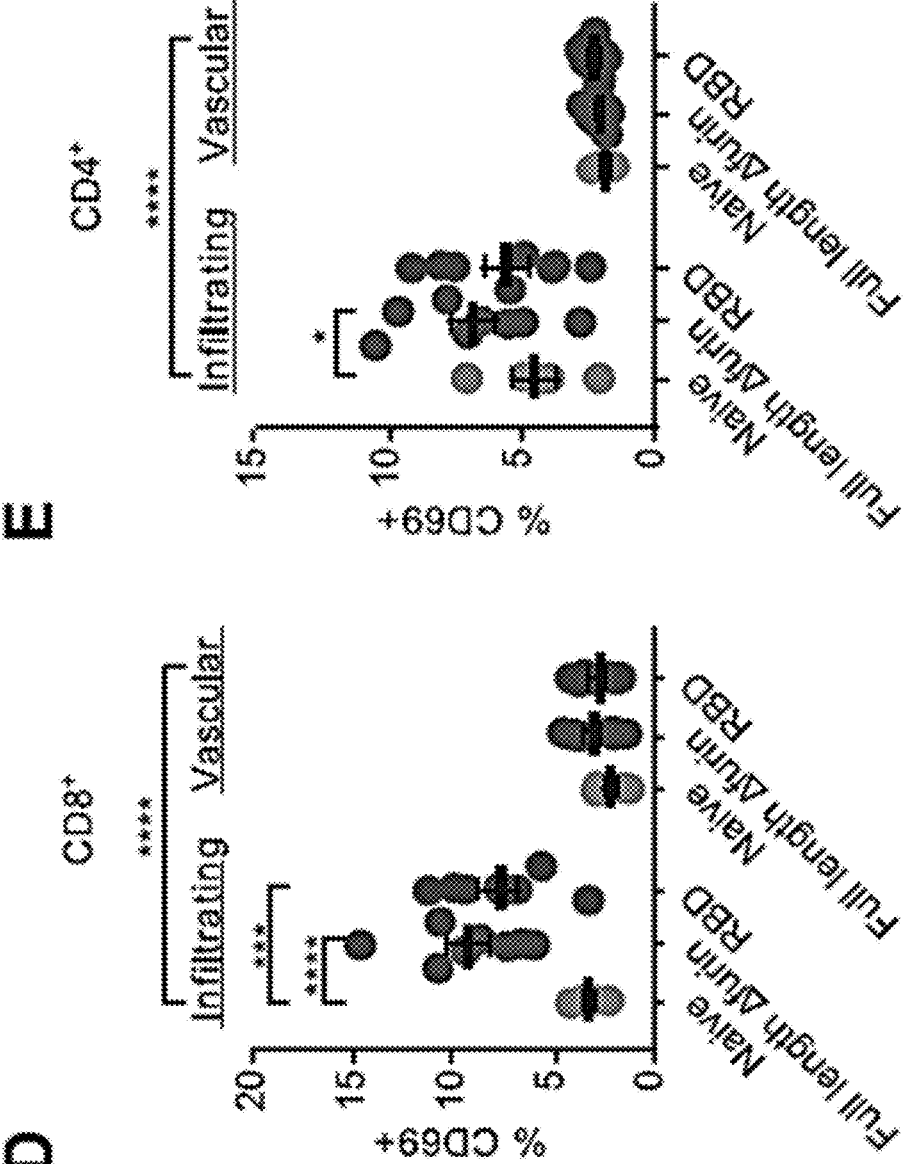
Figures 2F, 2G:
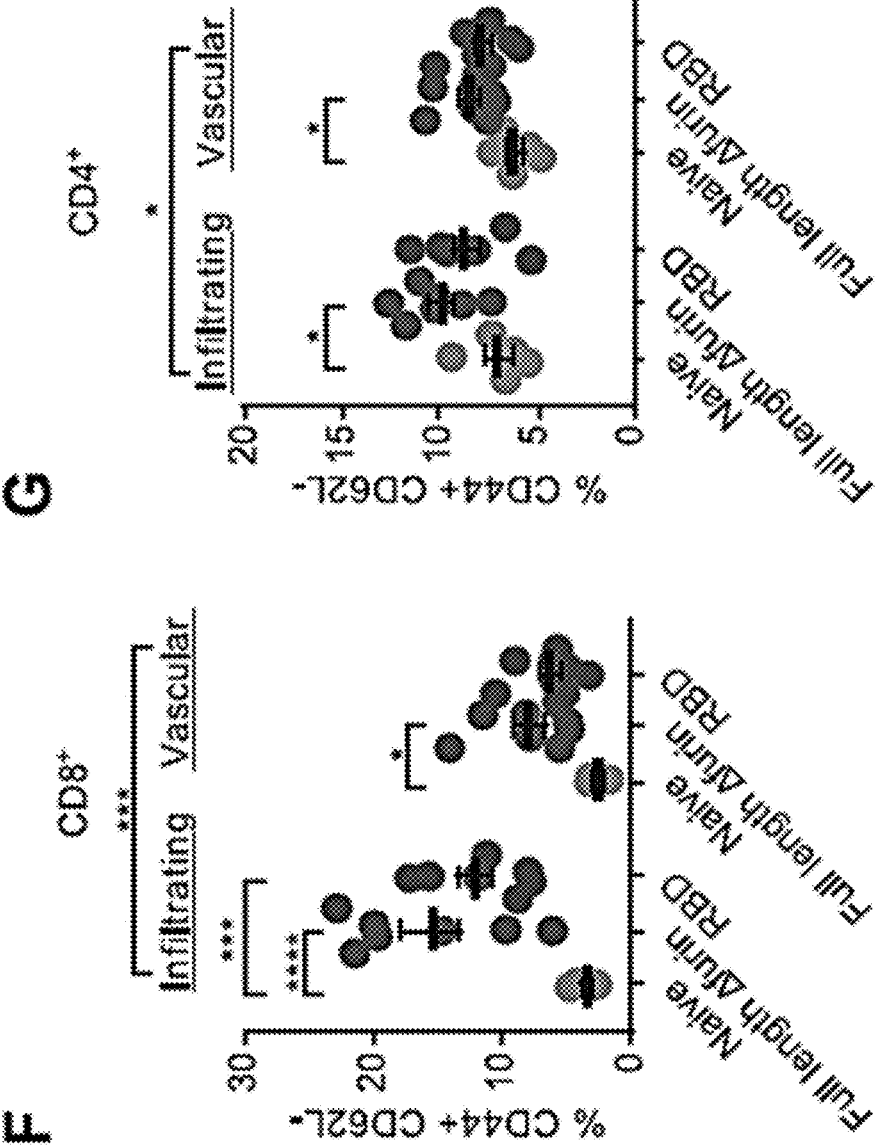

FIG. 2A through FIG. 2G depict exemplary experimental results demonstrating SARS-CoV-2 mRNA vaccines induce S protein-specific type 1 cellular responses. BALB/c mice were vaccinated i.m. with a single dose of 30 µg of mRNA-LNP vaccines. In FIG. 2A through FIG. 2C, spleen and lungs were harvested and stimulated with SARS-CoV-2 S protein peptide pools 10 days after immunization. T cells were stained for (FIG. 2A and FIG. 2B) type 1 intracellular cytokine expression and (FIG. 2C) cytolytic markers granzyme B and CD107a. In FIG. 2D through FIG. 2G, cells were stained directly ex vivo for activation markers, showing the proportion of i.v.-label negative (tissue-"infiltrating") and i.v.-label positive ("vascular") T cells that are (FIG. 2D and FIG. 2E) CD69$^+$ and (FIG. 2F and FIG. 2G) CD44$^+$ CD62L$^-$ in lung. n=8 mice per vaccine group and n=5 naive mice, pooled from two independent experiments. Naive mice were age matched, non-immunized BALB/c mice. For FIG. 2C through FIG. 2G, symbols represent individual animals. Data shown are mean plus SEM. Statistical analysis: (FIG. 2A through FIG. 2C) Kruskal-Wallis and post-hoc Mann Whitney U tests with Bonferroni correction and (FIG. 2D through FIG. 2G) two-way repeated measures ANOVA test with multiple post-hoc comparisons with Dunnett's correction. *P<0.05, P<0.01, *P<0.001, ****P<0.0001.

Figure 3A:
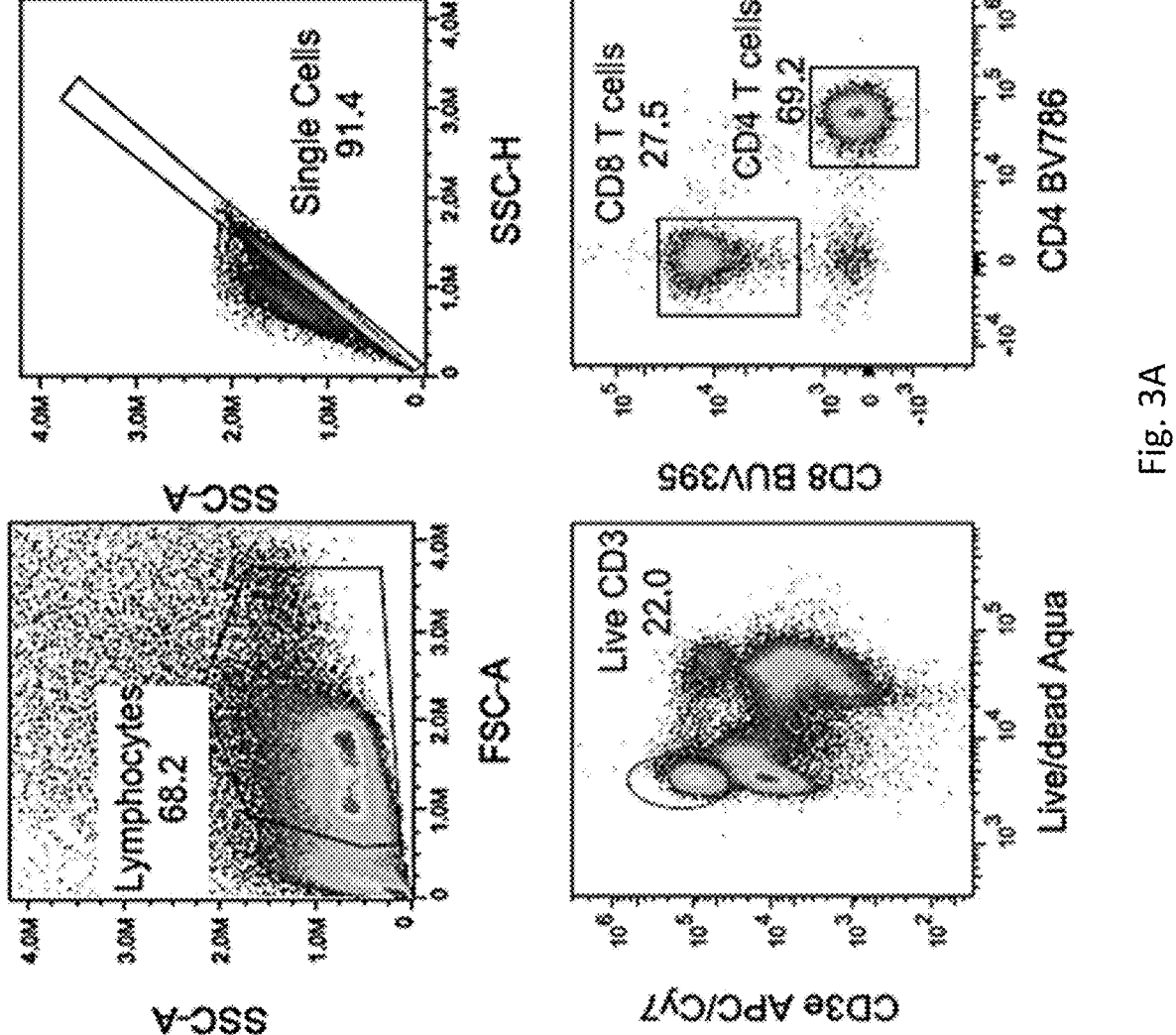
Figure 3B:
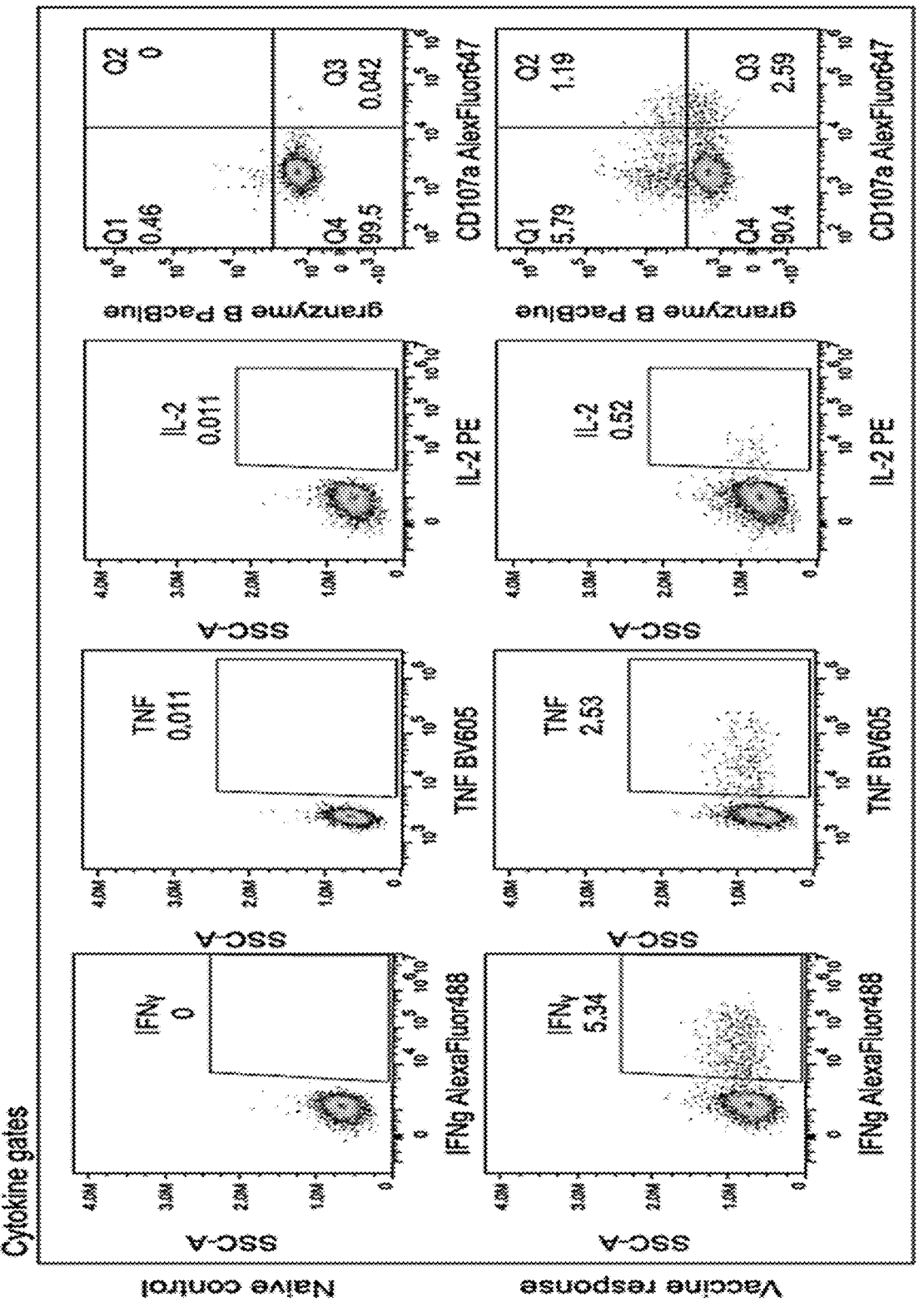
Figure 3C:
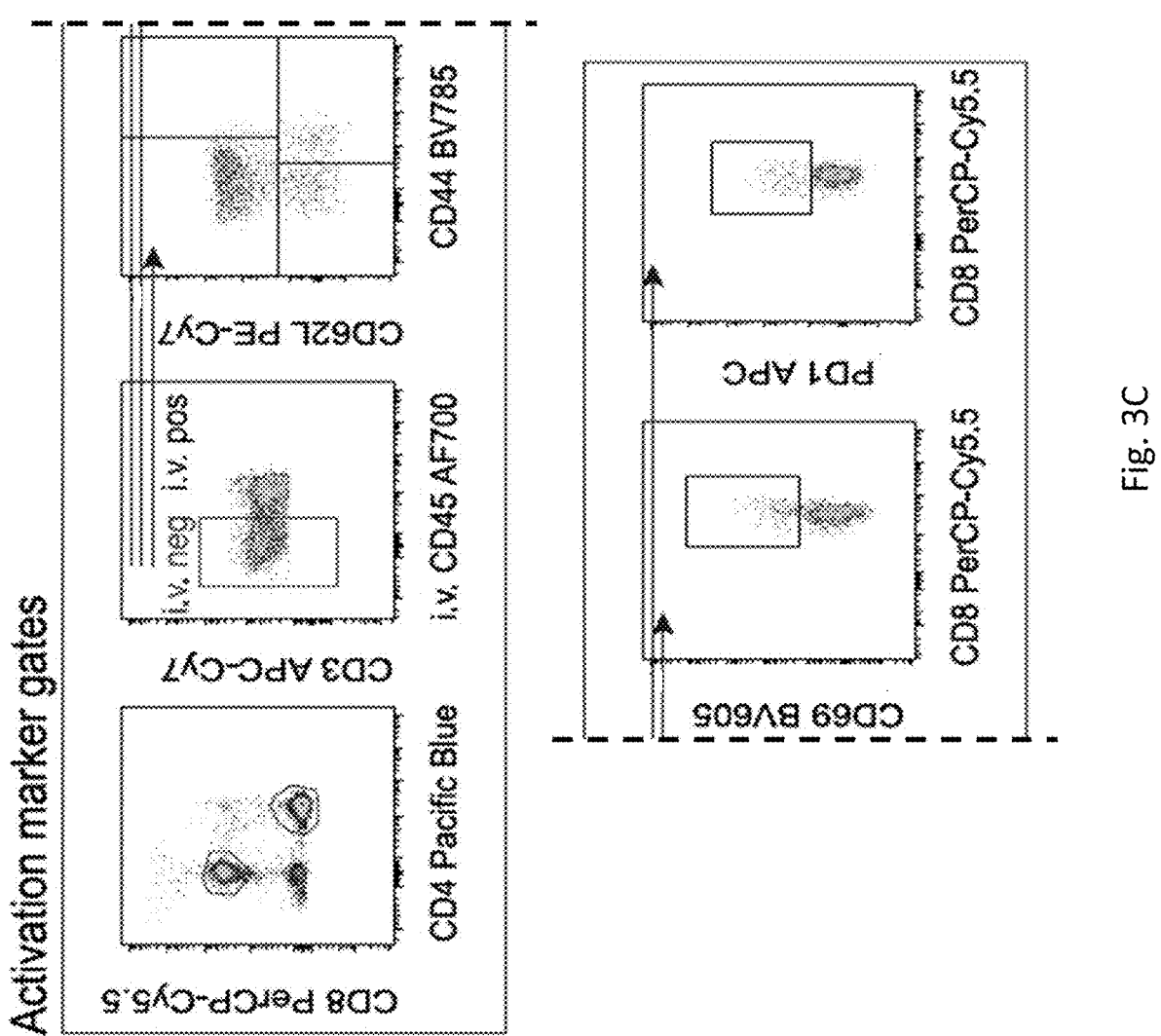

FIG. 3A through FIG. 3C depict exemplary experimental results demonstrating the gating strategy for intracellular cytokine staining and activation marker staining in CD8+ and CD4+ T cells. In FIG. 3A and FIG. 3B, the intracellular cytokine gating examples are lung cells from a naïve mouse and a representative CD8+ T cell cytokine response to the full length Δfurin mRNA-LNP vaccine. Spleen cells and CD4+ T cell acytokine responses were gated similarly. In FIG. 3C, the activation marker examples are lung cells from one representative full length Δfurin mRNA-LNP vaccine mouse, displaying the gating for i.v.-label negative CD8+ T cells. CD4+ T cells and i.v.-label positive cells were gated similarly.

FIG. 4A through FIG. 4D depict exemplary experimental results demonstrating T cell intracellular cytokine responses to individual peptide pools and PD-1 expression by lung T cells. For FIG. 4A and FIG. 4B, 10 days after vaccination, lung and spleen cells were stimulated ex vivo with JPT PepMix™ SARS-CoV-2 Spike Glycoprotein peptide pool 1 (N-terminal half of spike protein) and pool 2 (C-terminal half of spike protein). The frequency of sum total (FIG. 4A) IFN-γ, TNF, and IL-2 cytokine responses and (FIG. 4B) granzyme B+CD107a+ cells are shown for CD8+ and CD4+ T cells. For, FIG. 4C and FIG. 4D, the proportion of i.v. label-negative (tissue-"infiltrating") and i.v. label-positive ("vascular") CD8+ and CD4+ T cells from lung expressing PD-1, measured by ex vivo flow cytometry analysis 10 days after vaccination. n=5 mice for naive and n=8 mice per vaccine group, pooled from 2 experiments. Data shown are mean plus SEM, analyzed by two-way repeated measures ANOVA test with post-hoc multiple comparisons with Dunnett's correction. *P<0.05, ****P<0.0001.

FIG. 5A through FIG. 5D depict exemplary experimental results demonstrating humoral immune responses after SARS-CoV-2 mRNA vaccination. BALB/c mice received a single i.m. immunization with 30 µg of SARS-CoV-2 or Luc mRNA-LNP vaccines. For FIG. 5A, S protein-specific IgG levels were determined by endpoint dilution ELISA and for FIG. 5B, neutralizing antibody (Nab) levels were measured by a VSV-based pseudovirus neutralization assay before immunization and 4 and 9 weeks post immunization. For FIG. 5C, Nab levels were further confirmed by microneutralization assay using serum obtained 9 weeks post vaccination. n=10 mice/group. Naive mice were age matched, non-immunized BALB/c mice. For FIG. 5A through FIG. 5C, symbols represent individual animals. Horizontal lines represent the limit of detection. End-point dilution ELISA, $FRNT_{50}$ and $IC_{50}$ titers below the limit of detection are reported as half of the limit of detection. Data shown are mean plus SEM. For FIG. 5D, HEK293T cells transfected to express mFcγR1 were infected with SARS-CoV-2 pseudovirus or ZIKV virus-like particles preincubated with serially diluted anti-SARS-CoV-2 sera obtained 9 weeks post immunization or anti-ZIKV sera, respectively. Serum samples were pooled from 5 mice belonging to the same experimental group. Infection level was measured by luciferase assays. Mean±SEM of three independent experiments is presented. Statistical analysis: (FIG. 5A and FIG. 5B) two-way ANOVA and (FIG. 5C) one-way ANOVA with Tukey's multiple comparison on log-transformed data. (FIG. 5D) SARS-CoV-2: there are no significant differences when analyzed by two-way ANOVA with Tukey's multiple comparisons test; ZIKV: two-way ANOVA with Sidak's multiple comparisons test. *P<0.05, P<0.01, *P<0.001, ****P<0.0001. See also FIG. 6.

Figures 6A, 6B:
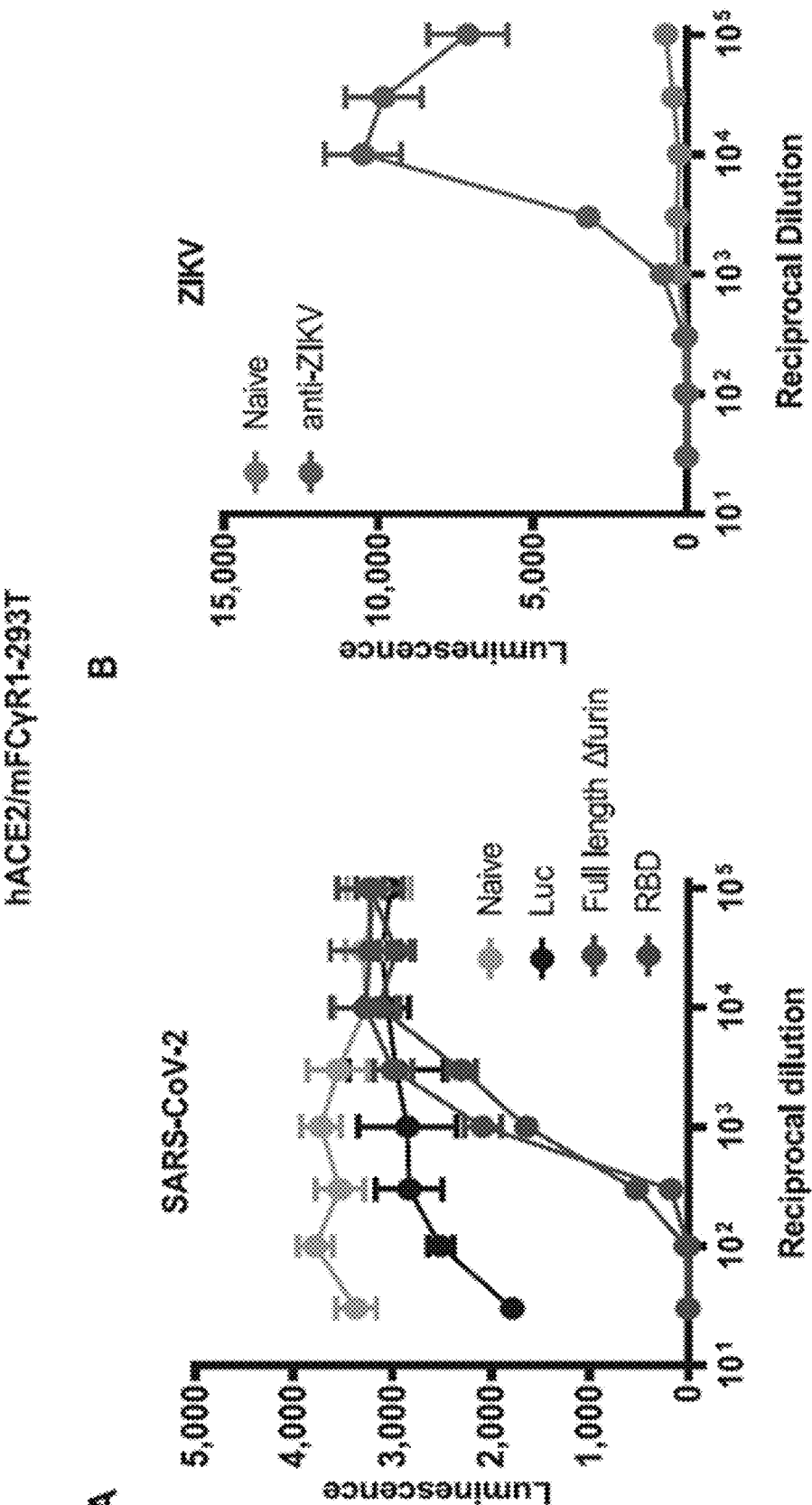

FIG. 6A through FIG. 6C depict exemplary experimental results demonstrating antisera from mRNA-LNP vaccinated mice does not promote antibody-dependent enhancement. HEK293T cells stably expressing human ACE2 transfected to express mFcγRI were infected with (FIG. 6A) SARS-CoV-2 pseudovirus preincubated with the serially diluted anti-SARS-CoV-2 sera obtained 9 weeks post immunization or (FIG. 6B) ZIKV virus-like particles preincubated with anti-ZIKV mouse sera. Serum samples were pooled from 5 mice belonging to the same experimental group. Infection level was measured by luciferase assays. Mean±SEM of three independent experiments is presented. Data were analyzed by two-way ANOVA with Tukey's multiple comparisons test (FIG. 6A) or by two-way ANOVA with Sidak's multiple comparisons test (FIG. 6B), and P values are presented (FIG. 6C).

Figure 7A:
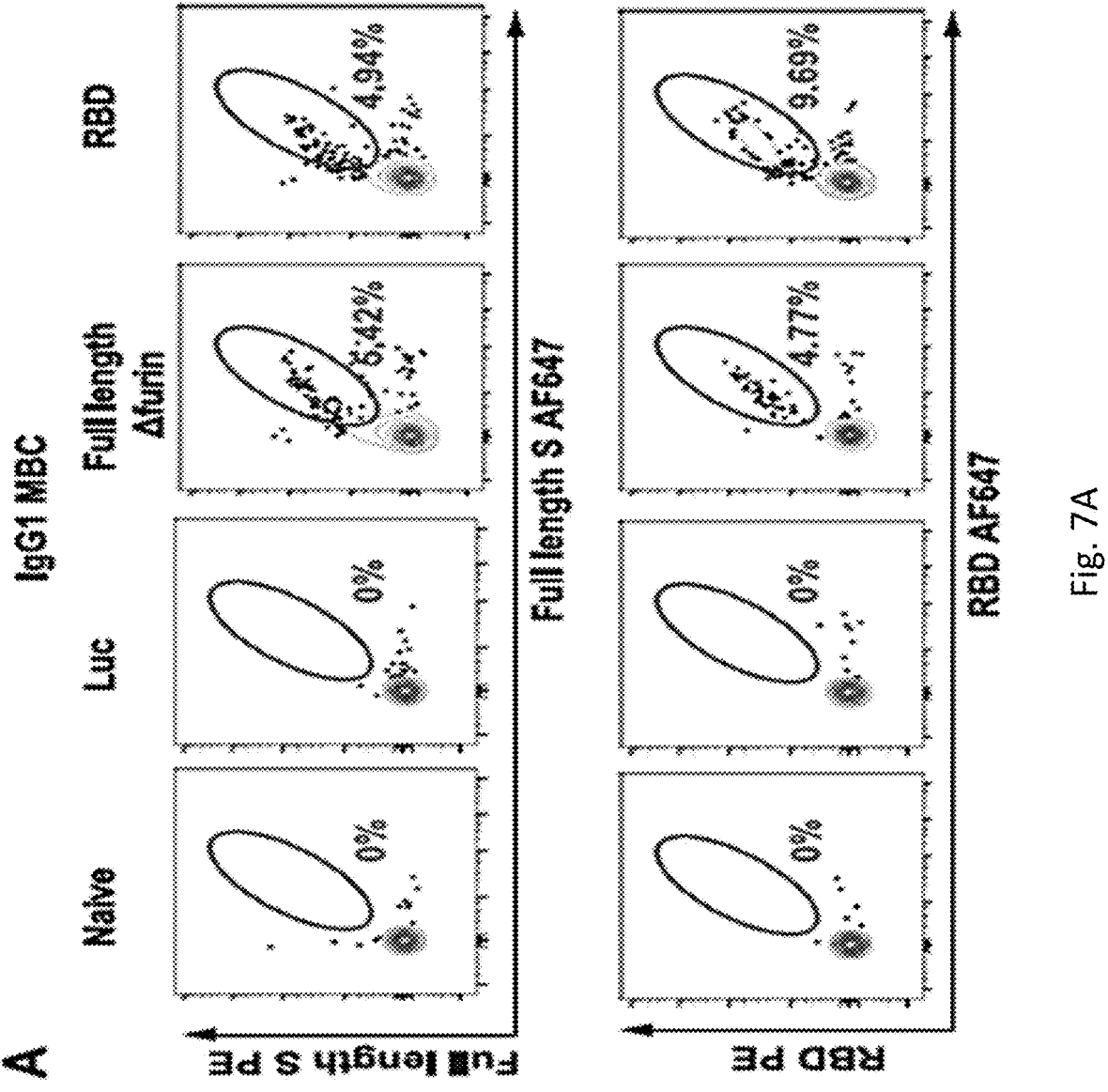
Figure 7B:
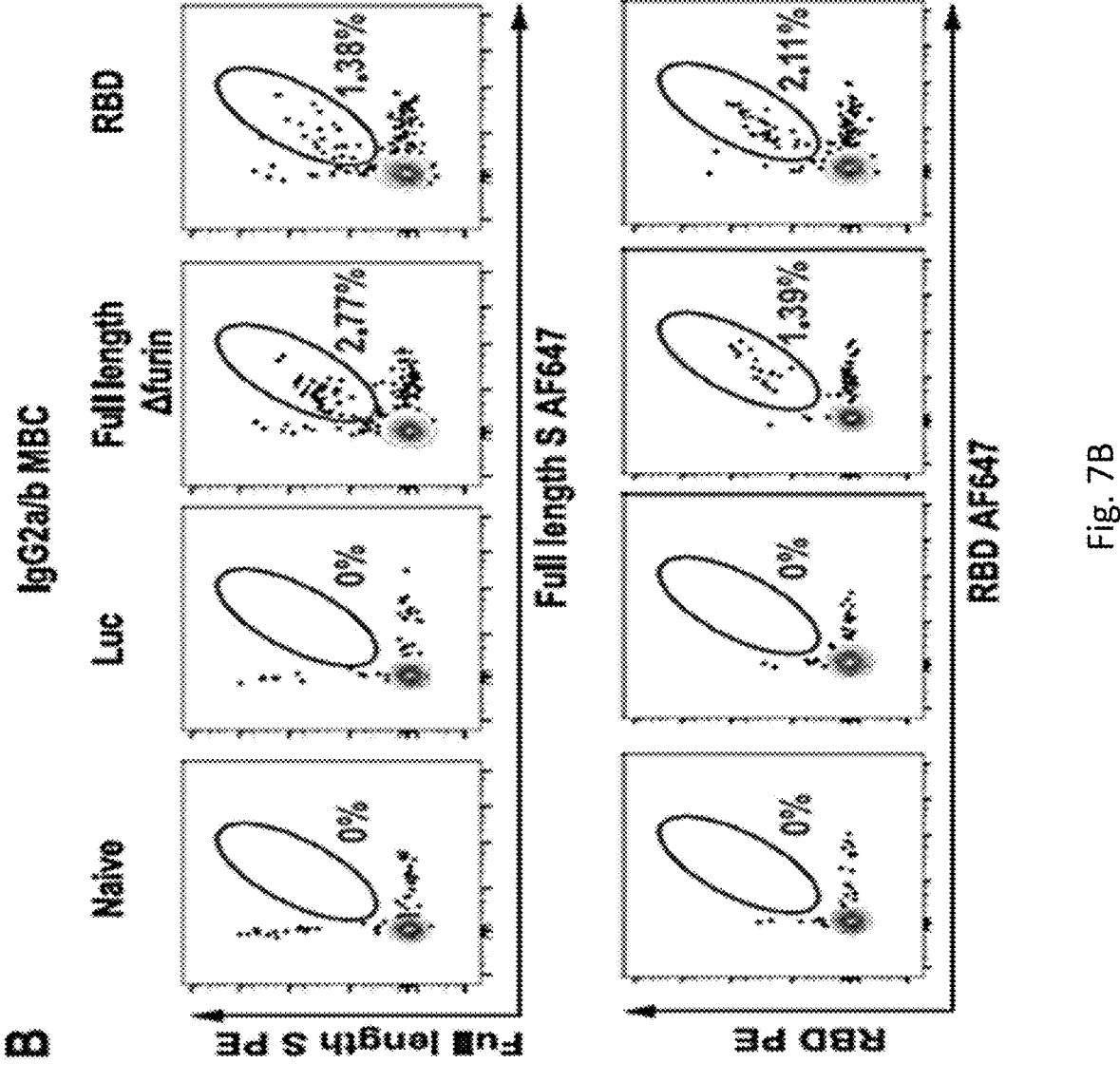
Figures 7C, 7D, 7E:
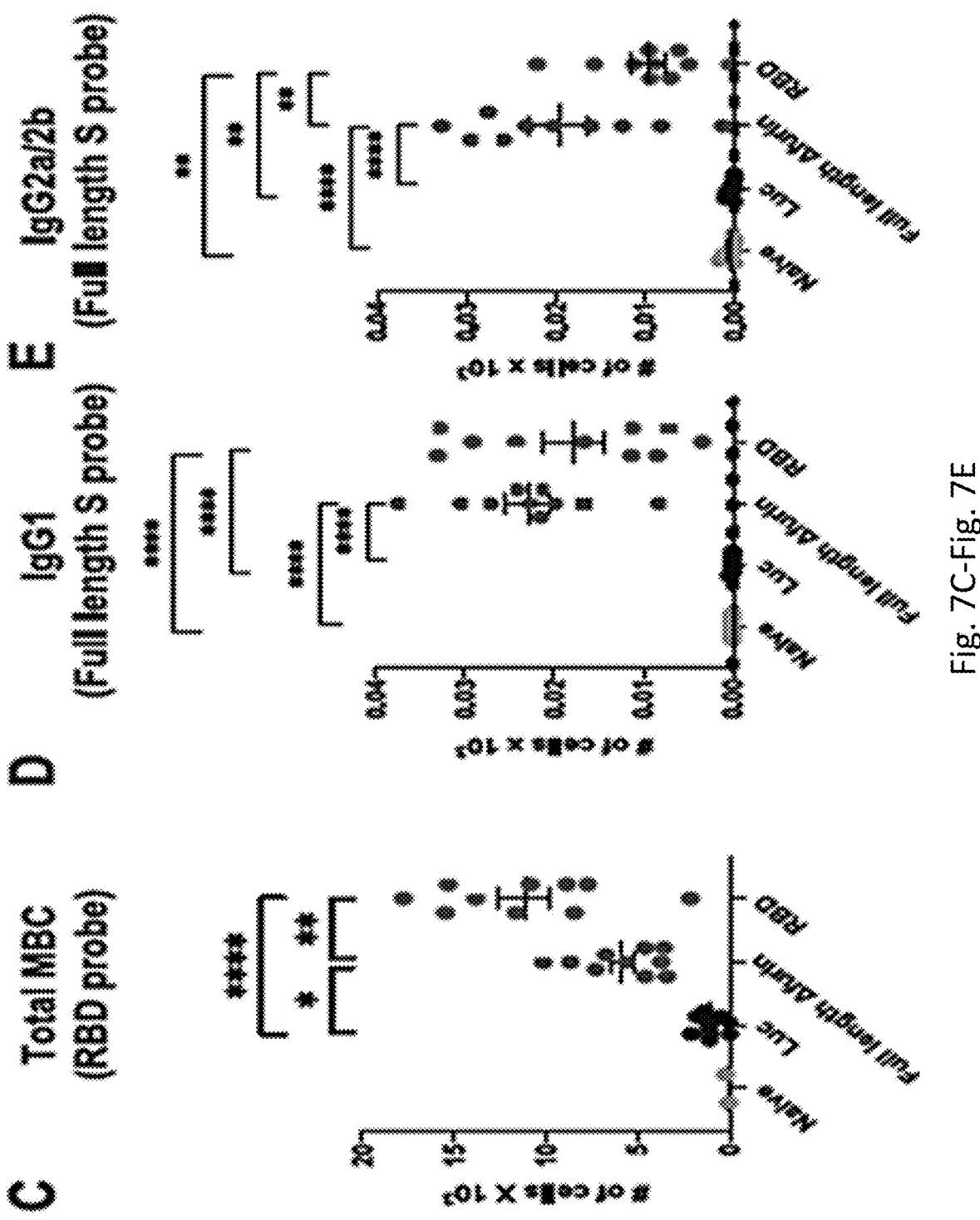
Figures 7F, 7G:
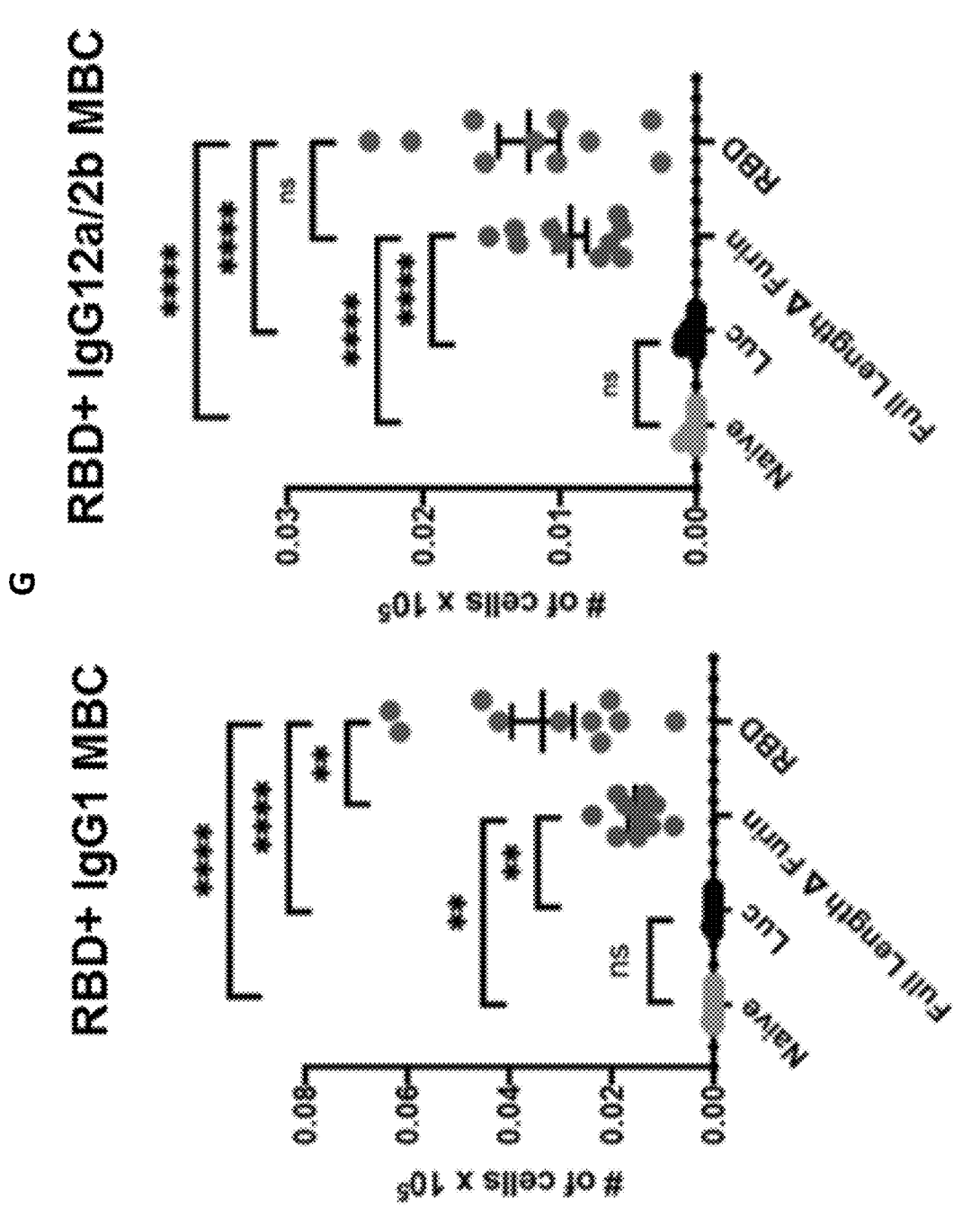
Figures 7H, 7I:
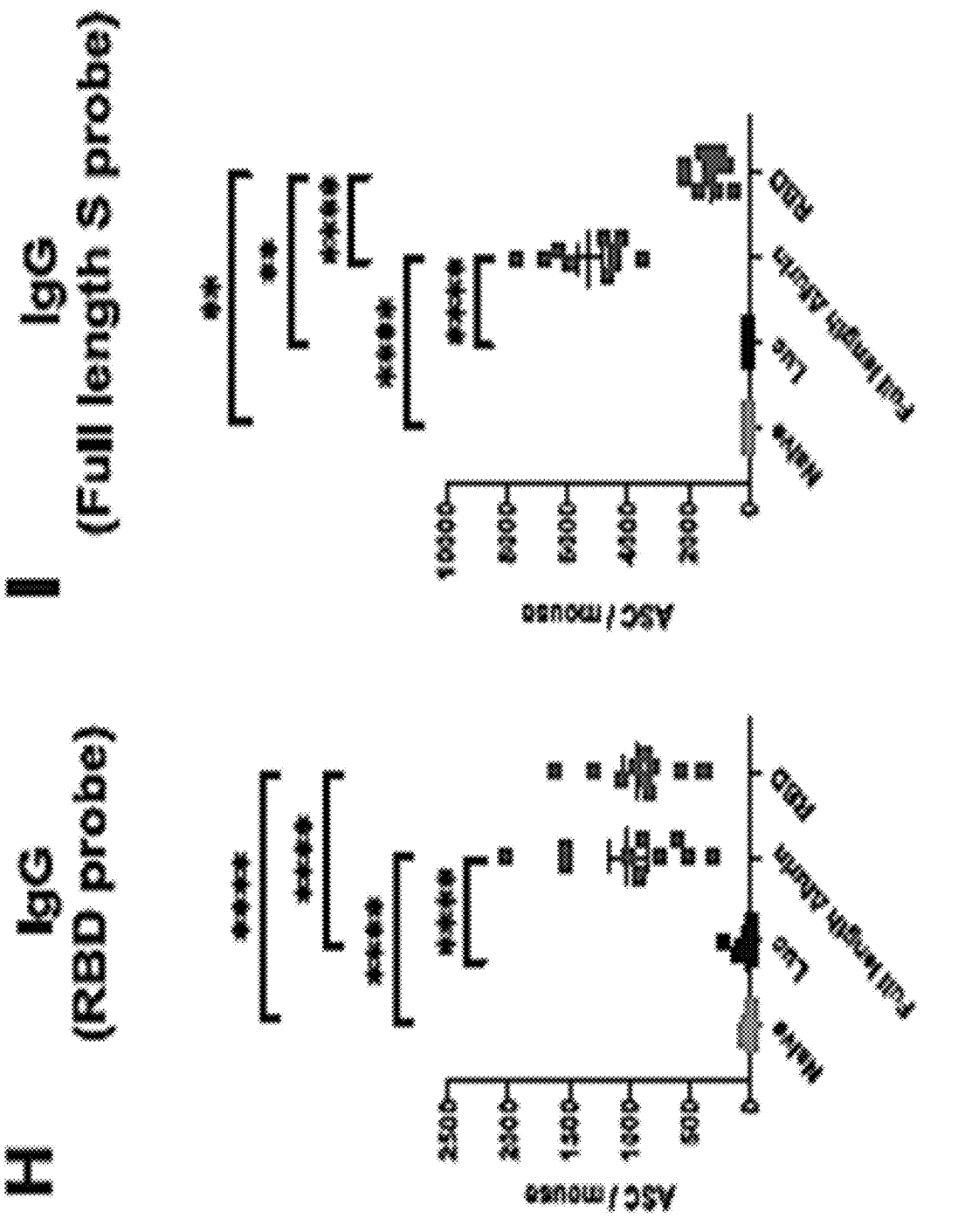
Figure 7J:
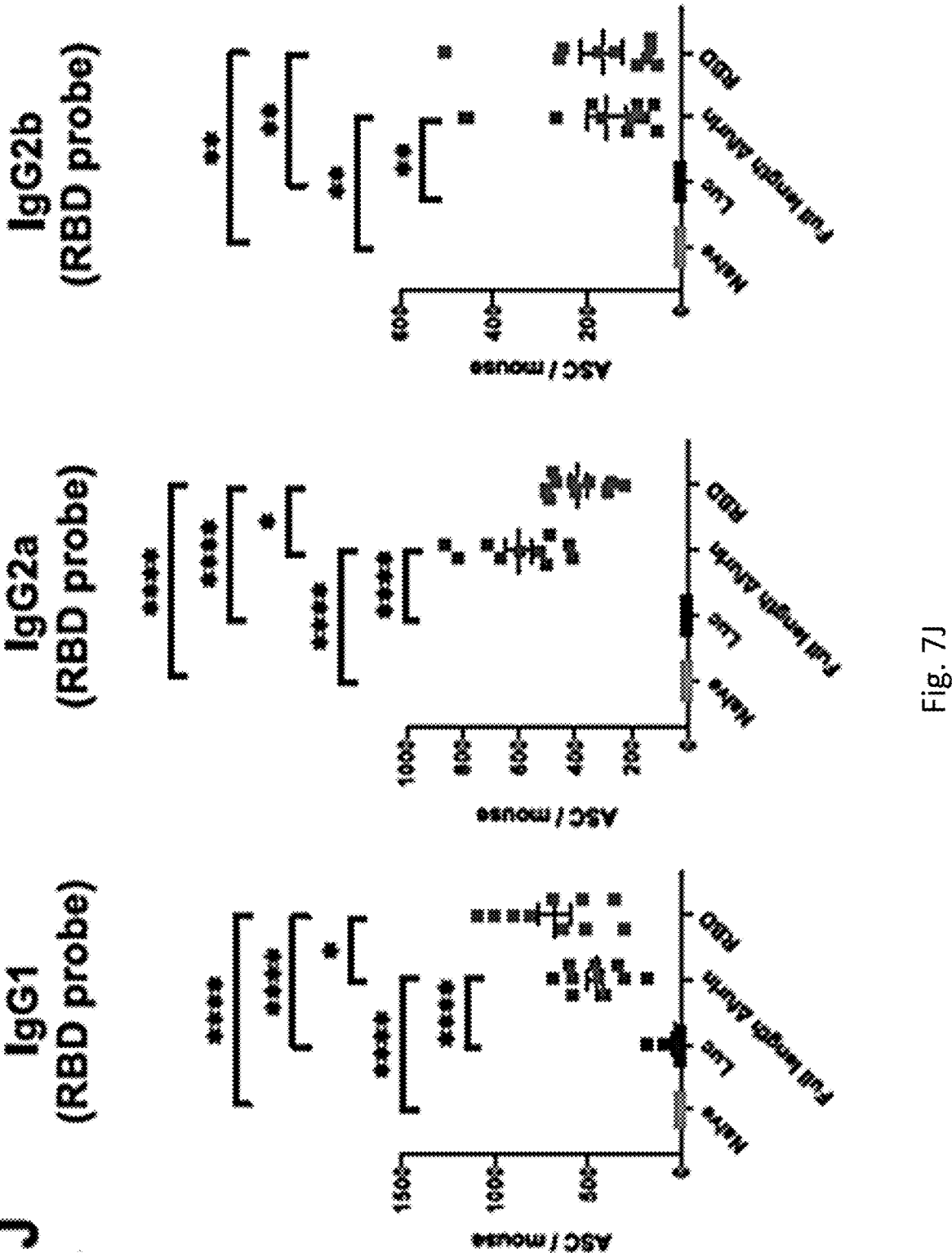
Figure 7J:
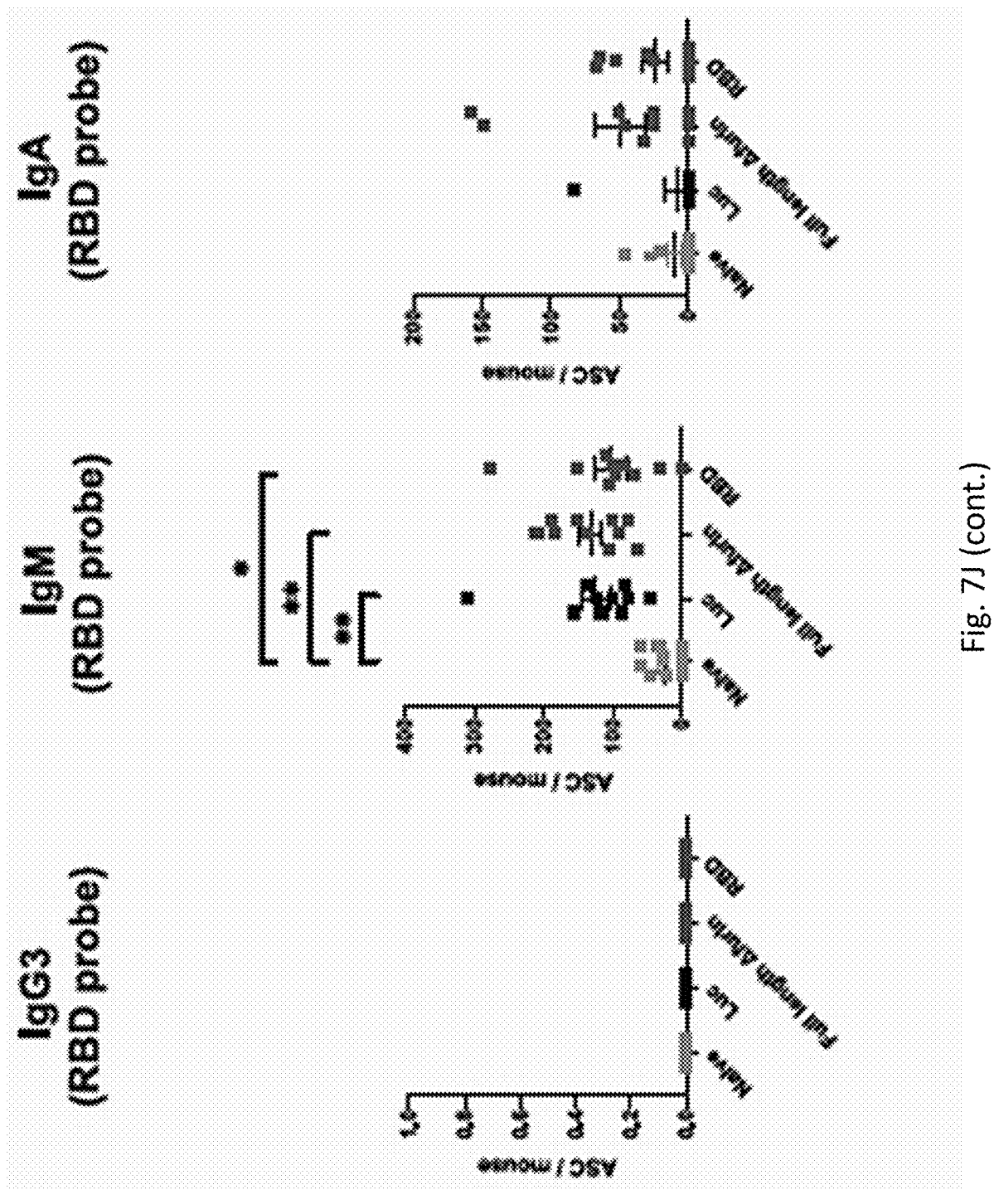

FIG. 7A through FIG. 7J depict exemplary experimental results demonstrating SARS-CoV-2 mRNA vaccines elicit antigen-specific MBC and LLPC responses. BALB/c mice received a single i.m. immunization with 30 µg of SARS-CoV-2 or Luc mRNA-LNP vaccines and sacrificed 9 weeks post immunization. FIG. 7A and FIG. 7B depict representative flow cytometry staining of full length Δfurin and RBD-specific splenic (FIG. 7A) IgG1 and (FIG. 7B) IgG2a/2b memory B cells (MBC). FIG. 7C depicts a quantification of total splenic RBD-specific MBC. FIG. 7D and FIG. 7E depict a quantitation of splenic full length Δfurin-specific (FIG. 7D) IgG1 and (FIG. 7E) IgG2a/2b MBC. FIG. 7F and FIG. 7G depict a quantification of RBD-specific splenic (FIG. 7F) IgG1 and (FIG. 7G) IgG2a/2b MBC. FIG. 7H and FIG. 7I depict a quantification of bone-marrow (FIG. 7H) RBD and (FIG. 7I) full length Δfurin-specific IgG Ab secreting cells (ASC). FIG. 7J depicts a quantification of bone-marrow RBD-specific IgG1, IgG2a, IgG2b, IgG3, IgM and IgA ASCs. n=10 mice per group, pooled from two independent experiments. Naive mice were age matched, non-immunized BALB/c mice. Symbols represent individual animals. Data shown are mean plus SEM. Statistical analysis: one-way ANOVA with Bonferroni correction, *P<0.05, P<0.01, *P<0.001, ****P<0.0001. See also FIG. 8 and FIG. 9.

Figure 8:
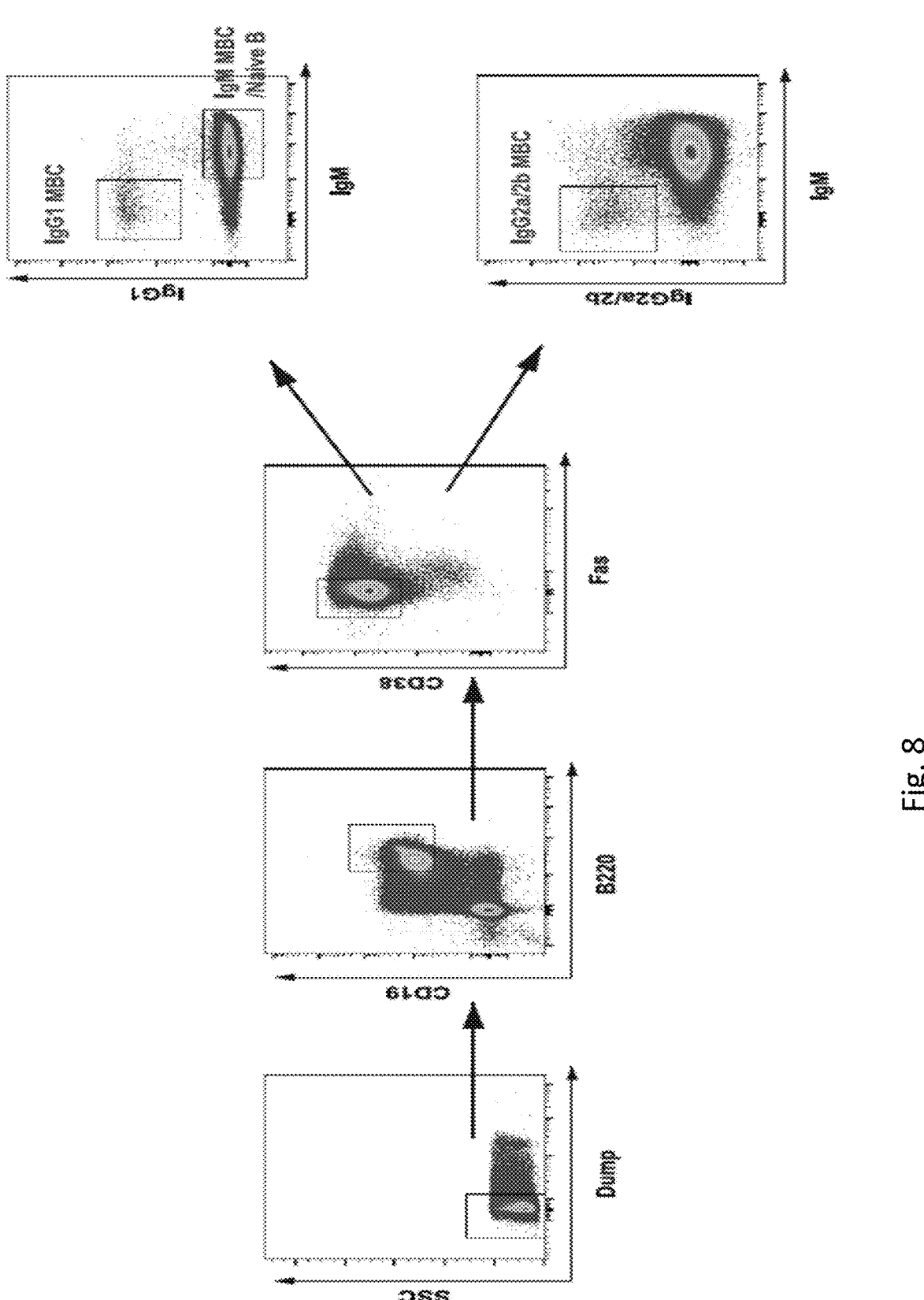

FIG. 8 depicts exemplary experimental results demonstrating a representative gating strategy for the investigation of MBCs. Flow cytometric gating strategy for splenic IgG1 MBC, IgG2a/2b MBC and IgM MBC/naive B cells is shown.

Figure 9A:
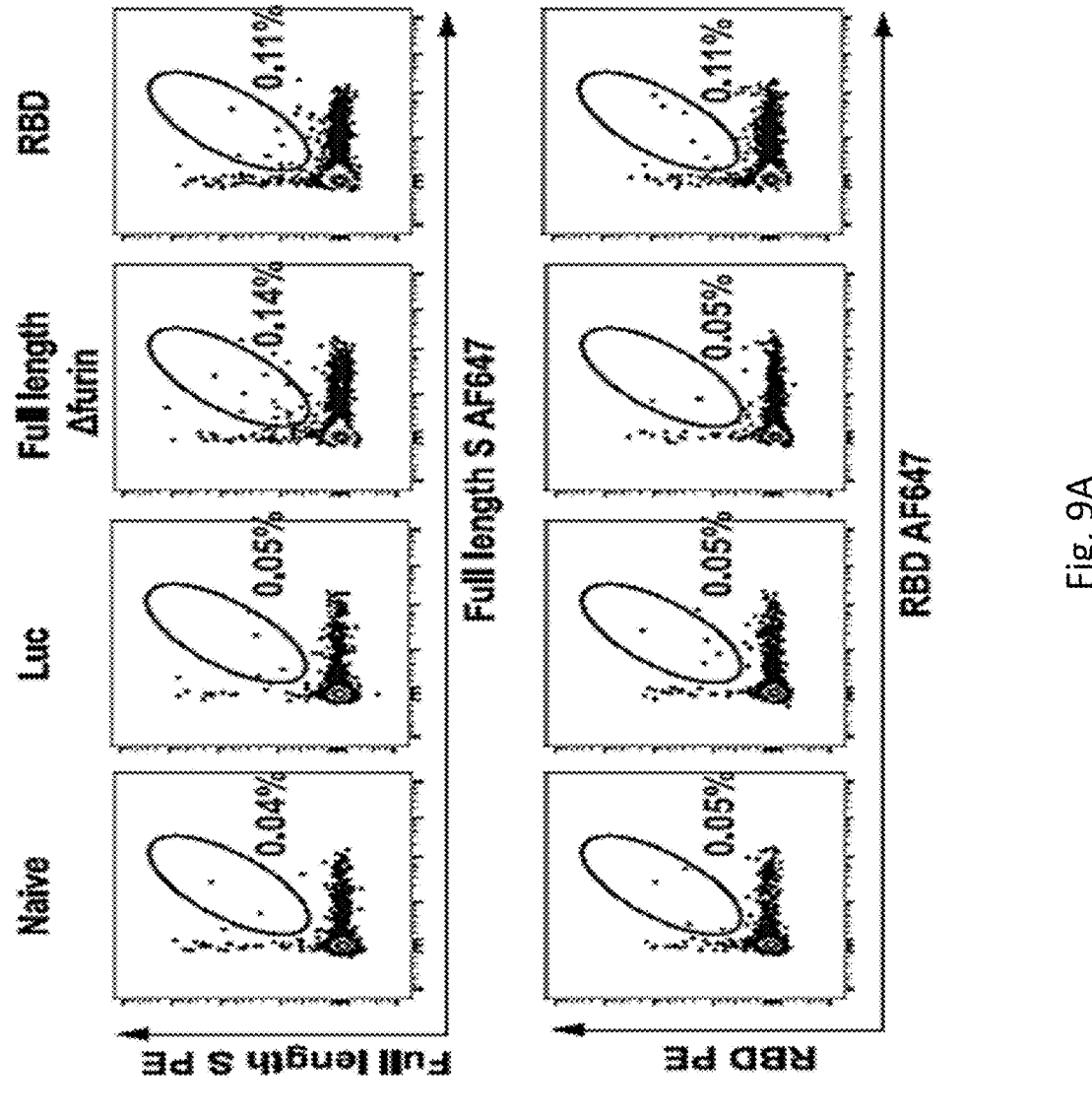
Figure 9B:
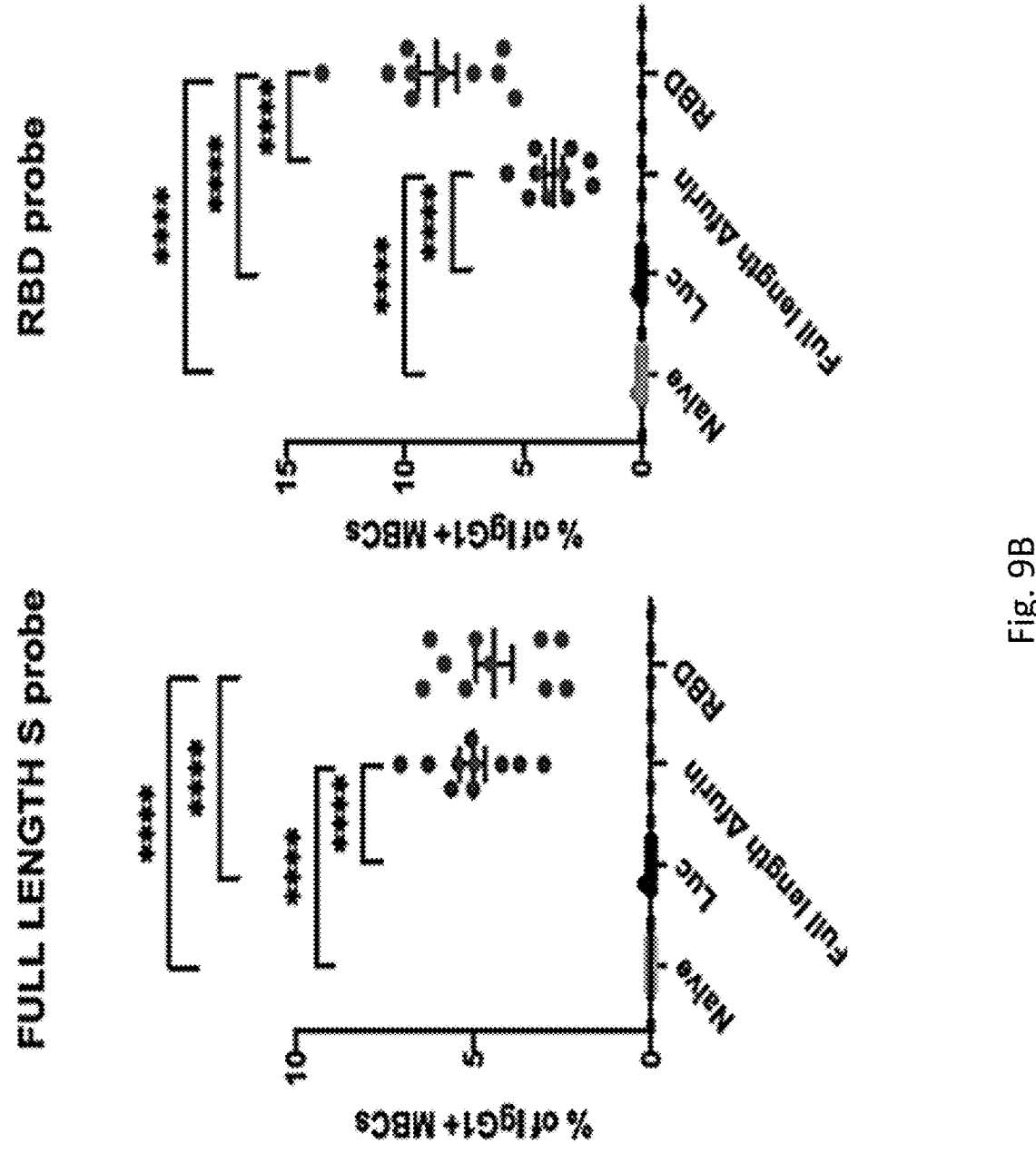
Figure 9B:
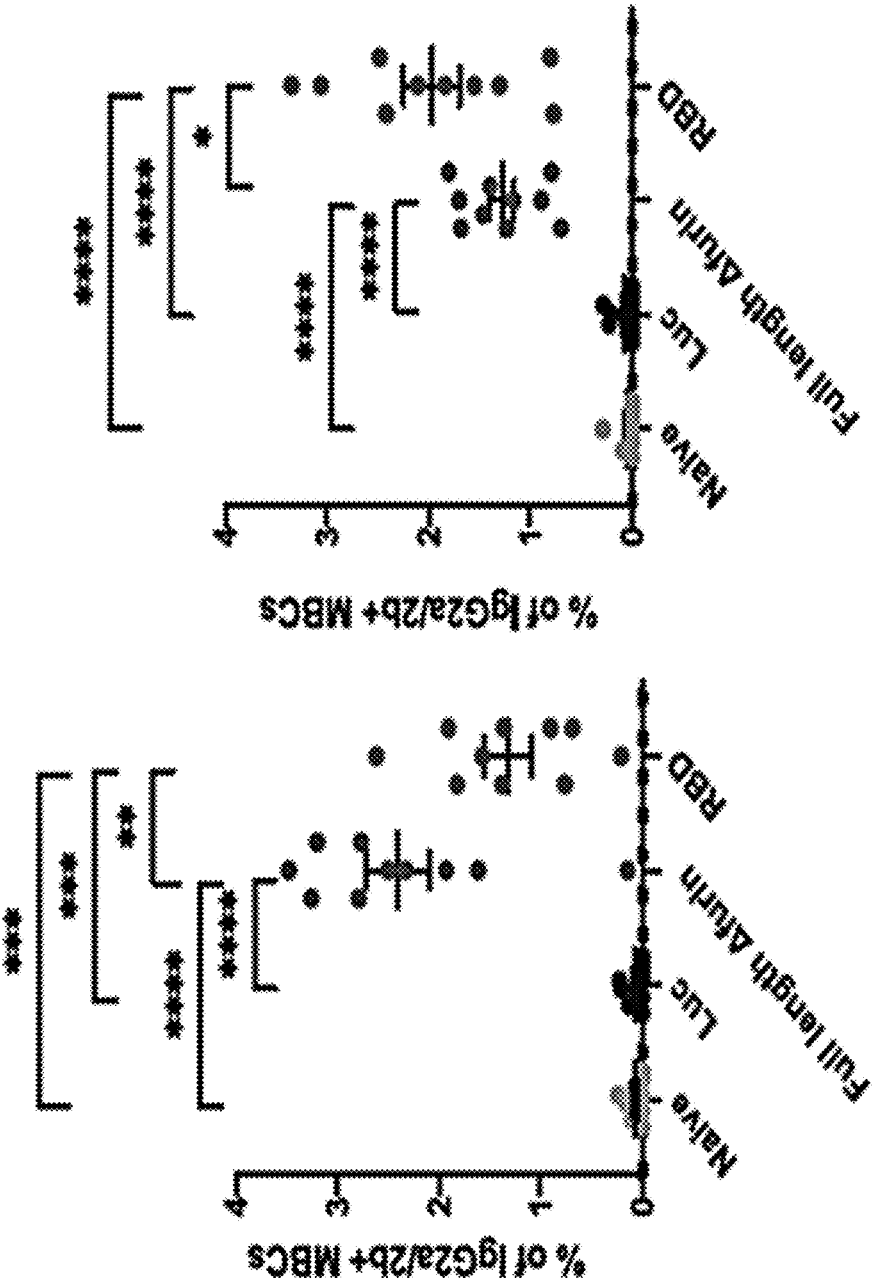
Figure 9B:
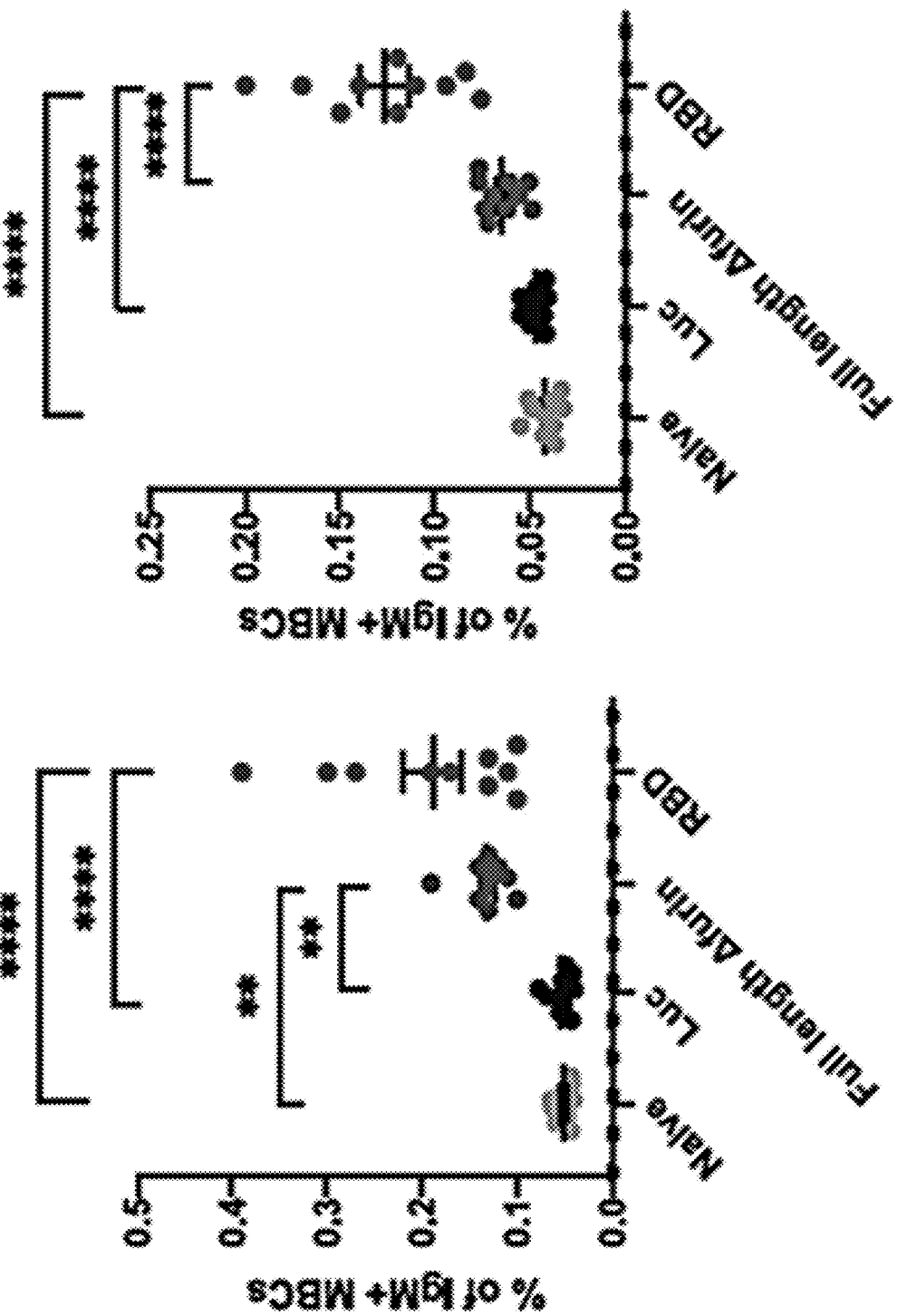
Figure 9C:
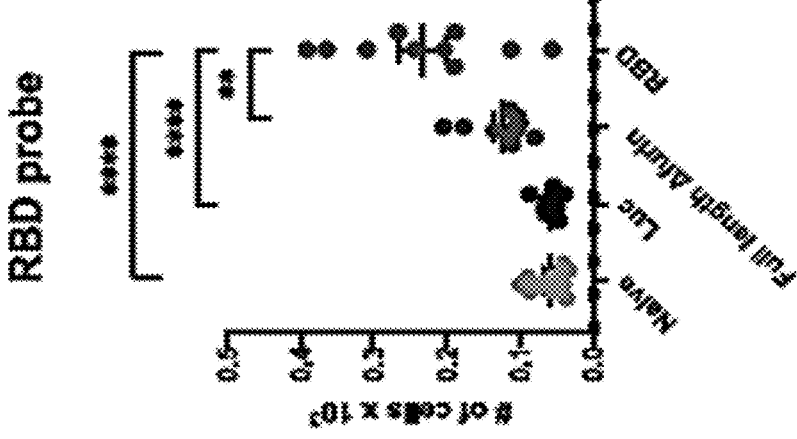
Figure 9C:
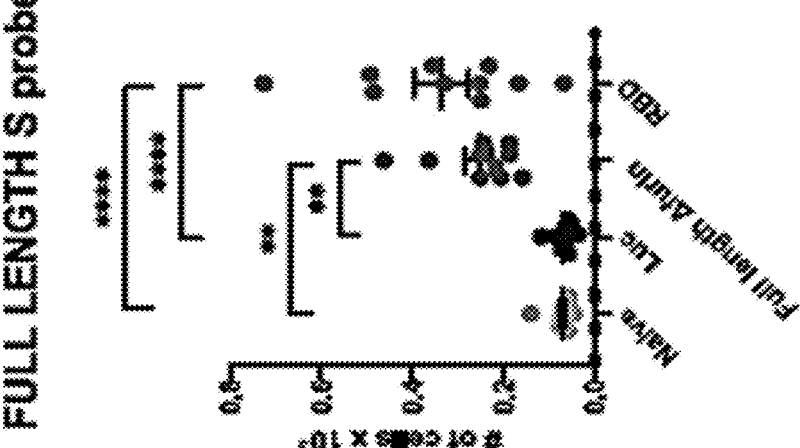

FIG. 9A through FIG. 9C depict exemplary experimental results demonstrating SARS-CoV-2 mRNA vaccines elicit antigen-specific MBCs. BALB/c mice received a single i.m. immunization with 30 μg of SARS-CoV-2 or Luc mRNA-LNP vaccines and sacrificed 9 weeks post immunization. FIG. 9A depicts a representative flow cytometry staining of full length S protein and RBD-specific IgM MBC/naive B cells. FIG. 9B depicts the frequencies of full length S protein and RBD-specific IgG1 MBC (upper panel), IgG2a/2b MBC (middle panel) and IgM MBC/naive B cells (lower panel). FIG. 9C depicts a quantification of full length S protein-specific IgM MBC/naive B cells. n=10 mice per vaccine group and n=5 naive mice, pooled from two independent experiments. Symbols represent individual animals. Data shown are mean plus SEM. Statistical analysis: one-way ANOVA with Bonferroni correction, *P<0.05, P<0.01, *P<0.001, ****P<0.0001.

Figures 10A, 10B:
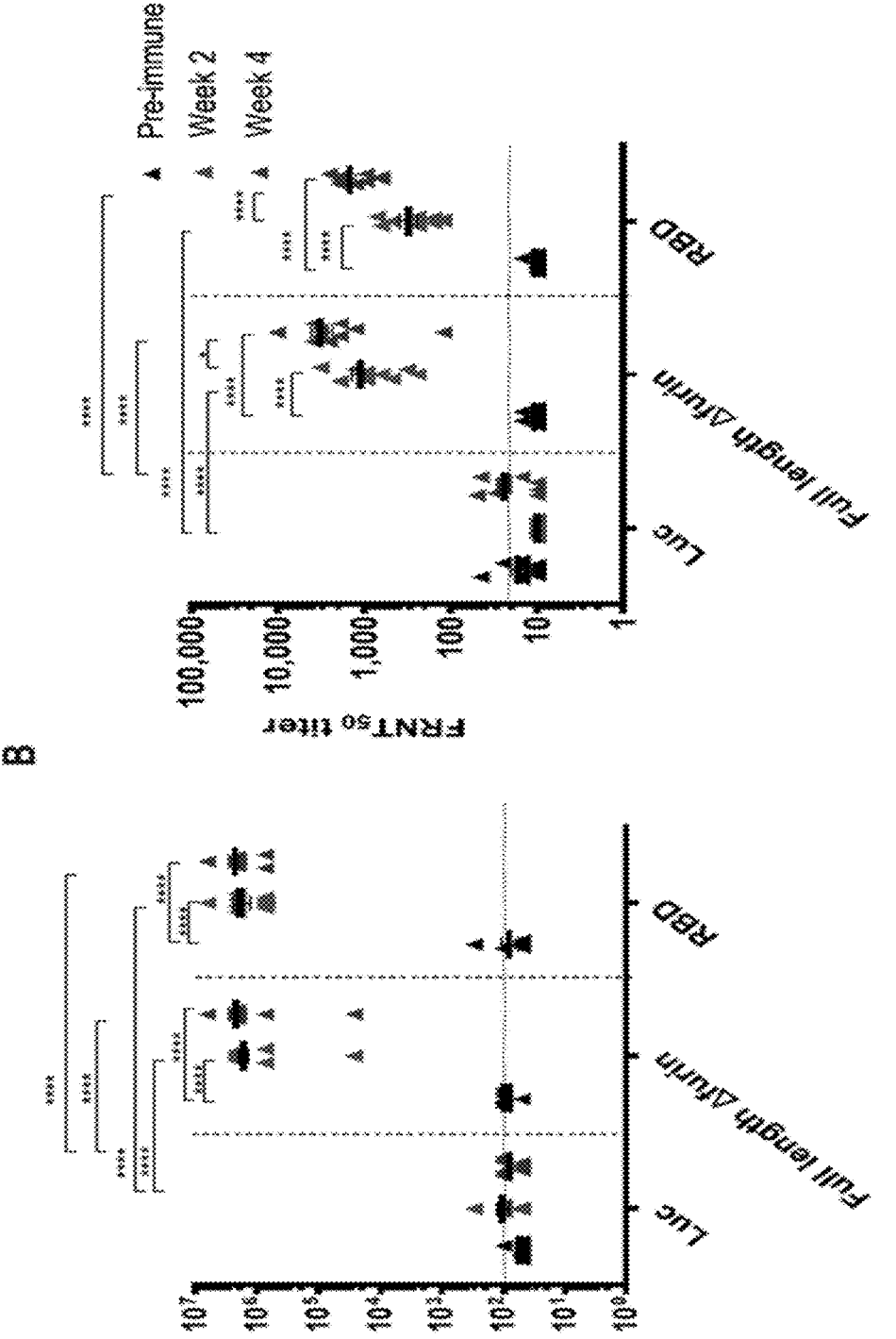
Figures 10C, 10D:
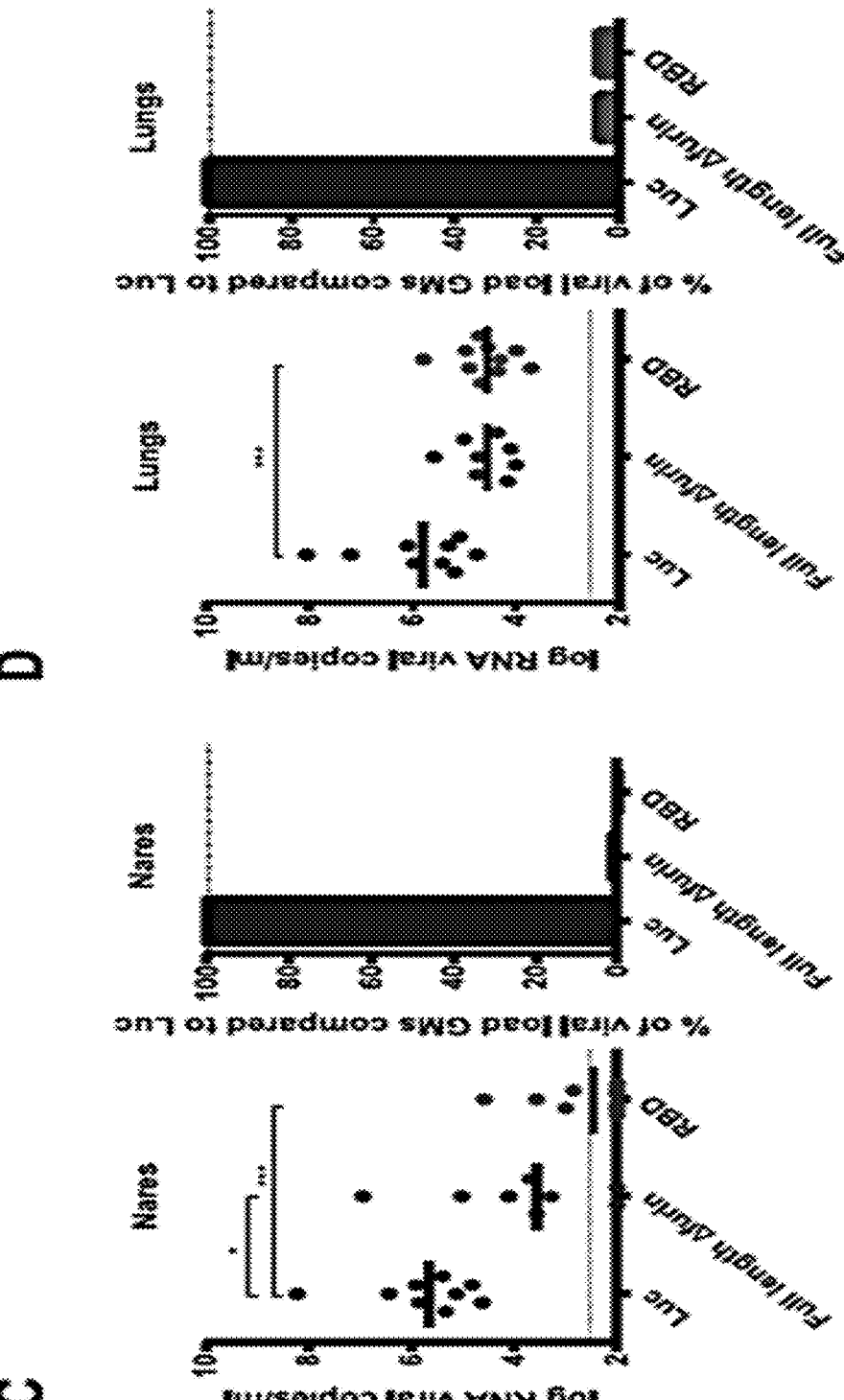
Figure 10E:
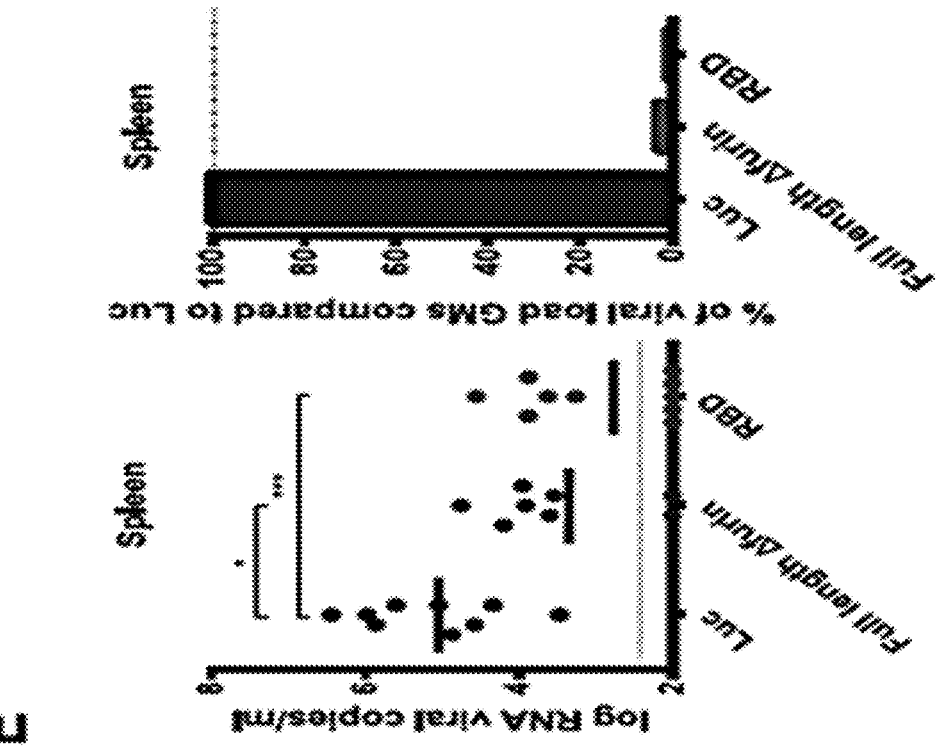

FIG. 10A through FIG. 10E depict exemplary experimental results demonstrating SARS-CoV-2 mRNA vaccines induce protective immune responses from SARS-CoV-2 replication. BALB/c mice received a single i.m. immunization with 30 μg of SARS-CoV-2 or Luc mRNA-LNP vaccines and intranasally challenged with SARS-CoV-2 virus 4 weeks after vaccine administration. S protein-specific IgG titers (FIG. 10A) and (FIG. 10B) neutralization titers were determined in pre-immune, week 2 and week 4 post immunization sera by endpoint dilution ELISA and VSV pseudovirus neutralization assays, respectively. Data shown are mean plus SEM. Viral loads in (FIG. 10C) nares, (FIG. 10D) lungs and (FIG. 10E) spleen were assessed 2 days after viral challenge by qRT-PCR. Log viral RNA copies/ml (left panels) and percentages of viral load geometric means (GMs) in SARS-CoV-2 mRNA vaccinated animals compared to Luc (right panels) are graphed. Dotted line represents the limit of detection (200 viral RNA copies/ml). End-point dilution ELISA, $FRNT_{50}$ and viral titers below the limit of detection are reported as half of the limit of detection. Horizontal lines represent geometric means of viral loads (FIG. 10C through FIG. 10E). Symbols represent individual mice. n=8-10 mice/group. Statistical analysis: (FIG. 10A and FIG. 10B) two-way ANOVA with Tukey's multiple comparison on log-transformed data, (FIG. 10C through FIG. 10E) Kruskal-Wallis test with Dunn's multiple comparison. *P<0.05, P<0.01, *P<0.001, ****P<0.0001.

Figure 11:
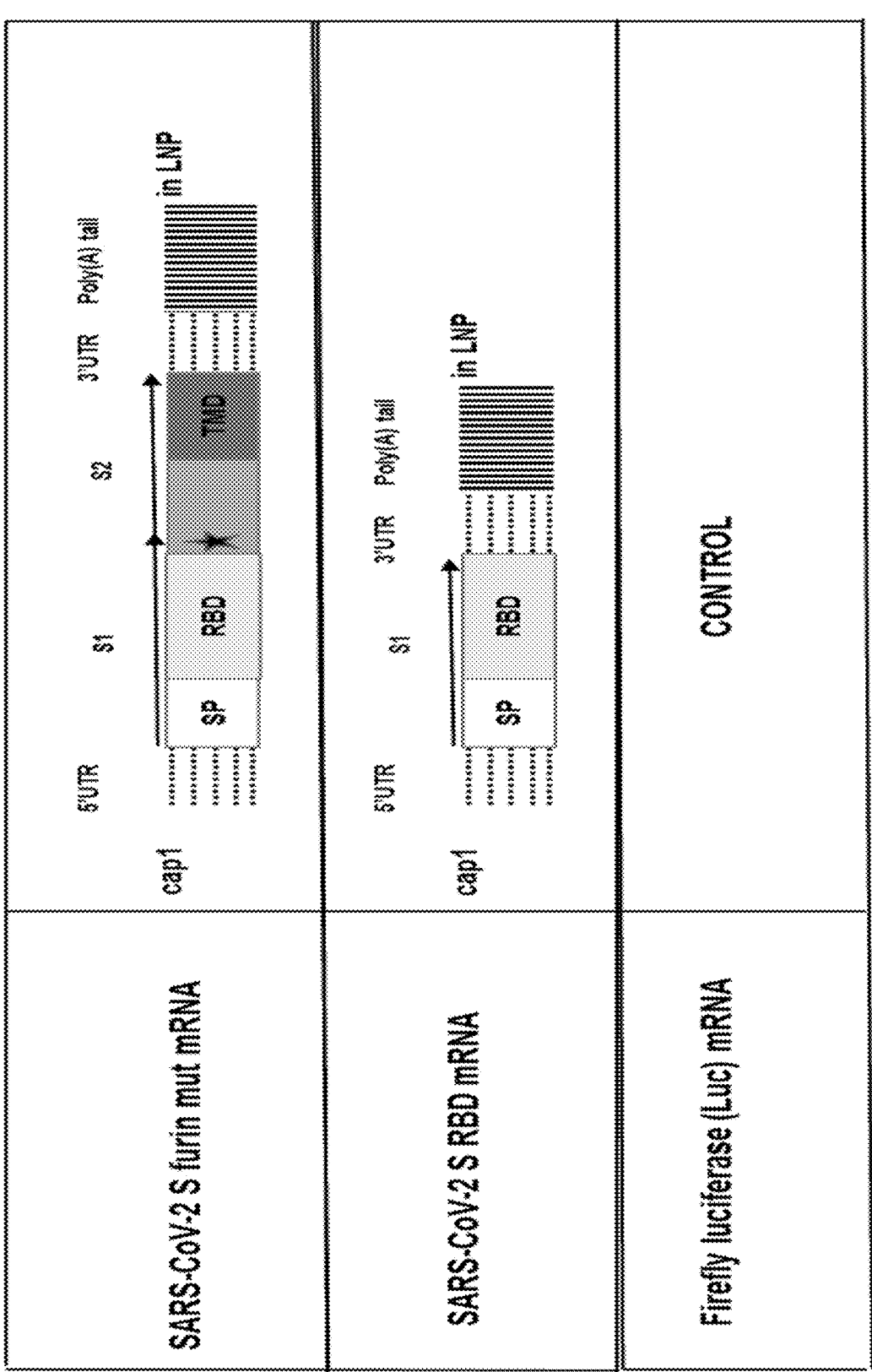
Figure 11:
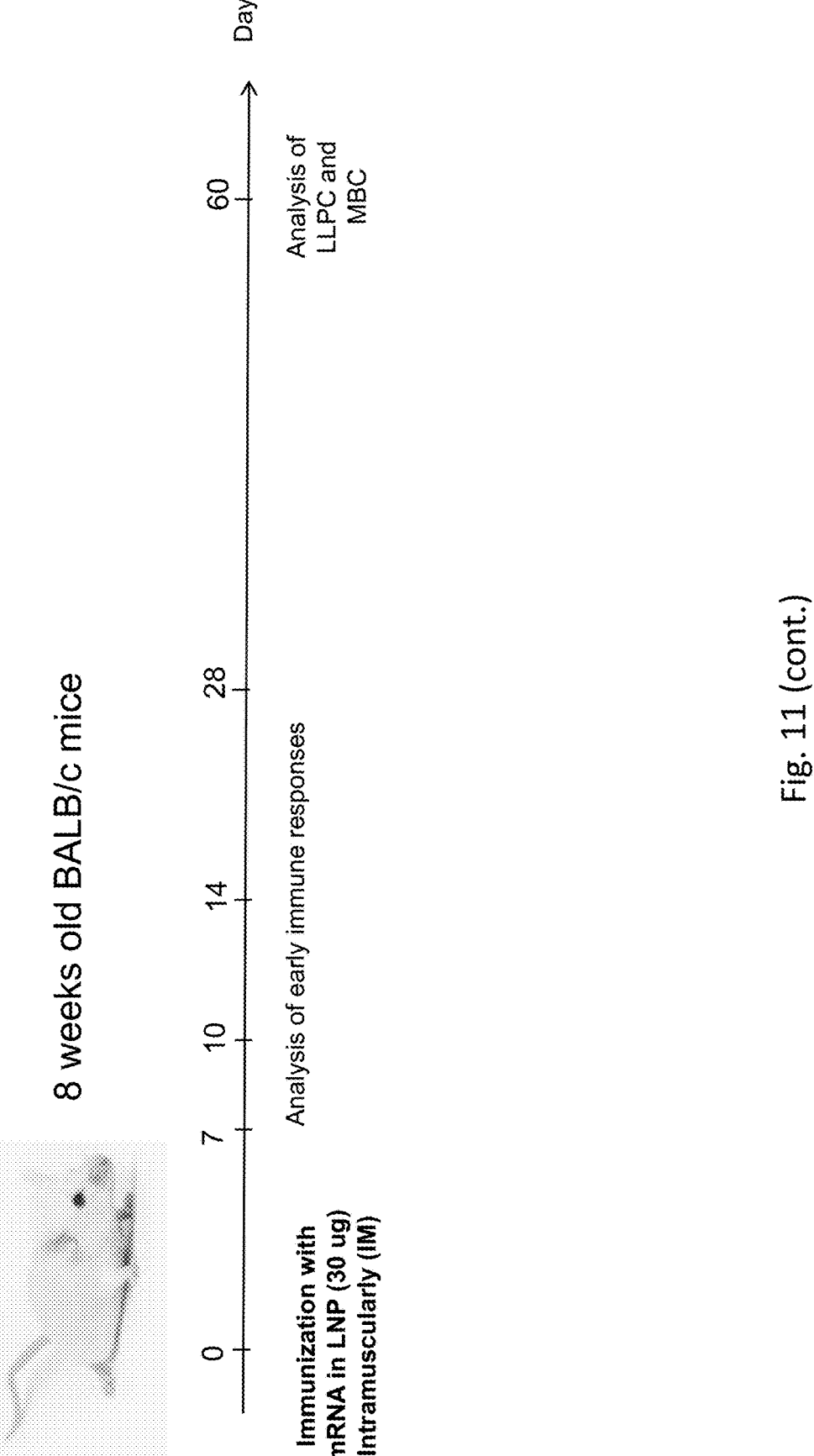

FIG. 11 depicts a schematic diagram of SARS-CoV-2 S protein-encoding mRNA-LNP vaccines.

Figure 12:
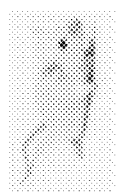

FIG. 12 depicts exemplary experimental data demonstrating that there was moderate induction of short-live Plasma Cell (PC) upon SARS-CoV-2 mRNA-LNP vaccination.

Figure 13:
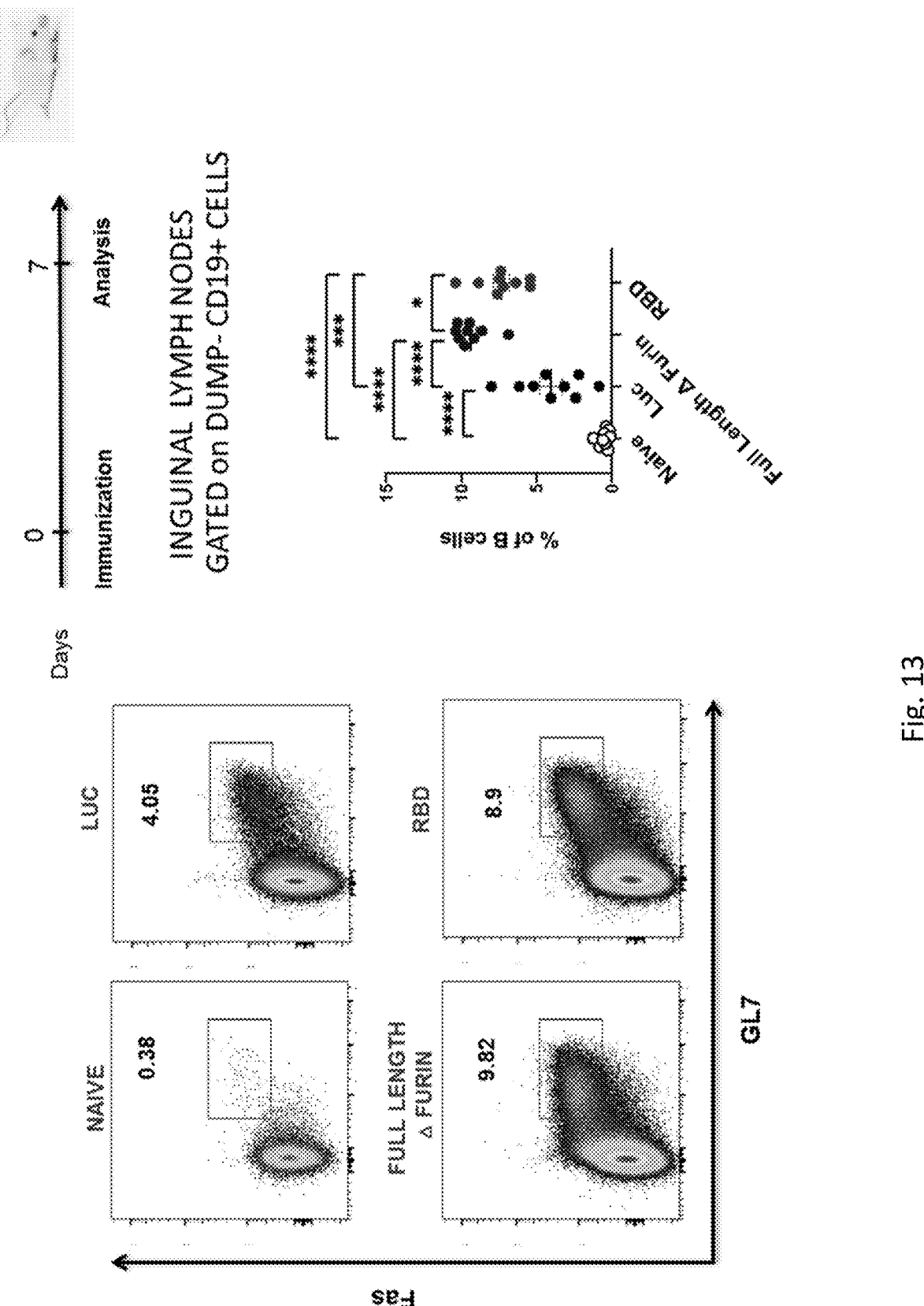

FIG. 13 depicts exemplary experimental data demonstrating that SARS-CoV-2 mRNA-LNP vaccines elicit strong germinal center (GC) responses.

Figure 14:
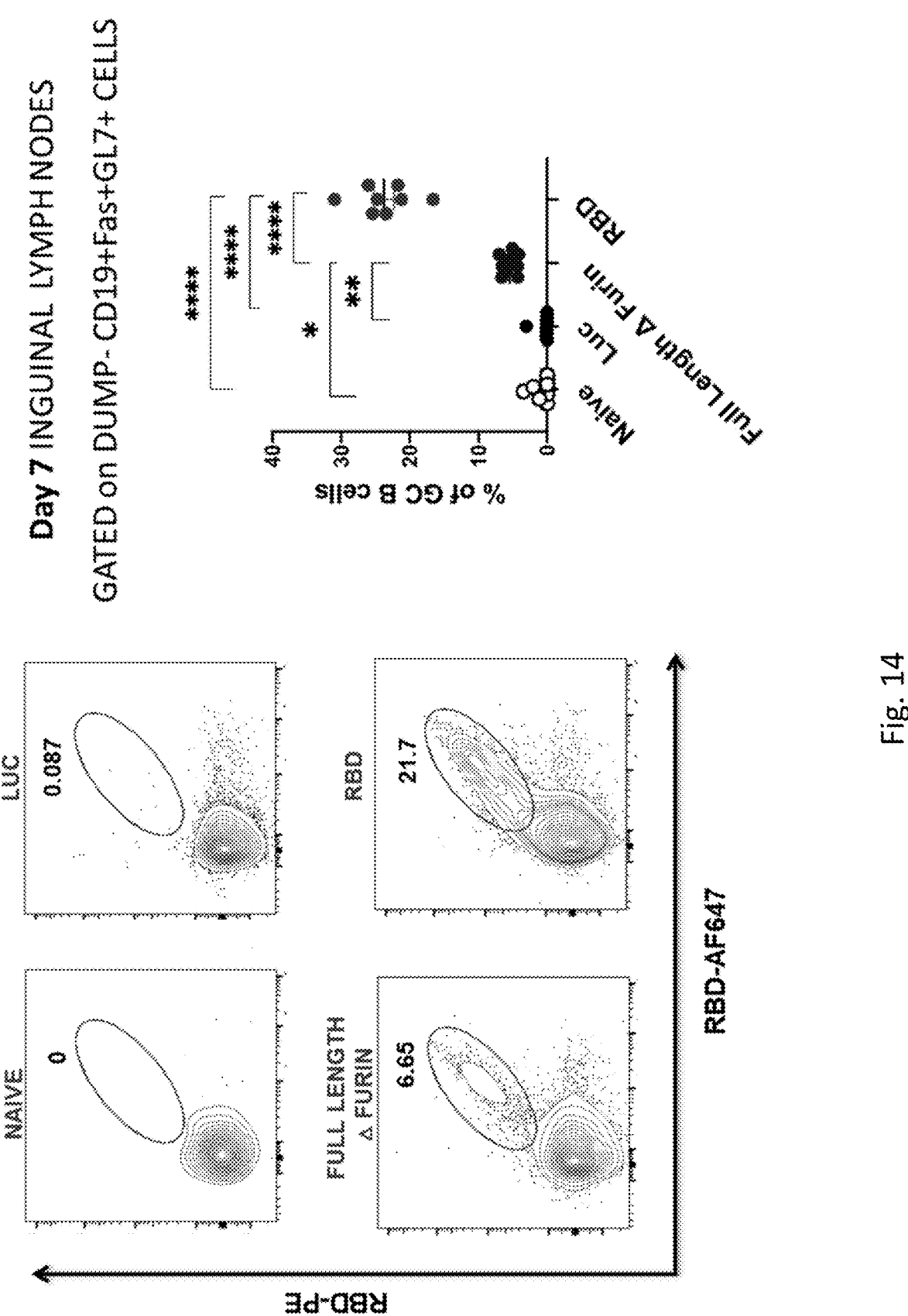

FIG. 14 depicts exemplary experimental data demonstrating that GC B cells induced by SARS-CoV-2 mRNA-LNP vaccines are antigen specific.

Figure 15:
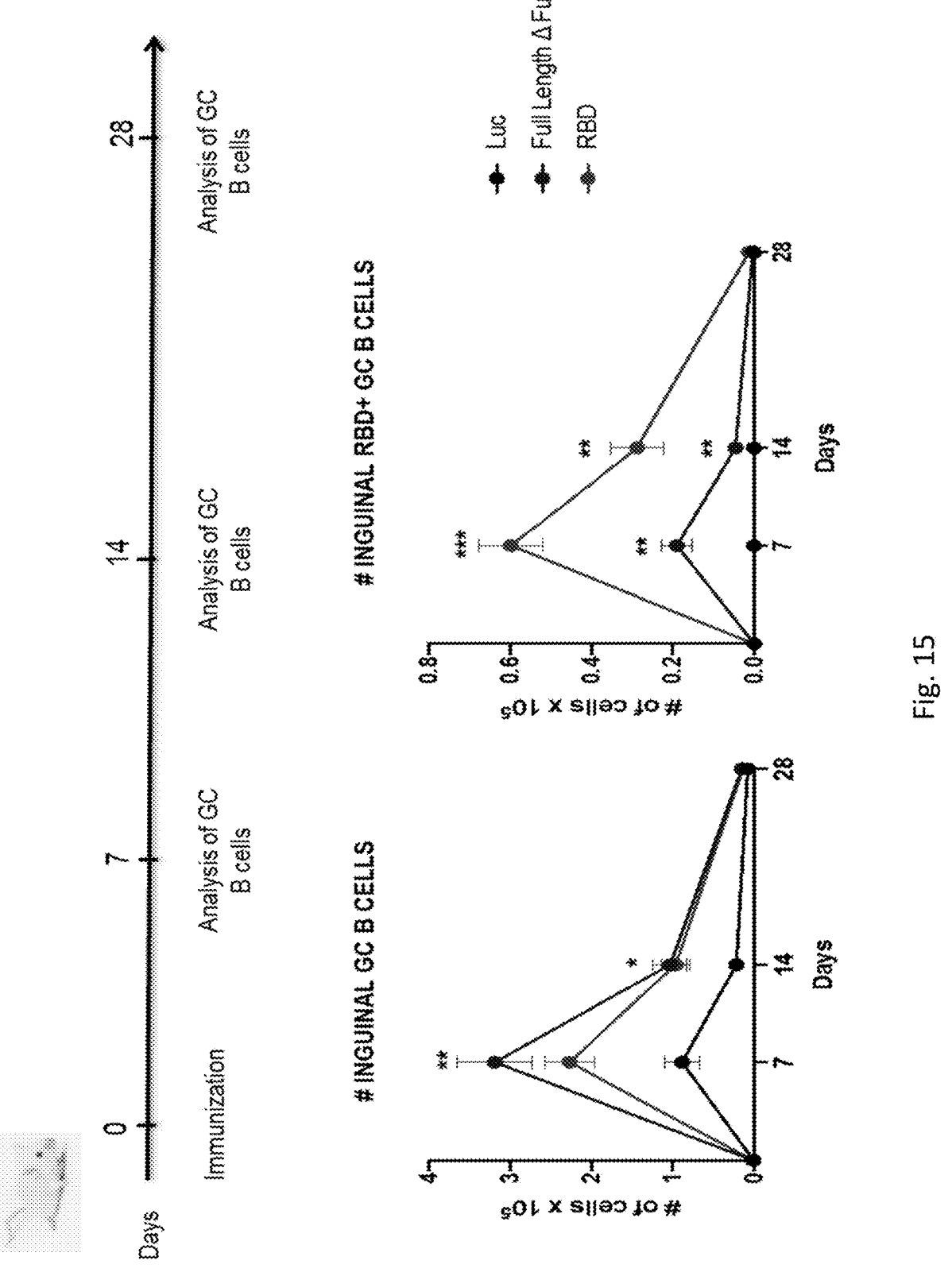

FIG. 15 depicts exemplary experimental data demonstrating that SARS-CoV-2 mRNA-LNP vaccines trigger potent GC responses that wane by day 28.

Figure 16:
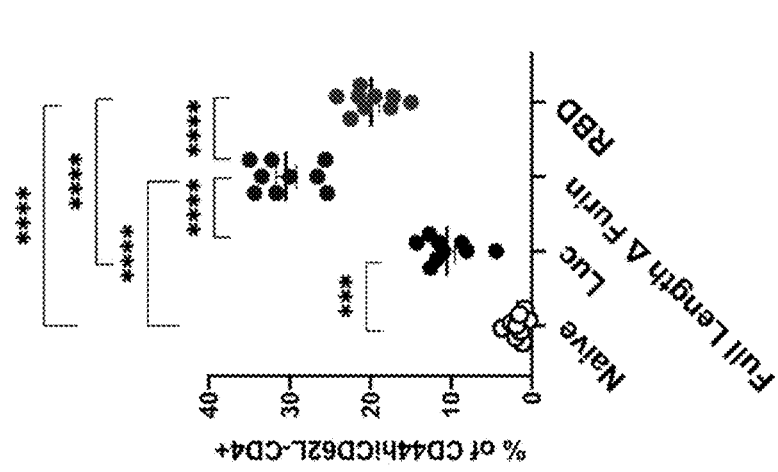
Figure 16:
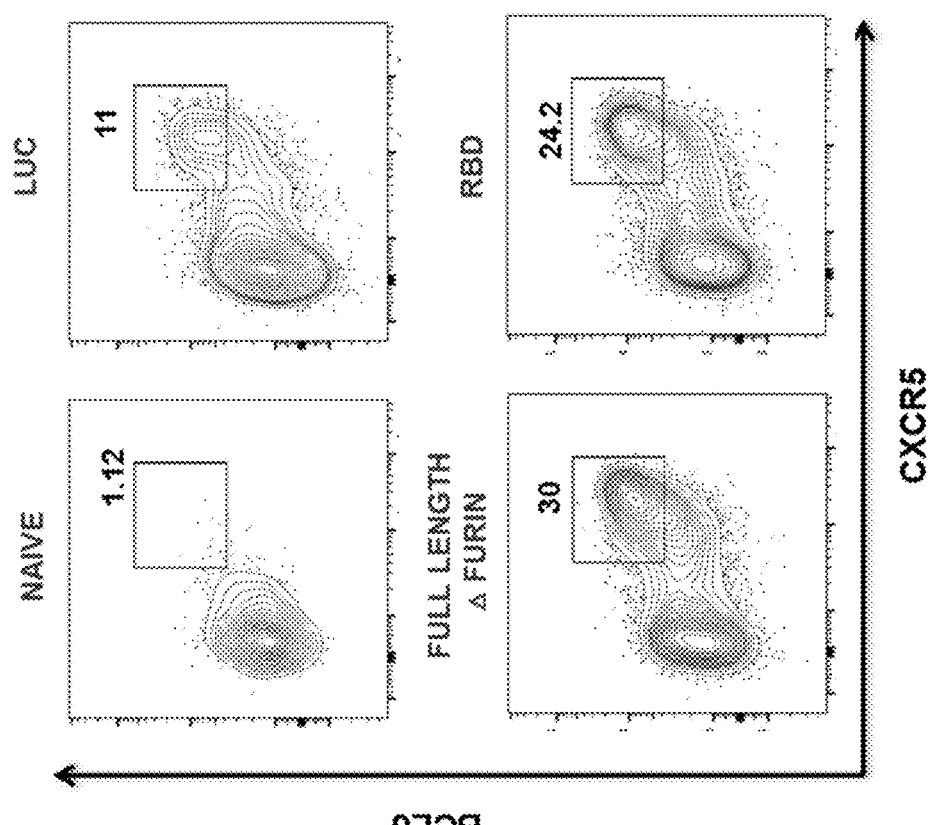

FIG. 16 depicts exemplary experimental data demonstrating that SARS-CoV-2 mRNA-LNP vaccines promote GC Tfh formation.

Figure 17:
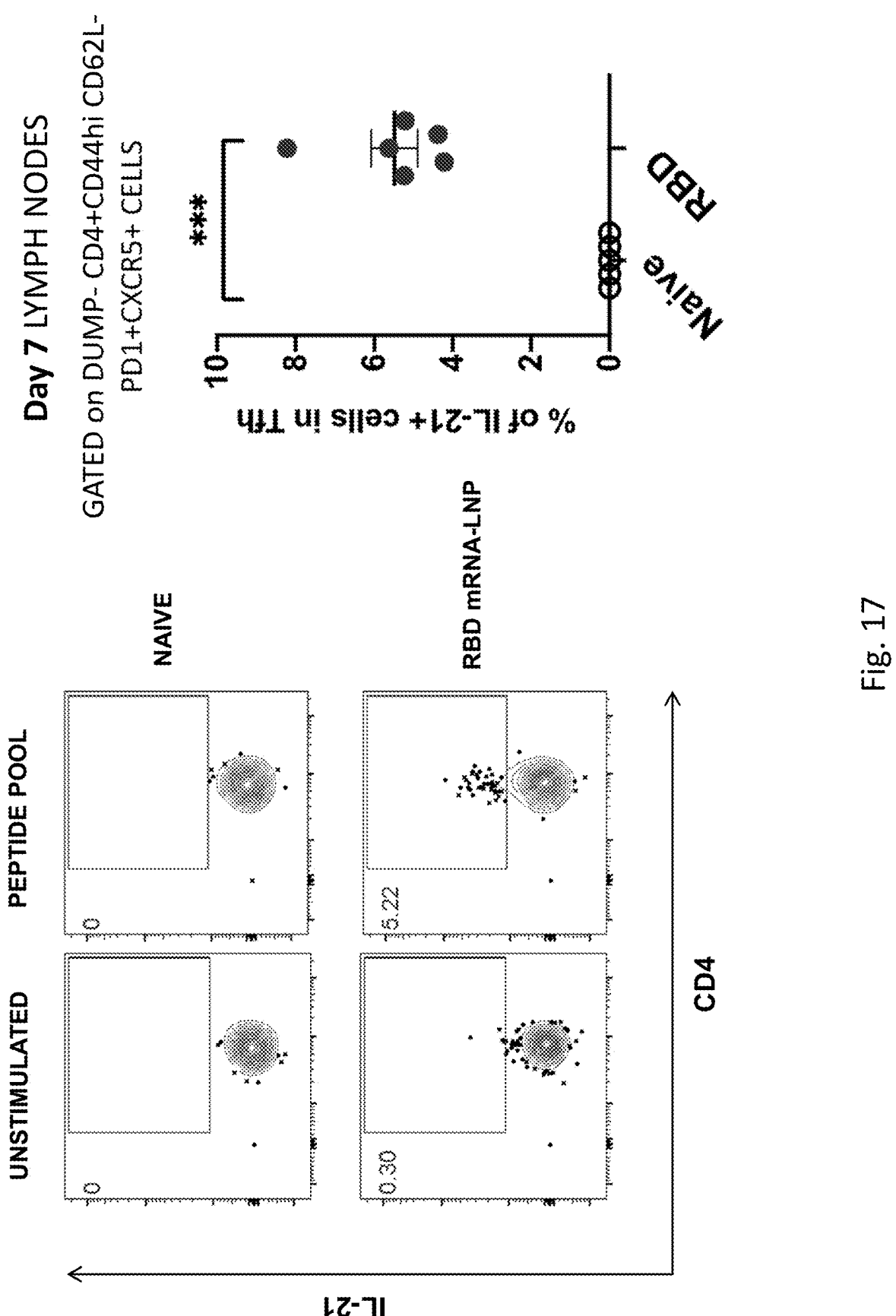

FIG. 17 depicts exemplary experimental data demonstrating that GC Tfh cells induced by SARS-CoV-2 mRNA-LNP vaccine are antigen specific.

Figure 18:
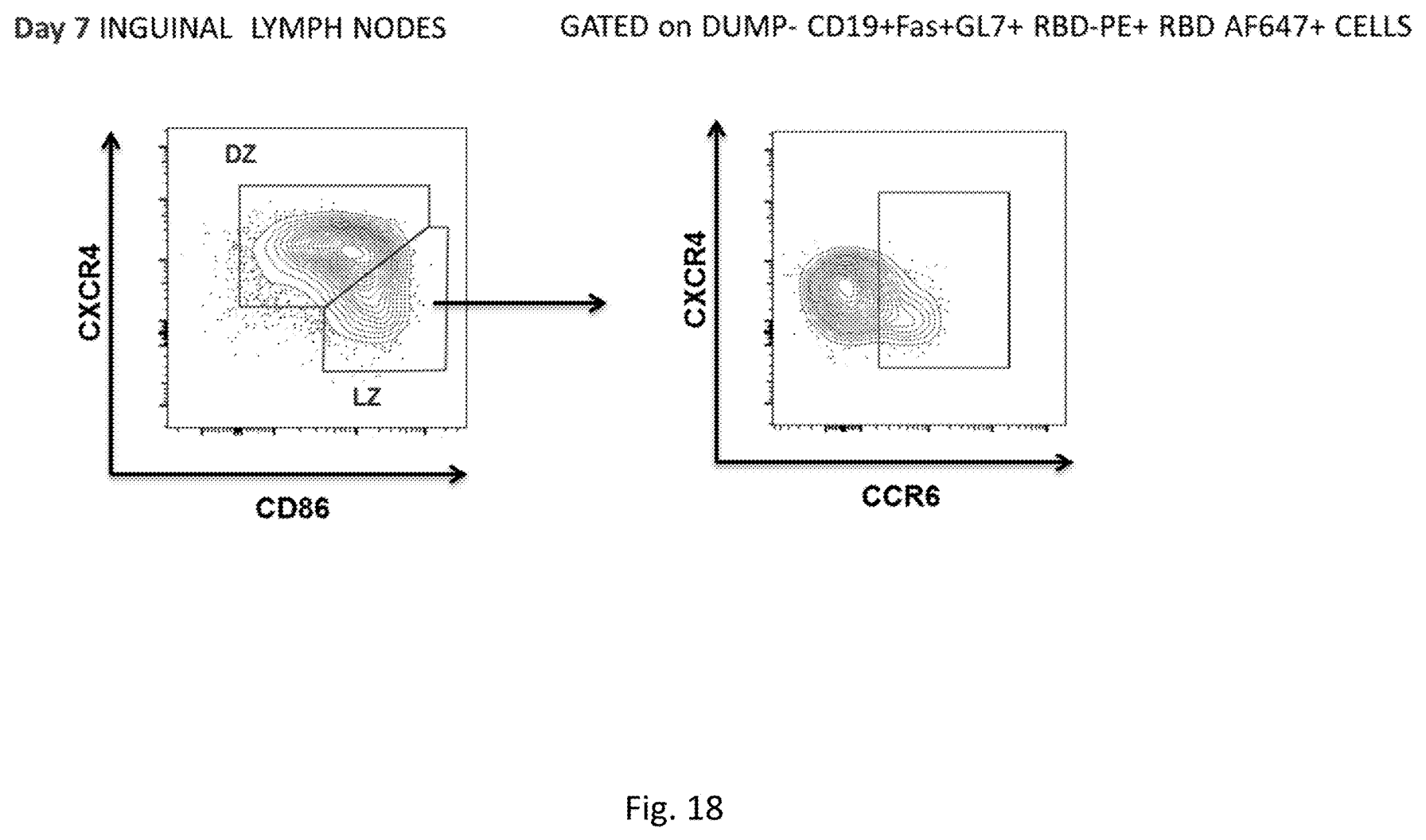

FIG. 18 depicts exemplary experimental data demonstrating the gating strategy use to detect RBD-specific MBC precursors.

Figure 19:

FIG. 19 depicts exemplary experimental data demonstrating that SARS-CoV-2 mRNA-LNP vaccines can generate RBD-specific MBC precursors.

Figure 20:
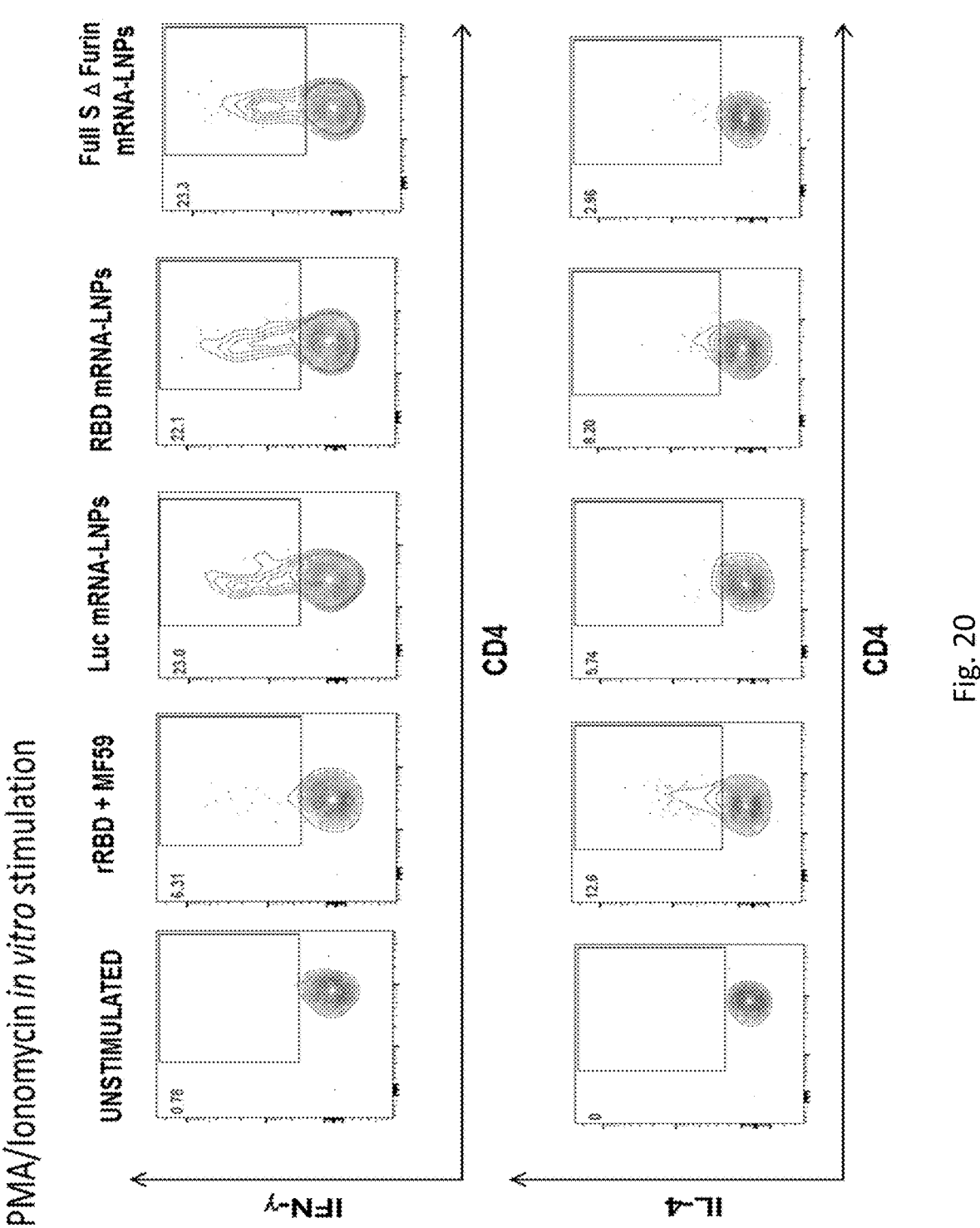

FIG. 20 depicts exemplary experimental data demonstrating that GC Tfh cells induced by SARS-CoV-2 mRNA-LNP vaccines have a stronger Th1 polarization.

Figure 21:
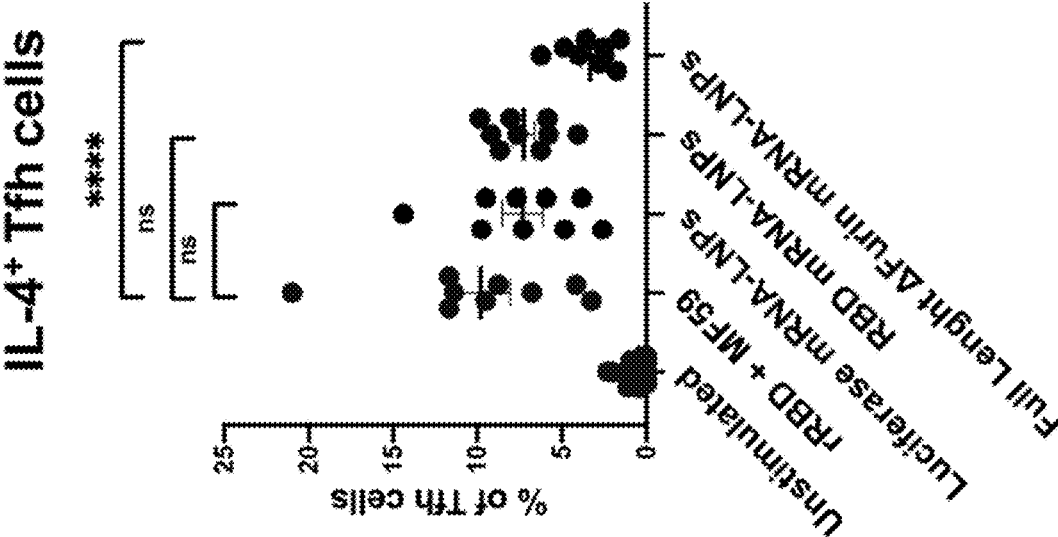
Figure 21:
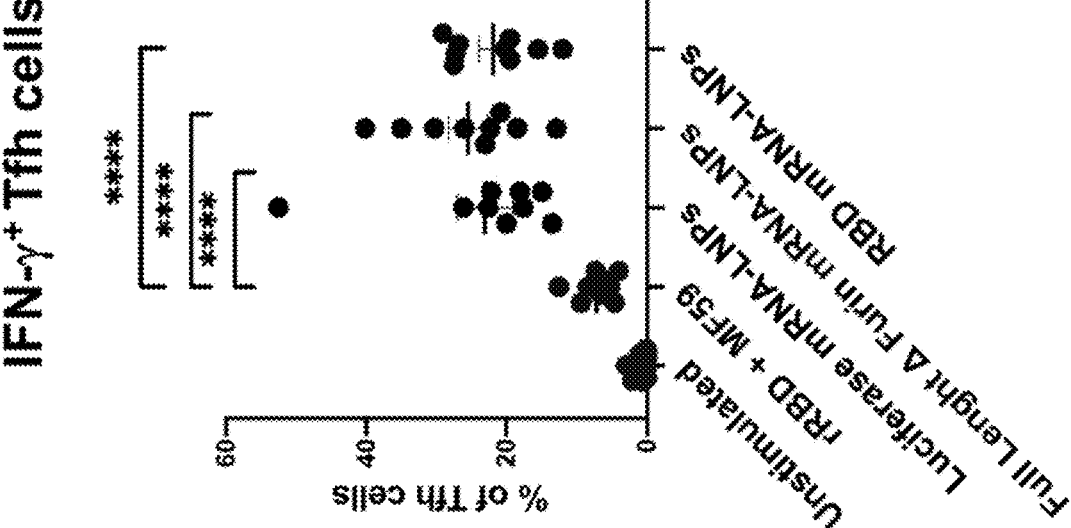

FIG. 21 depicts exemplary experimental data demonstrating that GC Tfh cells induced by SARS-CoV-2 mRNA-LNP vaccines have a stronger Th1 polarization.

DETAILED DESCRIPTION

The present invention relates to compositions and methods for inducing an immune response against SARS-CoV-2 in a subject. In certain embodiments, the invention provides a composition comprising at least one nucleoside-modified RNA encoding at least one SARS-CoV-2 antigen. In one embodiment, the composition is a vaccine comprising at least one nucleoside-modified RNA encoding at least one SARS-CoV-2 antigen, where the vaccine induces an immune response in the subject to the at least one SARS-CoV-2 antigen, and therefore induces an immune response in the subject to SARS-CoV-2 virus or pathology associated with SARS-CoV-2. In one embodiment, the vaccine prevents the development of COVID-19, or a comorbidity of COVID-19. In one embodiment, the vaccine treats COVID-19, or a comorbidity of COVID-19.

In certain embodiments, the at least one nucleoside-modified RNA encodes a SARS-CoV-2 spike antigen or a fragment thereof. In one embodiment, the at least one nucleoside-modified RNA encodes a receptor binding domain (RBD) of a SARS-CoV-2 spike antigen. In one embodiment, the nucleoside-modified RNA encodes a SARS-CoV-2 spike antigen comprising a mutation of the furin cleavage site. In one embodiment, the nucleoside-modified RNA encodes a full-length SARS-CoV-2 S protein comprising a deletion of an AA sequence in the furin cleavage site (referred to herein as "Δfurin"). In certain embodiments, the at least one nucleoside-modified RNA is encapsulated in a lipid nanoparticle (LNP).

In some embodiments, the invention is a method of administering to a subject a composition comprising at least one nucleoside-modified RNA encoding at least one SARS-CoV-2 antigen. In some embodiments, the invention is a method of administering to a subject a composition comprising at least one nucleoside-modified RNA encoding at least one SARS-CoV-2 antigen, wherein the subject is infected with severe acute respiratory syndrome coronavirus 2 (SARS-CoV-2).

Definitions

Unless defined otherwise, all technical and scientific terms used herein have the same meaning as commonly understood by one of ordinary skill in the art to which this invention belongs.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

The term "antibody," as used herein, refers to an immunoglobulin molecule, which specifically binds with an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, New York; Houston et al., 1988, Proc. Natl. Acad. Sci. USA 85:5879-5883; Bird et al., 1988, Science 242:423-426).

The term "antibody fragment" refers to a portion of an intact antibody and refers to the antigenic determining variable regions of an intact antibody. Examples of antibody fragments include, but are not limited to, Fab, Fab', F(ab')2, and Fv fragments, linear antibodies, scFv antibodies, and multispecific antibodies formed from antibody fragments.

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations. x and X light chains refer to the two major antibody light chain isotypes.

By the term "synthetic antibody" as used herein, is meant an antibody, which is generated using recombinant DNA technology, such as, for example, an antibody expressed by a bacteriophage. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art. The term should also be construed to mean an antibody, which has been generated by the synthesis of an RNA molecule encoding the antibody. The RNA molecule expresses an antibody protein, or an amino acid sequence specifying the antibody, wherein the RNA has been obtained by transcribing DNA (synthetic or cloned) or other technology, which is available and well known in the art.

The term "antigen" or "Ag" as used herein is defined as a molecule that provokes an adaptive immune response. This immune response may involve either antibody production, or the activation of specific immunogenically-competent cells, or both. The skilled artisan will understand that any macromolecule, including virtually all proteins or peptides, can serve as an antigen. Furthermore, antigens can be derived from recombinant or genomic DNA or RNA. A skilled artisan will understand that any DNA or RNA, which comprises a nucleotide sequence or a partial nucleotide sequence encoding a protein that elicits an adaptive immune response therefore encodes an "antigen" as that term is used herein. Furthermore, one skilled in the art will understand that an antigen need not be encoded solely by a full-length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

The term "adjuvant" as used herein is defined as any molecule to enhance an antigen-specific adaptive immune response.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

An "effective amount" as used herein, means an amount which provides a therapeutic or prophylactic benefit.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) RNA, and viruses (e.g., lentiviruses, retroviruses, adenoviruses, and adeno-associated viruses) that incorporate the recombinant polynucleotide.

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared X 100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

"Immunogen" refers to any substance introduced into the body in order to generate an immune response. That substance can a physical molecule, such as a protein, or can be encoded by a vector, such as DNA, mRNA, or a virus.

"Immune response," as the term is used herein, means a process involving the activation and/or induction of an effector function in, by way of non-limiting examples, a T cell, B cell, natural killer (NK) cell, and/or antigen-presenting cells (APC). Thus, an immune response, as would be understood by the skilled artisan, includes, but is not limited to, any detectable antigen-specific activation and/or induction of a helper T cell or cytotoxic T cell activity or response, production of antibodies, antigen presenting cell activity or infiltration, macrophage activity or infiltration, neutrophil activity or infiltration, and the like.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleosides (nucleobase bound to ribose or deoxyribose sugar via N-glycosidic linkage) are used. "A" refers to adenosine, "C" refers to cytidine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, such as, a human.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns. In addition, the nucleotide sequence may contain modified nucleosides that are capable of being translation by translational machinery in a cell. For example, an mRNA where all of the uridines have been replaced with pseudouridine, 1-methyl psuedouridine, or another modified nucleoside.

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA or RNA sequences are contiguous and, where necessary to join two protein coding regions, in the same reading frame.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

In certain instances, the polynucleotide or nucleic acid of the invention is a "nucleoside-modified nucleic acid," which refers to a nucleic acid comprising at least one modified nucleoside. A "modified nucleoside" refers to a nucleoside with a modification. For example, over one hundred different nucleoside modifications have been identified in RNA (Rozenski, et al., 1999, The RNA Modification Database: 1999 update. Nucl Acids Res 27: 196-197).

In certain embodiments, "pseudouridine" refers, in another embodiment, to $m^1acp^3\Psi$ (1-methyl-3-(amino-3-carboxypropyl) pseudouridine. In another embodiment, the term refers to $m^1\Psi$ (1-methylpseudouridine). In another embodiment, the term refers to $\Psi m$ (2'-O-methylpseudouridine. In another embodiment, the term refers to $m^5D$ (5-methyldihydrouridine). In another embodiment, the term refers to $m^3\Psi$ (3-methylpseudouridine). In another embodiment, the term refers to a pseudouridine moiety that is not further modified. In another embodiment, the term refers to a monophosphate, diphosphate, or triphosphate of any of the above pseudouridines. In another embodiment, the term refers to any other pseudouridine known in the art. Each possibility represents a separate embodiment of the present invention.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "promoter" as used herein is defined as a DNA sequence recognized by the synthetic machinery of the cell, or introduced synthetic machinery, required to initiate the specific transcription of a polynucleotide sequence. For example, the promoter that is recognized by bacteriophage RNA polymerase and is used to generate the mRNA by in vitro transcription.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more other species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

The term "therapeutic" as used herein means a treatment and/or prophylaxis. A therapeutic effect is obtained by suppression, diminution, remission, or eradication of at least one sign or symptom of a disease or disorder.

The term "therapeutically effective amount" refers to the amount of the subject compound that will elicit the biological or medical response of a tissue, system, or subject that is being sought by the researcher, veterinarian, medical doctor or other clinician. The term "therapeutically effective amount" includes that amount of a compound that, when administered, is sufficient to prevent development of, or alleviate to some extent, one or more of the signs or symptoms of the disorder or disease being treated. The therapeutically effective amount will vary depending on the compound, the disease and its severity and the age, weight, etc., of the subject to be treated.

To "treat" a disease as the term is used herein, means to reduce the frequency or severity of at least one sign or symptom of a disease or disorder experienced by a subject.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The phrase "under transcriptional control" or "operatively linked" as used herein means that the promoter is in the correct location and orientation in relation to a polynucleotide to control the initiation of transcription by RNA polymerase and expression of the polynucleotide.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention relates to compositions and methods for inducing an immune response against SARS-CoV-2 in a subject. In certain embodiments, the present invention provides a composition comprising a nucleic acid molecule encoding a SARS-CoV-2 antigen, where the SARS-CoV-2 antigen induces an immune response against SARS-CoV-2 in the subject. In some embodiments, the induced immune response is an adaptive immune response. For example, in certain embodiments, the composition comprises a vaccine comprising a nucleic acid molecule encoding a SARS-CoV-2 antigen. In certain embodiments, the SARS-CoV-2 antigen induces expression of a protective antibody. In certain embodiments, the SARS-CoV-2 antigen provides an adjuvant function.

In one embodiment, the composition of the invention comprises in vitro transcribed (IVT) RNA. For example, in certain embodiments, the composition of the invention comprises IVT RNA which encodes a SARS-CoV-2 antigen, where the SARS-CoV-2 antigen induces an adaptive immune response.

In certain embodiments, the SARS-CoV-2 antigen is a SARS-CoV-2 spike antigen, or a fragment or variant thereof. In one embodiment, the SARS-CoV-2 antigen is a SARS-CoV-2 spike protein receptor binding domain. In one embodiment, the SARS-CoV-2 antigen is a SARS-CoV-2 spike protein comprising a mutation in the furin cleavage site.

In certain embodiments, the antigen-encoding nucleic acid of the present composition is a nucleoside-modified RNA. The present invention is based in part on the finding that nucleoside-modified RNA encoding a SARS-CoV-2 antigen induces a robust and durable immune response against SARS-CoV-2. Further, the SARS-CoV-2 antigen-encoding nucleoside-modified RNA was observed to induce antigen-specific antibody production. The nucleoside-modified RNA is demonstrated to induce adaptive immune responses that are comparable or superior to current SARS-CoV-2 vaccine strategies.

In certain embodiments, the antigen-encoding nucleic acid of the present composition is a purified nucleoside-modified RNA. For example, in certain embodiments, the composition is purified such that is free of double-stranded contaminants.

In certain embodiments, the composition comprises a lipid nanoparticle (LNP). For example, in one embodiment, the composition comprises a SARS-CoV-2 antigen-encoding nucleic acid molecule encapsulated within a LNP. In certain instances, the LNP enhances cellular uptake of the nucleic acid molecule.

In certain embodiments, the composition comprises an adjuvant. In certain embodiments, the composition comprises a nucleic acid molecule encoding an adjuvant. For example, in one embodiment, the composition comprises a nucleoside-modified RNA encoding an adjuvant. In one embodiment, the composition comprises a nucleoside-modified RNA encoding a SARS-CoV-2 antigen and an adjuvant. In one embodiment, the composition comprises a first nucleoside-modified RNA, which encodes a SARS-CoV-2 antigen, and a second nucleoside-modified RNA, which encodes an adjuvant. In one embodiment, the composition comprises a nucleoside-modified RNA encoding an adjuvant and a LNP, wherein the LNP has adjuvant activity.

In one embodiment, the present invention provides a method for inducing an immune response against SARS-CoV-2 in a subject. In some embodiments, the method comprises administering to the subject a composition comprising one or more nucleoside-modified RNA encoding a SARS-CoV-2 antigen, adjuvant, or a combination thereof.

In one embodiment, the method comprises the systemic administration of the composition into the subject, including for example intradermal administration or intradermal administration. In certain embodiments, the method comprises administering a plurality of doses to the subject. In another embodiment, the method comprises administering a single dose of the composition, where the single dose is effective in inducing an adaptive immune response. In one embodiment, the method provides a sustained or prolonged immune response.

Vaccine

In one embodiment, the present invention provides an immunogenic composition for inducing an immune response against SARS-CoV-2 in a subject. For example, in one embodiment, the immunogenic composition is a vaccine. For a composition to be useful as a vaccine, the composition must induce an immune response to the SARS-CoV-2 antigen in a cell, tissue or mammal (e.g., a human). In certain instances, the vaccine induces a protective immune response in the mammal. As used herein, an "immunogenic composition" may comprise an antigen (e.g., a peptide or polypeptide), a nucleic acid encoding an antigen, a cell expressing or presenting an antigen or cellular component, or a combination thereof. In particular embodiments, the composition comprises or encodes all or part of any peptide antigen described herein, or an immunogenically functional equivalent thereof. In other embodiments, the composition is in a mixture that comprises an additional immunostimulatory agent or nucleic acids encoding such an agent. Immunostimulatory agents include but are not limited to an additional antigen, an immunomodulator, an antigen presenting cell, lipid nanoparticle, or an adjuvant. In other embodiments, one or more of the additional agent(s) is covalently bonded to the antigen or an immunostimulatory agent, in any combination.

In the context of the present invention, the term "vaccine" refers to a composition that induces an immune response upon inoculation into animals. In some embodiments, the induced immune response provides protective immunity.

A vaccine of the present invention may vary in its composition of nucleic acid and/or cellular components. In a non-limiting example, a nucleic acid encoding a SARS-CoV-2 antigen might also be formulated with an adjuvant. Of course, it will be understood that various compositions described herein may further comprise additional components. For example, one or more vaccine components may be comprised in a lipid, liposome, or lipid nanoparticle. In another non-limiting example, a vaccine may comprise one or more adjuvants. A vaccine of the present invention, and its various components, may be prepared and/or administered by any method disclosed herein or as would be known to one of ordinary skill in the art, in light of the present disclosure.

The induction of the immunity by the expression of the SARS-CoV-2 antigen can be detected by observing in vivo or in vitro the response of all or any part of the immune system in the host against the SARS-CoV-2 antigen.

For example, a method for detecting the induction of cytotoxic T lymphocytes is well known. A foreign substance that enters the living body is presented to T cells and B cells by the action of APCs. T cells that respond to the antigen presented by APC in an antigen specific manner differentiate into cytotoxic T cells (also referred to as cytotoxic T lymphocytes or CTLs) due to stimulation by the antigen. These antigen-stimulated cells then proliferate. This process is referred to herein as "activation" of T cells. Therefore, CTL induction by an epitope of a polypeptide or peptide or combinations thereof can be evaluated by presenting an epitope of a polypeptide or peptide or combinations thereof to a T cell by APC, and detecting the induction of CTL. Furthermore, APCs have the effect of activating B cells, CD4+ T cells, CD8+ T cells, macrophages, eosinophils and NK cells.

A method for evaluating the inducing action of CTL using dendritic cells (DCs) as APC is well known in the art. DC is a representative APC having a robust CTL inducing action among APCs. In the methods of the invention, the epitope of a polypeptide or peptide or combinations thereof is initially expressed by the DC and then this DC is contacted with T cells. Detection of T cells having cytotoxic effects against the cells of interest after the contact with DC shows that the epitope of a polypeptide or peptide or combinations thereof has an activity of inducing the cytotoxic T cells. Furthermore, the induced immune response can be also examined by measuring IFN-gamma produced and released by CTL in the presence of antigen-presenting cells that carry immobilized peptide or combination of peptides by visualizing using anti-IFN-gamma antibodies, such as an ELISPOT assay.

Apart from DC, peripheral blood mononuclear cells (PBMCs) may also be used as the APC. The induction of CTL is reported to be enhanced by culturing PBMC in the presence of GM-CSF and IL-4. Similarly, CTL has been shown to be induced by culturing PBMC in the presence of keyhole limpet hemocyanin (KLH) and IL-7.

The antigens confirmed to possess CTL-inducing activity by these methods are antigens having DC activation effect and subsequent CTL-inducing activity. Furthermore, CTLs that have acquired cytotoxicity due to presentation of the antigen by APC can be also used as vaccines against antigen-associated disorders.

The induction of immunity by expression of the SARS-CoV-2 antigen can be further confirmed by observing the induction of antibody production against the SARS-CoV-2 antigen. For example, when antibodies against an antigen are induced in a laboratory animal immunized with the composition encoding the antigen, and when antigen-associated pathology is suppressed by those antibodies, the composition is determined to induce immunity.

The induction of immunity by expression of the SARS-CoV-2 antigen can be further confirmed by observing the induction of CD4+ T cells. CD4+ T cells can also lyse target cells, but mainly supply help in the induction of other types of immune responses, including CTL and antibody generation. The type of CD4+ T cell help can be characterized, as Th1, Th2, Th9, Th17, T regulatory, or T follicular helper (T$_{fh}$) cells. Each subtype of CD4+ T cell supplies help to certain types of immune responses. In one embodiment, the composition selectively induces T follicular helper cells, which drive potent antibody responses.

The therapeutic compounds or compositions of the invention may be administered prophylactically (i.e., to prevent a disease or disorder) or therapeutically (i.e., to treat a disease or disorder) to subjects suffering from, or at risk of (or susceptible to) developing the disease or disorder. Such subjects may be identified using standard clinical methods. In the context of the present invention, prophylactic administration occurs prior to the manifestation of overt clinical symptoms of disease, such that a disease or disorder is prevented or alternatively delayed in its progression. In the context of the field of medicine, the term "prevent" encompasses any activity, which reduces the burden of mortality or morbidity from disease. Prevention can occur at primary, secondary and tertiary prevention levels. While primary prevention avoids the development of a disease, secondary and tertiary levels of prevention encompass activities aimed at preventing the progression of a disease and the emergence of symptoms as well as reducing the negative impact of an already established disease by restoring function and reducing disease-related complications.

Antigen

The present invention provides a composition that induces an immune response in a subject. In one embodiment, the composition comprises a SARS-CoV-2 antigen. In one embodiment, the composition comprises a nucleic acid sequence, which encodes a SARS-CoV-2 antigen. For example, in certain embodiments, the composition comprises a nucleoside-modified RNA encoding a SARS-CoV-2 antigen. In certain embodiments, the composition comprises a purified, nucleoside-modified RNA encoding a SARS-CoV-2 antigen. The antigen may include, but is not limited to a polypeptide, peptide or protein that induces an immune response in a subject.

In one embodiment, the antigen comprises a polypeptide or peptide associated with SARS-CoV-2, such that the antigen induces an immune response against the antigen, and therefore SARS-CoV-2. In one embodiment, the antigen comprises a fragment of a polypeptide or peptide associated with SARS-CoV-2, such that the antigen induces an immune response against SARS-CoV-2.

In certain embodiments, the antigen is a SARS-CoV-2 spike antigen or a fragment thereof. In one embodiment, the antigen is the receptor binding domain of a SARS-CoV-2 spike antigen. In one embodiment, antigen is a SARS-CoV-2 spike antigen comprising a mutation of the furin cleavage site. In one embodiment, antigen is the full-length SARS-CoV-2 S protein comprising a deletion of an AA sequence in the furin cleavage site (referred to herein as "Δfurin"). In certain embodiments, the antigen comprises an amino acid sequence of SEQ ID NO:3, SEQ ID NO:6 or SEQ ID NO:9, or a fragment or variant thereof.

In one embodiment, the composition comprises a nucleic acid sequence encoding a SARS-CoV-2 spike antigen or a fragment thereof. In one embodiment, the antigen is the receptor binding domain of a SARS-CoV-2 spike antigen. In one embodiment, antigen is a SARS-CoV-2 spike antigen comprising a mutation of the furin cleavage site. In one embodiment, antigen is the full-length SARS-CoV-2 S protein comprising a deletion of an AA sequence in the furin cleavage site (referred to herein as "Δfurin"). In certain embodiments, composition comprises a nucleic acid sequence encoding an amino acid sequence of SEQ ID NO:3, SEQ ID NO:6 or SEQ ID NO:9, or a fragment or variant thereof.

In one embodiment, the composition comprises a nucleic acid sequence encoding a SARS-CoV-2 spike antigen, where the nucleic acid sequence comprises an mRNA nucleotide sequence transcribed from SEQ ID NO:1 or SEQ ID NO:2. In one embodiment, the composition comprises a nucleoside-modified mRNA nucleotide sequence transcribed from SEQ ID NO:1 or SEQ ID NO:2, wherein one or more residues are replaced with a modified nucleoside as described elsewhere herein.

In one embodiment, the composition comprises a nucleic acid sequence encoding a SARS-CoV-2 spike antigen with a mutation in the furin cleavage site, where the nucleic acid sequence comprises an mRNA nucleotide sequence transcribed from SEQ ID NO:4 or SEQ ID NO:5. In one embodiment, the composition comprises a nucleoside-modified mRNA nucleotide sequence transcribed from SEQ ID NO:4 or SEQ ID NO:5, wherein one or more residues are replaced with a modified nucleoside as described elsewhere herein.

In one embodiment, the composition comprises a nucleic acid sequence encoding a SARS-CoV-2 spike antigen receptor binding domain, where the nucleic acid sequence comprises an mRNA nucleotide sequence transcribed from SEQ ID NO:7 or SEQ ID NO:8. In one embodiment, the composition comprises a nucleoside-modified mRNA nucleotide sequence transcribed from SEQ ID NO:7 or SEQ ID NO:8, wherein one or more residues are replaced with a modified nucleoside as described elsewhere herein.

The SARS-CoV-2 antigen may be of any type or strain of SARS-CoV-2. For example, in one embodiment, the SARS-CoV-2 antigen is a protein, or fragment thereof, of a SARS-CoV-2 strain including, but not limited to, Wuhan-Hu-1 (GenBank: MN908947.3).

In certain embodiments, the SARS-CoV-2 antigen comprises an amino acid sequence that is substantially homologous to the amino acid sequence of a SARS-CoV-2 antigen described herein and retains the immunogenic function of the original amino acid sequence. For example, in certain embodiments, the amino acid sequence of the SARS-CoV-2 antigen has a degree of identity with respect to the original amino acid sequence of at least 60%, of at least 65%, of at least 70%, of at least 75%, of at least 80%, of at least 85%, of at least 90%, of at least 91%, of at least 92%, of at least 93%, of at least 94%, of at least 95%, of at least 96%, of at least 97%, of at least 98%, of at least 99%, or of at least 99.5% In one embodiment, the SARS-CoV-2 antigen is encoded by a nucleic acid sequence of a nucleic acid molecule. In certain embodiments, the nucleic acid sequence comprises DNA, RNA, cDNA, a variant thereof, a fragment thereof, or a combination thereof. In one embodiment, the nucleic acid sequence comprises a modified nucleic acid sequence. For example, in one embodiment the SARS-CoV-2 antigen-encoding nucleic acid sequence comprises nucleoside-modified RNA, as described in detail elsewhere herein. In certain instances, the nucleic acid sequence comprises include additional sequences that encode linker or tag sequences that are linked to the antigen by a peptide bond.

Adjuvant

In one embodiment, the composition comprises an adjuvant. In one embodiment, the composition comprises a nucleic acid molecule encoding an adjuvant. In one embodiment, the adjuvant-encoding nucleic acid molecule is IVT RNA. In one embodiment, the adjuvant-encoding nucleic acid molecule is nucleoside-modified RNA.

Exemplary adjuvants include, but are not limited to, alpha-interferon, gamma-interferon, platelet derived growth factor (PDGF), TNFα, TNFβ, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15, MHC, CD80, CD86. Other genes which may be useful adjuvants include those encoding: MCP-I, MIP-Ia, MIP-Ip, IL-8, RANTES, L-selectin, P-selectin, E-selectin, CD34, GlyCAM-1, MadCAM-1, LFA-I, VLA-I, Mac-1, p150.95, PECAM, ICAM-I, ICAM-2, ICAM-3, CD2, LFA-3, M-CSF, G-CSF, IL-4, mutant forms of IL-18, CD40, CD40L, vascular growth factor, fibroblast growth factor, IL-7, nerve growth factor, vascular endothelial growth factor, Fas, TNF receptor, Fit, Apo-1, p55, WSL-I, DR3, TRAMP, Apo-3, AIR, LARD, NGRF, DR4, DR5, KILLER, TRAIL-R2, TRICK2, DR6, Caspase ICE, Fos, c-jun, Sp-I, Ap-I, Ap-2, p38, p65Rel, MyD88, IRAK, TRAF6, IkB, Inactive NIK, SAP K, SAP-I, JNK, interferon response genes, NFkB, Bax, TRAIL, TRAILrec, TRAILrecDRC5, TRAIL-R³, TRAIL-R⁴, RANK, RANK LIGAND, Ox40, Ox40 LIGAND, NKG2D, MICA, MICB, NKG2A, NKG2B, NKG2C, NKG2E, NKG2F, TAP 1, TAP2, anti-CTLA4-sc, anti-LAG3-Ig, anti-TIM3-Ig, and functional fragments thereof.

In certain embodiments, the composition comprises a lipid nanoparticle, where the lipid nanoparticle acts as an adjuvant.

Nucleic Acids

In one embodiment, the invention includes a nucleoside-modified nucleic acid molecule. In one embodiment, the nucleoside-modified nucleic acid molecule encodes a SARS-CoV-2 antigen. In one embodiment, the nucleoside-modified nucleic acid molecule encodes a plurality of antigens, including one or more SARS-CoV-2 antigens. In certain embodiments, the nucleoside-modified nucleic acid molecule encodes a SARS-CoV-2 antigen that induces an adaptive immune response against the SARS-CoV-2 antigen. In one embodiment, the invention includes a nucleoside-modified nucleic acid molecule encoding an adjuvant.

The nucleotide sequences encoding a SARS-CoV-2 antigen or adjuvant, as described herein, can alternatively comprise sequence variations with respect to the original nucleotide sequences, for example, substitutions, insertions and/or deletions of one or more nucleotides, with the condition that the resulting polynucleotide encodes a polypeptide according to the invention. Therefore, the scope of the present invention includes nucleotide sequences that are substantially homologous to the nucleotide sequences recited herein and encode a SARS-CoV-2 antigen or adjuvant of interest.

As used herein, a nucleotide sequence is "substantially homologous" to any of the nucleotide sequences described herein when its nucleotide sequence has a degree of identity with respect to the nucleotide sequence of at least 60%, of at least 65%, of at least 70%, of at least 65%, of at least 80%, of at least 85%, of at least 90%, of at least 95%, of at least 96%, of at least 97%, of at least 98%, or of at least 99%. A nucleotide sequence that is substantially homologous to a nucleotide sequence encoding an antigen can typically be isolated from a producer organism of the antigen based on the information contained in the nucleotide sequence by means of introducing conservative or non-conservative substitutions, for example. Other examples of possible modifications include the insertion of one or more nucleotides in the sequence, the addition of one or more nucleotides in any of the ends of the sequence, or the deletion of one or more nucleotides in any end or inside the sequence. The degree of identity between two polynucleotides is determined using computer algorithms and methods that are widely known for the persons skilled in the art.

Further, the scope of the invention includes nucleotide sequences that encode amino acid sequences that are substantially homologous to the amino acid sequences recited herein and preserve the immunogenic function of the original amino acid sequence.

As used herein, an amino acid sequence is "substantially homologous" to any of the amino acid sequences described herein when its amino acid sequence has a degree of identity with respect to the amino acid sequence of at least 60%, of at least 65%, of at least 70%, of at least 65%, of at least 80%, of at least 85%, of at least 90%, of at least 95%, of at least 96%, of at least 97%, of at least 98%, or of at least 99%. The identity between two amino acid sequences can be determined by using the BLASTN algorithm (BLAST Manual, Altschul, S., et al., NCBI NLM NIH Bethesda, Md. 20894, Altschul, S., et al., J. Mol. Biol. 215: 403-410 (1990)).

In one embodiment, the invention relates to a construct, comprising a nucleotide sequence encoding a SARS-CoV-2 antigen. In one embodiment, the construct comprises a plurality of nucleotide sequences encoding a plurality of SARS-CoV-2 antigens. For example, in certain embodiments, the construct encodes 1 or more, 2 or more, 5 or more, or more SARS-CoV-2 antigens. In one embodiment, the invention relates to a construct, comprising a nucleotide sequence encoding an adjuvant. In one embodiment, the construct comprises a first nucleotide sequence encoding a SARS-CoV-2 antigen and a second nucleotide sequence encoding an adjuvant.

In one embodiment, the composition comprises a plurality of constructs, each construct encoding one or more SARS-CoV-2 antigens. In certain embodiments, the composition comprises 1 or more, 2 or more, 3 or more, 4 or more, 5 or more, 6 or more, 7 or more, 8 or more, 9 or more, 10 or more, 15 or more, or 20 or more constructs. In one embodiment, the composition comprises a first construct, comprising a nucleotide sequence encoding a SARS-CoV-2 antigen; and a second construct, comprising a nucleotide sequence encoding an adjuvant.

In another particular embodiment, the construct is operatively bound to a translational control element. The construct can incorporate an operatively bound regulatory sequence for the expression of the nucleotide sequence of the invention, thus forming an expression cassette.

Vectors

The nucleic acid sequences coding for the SARS-CoV-2 antigen or adjuvant can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically.

The nucleic acid can be cloned into a number of types of vectors. For example, the nucleic acid can be cloned into a vector including, but not limited to a plasmid, a phagemid, a phage derivative, an animal virus, a PCR-generated linear DNA sequence, and a cosmid. Vectors of particular interest include expression vectors, replication vectors, probe generation vectors, sequencing vectors and vectors optimized for in vitro transcription.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, carbohydrates, peptides, cationic polymers, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/RNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, MO; dicetyl phosphate ("DCP") can be obtained from K & K Laboratories (Plainview, NY); cholesterol ("Chol") can be obtained from Calbiochem-Behring; dimyristyl phosphatidylglycerol ("DMPG") and other lipids may be obtained from Avanti Polar Lipids, Inc. (Birmingham, AL). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell or otherwise expose a cell to the inhibitor of the present invention, in order to confirm the presence of the mRNA sequence in the host cell, a variety of assays may be performed. Such assays include, for example, "molecular biological" assays well known to those of skill in the art, such as Northern blotting and RT-PCR; "biochemical" assays, such as detecting the presence or absence of a particular peptide, e.g., by immunogenic means (ELISAs and Western blots) or by assays described herein to identify agents falling within the scope of the invention.

In Vitro Transcribed RNA

In one embodiment, the composition of the invention comprises in vitro transcribed (IVT) RNA encoding a SARS-CoV-2 antigen. In one embodiment, the composition of the invention comprises IVT RNA encoding a plurality of SARS-CoV-2 antigens. In one embodiment, the composition of the invention comprises IVT RNA encoding an adjuvant. In one embodiment, the composition of the invention comprises IVT RNA encoding one or more SARS-CoV-2 antigens and one or more adjuvants.

In one embodiment, an IVT RNA can be introduced to a cell as a form of transient transfection. The RNA is produced by in vitro transcription using a plasmid DNA template generated synthetically. DNA of interest from any source can be directly converted by PCR into a template for in vitro mRNA synthesis using appropriate primers and RNA polymerase. The source of the DNA can be, for example, genomic DNA, plasmid DNA, phage DNA, cDNA, synthetic DNA sequence or any other appropriate source of DNA. In one embodiment, the desired template for in vitro transcription is a SARS-CoV-2 antigen capable of inducing an adaptive immune response. In one embodiment, the desired template for in vitro transcription is an adjuvant capable of enhancing an adaptive immune response.

In one embodiment, the DNA to be used for PCR contains an open reading frame. The DNA can be from a naturally occurring DNA sequence from the genome of an organism. In one embodiment, the DNA is a full length gene of interest of a portion of a gene. The gene can include some or all of the 5' and/or 3' untranslated regions (UTRs). The gene can include exons and introns. In one embodiment, the DNA to be used for PCR is a human gene. In another embodiment, the DNA to be used for PCR is a human gene including the 5' and 3' UTRs. In another embodiment, the DNA to be used for PCR is a gene from a pathogenic or commensal organism, including bacteria, viruses, parasites, and fungi. In another embodiment, the DNA to be used for PCR is from a pathogenic or commensal organism, including bacteria, viruses, parasites, and fungi, including the 5' and 3' UTRs. The DNA can alternatively be an artificial DNA sequence that is not normally expressed in a naturally occurring organism. An exemplary artificial DNA sequence is one that contains portions of genes that are ligated together to form an open reading frame that encodes a fusion protein. The portions of DNA that are ligated together can be from a single organism or from more than one organism.

Genes that can be used as sources of DNA for PCR include genes that encode polypeptides that induce or enhance an adaptive immune response in an organism. In certain instances, the genes are useful for a short term treatment. In certain instances, the genes have limited safety concerns regarding dosage of the expressed gene.

In various embodiments, a plasmid is used to generate a template for in vitro transcription of mRNA, which is used for transfection.

Chemical structures with the ability to promote stability and/or translation efficiency may also be used. In certain embodiments, the RNA has 5' and 3' UTRs. In one embodiment, the 5' UTR is between zero and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the gene of interest. Alternatively, UTR sequences that are not endogenous to the gene of interest can be added by incorporating the UTR sequences into the forward and reverse primers or by any other modifications of the template. The use of UTR sequences that are not endogenous to the gene of interest can be useful for modifying the stability and/or translation efficiency of the RNA. For example, it is known that AU-rich elements in 3' UTR sequences can decrease the stability of mRNA. Therefore, 3' UTRs can be selected or designed to increase the stability of the transcribed RNA based on properties of UTRs that are well known in the art.

In one embodiment, the 5' UTR can contain the Kozak sequence of the endogenous gene. Alternatively, when a 5' UTR that is not endogenous to the gene of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many mRNAs is known in the art. In other embodiments, the 5' UTR can be derived from an RNA virus whose RNA genome is stable in cells. In other embodiments, various nucleotide analogues can be used in the 3' or 5' UTR to impede exonuclease degradation of the mRNA.

To enable synthesis of RNA from a DNA template without the need for gene cloning, a promoter of transcription should be attached to the DNA template upstream of the sequence to be transcribed. When a sequence that functions as a promoter for an RNA polymerase is added to the 5' end of the forward primer, the RNA polymerase promoter becomes incorporated into the PCR product upstream of the open reading frame that is to be transcribed. In one embodiment, the promoter is a T7 RNA polymerase promoter, as described elsewhere herein. Other useful promoters include, but are not limited to, T3 and SP6 RNA polymerase promoters. Consensus nucleotide sequences for T7, T3 and SP6 promoters are known in the art.

In one embodiment, the mRNA has both a cap on the 5' end and a 3' poly(A) tail which determine ribosome binding, initiation of translation and stability mRNA in the cell. On a circular DNA template, for instance, plasmid DNA, RNA polymerase produces a long concatameric product, which is not suitable for expression in eukaryotic cells. The transcription of plasmid DNA linearized at the end of the 3' UTR results in normal sized mRNA, which is effective in eukaryotic transfection when it is polyadenylated after transcription.

On a linear DNA template, phage T7 RNA polymerase can extend the 3' end of the transcript beyond the last base of the template (Schenborn and Mierendorf, Nuc Acids Res., 13:6223-36 (1985); Nacheva and Berzal-Herranz, Eur. J. Biochem., 270:1485-65 (2003).

The conventional method of integration of polyA/T stretches into a DNA template is molecular cloning. However, polyA/T sequence integrated into plasmid DNA can cause plasmid instability, which can be ameliorated through the use of recombination incompetent bacterial cells for plasmid propagation.

Poly(A) tails of RNAs can be further extended following in vitro transcription with the use of a poly(A) polymerase, such as *E. coli* polyA polymerase (E-PAP) or yeast polyA polymerase. In one embodiment, increasing the length of a poly(A) tail from 100 nucleotides to between 300 and 400 nucleotides results in about a two-fold increase in the translation efficiency of the RNA. Additionally, the attachment of different chemical groups to the 3' end can increase mRNA stability. Such attachment can contain modified/ artificial nucleotides, aptamers and other compounds. For example, ATP analogs can be incorporated into the poly(A) tail using poly(A) polymerase. ATP analogs can further increase the stability of the RNA.

5' caps on also provide stability to mRNA molecules. In one embodiment, RNAs produced by the methods to include a 5' cap1 structure. Such cap1 structure can be generated using Vaccinia capping enzyme and 2'-O-methyltransferase enzymes (CellScript, Madison, WI). Alternatively, 5' cap is provided using techniques known in the art and described herein (Cougot, et al., Trends in Biochem. Sci., 29:436-444 (2001); Stepinski, et al., RNA, 7:1468-95 (2001); Elango, et al., Biochim. Biophys. Res. Commun., 330:958-966 (2005)).

RNA can be introduced into target cells using any of a number of different methods, for instance, commercially available methods which include, but are not limited to, electroporation (Amaxa Nucleofector-II (Amaxa Biosystems, Cologne, Germany)), (ECM 830 (BTX) (Harvard Instruments, Boston, Mass.) or the Gene Pulser II (BioRad, Denver, Colo.), Multiporator (Eppendort, Hamburg Germany), cationic liposome mediated transfection using lipofection, polymer encapsulation, peptide mediated transfection, or biolistic particle delivery systems such as "gene guns" (see, for example, Nishikawa, et al. Hum Gene Ther., 12(8):861-70 (2001). In certain embodiments RNA of the invention is introduced to a cell with a method comprising the use of TransIT®-mRNA transfection Kit (Mirus, Madison WI), which, in some instances, provides high efficiency, low toxicity, transfection.

Nucleoside-Modified RNA

In one embodiment, the composition of the present invention comprises a nucleoside-modified nucleic acid encoding a SARS-CoV-2 antigen as described herein. In one embodiment, the composition of the present invention comprises a nucleoside-modified nucleic acid encoding a plurality of antigens, including one or more SARS-CoV-2 antigens. In one embodiment, the composition of the present invention comprises a nucleoside-modified nucleic acid encoding an adjuvant as described herein. In one embodiment, the composition of the present invention comprises a nucleoside-modified nucleic acid encoding one or more SARS-CoV-2 antigens and one or more adjuvants.

For example, in one embodiment, the composition comprises a nucleoside-modified RNA. In one embodiment, the composition comprises a nucleoside-modified mRNA. Nucleoside-modified mRNA have particular advantages over non-modified mRNA, including for example, increased stability, low or absent innate immunogenicity, and enhanced translation. Nucleoside-modified mRNA useful in the present invention is further described in U.S. Pat. Nos. 8,278,036, 8,691,966, and 8,835,108, each of which is incorporated by reference herein in its entirety.

In certain embodiments, nucleoside-modified mRNA does not activate any pathophysiologic pathways, translates very efficiently and almost immediately following delivery, and serve as templates for continuous protein production in vivo lasting for several days (Karikó et al., 2008, Mol Ther 16:1833-1840; Karikó et al., 2012, Mol Ther 20:948-953). The amount of mRNA required to exert a physiological effect is small and that makes it applicable for human therapy. For example, as described herein, nucleoside-modified mRNA encoding a SARS-CoV-2 antigen has demonstrated the ability to antigen-specific antibody production. For example, in certain instances, antigen encoded by nucleoside-modified mRNA induces greater production of antigen-specific antibody production as compared to antigen encoded by non-modified mRNA.

In certain instances, expressing a protein by delivering the encoding mRNA has many benefits over methods that use protein, plasmid DNA or viral vectors. During mRNA transfection, the coding sequence of the desired protein is the only substance delivered to cells, thus avoiding all the side effects associated with plasmid backbones, viral genes, and viral proteins. More importantly, unlike DNA- and viral-based vectors, the mRNA does not carry the risk of being incorporated into the genome and protein production starts immediately after mRNA delivery. For example, high levels of circulating proteins have been measured within 15 to 30 minutes of in vivo injection of the encoding mRNA. In certain embodiments, using mRNA rather than the protein also has many advantages. Half-lives of proteins in the circulation are often short, thus protein treatment would need frequent dosing, while mRNA provides a template for continuous protein production for several days. Purification of proteins is problematic and they can contain aggregates and other impurities that cause adverse effects (Kromminga and Schellekens, 2005, Ann NY Acad Sci 1050:257-265).

In certain embodiments, the nucleoside-modified RNA comprises the naturally occurring modified-nucleoside pseudouridine. In certain embodiments, inclusion of pseudouridine makes the mRNA more stable, non-immunogenic, and highly translatable (Karikó et al., 2008, Mol Ther 16:1833-1840; Anderson et al., 2010, Nucleic Acids Res 38:5884-5892; Anderson et al., 2011, Nucleic Acids Research 39:9329-9338; Karikó et al., 2011, Nucleic Acids Research 39:e142; Karikó et al., 2012, Mol Ther 20:948-953; Karikó et al., 2005, Immunity 23:165-175).

It has been demonstrated that the presence of modified nucleosides, including pseudouridines in RNA suppress their innate immunogenicity (Karikó et al., 2005, Immunity 23:165-175). Further, protein-encoding, in vitro-transcribed RNA containing pseudouridine can be translated more efficiently than RNA containing no or other modified nucleosides (Karikó et al., 2008, Mol Ther 16:1833-1840). Subsequently, it is shown that the presence of pseudouridine improves the stability of RNA (Anderson et al., 2011, Nucleic Acids Research 39:9329-9338) and abates both activation of PKR and inhibition of translation (Anderson et al., 2010, Nucleic Acids Res 38:5884-5892).

In certain embodiments, the nucleoside-modified nucleic acid molecule is a purified nucleoside-modified nucleic acid molecule. For example, in certain embodiments, the composition is purified to remove double-stranded contaminants. In certain instances, a preparative high performance liquid chromatography (HPLC) purification procedure is used to obtain pseudouridine-containing RNA that has superior translational potential and no innate immunogenicity (Karikó et al., 2011, Nucleic Acids Research 39:e142). Administering HPLC-purified, pseudourine-containing RNA coding for erythropoietin into mice and macaques resulted in a significant increase of serum EPO levels (Karikó et al., 2012, Mol Ther 20:948-953), thus confirming that pseudouridine-containing mRNA is suitable for in vivo protein therapy. In certain embodiments, the nucleoside-modified nucleic acid molecule is purified using non-HPLC methods. In certain instances, the nucleoside-modified nucleic acid molecule is purified using chromatography methods, including but not limited to HPLC and fast protein liquid chromatography (FPLC). An exemplary FPLC-based purification procedure is described in Weissman et al., 2013, Methods Mol Biol, 969: 43-54. Exemplary purification procedures are also described in U.S. Patent Application Publication No. US2016/0032316, which is hereby incorporated by reference in its entirety.

The present invention encompasses RNA, oligoribonucleotide, and polyribonucleotide molecules comprising pseudouridine or a modified nucleoside. In certain embodiments, the composition comprises an isolated nucleic acid encoding an antigen, wherein the nucleic acid comprises a pseudouridine or a modified nucleoside. In certain embodiments, the composition comprises a vector, comprising an isolated nucleic acid encoding an antigen, adjuvant, or combination thereof, wherein the nucleic acid comprises a pseudouridine or a modified nucleoside.

In one embodiment, the nucleoside-modified RNA of the invention is IVT RNA, as described elsewhere herein. For example, in certain embodiments, the nucleoside-modified RNA is synthesized by T7 phage RNA polymerase. In another embodiment, the nucleoside-modified mRNA is synthesized by SP6 phage RNA polymerase. In another embodiment, the nucleoside-modified RNA is synthesized by T3 phage RNA polymerase.

In one embodiment, the modified nucleoside is $m^1acp^3\Psi$ (1-methyl-3-(3-amino-3-carboxypropyl) pseudouridine. In another embodiment, the modified nucleoside is $m^1\Psi$ (1-methylpseudouridine). In another embodiment, the modified nucleoside is $\Psi m$ (2'-O-methylpseudouridine). In another embodiment, the modified nucleoside is $m^5D$ (5-methyldihydrouridine). In another embodiment, the modified nucleoside is $m^3\Psi$ (3-methylpseudouridine). In another embodiment, the modified nucleoside is a pseudouridine moiety that is not further modified. In another embodiment, the modified nucleoside is a monophosphate, diphosphate, or triphosphate of any of the above pseudouridines. In another embodiment, the modified nucleoside is any other pseudouridine-like nucleoside known in the art.

In another embodiment, the nucleoside that is modified in the nucleoside-modified RNA the present invention is uridine (U). In another embodiment, the modified nucleoside is cytidine (C). In another embodiment, the modified nucleoside is adenosine (A). In another embodiment, the modified nucleoside is guanosine (G).

In another embodiment, the modified nucleoside of the present invention is $m^5C$ (5-methylcytidine). In another embodiment, the modified nucleoside is $m^5U$ (5-methyluridine). In another embodiment, the modified nucleoside is $m^6A$ ($N^6$-methyladenosine). In another embodiment, the modified nucleoside is $s^2U$ (2-thiouridine). In another embodiment, the modified nucleoside is $\Psi$ (pseudouridine). In another embodiment, the modified nucleoside is Um (2'-O-methyluridine).

In other embodiments, the modified nucleoside is $m^1A$ (1-methyladenosine); $m^2A$ (2-methyladenosine); Am (2'-O-methyladenosine); $ms^2m^6A$ (2-methylthio-$N^6$-methyladenosine); $i^6A$ ($N^6$-isopentenyladenosine); $ms^2i6A$ (2-methylthio-$N^6$isopentenyladenosine); $io^6A$ ($N^6$-(cis-hydroxyisopentenyl)adenosine); $ms^2io^6A$ (2-methylthio-$N^6$-(cis-hydroxyisopentenyl) adenosine); $g^6A$ ($N^6$- glycinylcarbamoyladenosine); t$^6$A (N$^6$-threonylcarbamoyladenosine); ms$^2$t$^6$A (2-methylthio-N$^6$-threonyl carbamoyladenosine); m$^6$t$^6$A (N$^6$-methyl-N$^6$-threonylcarbamoyladenosine); hn$^6$A (N$^6$-hydroxynorvalylcarbamoyladenosine); ms$^2$hn$^6$A (2-methylthio-N$^6$-hydroxynorvalyl carbamoyladenosine); Ar(p) (2'-O-ribosyladenosine (phosphate)); I (inosine); m$^1$I (1-methylinosine); m$^1$Im (1,2'-O-dimethylinosine); m$^3$C (3-methylcytidine); Cm (2'-O-methylcytidine); s$^2$C (2-thio-cytidine); ac$^4$C (N$^4$-acetylcytidine); f$^5$C (5-formylcytidine); m$^5$Cm (5,2'-O-dimethylcytidine); ac$^4$Cm (N$^4$-acetyl-2'-O-methylcytidine); k$^2$C (lysidine); m$^1$G (1-methylguanosine); m$^2$G (N$^2$-methylguanosine); m$^7$G (7-methylguanosine); Gm (2'-O-methylguanosine); m$^2$2G (N$^2$,N$^2$-dimethylguanosine); m$^2$Gm (N$^2$,2'-O-dimethylguanosine); m$^2$2Gm (N$^2$,N$^2$,2'-O-trimethylguanosine); Gr(p) (2'-O-ribosylguanosine (phosphate)); yW (wybutosine); o$_2$yW (peroxywybutosine); OHyW (hydroxywybutosine); OHyW* (undermodified hydroxywybutosine); imG (wyosine); mimG (methyl-wyosine); Q (queuosine); oQ (epoxyqueuosine); galQ (galactosyl-queuosine); manQ (mannosyl-queuosine); preQ$_0$ (7-cyano-7-deazaguanosine); preQ$_1$ (7-aminomethyl-7-deazaguanosine); G$^+$ (archaeosine); D (dihydrouridine); m$^5$Um (5,2'-O-dimethyluridine); s$^4$U (4-thiouridine); m$^5$s$^2$U (5-methyl-2-thiouridine); s$^2$Um (2-thio-2'-O-methyluridine); acp$^3$U (3-(3-amino-3-carboxypropyl)uridine); ho$^5$U (5-hydroxyuridine); mo$^5$U (5-methoxyuridine); cmo$^5$U (uridine 5-oxyacetic acid); mcmo$^5$U (uridine 5-oxyacetic acid methyl ester); chm$^5$U (5-(carboxyhydroxymethyl)uridine)); mchm$^5$U (5-(carboxyhydroxymethyl)uridine methyl ester); mcm$^5$U (5-methoxycarbonylmethyluridine); mcm$^5$Um (5-methoxycarbonylmethyl-2'-O-methyluridine); mcm$^5$s$^2$U (5-methoxycarbonylmethyl-2-thiouridine); nm$^5$s$^2$U (5-aminomethyl-2-thiouridine); mnm$^5$U (5-methylaminomethyluridine); mnm$^5$s$^2$U (5-methylaminomethyl-2-thiouridine); mnm$^5$se$^2$U (5-methylaminomethyl-2-selenouridine); ncm$^5$U (5-carbamoylmethyluridine); ncm$^5$Um (5-carbamoylmethyl-2'-O-methyluridine); cmnm$^5$U (5-carboxymethylaminomethyluridine); cmnm$^5$Um (5-carboxymethylaminomethyl-2'-O-methyluridine); cmnm$^5$s$^2$U (5-carboxymethylaminomethyl-2-thiouridine); m$^6_2$A (N$^6$,N$^6$-dimethyladenosine); Im (2'-O-methylinosine); m$^4$C (N$^4$-methylcytidine); m$^4$Cm (N$^4$,2'-O-dimethylcytidine); hm$^5$C (5-hydroxymethylcytidine); m$^3$U (3-methyluridine); cm$^5$U (5-carboxymethyluridine); m$^6$Am (N$^6$,2'-O-dimethyladenosine); m$^6_2$Am (N$^6$,N$^6$,O-2'-trimethyladenosine); m$^{2,7}$G (N$^2$,7-dimethylguanosine); m$^{2,2,7}$G (N$^2$,N$^2$,7-trimethylguanosine); m$^3$Um (3,2'-O-dimethyluridine); m$^5$D (5-methyldihydrouridine); f$^5$Cm (5-formyl-2'-O-methylcytidine); m$^1$Gm (1,2'-O-dimethylguanosine); m$^1$Am (1,2'-0-dimethyladenosine); τm$^5$U (5-taurinomethyluridine); τm$^5$s$^2$U (5-taurinomethyl-2-thiouridine)); imG-14 (4-demethyl-wyosine); imG2 (isowyosine); or ac$^6$A (N$^6$-acetyladenosine).

In another embodiment, a nucleoside-modified RNA of the present invention comprises a combination of 2 or more of the above modifications. In another embodiment, the nucleoside-modified RNA comprises a combination of 3 or more of the above modifications. In another embodiment, the nucleoside-modified RNA comprises a combination of more than 3 of the above modifications.

In various embodiments, between 0.1% and 100% of the residues in the nucleoside-modified of the present invention are modified (e.g., either by the presence of pseudouridine or another modified nucleoside base). In one embodiment, the fraction of modified residues is 0.1%. In another embodiment, the fraction of modified residues is 0.2%. In another embodiment, the fraction is 0.3%. In another embodiment, the fraction is 0.4%. In another embodiment, the fraction is 0.5%. In another embodiment, the fraction is 0.6%. In another embodiment, the fraction is 0.7%. In another embodiment, the fraction is 0.8%. In another embodiment, the fraction is 0.9%. In another embodiment, the fraction is 1%. In another embodiment, the fraction is 1.5%. In another embodiment, the fraction is 2%. In another embodiment, the fraction is 2.5%. In another embodiment, the fraction is 3%. In another embodiment, the fraction is 4%. In another embodiment, the fraction is 5%. In another embodiment, the fraction is 6%. In another embodiment, the fraction is 7%. In another embodiment, the fraction is 8%. In another embodiment, the fraction is 9%. In another embodiment, the fraction is 10%. In another embodiment, the fraction is 12%. In another embodiment, the fraction is 14%. In another embodiment, the fraction is 16%. In another embodiment, the fraction is 18%. In another embodiment, the fraction is 20%. In another embodiment, the fraction is 25%. In another embodiment, the fraction is 30%. In another embodiment, the fraction is 35%. In another embodiment, the fraction is 40%. In another embodiment, the fraction is 45%. In another embodiment, the fraction is 50%. In another embodiment, the fraction is 55%. In another embodiment, the fraction is 60%. In another embodiment, the fraction is 65%. In another embodiment, the fraction is 70%. In another embodiment, the fraction is 75%. In another embodiment, the fraction is 80%. In another embodiment, the fraction is 85%. In another embodiment, the fraction is 90%. In another embodiment, the fraction is 91%. In another embodiment, the fraction is 92%. In another embodiment, the fraction is 93%. In another embodiment, the fraction is 94%. In another embodiment, the fraction is 95%. In another embodiment, the fraction is 96%. In another embodiment, the fraction is 97%. In another embodiment, the fraction is 98%. In another embodiment, the fraction is 99%. In another embodiment, the fraction is 100%.

In another embodiment, the fraction is less than 5%. In another embodiment, the fraction is less than 3%. In another embodiment, the fraction is less than 1%. In another embodiment, the fraction is less than 2%. In another embodiment, the fraction is less than 4%. In another embodiment, the fraction is less than 6%. In another embodiment, the fraction is less than 8%. In another embodiment, the fraction is less than 10%. In another embodiment, the fraction is less than 12%. In another embodiment, the fraction is less than 15%. In another embodiment, the fraction is less than 20%. In another embodiment, the fraction is less than 30%. In another embodiment, the fraction is less than 40%. In another embodiment, the fraction is less than 50%. In another embodiment, the fraction is less than 60%. In another embodiment, the fraction is less than 70%.

In another embodiment, 0.1% of the residues of a given nucleoside (i.e., uridine, cytidine, guanosine, or adenosine) are modified. In another embodiment, the fraction of modified residues is 0.2%. In another embodiment, the fraction is 0.3%. In another embodiment, the fraction is 0.4%. In another embodiment, the fraction is 0.5%.

In another embodiment, the fraction is 0.6%. In another embodiment, the fraction is 0.7%. In another embodiment, the fraction is 0.8%. In another embodiment, the fraction is 0.9%. In another embodiment, the fraction is 1%. In another embodiment, the fraction is 1.5%. In another embodiment, the fraction is 2%. In another embodiment, the fraction is 2.5%. In another embodiment, the fraction is 3%. In another embodiment, the fraction is 4%. In another embodiment, the fraction is 5%. In another embodiment, the fraction is 6%. In another embodiment, the fraction is 7%. In another embodiment, the fraction is 8%. In another embodiment, the fraction is 9%. In another embodiment, the fraction is 10%. In another embodiment, the fraction is 12%. In another embodiment, the fraction is 14%. In another embodiment, the fraction is 16%. In another embodiment, the fraction is 18%. In another embodiment, the fraction is 20%. In another embodiment, the fraction is 25%. In another embodiment, the fraction is 30%. In another embodiment, the fraction is 35%. In another embodiment, the fraction is 40%. In another embodiment, the fraction is 45%. In another embodiment, the fraction is 50%. In another embodiment, the fraction is 55%. In another embodiment, the fraction is 60%. In another embodiment, the fraction is 65%. In another embodiment, the fraction is 70%. In another embodiment, the fraction is 75%. In another embodiment, the fraction is 80%. In another embodiment, the fraction is 85%. In another embodiment, the fraction is 90%. In another embodiment, the fraction is 91%. In another embodiment, the fraction is 92%. In another embodiment, the fraction is 93%. In another embodiment, the fraction is 94%. In another embodiment, the fraction is 95%. In another embodiment, the fraction is 96%. In another embodiment, the fraction is 97%. In another embodiment, the fraction is 98%. In another embodiment, the fraction is 99%. In another embodiment, the fraction is 100%. In another embodiment, the fraction of the given nucleotide that is modified is less than 8%. In another embodiment, the fraction is less than 10%. In another embodiment, the fraction is less than 5%. In another embodiment, the fraction is less than 3%. In another embodiment, the fraction is less than 1%. In another embodiment, the fraction is less than 2%. In another embodiment, the fraction is less than 4%. In another embodiment, the fraction is less than 6%. In another embodiment, the fraction is less than 12%. In another embodiment, the fraction is less than 15%. In another embodiment, the fraction is less than 20%. In another embodiment, the fraction is less than 30%. In another embodiment, the fraction is less than 40%. In another embodiment, the fraction is less than 50%. In another embodiment, the fraction is less than 60%. In another embodiment, the fraction is less than 70%.

In another embodiment, a nucleoside-modified RNA of the present invention is translated in the cell more efficiently than an unmodified RNA molecule with the same sequence. In another embodiment, the nucleoside-modified RNA exhibits enhanced ability to be translated by a target cell. In another embodiment, translation is enhanced by a factor of 2-fold relative to its unmodified counterpart. In another embodiment, translation is enhanced by a 3-fold factor. In another embodiment, translation is enhanced by a 4-fold factor. In another embodiment, translation is enhanced by a 5-fold factor. In another embodiment, translation is enhanced by a 6-fold factor. In another embodiment, translation is enhanced by a 7-fold factor. In another embodiment, translation is enhanced by a 8-fold factor. In another embodiment, translation is enhanced by a 9-fold factor. In another embodiment, translation is enhanced by a 10-fold factor. In another embodiment, translation is enhanced by a 15-fold factor. In another embodiment, translation is enhanced by a 20-fold factor. In another embodiment, translation is enhanced by a 50-fold factor. In another embodiment, translation is enhanced by a 100-fold factor. In another embodiment, translation is enhanced by a 200-fold factor. In another embodiment, translation is enhanced by a 500-fold factor. In another embodiment, translation is enhanced by a 1000-fold factor. In another embodiment, translation is enhanced by a 2000-fold factor. In another embodiment, the factor is 10-1000-fold. In another embodiment, the factor is 10-100-fold. In another embodiment, the factor is 10-200-fold. In another embodiment, the factor is 10-300-fold. In another embodiment, the factor is 10-500-fold. In another embodiment, the factor is 20-1000-fold. In another embodiment, the factor is 30-1000-fold. In another embodiment, the factor is 50-1000-fold. In another embodiment, the factor is 100-1000-fold. In another embodiment, the factor is 200-1000-fold. In another embodiment, translation is enhanced by any other significant amount or range of amounts.

In another embodiment, the nucleoside-modified antigen-encoding RNA of the present invention induces a significantly more robust adaptive immune response as compared with an unmodified in vitro-synthesized RNA molecule of the same sequence.

In another embodiment, the modified RNA molecule induces an adaptive immune response that is 2-fold greater than its unmodified counterpart. In another embodiment, the adaptive immune response is increased by a 3-fold factor. In another embodiment, the adaptive immune response is increased by a 4-fold factor. In another embodiment the adaptive immune response is increased by a 5-fold factor. In another embodiment, the adaptive immune response is increased by a 6-fold factor. In another embodiment, the adaptive immune response is increased by a 7-fold factor. In another embodiment, the adaptive immune response is increased by a 8-fold factor. In another embodiment, the adaptive immune response is increased by a 9-fold factor. In another embodiment, the adaptive immune response is increased by a 10-fold factor. In another embodiment, the adaptive immune response is increased by a 15-fold factor. In another embodiment, the adaptive immune response is increased by a 20-fold factor. In another embodiment, the adaptive immune response is increased by a 50-fold factor. In another embodiment, the adaptive immune response is increased by a 100-fold factor. In another embodiment, the adaptive immune response is increased by a 200-fold factor. In another embodiment, the adaptive immune response is increased by a 500-fold factor. In another embodiment, the adaptive immune response is increased by a 1000-fold factor. In another embodiment, the adaptive immune response is increased by a 2000-fold factor. In another embodiment, the adaptive immune response is increased by another fold difference.

In another embodiment, "induces significantly more robust adaptive immune response" refers to a detectable increase in an adaptive immune response. In another embodiment, the term refers to a fold increase in the adaptive immune response (e.g., 1 of the fold increases enumerated above). In another embodiment, the term refers to an increase such that the nucleoside-modified RNA can be administered at a lower dose or frequency than an unmodified RNA molecule while still inducing a similarly effective adaptive immune response. In another embodiment, the increase is such that the nucleoside-modified RNA can be administered using a single dose to induce an effective adaptive immune response.

In another embodiment, the nucleoside-modified RNA of the present invention exhibits significantly less innate immunogenicity than an unmodified in vitro-synthesized RNA molecule of the same sequence. In another embodiment, the modified RNA molecule exhibits an innate immune response that is 2-fold less than its unmodified counterpart. In another embodiment, innate immunogenicity is reduced by a 3-fold factor. In another embodiment, innate immunogenicity is reduced by a 4-fold factor. In another embodiment, innate immunogenicity is reduced by a 5-fold factor. In another embodiment, innate immunogenicity is reduced by a 6-fold factor. In another embodiment, innate immunogenicity is reduced by a 7-fold factor. In another embodiment, innate immunogenicity is reduced by a 8-fold factor. In another embodiment, innate immunogenicity is reduced by a 9-fold factor. In another embodiment, innate immunogenicity is reduced by a 10-fold factor. In another embodiment, innate immunogenicity is reduced by a 15-fold factor. In another embodiment, innate immunogenicity is reduced by a 20-fold factor. In another embodiment, innate immunogenicity is reduced by a 50-fold factor. In another embodiment, innate immunogenicity is reduced by a 100-fold factor. In another embodiment, innate immunogenicity is reduced by a 200-fold factor. In another embodiment, innate immunogenicity is reduced by a 500-fold factor. In another embodiment, innate immunogenicity is reduced by a 1000-fold factor. In another embodiment, innate immunogenicity is reduced by a 2000-fold factor. In another embodiment, innate immunogenicity is reduced by another fold difference.

In another embodiment, "exhibits significantly less innate immunogenicity" refers to a detectable decrease in innate immunogenicity. In another embodiment, the term refers to a fold decrease in innate immunogenicity (e.g., 1 of the fold decreases enumerated above). In another embodiment, the term refers to a decrease such that an effective amount of the nucleoside-modified RNA can be administered without triggering a detectable innate immune response. In another embodiment, the term refers to a decrease such that the nucleoside-modified RNA can be repeatedly administered without eliciting an innate immune response sufficient to detectably reduce production of the protein encoded by the modified RNA. In another embodiment, the decrease is such that the nucleoside-modified RNA can be repeatedly administered without eliciting an innate immune response sufficient to eliminate detectable production of the protein encoded by the modified RNA.

In some embodiments, the vaccine does not elicit antibodies with antibody-dependent enhancement (ADE) activity. Vaccine-induced enhancement of susceptibility to virus infection or of aberrant viral pathogenesis have been documented for infections by members of different virus families including, but not limited to Dengue virus, Zika virus and feline coronavirus. In some embodiments, "antibodies with ADE activity" refers to antibodies that enhance the entry of virus, and in some cases the replication of virus, into monocytes/macrophages and granulocytic cells through interaction with Fc and/or complement receptors. Therefore, in one embodiment, the vaccine elicits antibodies that do not enhance or cause ADE of disease associated with the antigen, but still neutralize the antigen.

Lipid Nanoparticle

In one embodiment, delivery of nucleoside-modified RNA comprises any suitable delivery method, including exemplary RNA transfection methods described elsewhere herein. In certain embodiments, delivery of a nucleoside-modified RNA to a subject comprises mixing the nucleoside-modified RNA with a transfection reagent prior to the step of contacting. In another embodiment, a method of present invention further comprises administering nucleoside-modified RNA together with the transfection reagent. In another embodiment, the transfection reagent is a cationic lipid reagent. In another embodiment, the transfection reagent is a cationic polymer reagent.

In another embodiment, the transfection reagent is a lipid-based transfection reagent. In another embodiment, the transfection reagent is a protein-based transfection reagent. In another embodiment, the transfection reagent is a carbohydrate-based transfection reagent. In another embodiment, the transfection reagent is a cationic lipid-based transfection reagent. In another embodiment, the transfection reagent is a cationic polymer-based transfection reagent. In another embodiment, the transfection reagent is a polyethyleneimine based transfection reagent. In another embodiment, the transfection reagent is calcium phosphate. In another embodiment, the transfection reagent is Lipofectin®, Lipofectamine®, or TransIT®. In another embodiment, the transfection reagent is any other transfection reagent known in the art.

In another embodiment, the transfection reagent forms a liposome.

Liposomes, in another embodiment, increase intracellular stability, increase uptake efficiency and improve biological activity. In another embodiment, liposomes are hollow spherical vesicles composed of lipids arranged in a similar fashion as those lipids, which make up the cell membrane. They have, in another embodiment, an internal aqueous space for entrapping water-soluble compounds and range in size from 0.05 to several microns in diameter. In another embodiment, liposomes can deliver RNA to cells in a biologically active form.

In one embodiment, the composition comprises a lipid nanoparticle (LNP) and one or more nucleic acid molecules described herein. For example, in one embodiment, the composition comprises an LNP and one or more nucleoside-modified RNA molecules encoding one or more antigens, adjuvants, or a combination thereof.

The term "lipid nanoparticle" refers to a particle having at least one dimension on the order of nanometers (e.g., 1-1,000 nm), which includes one or more lipids, for example a lipid of Formula (I), (II) or (III). In some embodiments, lipid nanoparticles are included in a formulation comprising a nucleoside-modified RNA as described herein. In some embodiments, such lipid nanoparticles comprise a cationic lipid (e.g., a lipid of Formula (I), (II) or (III)) and one or more excipient selected from neutral lipids, charged lipids, steroids and polymer conjugated lipids (e.g., a pegylated lipid such as a pegylated lipid of structure (IV), such as compound Iva). In some embodiments, the nucleoside-modified RNA is encapsulated in the lipid portion of the lipid nanoparticle or an aqueous space enveloped by some or all of the lipid portion of the lipid nanoparticle, thereby protecting it from enzymatic degradation or other undesirable effects induced by the mechanisms of the host organism or cells, e.g., an adverse immune response.

In various embodiments, the lipid nanoparticles have a mean diameter of from about 30 nm to about 150 nm, from about 40 nm to about 150 nm, from about 50 nm to about 150 nm, from about 60 nm to about 130 nm, from about 70 nm to about 110 nm, from about 70 nm to about 100 nm, from about 80 nm to about 100 nm, from about 90 nm to about 100 nm, from about 70 to about 90 nm, from about 80 nm to about 90 nm, from about 70 nm to about 80 nm, or about 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, or 150 nm, and are substantially non-toxic. In certain embodiments, the nucleoside-modified RNA, when present in the lipid nanoparticles, is resistant in aqueous solution to degradation with a nuclease.

The LNP may comprise any lipid capable of forming a particle to which the one or more nucleic acid molecules are attached, or in which the one or more nucleic acid molecules are encapsulated. The term "lipid" refers to a group of organic compounds that are derivatives of fatty acids (e.g., esters) and are generally characterized by being insoluble in water but soluble in many organic solvents. Lipids are usually divided in at least three classes: (1) "simple lipids" which include fats and oils as well as waxes; (2) "compound lipids" which include phospholipids and glycolipids; and (3) "derived lipids" such as steroids.

In one embodiment, the LNP comprises one or more cationic lipids, and one or more stabilizing lipids. Stabilizing lipids include neutral lipids and pegylated lipids.

In one embodiment, the LNP comprises a cationic lipid. As used herein, the term "cationic lipid" refers to a lipid that is cationic or becomes cationic (protonated) as the pH is lowered below the pK of the ionizable group of the lipid, but is progressively more neutral at higher pH values. At pH values below the pK, the lipid is then able to associate with negatively charged nucleic acids. In certain embodiments, the cationic lipid comprises a zwitterionic lipid that assumes a positive charge on pH decrease.

In certain embodiments, the cationic lipid comprises any of a number of lipid species which carry a net positive charge at a selective pH, such as physiological pH. Such lipids include, but are not limited to, N,N-dioleyl-N,N-dimethylammonium chloride (DODAC); N-(2,3-dioley-loxy)propyl)-N,N,N-trimethylammonium chloride (DOTMA); N,N-distearyl-N,N-dimethylammonium bromide (DDAB); N-(2,3-dioleoyloxy)propyl)-N,N,N-trimeth-ylammonium chloride (DOTAP); 3-(N—(N',N'-dimethyl-aminoethane)-carbamoyl)cholesterol (DC-Chol), N-(1-(2,3-dioleoyloxy)propyl)-N-2-(sperminecarboxamido)ethyl)-N, N-dimethylammonium trifluoracetate (DOSPA), dioctadecylamidoglycyl carboxyspermine (DOGS), 1,2-dio-leoyl-3-dimethylammonium propane (DODAP), N,N-dim-ethyl-2,3-dioleoyloxy)propylamine (DODMA), and N-(1,2-dimyristyloxyprop-3-yl)-N,N-dimethyl-N-hydroxyethyl ammonium bromide (DMRIE). Additionally, a number of commercial preparations of cationic lipids are available which can be used in the present invention. These include, for example, LIPOFECTIN® (commercially available cationic liposomes comprising DOTMA and 1,2-dioleoyl-sn-3-phosphoethanolamine (DOPE), from GIBCO/BRL, Grand Island, N.Y.); LIPOFECTAMINE® (commercially available cationic liposomes comprising N-(1-(2,3-dioleyloxy)pro-pyl)-N-(2-(sperminecarboxamido)ethyl)-N,N-dimethylam-monium trifluoroacetate (DOSPA) and (DOPE), from GIBCO/BRL); and TRANSFECTAM® (commercially available cationic lipids comprising dioctadecylamidoglycyl carboxyspermine (DOGS) in ethanol from Promega Corp., Madison, Wis.). The following lipids are cationic and have a positive charge at below physiological pH: DODAP, DODMA, DMDMA, 1,2-dilinoleyloxy-N,N-dimethylami-nopropane (DLinDMA), 1,2-dilinolenyloxy-N,N-dimethyl-aminopropane (DLenDMA).

In one embodiment, the cationic lipid is an amino lipid. Suitable amino lipids useful in the invention include those described in WO 2012/016184, incorporated herein by reference in its entirety. Representative amino lipids include, but are not limited to, 1,2-dilinoleyoxy-3-(dimethylamino) acetoxypropane (DLin-DAC), 1,2-dilinoleyoxy-3-mor-pholinopropane (DLin-MA), 1,2-dilinoleoyl-3-dimethyl-aminopropane (DLinDAP), 1,2-dilinoleylthio-3-dimethylaminopropane (DLin-S-DMA), 1-linoleoyl-2-linoleyloxy-3-dimethylaminopropane (DLin-2-DMAP), 1,2-dilinoleyloxy-3-trimethylaminopropane chloride salt (DLin-TMA·Cl), 1,2-dilinoleoyl-3-trimethylaminopropane chloride salt (DLin-TAP·Cl), 1,2-dilinoleyloxy-3-(N-methylpiperazino)propane (DLin-MPZ), 3-(N,N-dilinoley-lamino)-1,2-propanediol (DLinAP), 3-(N,N-dioleylamino)-1,2-propanediol (DOAP), 1,2-dilinoleyloxo-3-(2-N,N-dimethylamino)ethoxypropane (DLin-EG-DMA), and 2,2-dilinoleyl-4-dimethylaminomethyl-[1,3]-dioxolane (DLin-K-DMA).

Suitable amino lipids include those having the formula:

wherein $R_1$ and $R_2$ are either the same or different and independently optionally substituted $C_{10}$-$C_{24}$ alkyl, optionally substituted $C_{10}$-$C_{24}$ alkenyl, optionally substituted $C_{10}$-$C_{24}$ alkynyl, or optionally substituted $C_{10}$-$C_{24}$ acyl;

$R_3$ and $R_4$ are either the same or different and independently optionally substituted $C_1$-$C_6$ alkyl, optionally substituted $C_2$-$C_6$ alkenyl, or optionally substituted $C_2$-$C_6$ alkynyl or $R_3$ and $R_4$ may join to form an optionally substituted heterocyclic ring of 4 to 6 carbon atoms and 1 or 2 heteroatoms chosen from nitrogen and oxygen;

$R_5$ is either absent or present and when present is hydrogen or $C_1$-$C_6$ alkyl;

m, n, and p are either the same or different and independently either 0 or 1 with the proviso that m, n, and p are not simultaneously 0;

q is 0, 1, 2, 3, or 4; and

Y and Z are either the same or different and independently O, S, or NH.

In one embodiment, $R_1$ and $R_2$ are each linoleyl, and the amino lipid is a dilinoleyl amino lipid. In one embodiment, the amino lipid is a dilinoleyl amino lipid.

A representative useful dilinoleyl amino lipid has the formula:

DLin-K-DMA wherein n is 0, 1, 2, 3, or 4.

In one embodiment, the cationic lipid is a DLin-K-DMA. In one embodiment, the cationic lipid is DLin-KC2-DMA (DLin-K-DMA above, wherein n is 2).

In one embodiment, the cationic lipid component of the LNPs has the structure of Formula (I):

(I)

or a pharmaceutically acceptable salt, tautomer, prodrug or stereoisomer thereof, wherein:

$L^1$ and $L^2$ are each independently —O(C=O)—, —(C=O)O— or a carbon-carbon double bond;

$R^{1a}$ and $R^{1b}$ are, at each occurrence, independently either (a) H or $C_1$-$C_{12}$ alkyl, or (b) $R^{1a}$ is H or $C_1$-$C_{12}$ alkyl, and $R^{1b}$ together with the carbon atom to which it is bound is taken together with an adjacent $R^{1b}$ and the carbon atom to which it is bound to form a carbon-carbon double bond;

$R^{2a}$ and $R^{2b}$ are, at each occurrence, independently either (a) H or $C_1$-$C_{12}$ alkyl, or (b) $R^{2a}$ is H or $C_1$-$C_{12}$ alkyl, and $R^{2b}$ together with the carbon atom to which it is bound is taken together with an adjacent $R^{2b}$ and the carbon atom to which it is bound to form a carbon-carbon double bond;

$R^{3a}$ and $R^{3b}$ are, at each occurrence, independently either (a) H or $C_1$-$C_{12}$ alkyl, or (b) $R^{3a}$ is H or $C_1$-$C_{12}$ alkyl, and $R^{3b}$ together with the carbon atom to which it is bound is taken together with an adjacent $R^{3b}$ and the carbon atom to which it is bound to form a carbon-carbon double bond;

$R^{4a}$ and $R^{4b}$ are, at each occurrence, independently either (a) H or $C_1$-$C_{12}$ alkyl, or (b) $R^{4a}$ is H or $C_1$-$C_{12}$ alkyl, and $R^{4b}$ together with the carbon atom to which it is bound is taken together with an adjacent $R^{4b}$ and the carbon atom to which it is bound to form a carbon-carbon double bond;

$R^5$ and $R^6$ are each independently methyl or cycloalkyl;

$R^7$ is, at each occurrence, independently H or $C_1$-$C_{12}$ alkyl;

$R^8$ and $R^9$ are each independently $C_1$-$C_{12}$ alkyl; or $R^8$ and $R^9$, together with the nitrogen atom to which they are attached, form a 5, 6 or 7-membered heterocyclic ring comprising one nitrogen atom;

a and d are each independently an integer from 0 to 24;

b and c are each independently an integer from 1 to 24; and e is 1 or 2.

In certain embodiments of Formula (I), at least one of $R^{1a}$, $R^{2a}$, $R^{3a}$ or $R^{4a}$ is $C_1$-$C_{12}$ alkyl, or at least one of $L^1$ or $L^2$ is —O(C=O)— or —(C=O)O—. In other embodiments, $R^{1a}$ and $R^{1b}$ are not isopropyl when a is 6 or n-butyl when a is 8.

In still further embodiments of Formula (I), at least one of $R^{1a}$, $R^{2a}$, $R^{3a}$ or $R^{4a}$ is $C_1$-$C_{12}$ alkyl, or at least one of $L^1$ or $L^2$ is —O(C=O)— or —(C=O)O—; and $R^{1a}$ and $R^{1b}$ are not isopropyl when a is 6 or n-butyl when a is 8.

In other embodiments of Formula (I), $R^8$ and $R^9$ are each independently unsubstituted $C_1$-$C_{12}$ alkyl; or $R^8$ and $R^9$, together with the nitrogen atom to which they are attached, form a 5, 6 or 7-membered heterocyclic ring comprising one nitrogen atom;

In certain embodiments of Formula (I), any one of $L^1$ or $L^2$ may be —O(C=O)— or a carbon-carbon double bond. $L^1$ and $L^2$ may each be —O(C=O)— or may each be a carbon-carbon double bond.

In some embodiments of Formula (I), one of $L^1$ or $L^2$ is —O(C=O)—. In other embodiments, both $L^1$ and $L^2$ are —O(C=O)—.

In some embodiments of Formula (I), one of $L^1$ or $L^2$ is —(C=O)O—. In other embodiments, both $L^1$ and $L^2$ are —(C=O)O—.

In some other embodiments of Formula (I), one of $L^1$ or $L^2$ is a carbon-carbon double bond. In other embodiments, both $L^1$ and $L^2$ are a carbon-carbon double bond.

In still other embodiments of Formula (I), one of $L^1$ or $L^2$ is —O(C=O)— and the other of $L^1$ or $L^2$ is —(C=O)O—. In more embodiments, one of $L^1$ or $L^2$ is —O(C=O)— and the other of $L^1$ or $L^2$ is a carbon-carbon double bond. In yet more embodiments, one of $L^1$ or $L^2$ is —(C=O)O— and the other of $L^1$ or $L^2$ is a carbon-carbon double bond.

It is understood that "carbon-carbon" double bond, as used throughout the specification, refers to one of the following structures:

wherein $R^a$ and $R^b$ are, at each occurrence, independently H or a substituent. For example, in some embodiments $R^a$ and $R^b$ are, at each occurrence, independently H, $C_1$-$C_{12}$ alkyl or cycloalkyl, for example H or $C_1$-$C_{12}$ alkyl.

In other embodiments, the lipid compounds of Formula (I) have the following structure (Ia):

(Ia)

In other embodiments, the lipid compounds of Formula (I) have the following structure (Ib):

(Ib)

In yet other embodiments, the lipid compounds of Formula (I) have the following structure (Ic):

$$(Ic)$$

In certain embodiments of the lipid compound of Formula (I), a, b, c and d are each independently an integer from 2 to 12 or an integer from 4 to 12. In other embodiments, a, b, c and d are each independently an integer from 8 to 12 or 5 to 9. In some certain embodiments, a is 0. In some embodiments, a is 1. In other embodiments, a is 2. In more embodiments, a is 3. In yet other embodiments, a is 4. In some embodiments, a is 5. In other embodiments, a is 6. In more embodiments, a is 7. In yet other embodiments, a is 8. In some embodiments, a is 9. In other embodiments, a is 10. In more embodiments, a is 11. In yet other embodiments, a is 12. In some embodiments, a is 13. In other embodiments, a is 14. In more embodiments, a is 15. In yet other embodiments, a is 16.

In some other embodiments of Formula (I), b is 1. In other embodiments, b is 2. In more embodiments, b is 3. In yet other embodiments, b is 4. In some embodiments, b is 5. In other embodiments, b is 6. In more embodiments, b is 7. In yet other embodiments, b is 8. In some embodiments, b is 9. In other embodiments, b is 10. In more embodiments, b is 11. In yet other embodiments, b is 12. In some embodiments, b is 13. In other embodiments, b is 14. In more embodiments, b is 15. In yet other embodiments, b is 16.

In some more embodiments of Formula (I), c is 1. In other embodiments, c is 2. In more embodiments, c is 3. In yet other embodiments, c is 4. In some embodiments, c is 5. In other embodiments, c is 6. In more embodiments, c is 7. In yet other embodiments, c is 8. In some embodiments, c is 9. In other embodiments, c is 10. In more embodiments, c is 11. In yet other embodiments, c is 12. In some embodiments, c is 13. In other embodiments, c is 14. In more embodiments, c is 15. In yet other embodiments, c is 16.

In some certain other embodiments of Formula (I), d is 0. In some embodiments, d is 1. In other embodiments, d is 2. In more embodiments, d is 3. In yet other embodiments, d is 4. In some embodiments, d is 5. In other embodiments, d is 6. In more embodiments, d is 7. In yet other embodiments, d is 8. In some embodiments, d is 9. In other embodiments, d is 10. In more embodiments, d is 11. In yet other embodiments, d is 12. In some embodiments, d is 13. In other embodiments, d is 14. In more embodiments, d is 15. In yet other embodiments, d is 16.

In some other various embodiments of Formula (I), a and d are the same. In some other embodiments, b and c are the same. In some other specific embodiments, a and d are the same and b and c are the same.

The sum of a and b and the sum of c and d in Formula (I) are factors which may be varied to obtain a lipid of Formula (I) having the desired properties. In one embodiment, a and b are chosen such that their sum is an integer ranging from 14 to 24. In other embodiments, c and d are chosen such that their sum is an integer ranging from 14 to 24. In further embodiment, the sum of a and b and the sum of c and d are the same. For example, in some embodiments the sum of a and b and the sum of c and d are both the same integer which may range from 14 to 24. In still more embodiments, a. b, c and d are selected such the sum of a and b and the sum of c and d is 12 or greater.

In some embodiments of Formula (I), e is 1. In other embodiments, e is 2.

The substituents at $R^{1a}$, $R^{2a}$, $R^{3a}$ and $R^{4a}$ of Formula (I) are not particularly limited. In certain embodiments $R^{1a}$, $R^{2a}$, $R^{3a}$ and $R^{4a}$ are H at each occurrence. In certain other embodiments, at least one of $R^{1a}$, $R^{2a}$, $R^{3a}$ and $R^{4a}$ is $C_1$-$C_{12}$ alkyl. In certain other embodiments, at least one of $R^{1a}$, $R^{2a}$, $R^{3a}$ and $R^{4a}$ is $C_1$-$C_8$ alkyl. In certain other embodiments, at least one of $R^{1a}$, $R^{2a}$, $R^{3a}$ and $R^{4a}$ is $C_1$-$C_6$ alkyl. In some of the foregoing embodiments, the $C_1$-$C_8$ alkyl is methyl, ethyl, n-propyl, iso-propyl, n-butyl, iso-butyl, tert-butyl, n-hexyl or n-octyl.

In certain embodiments of Formula (I), $R^{1a}$, $R^{1b}$, $R^{4a}$ and $R^{4b}$ are $C_1$-$C_{12}$ alkyl at each occurrence.

In further embodiments of Formula (I), at least one of $R^{1b}$, $R^{2b}$, $R^{3b}$ and $R^{4b}$ is H or $R^{1b}$, $R^{2b}$, $R^{3b}$ and $R^{4b}$ are H at each occurrence.

In certain embodiments of Formula (I), $R^{1b}$ together with the carbon atom to which it is bound is taken together with an adjacent $R^{1b}$ and the carbon atom to which it is bound to form a carbon-carbon double bond. In other embodiments of the foregoing $R^{4b}$ together with the carbon atom to which it is bound is taken together with an adjacent $R^{4b}$ and the carbon atom to which it is bound to form a carbon-carbon double bond.

The substituents at $R^5$ and $R^6$ of Formula (I) are not particularly limited in the foregoing embodiments. In certain embodiments one or both of $R^5$ or $R^6$ is methyl. In certain other embodiments one or both of $R^5$ or $R^6$ is cycloalkyl for example cyclohexyl. In these embodiments, the cycloalkyl may be substituted or not substituted. In certain other embodiments, the cycloalkyl is substituted with $C_1$-$C_{12}$ alkyl, for example tert-butyl.

The substituents at $R^7$ are not particularly limited in the foregoing embodiments of Formula (I). In certain embodiments, at least one $R^7$ is H. In some other embodiments, $R^7$ is H at each occurrence. In certain other embodiments $R^7$ is $C_1$-$C_{12}$ alkyl.

In certain other of the foregoing embodiments of Formula (I), one of $R^8$ or $R^9$ is methyl. In other embodiments, both Ru and $R^9$ are methyl.

In some different embodiments of Formula (I), $R^8$ and $R^9$, together with the nitrogen atom to which they are attached, form a 5, 6 or 7-membered heterocyclic ring. In some embodiments of the foregoing, $R^8$ and $R^9$, together with the nitrogen atom to which they are attached, form a 5-membered heterocyclic ring, for example a pyrrolidinyl ring.

In various different embodiments, the lipid of Formula (I) has one of the structures set forth in Table 1 below.

TABLE 1

| | Representative Lipids of Formula (I) | |
|---|---|---|
| No. | Structure | Prep. Method |
| I-1 | | B |
| I-2 | | A |
| I-3 | | A |
| I-4 | | B |
| I-5 | | B |
| I-6 | | B |

TABLE 1-continued

Representative Lipids of Formula (I)

| No. | Structure | Prep. Method |
|---|---|---|
| I-7 | | A |
| I-8 | | A |
| I-9 | | B |
| I-10 | | A |
| I-11 | | A |

TABLE 1-continued

| | Representative Lipids of Formula (I) | |
|---|---|---|
| No. | Structure | Prep. Method |
| I-12 | | A |
| I-13 | | A |
| I-14 | | A |
| I-15 | | A |
| I-16 | | A |
| I-17 | | A |

TABLE 1-continued

| | Representative Lipids of Formula (I) | |
|---|---|---|
| No. | Structure | Prep. Method |
| I-18 | | A |
| I-19 | | A |
| I-20 | | A |
| I-21 | | A |
| I-22 | | A |
| I-23 | | A |

TABLE 1-continued

Representative Lipids of Formula (I)

| No. | Structure | Prep. Method |
|-----|-----------|--------------|
| I-24 | | A |
| I-25 | | A |
| I-26 | | A |
| I-27 | | A |
| I-28 | | A |
| I-29 | | A |

TABLE 1-continued

Representative Lipids of Formula (I)

| No. | Structure | Prep. Method |
|---|---|---|
| I-30 | | A |
| I-31 | | C |
| I-32 | | C |
| I-33 | | C |
| I-34 | | B |
| I-35 | | B |

TABLE 1-continued

Representative Lipids of Formula (I)

| No. | Structure | Prep. Method |
|-----|-----------|--------------|
| I-36 | | C |
| I-37 | | C |
| I-38 | | B |
| I-39 | | B |
| I-40 | | B |

TABLE 1-continued

Representative Lipids of Formula (I)

| No. | Structure | Prep. Method |
|---|---|---|
| I-41 | | B |

In some embodiments, the LNPs comprise a lipid of Formula (I), a nucleoside-modified RNA and one or more excipients selected from neutral lipids, steroids and pegylated lipids. In some embodiments the lipid of Formula (I) is compound I-5. In some embodiments the lipid of Formula (I) is compound I-6.

In some other embodiments, the cationic lipid component of the LNPs has the structure of Formula (II):

or a pharmaceutically acceptable salt, tautomer, prodrug or stereoisomer thereof, wherein:

$L^1$ and $L^2$ are each independently —O(C=O)—, —(C=O)O—, —C(=O)—, —O—, —S(O)$_x$—, —S—S—, —C(=O)S—, —SC(=O)—, —NR$^a$C(=O)—, —C(=O)NR$^a$—, —NR$^a$C(=O)NR$^a$, —OC(=O)NR$^a$—, —NR$^a$C(=O)O—, or a direct bond;

$G^1$ is $C_1$-$C_2$ alkylene, —(C=O)—, —O(C=O)—, —SC(=O)—, —NR$^a$C(=O)— or a direct bond;

$G^2$ is —C(=O)—, —(C=O)O—, —C(=O)S—, —C(=O)NR$^a$ or a direct bond;

$G^3$ is $C_1$-$C_6$ alkylene;

$R^a$ is H or $C_1$-$C_{12}$ alkyl;

$R^{1a}$ and $R^{1b}$ are, at each occurrence, independently either: (a) H or $C_1$-$C_{12}$ alkyl; or (b) $R^{1a}$ is H or $C_1$-$C_{12}$ alkyl, and $R^{1b}$ together with the carbon atom to which it is bound is taken together with an adjacent $R^{1b}$ and the carbon atom to which it is bound to form a carbon-carbon double bond;

$R^{2a}$ and $R^{2b}$ are, at each occurrence, independently either: (a) H or $C_1$-$C_{12}$ alkyl; or (b) $R^{2a}$ is H or $C_1$-$C_{12}$ alkyl, and $R^{2b}$ together with the carbon atom to which it is bound is taken together with an adjacent $R^{2b}$ and the carbon atom to which it is bound to form a carbon-carbon double bond;

$R^{3a}$ and $R^{3b}$ are, at each occurrence, independently either: (a) H or $C_1$-$C_{12}$ alkyl; or (b) $R^{3a}$ is H or $C_1$-$C_{12}$ alkyl, and $R^{3b}$ together with the carbon atom to which it is bound is taken together with an adjacent $R^{3b}$ and the carbon atom to which it is bound to form a carbon-carbon double bond;

$R^{4a}$ and $R^{4b}$ are, at each occurrence, independently either: (a) H or $C_1$-$C_{12}$ alkyl; or (b) $R^{4a}$ is H or $C_1$-$C_{12}$ alkyl, and $R^{4b}$ together with the carbon atom to which it is bound is taken together with an adjacent $R^{4b}$ and the carbon atom to which it is bound to form a carbon-carbon double bond;

$R^5$ and $R^6$ are each independently H or methyl;

$R^7$ is $C_4$-$C_{20}$ alkyl;

$R^8$ and $R^9$ are each independently $C_1$-$C_{12}$ alkyl; or $R^8$ and $R^9$, together with the nitrogen atom to which they are attached, form a 5, 6 or 7-membered heterocyclic ring;

a, b, c and d are each independently an integer from 1 to 24; and x is 0, 1 or 2.

In some embodiments of Formula (II), $L^1$ and $L^2$ are each independently —O(C=O)—, —(C=O)O— or a direct bond. In other embodiments, $G^1$ and $G^2$ are each independently —(C=O)— or a direct bond. In some different embodiments, $L^1$ and $L^2$ are each independently —O(C=O)—, —(C=O)O— or a direct bond; and $G^1$ and $G^2$ are each independently —(C=O)— or a direct bond.

In some different embodiments of Formula (II), $L^1$ and $L^2$ are each independently —C(=O)—, —O—, —S(O)$_x$—, —S—S—, —C(=O)S—, —SC(=O)—, —NR$^a$—, —NR$^a$C(=O)—, —C(=O)NR$^a$—, —NR$^a$C(=O)NR$^a$, —OC(=O)NR$^a$—, —NR$^a$C(=O)O—, —NR$^a$S(O)$_x$NR$^a$—, —NR$^a$S(O)$_x$— or —S(O)$_x$NR$^a$—.

In other of the foregoing embodiments of Formula (II), the lipid compound has one of the following structures (IIA) or (IIB):

or (IIA)

-continued (IIB)

In some embodiments of Formula (II), the lipid compound has structure (IIA). In other embodiments, the lipid compound has structure (IIB).

In any of the foregoing embodiments of Formula (II), one of $L^1$ or $L^2$ is —O(C=O)—. For example, in some embodiments each of $L^1$ and $L^2$ are —O(C=O)—.

In some different embodiments of Formula (II), one of $L^1$ or $L^2$ is —(C=O)O—. For example, in some embodiments each of $L^1$ and $L^2$ is —(C=O)O—.

In different embodiments of Formula (II), one of $L^1$ or $L^2$ is a direct bond. As used herein, a "direct bond" means the group (e.g., $L^1$ or $L^2$) is absent. For example, in some embodiments each of $L^1$ and $L^2$ is a direct bond.

In other different embodiments of Formula (II), for at least one occurrence of $R^{1a}$ and $R^{1b}$, $R^{1a}$ is H or $C_1$-$C_{12}$ alkyl, and $R^{1b}$ together with the carbon atom to which it is bound is taken together with an adjacent $R^{1b}$ and the carbon atom to which it is bound to form a carbon-carbon double bond.

In still other different embodiments of Formula (II), for at least one occurrence of $R^{4a}$ and $R^{4b}$, $R^{4a}$ is H or $C_1$-$C_{12}$ alkyl, and $R^{4b}$ together with the carbon atom to which it is bound is taken together with an adjacent $R^{4b}$ and the carbon atom to which it is bound to form a carbon-carbon double bond.

In more embodiments of Formula (II), for at least one occurrence of $R^{2a}$ and $R^{2b}$, $R^{2a}$ is H or $C_1$-$C_{12}$ alkyl, and $R^{2b}$ together with the carbon atom to which it is bound is taken together with an adjacent $R^{2b}$ and the carbon atom to which it is bound to form a carbon-carbon double bond.

In other different embodiments of Formula (II), for at least one occurrence of $R^{3a}$ and $R^{3b}$, $R^{3a}$ is H or $C_1$-$C_{12}$ alkyl, and $R^{3b}$ together with the carbon atom to which it is bound is taken together with an adjacent $R^{3b}$ and the carbon atom to which it is bound to form a carbon-carbon double bond.

In various other embodiments of Formula (II), the lipid compound has one of the following structures (IIC) or (IID):

(IIC)

or

-continued (IID)

wherein e, f, g and h are each independently an integer from 1 to 12.

In some embodiments of Formula (II), the lipid compound has structure (IIC). In other embodiments, the lipid compound has structure (IID).

In various embodiments of structures (IIC) or (IID), e, f, g and h are each independently an integer from 4 to 10.

In certain embodiments of Formula (II), a, b, c and d are each independently an integer from 2 to 12 or an integer from 4 to 12. In other embodiments, a, b, c and d are each independently an integer from 8 to 12 or 5 to 9. In some certain embodiments, a is 0. In some embodiments, a is 1. In other embodiments, a is 2. In more embodiments, a is 3. In yet other embodiments, a is 4. In some embodiments, a is 5. In other embodiments, a is 6. In more embodiments, a is 7. In yet other embodiments, a is 8. In some embodiments, a is 9. In other embodiments, a is 10. In more embodiments, a is 11. In yet other embodiments, a is 12. In some embodiments, a is 13. In other embodiments, a is 14. In more embodiments, a is 15. In yet other embodiments, a is 16.

In some embodiments of Formula (II), b is 1. In other embodiments, b is 2. In more embodiments, b is 3. In yet other embodiments, b is 4. In some embodiments, b is 5. In other embodiments, b is 6. In more embodiments, b is 7. In yet other embodiments, b is 8. In some embodiments, b is 9. In other embodiments, b is 10. In more embodiments, b is 11. In yet other embodiments, b is 12. In some embodiments, b is 13. In other embodiments, b is 14. In more embodiments, b is 15. In yet other embodiments, b is 16.

In some embodiments of Formula (II), c is 1. In other embodiments, c is 2. In more embodiments, c is 3. In yet other embodiments, c is 4. In some embodiments, c is 5. In other embodiments, c is 6. In more embodiments, c is 7. In yet other embodiments, c is 8. In some embodiments, c is 9. In other embodiments, c is 10.

In more embodiments, c is 11. In yet other embodiments, c is 12. In some embodiments, c is 13. In other embodiments, c is 14. In more embodiments, c is 15. In yet other embodiments, c is 16.

In some certain embodiments of Formula (II), d is 0. In some embodiments, d is 1. In other embodiments, d is 2. In more embodiments, d is 3. In yet other embodiments, d is 4. In some embodiments, d is 5. In other embodiments, d is 6. In more embodiments, d is 7. In yet other embodiments, d is 8. In some embodiments, d is 9. In other embodiments, d is 10. In more embodiments, d is 11. In yet other embodiments, d is 12. In some embodiments, d is 13. In other embodiments, d is 14. In more embodiments, d is 15. In yet other embodiments, d is 16.

In some embodiments of Formula (II), e is 1. In other embodiments, e is 2. In more embodiments, e is 3. In yet other embodiments, e is 4. In some embodiments, e is 5. In other embodiments, e is 6. In more embodiments, e is 7. In yet other embodiments, e is 8. In some embodiments, e is 9.

In other embodiments, e is 10. In more embodiments, e is 11. In yet other embodiments, e is 12.

In some embodiments of Formula (II), f is 1. In other embodiments, f is 2. In more embodiments, f is 3. In yet other embodiments, f is 4. In some embodiments, f is 5. In other embodiments, f is 6. In more embodiments, f is 7. In yet other embodiments, f is 8. In some embodiments, f is 9. In other embodiments, f is 10. In more embodiments, f is 11. In yet other embodiments, f is 12.

In some embodiments of Formula (II), g is 1. In other embodiments, g is 2. In more embodiments, g is 3. In yet other embodiments, g is 4. In some embodiments, g is 5. In other embodiments, g is 6. In more embodiments, g is 7. In yet other embodiments, g is 8. In some embodiments, g is 9. In other embodiments, g is 10. In more embodiments, g is 11. In yet other embodiments, g is 12.

In some embodiments of Formula (II), h is 1. In other embodiments, e is 2. In more embodiments, h is 3. In yet other embodiments, h is 4. In some embodiments, e is 5. In other embodiments, h is 6. In more embodiments, h is 7. In yet other embodiments, h is 8. In some embodiments, h is 9. In other embodiments, h is 10. In more embodiments, h is 11. In yet other embodiments, h is 12.

In some other various embodiments of Formula (II), a and d are the same. In some other embodiments, b and c are the same. In some other specific embodiments and a and d are the same and b and c are the same.

The sum of a and b and the sum of c and d of Formula (II) are factors which may be varied to obtain a lipid having the desired properties. In one embodiment, a and b are chosen such that their sum is an integer ranging from 14 to 24. In other embodiments, c and d are chosen such that their sum is an integer ranging from 14 to 24. In further embodiment, the sum of a and b and the sum of c and d are the same. For example, in some embodiments the sum of a and b and the sum of c and d are both the same integer which may range from 14 to 24. In still more embodiments, a. b, c and d are selected such that the sum of a and b and the sum of c and d is 12 or greater.

The substituents at $R^{1a}$, $R^2$, $R^{3a}$ and $R^{4a}$ of Formula (II) are not particularly limited. In some embodiments, at least one of $R^{1a}$, $R^{2a}$, $R^{3a}$ and $R^{4a}$ is H. In certain embodiments $R^{1a}$, $R^{2a}$, $R^{3a}$ and $R^{4a}$ are H at each occurrence. In certain other embodiments, at least one of $R^{1a}$, $R^{2a}$, $R^{3a}$ and $R^{4a}$ is $C_1$-$C_{12}$ alkyl. In certain other embodiments, at least one of $R^{1a}$, $R^{2a}$, $R^{3a}$ and $R^{4a}$ is $C_1$-$C_8$ alkyl. In certain other embodiments, at least one of $R^{1a}$, $R^{2a}$, $R^{3a}$ and $R^{4a}$ is $C_1$-$C_6$ alkyl. In some of the foregoing embodiments, the $C_1$-$C_8$ alkyl is methyl, ethyl, n-propyl, iso-propyl, n-butyl, iso-butyl, tert-butyl, n-hexyl or n-octyl.

In certain embodiments of Formula (II), $R^{1a}$, $R^{1b}$, $R^{4a}$ and $R^{4b}$ are $C_1$-$C_{12}$ alkyl at each occurrence.

In further embodiments of Formula (II), at least one of $R^{1b}$, $R^{2b}$, $R^{3b}$ and $R^{4b}$ is H or $R^{1b}$, $R^{2b}$, $R^{3b}$ and $R^{4b}$ are H at each occurrence.

In certain embodiments of Formula (II), $R^{1b}$ together with the carbon atom to which it is bound is taken together with an adjacent $R^{1b}$ and the carbon atom to which it is bound to form a carbon-carbon double bond. In other embodiments of the foregoing $R^{4b}$ together with the carbon atom to which it is bound is taken together with an adjacent $R^{4b}$ and the carbon atom to which it is bound to form a carbon-carbon double bond.

The substituents at $R^5$ and $R^6$ of Formula (II) are not particularly limited in the foregoing embodiments. In certain embodiments one of $R^5$ or $R^6$ is methyl. In other embodiments, each of $R^5$ or $R^6$ is methyl.

The substituents at $R^7$ of Formula (II) are not particularly limited in the foregoing embodiments. In certain embodiments $R^7$ is $C_6$-$C_{16}$ alkyl. In some other embodiments, $R^7$ is $C_6$-$C_9$ alkyl. In some of these embodiments, $R^7$ is substituted with —(C=O)OR$^b$, —O(C=O)R$^b$, —C(=O)R$^b$, —OR$^b$, —S(O)$_x$R$^b$, —S—SR$^b$, —C(=O)SR$^b$, —SC(=O)R$^b$, —NR$^a$R$^b$, —NR$^a$C(=O)R$^b$, —C(=O)NR$^a$R$^b$, —NR$^a$C(=O)NR$^a$R$^b$, —OC(=O)NR$^a$R$^b$, —NR$^a$C(=O)OR$^b$, —NR$^a$S(O)$_x$NR$^a$R$^b$, —NR$^a$S(O)$_x$R$^b$ or —S(O)$_x$NR$^a$R$^b$, wherein: $R^a$ is H or $C_1$-$C_{12}$ alkyl; $R^b$ is $C_1$-$C_{15}$ alkyl; and x is 0, 1 or 2. For example, in some embodiments $R^7$ is substituted with —(C=O)OR$^b$ or —O(C=O)R$^b$.

In various of the foregoing embodiments of Formula (II), $R^b$ is branched $C_1$-$C_{15}$ alkyl. For example, in some embodiments $R^b$ has one of the following structures:

In certain other of the foregoing embodiments of Formula (II), one of $R^8$ or $R^9$ is methyl. In other embodiments, both $R^8$ and $R^9$ are methyl.

In some different embodiments of Formula (II), $R^8$ and $R^9$, together with the nitrogen atom to which they are attached, form a 5, 6 or 7-membered heterocyclic ring. In some embodiments of the foregoing, $R^8$ and $R^9$, together with the nitrogen atom to which they are attached, form a 5-membered heterocyclic ring, for example a pyrrolidinyl ring. In some different embodiments of the foregoing, $R^8$ and $R^9$, together with the nitrogen atom to which they are attached, form a 6-membered heterocyclic ring, for example a piperazinyl ring.

In still other embodiments of the foregoing lipids of Formula (II), $G^3$ is $C_2$-$C_4$ alkylene, for example $C_3$ alkylene.

In various different embodiments, the lipid compound has one of the structures set forth in Table 2 below.

TABLE 2

| No. | Structure | Prep. Method |
|---|---|---|
| II-1 | | D |
| II-2 | | D |
| II-3 | | D |
| II-4 | | E |
| II-5 | | D |
| II-6 | | D |
| II-7 | | D |
| II-8 | | D |

Representative Lipids of Formula (II)

TABLE 2-continued

Representative Lipids of Formula (II)

| No. | Structure | Prep. Method |
|-----|-----------|--------------|
| II-9 | | D |
| II-10 | | D |
| II-11 | | D |
| II-12 | | D |
| II-13 | | D |
| II-14 | | D |

TABLE 2-continued

Representative Lipids of Formula (II)

| No. | Structure | Prep. Method |
|-----|-----------|--------------|
| II-15 | | D |
| II-16 | | E |
| II-17 | | D |
| II-18 | | D |
| II-19 | | D |
| II-20 | | D |

TABLE 2-continued

Representative Lipids of Formula (II)

| No. | Structure | Prep. Method |
|---|---|---|
| II-21 | | D |
| II-22 | | D |
| II-23 | | D |
| II-24 | | D |
| II-25 | | E |

TABLE 2-continued

| | Representative Lipids of Formula (II) | |
|---|---|---|
| No. | Structure | Prep. Method |
| II-26 | | E |
| II-27 | | E |
| II-28 | | E |
| II-29 | | E |
| II-30 | | E |
| II-31 | | E |

TABLE 2-continued

Representative Lipids of Formula (II)

| No. | Structure | Prep. Method |
|---|---|---|
| II-32 | | E |
| II-33 | | E |
| II-34 | | E |

In some embodiments, the LNPs comprise a lipid of Formula (II), a nucleoside-modified RNA and one or more excipient selected from neutral lipids, steroids and pegylated lipids. In some embodiments, the lipid of Formula (II) is compound II-9. In some embodiments, the lipid of Formula (II) is compound II-10. In some embodiments, the lipid of Formula (II) is compound II-11. In some embodiments, the lipid of Formula (II) is compound II-12. In some embodiments, the lipid of Formula (II) is compound II-32.

In some other embodiments, the cationic lipid component of the LNPs has the structure of Formula (III):

$$\text{(III)}$$

or a pharmaceutically acceptable salt, tautomer, prodrug or stereoisomer thereof, wherein:

one of $L^1$ or $L^2$ is —O(C=O)—, —(C=O)O—, —C(=O)—, —O—, —S(O)$_x$—, —S—S—, —C(=O)S—, SC(=O)—, —NR$^a$C(=O)—, —C(=O)NR$^a$—, NR$^a$C(=O)NR$^a$, —OC(=O)NR$^a$— or —NR$^a$C(=O)O—, and the other of $L^1$ or $L^2$ is —O(C=O)—, —(C=O)O—, —C(=O)—, —O—, —S(O)$_x$—, —S—S—, —C(=O)S—, SC(=O)—, —NR$^a$C(=O)—, —C(=O)NR$^a$—, NR$^a$C(=O) NR$^a$—, —OC(=O)NR$^a$— or —NR$^a$C(=O)O— or a direct bond;

$G^1$ and $G^2$ are each independently unsubstituted $C_1$-$C_{12}$ alkylene or $C_1$-$C_{12}$ alkenylene;

$G^3$ is $C_1$-$C_{24}$ alkylene, $C_1$-$C_{24}$ alkenylene, $C_3$-$C_8$ cycloalkylene, $C_3$-$C_8$ cycloalkenylene;

$R^a$ is H or $C_1$-$C_{12}$ alkyl;

$R^1$ and $R^2$ are each independently $C_6$-$C_{24}$ alkyl or $C_6$-$C_{24}$ alkenyl;

$R^3$ is H, $OR^5$, CN, —C(=O)OR$^4$, —OC(=O)R$^4$ or —NR$^5$C(=O)R$^4$;

$R^4$ is $C_1$-$C_{12}$ alkyl;

$R^5$ is H or $C_1$-$C_6$ alkyl; and x is 0, 1 or 2.

In some of the foregoing embodiments of Formula (III), the lipid has one of the following structures (IIIA or IIIB):

$$\text{(IIIA)}$$

or $$\text{(IIIB)}$$

wherein:

A is a 3 to 8-membered cycloalkyl or cycloalkylene ring;

$R^6$ is, at each occurrence, independently H, OH or $C_1$-$C_{24}$ alkyl;

n is an integer ranging from 1 to 15.

In some of the foregoing embodiments of Formula (III), the lipid has structure (IIIA), and in other embodiments, the lipid has structure (IIIB).

In other embodiments of Formula (III), the lipid has one of the following structures (IIIC) or (IIID):

(IIIC)

or (IIID)

wherein y and z are each independently integers ranging from 1 to 12.

In any of the foregoing embodiments of Formula (III), one of $L^1$ or $L^2$ is —O(C=O)—. For example, in some embodiments each of $L^1$ and $L^2$ are —O(C=O)—. In some different embodiments of any of the foregoing, $L^1$ and $L^2$ are each independently —(C=O)O— or —O(C=O)—. For example, in some embodiments each of $L^1$ and $L^2$ is —(C=O)O—.

In some different embodiments of Formula (III), the lipid has one of the following structures (IIIE) or (IIIF):

(IIIE)

or (IIIF)

In some of the foregoing embodiments of Formula (III), the lipid has one of the following structures (IIIG), (IIIH), (IIII), or (IIIJ):

(IIIG)

(IIIH)

-continued (III)

or (IIIJ)

In some of the foregoing embodiments of Formula (III), n is an integer ranging from 2 to 12, for example from 2 to 8 or from 2 to 4. For example, in some embodiments, n is 3, 4, 5 or 6. In some embodiments, n is 3. In some embodiments, n is 4. In some embodiments, n is 5. In some embodiments, n is 6.

In some other of the foregoing embodiments of Formula (III), y and z are each independently an integer ranging from 2 to 10. For example, in some embodiments, y and z are each independently an integer ranging from 4 to 9 or from 4 to 6.

In some of the foregoing embodiments of Formula (III), $R^6$ is H. In other of the foregoing embodiments, $R^6$ is $C_1$-$C_{24}$ alkyl. In other embodiments, $R^6$ is OH.

In some embodiments of Formula (III), $G^3$ is unsubstituted. In other embodiments, $G^3$ is substituted. In various different embodiments, $G^3$ is linear $C_1$-$C_{24}$ alkylene or linear $C_1$-$C_{24}$ alkenylene.

In some other foregoing embodiments of Formula (III), $R^1$ or $R^2$, or both, is $C_6$-$C_{24}$ alkenyl. For example, in some embodiments, $R^1$ and $R^2$ each, independently have the following structure:

wherein:

$R^{7a}$ and $R^{7b}$ are, at each occurrence, independently H or $C_1$-$C_{12}$ alkyl; and a is an integer from 2 to 12, wherein $R^{7a}$, $R^{7b}$ and a are each selected such that $R^1$ and $R^2$ each independently comprise from 6 to 20 carbon atoms. For example, in some embodiments a is an integer ranging from 5 to 9 or from 8 to 12.

In some of the foregoing embodiments of Formula (III), at least one occurrence of $R^{7a}$ is H. For example, in some embodiments, $R^{7a}$ is H at each occurrence. In other different embodiments of the foregoing, at least one occurrence of $R^b$ is $C_1$-$C_8$ alkyl. For example, in some embodiments, $C_1$-$C_8$ alkyl is methyl, ethyl, n-propyl, iso-propyl, n-butyl, iso-butyl, tert-butyl, n-hexyl or n-octyl.

In different embodiments of Formula (III), $R^1$ or $R^2$, or both, has one of the following structures:

77

78

-continued

In some of the foregoing embodiments of Formula (III), $R^3$ is OH, CN, —C(=O)OR$^4$, —OC(=O)R$^4$ or —NHC(=O)R$^4$. In some embodiments, $R^4$ is methyl or ethyl.

In various different embodiments, the cationic lipid of Formula (III) has one of the structures set forth in Table 3 below.

TABLE 3

| No. | Representative Compounds of Formula (III) Structure | Prep. Method |
|---|---|---|
| III-1 | | F |
| III-2 | | F |

TABLE 3-continued

| | Representative Compounds of Formula (III) | |
|---|---|---|
| No. | Structure | Prep. Method |
| III-3 | | F |
| III-4 | | F |
| III-5 | | F |
| III-6 | | F |

TABLE 3-continued

| | Representative Compounds of Formula (III) | |
|---|---|---|
| No. | Structure | Prep. Method |
| III-7 | | F |
| III-8 | | F |
| III-9 | | F |
| III-10 | | F |
| III-11 | | F |

TABLE 3-continued

Representative Compounds of Formula (III)

| No. | Structure | Prep. Method |
|-----|-----------|--------------|
| III-12 | | F |
| III-13 | | F |
| III-14 | | F |
| III-15 | | F |
| III-16 | | F |
| III-17 | | F |

TABLE 3-continued

Representative Compounds of Formula (III)

| No. | Structure | Prep. Method |
|---|---|---|
| III-18 | | F |
| III-19 | | F |
| III-20 | | F |
| III-21 | | F |
| III-22 | | F |
| III-23 | | F |

TABLE 3-continued

| | Representative Compounds of Formula (III) | |
|---|---|---|
| No. | Structure | Prep. Method |
| III-24 | | F |
| III-25 | | F |
| III-26 | | F |
| III-27 | | F |
| III-28 | | F |

TABLE 3-continued

Representative Compounds of Formula (III)

| No. | Structure | Prep. Method |
| --- | --- | --- |
| III-29 | | F |
| III-30 | | F |
| III-31 | | F |
| III-32 | | F |

TABLE 3-continued

Representative Compounds of Formula (III)

| No. | Structure | Prep. Method |
|---|---|---|
| III-33 | | F |
| III-34 | | F |
| III-35 | | F |
| III-36 | | F |

In some embodiments, the LNPs comprise a lipid of Formula (III), a nucleoside-modified RNA and one or more excipient selected from neutral lipids, steroids and pegylated lipids. In some embodiments, the lipid of Formula (III) is compound III-3. In some embodiments, the lipid of Formula (III) is compound III-7.

In certain embodiments, the cationic lipid is present in the LNP in an amount from about 30 to about 95 mole percent. In one embodiment, the cationic lipid is present in the LNP in an amount from about 30 to about 70 mole percent. In one embodiment, the cationic lipid is present in the LNP in an amount from about 40 to about 60 mole percent. In one embodiment, the cationic lipid is present in the LNP in an amount of about 50 mole percent. In one embodiment, the LNP comprises only cationic lipids.

In certain embodiments, the LNP comprises one or more additional lipids which stabilize the formation of particles during their formation.

Suitable stabilizing lipids include neutral lipids and anionic lipids.

The term "neutral lipid" refers to any one of a number of lipid species that exist in either an uncharged or neutral zwitterionic form at physiological pH. Representative neutral lipids include diacylphosphatidylcholines, diacylphosphatidylethanolamines, ceramides, sphingomyelins, dihydro sphingomyelins, cephalins, and cerebrosides.

Exemplary neutral lipids include, for example, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoyl-phosphatidylethanolamine (POPE) and dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidylethanolamine (DSPE), 16-O-monomethyl PE, 16-O-dimethyl PE, 18-1-trans PE, 1-stearioyl-2-oleoyl-phosphatidyethanol amine (SOPE), and 1,2-dielaidoyl-sn-glycero-3-phophoethanolamine (transDOPE). In one embodiment, the neutral lipid is 1,2-distearoyl-sn-glycero-3-phosphocholine (DSPC).

In some embodiments, the LNPs comprise a neutral lipid selected from DSPC, DPPC, DMPC, DOPC, POPC, DOPE and SM. In various embodiments, the molar ratio of the cationic lipid (e.g., lipid of Formula (I)) to the neutral lipid ranges from about 2:1 to about 8:1.

In various embodiments, the LNPs further comprise a steroid or steroid analogue. A "steroid" is a compound comprising the following carbon skeleton:

In certain embodiments, the steroid or steroid analogue is cholesterol. In some of these embodiments, the molar ratio of the cationic lipid (e.g., lipid of Formula (I)) to cholesterol ranges from about 2:1 to 1:1.

The term "anionic lipid" refers to any lipid that is negatively charged at physiological pH. These lipids include phosphatidylglycerol, cardiolipin, diacylphosphatidylserine, diacylphosphatidic acid, N-dodecanoylphosphatidylethanolamines, N-succinylphosphatidylethanolamines, N-glutarylphosphatidylethanolamines, lysylphosphatidylglycerols, palmitoyloleyolphosphatidylglycerol (POPG), and other anionic modifying groups joined to neutral lipids.

In certain embodiments, the LNP comprises glycolipids (e.g., monosialoganglioside $GM_1$). In certain embodiments, the LNP comprises a sterol, such as cholesterol.

In some embodiments, the LNPs comprise a polymer conjugated lipid. The term "polymer conjugated lipid" refers to a molecule comprising both a lipid portion and a polymer portion. An example of a polymer conjugated lipid is a pegylated lipid. The term "pegylated lipid" refers to a molecule comprising both a lipid portion and a polyethylene glycol portion. Pegylated lipids are known in the art and include 1-(monomethoxy-polyethyleneglycol)-2,3-dimyristoylglycerol (PEG-s-DMG) and the like.

In certain embodiments, the LNP comprises an additional, stabilizing-lipid which is a polyethylene glycol-lipid (pegylated lipid). Suitable polyethylene glycol-lipids include PEG-modified phosphatidylethanolamine, PEG-modified phosphatidic acid, PEG-modified ceramides (e.g., PEG-CerC14 or PEG-CerC20), PEG-modified dialkylamines, PEG-modified diacylglycerols, PEG-modified dialkylglycerols. Representative polyethylene glycol-lipids include PEG-c-DOMG, PEG-c-DMA, and PEG-s-DMG. In one embodiment, the polyethylene glycol-lipid is N-[(methoxy poly(ethylene glycol)$_{2000}$)carbamyl]-1,2-dimyristyloxlpropyl-3-amine (PEG-c-DMA). In one embodiment, the polyethylene glycol-lipid is PEG-c-DOMG). In other embodiments, the LNPs comprise a pegylated diacylglycerol (PEG-DAG) such as 1-(monomethoxy-polyethyleneglycol)-2,3-dimyristoylglycerol (PEG-DMG), a pegylated phosphatidylethanoloamine (PEG-PE), a PEG succinate diacylglycerol (PEG-S-DAG) such as 4-O-(2',3'-di(tetradecanoyloxy)propyl-1-O-(m-methoxy(polyethoxy)ethyl)butanedioate (PEG-S-DMG), a pegylated ceramide (PEG-cer), or a PEG dialkoxypropylcarbamate such as ω-methoxy(polyethoxy)ethyl-N-(2,3-di(tetradecanoxy)propyl)carbamate or 2,3-di(tetradecanoxy)propyl-N-(ω-methoxy(polyethoxy)ethyl)carbamate. In various embodiments, the molar ratio of the cationic lipid to the pegylated lipid ranges from about 100:1 to about 25:1.

In some embodiments, the LNPs comprise a pegylated lipid having the following structure (IV):

(IV)

or a pharmaceutically acceptable salt, tautomer or stereoisomer thereof, wherein:

$R^{10}$ and $R^{11}$ are each independently a straight or branched, saturated or unsaturated alkyl chain containing from 10 to 30 carbon atoms, wherein the alkyl chain is optionally interrupted by one or more ester bonds; and z has mean value ranging from 30 to 60.

In some of the foregoing embodiments of the pegylated lipid (IV), $R^{10}$ and $R^{11}$ are not both n-octadecyl when z is 42. In some other embodiments, $R^{10}$ and $R^{11}$ are each independently a straight or branched, saturated or unsaturated alkyl chain containing from 10 to 18 carbon atoms. In some embodiments, $R^{10}$ and $R^{11}$ are each independently a straight or branched, saturated or unsaturated alkyl chain containing from 12 to 16 carbon atoms. In some embodiments, $R^{10}$ and $R^{11}$ are each independently a straight or branched, saturated or unsaturated alkyl chain containing 12 carbon atoms. In some embodiments, $R^{10}$ and $R^{11}$ are each independently a straight or branched, saturated or unsaturated alkyl chain containing 14 carbon atoms. In other embodiments, $R^{10}$ and $R^{11}$ are each independently a straight or branched, saturated or unsaturated alkyl chain containing 16 carbon atoms. In still more embodiments, $R^{10}$ and $R^{11}$ are each independently a straight or branched, saturated or unsaturated alkyl chain containing 18 carbon atoms. In still other embodiments, $R^{10}$ is a straight or branched, saturated or unsaturated alkyl chain containing 12 carbon atoms and $R^{11}$ is a straight or branched, saturated or unsaturated alkyl chain containing 14 carbon atoms.

In various embodiments, z spans a range that is selected such that the PEG portion of (II) has an average molecular weight of about 400 to about 6000 g/mol. In some embodiments, the average z is about 45.

In other embodiments, the pegylated lipid has one of the following structures:

(IVa)

(IVb)

(IVc)

(IVd)

wherein n is an integer selected such that the average molecular weight of the pegylated lipid is about 2500 g/mol.

In certain embodiments, the additional lipid is present in the LNP in an amount from about 1 to about 10 mole percent. In one embodiment, the additional lipid is present in the LNP in an amount from about 1 to about 5 mole percent. In one embodiment, the additional lipid is present in the LNP in about 1 mole percent or about 1.5 mole percent.

In some embodiments, the LNPs comprise a lipid of Formula (I), a nucleoside-modified RNA, a neutral lipid, a steroid and a pegylated lipid. In some embodiments the lipid of Formula (I) is compound I-6. In different embodiments, the neutral lipid is DSPC. In other embodiments, the steroid is cholesterol. In still different embodiments, the pegylated lipid is compound Va.

In certain embodiments, the LNP comprises one or more targeting moieties, which are capable of targeting the LNP to a cell or cell population. For example, in one embodiment, the targeting moiety is a ligand, which directs the LNP to a receptor found on a cell surface.

In certain embodiments, the LNP comprises one or more internalization domains. For example, in one embodiment, the LNP comprises one or more domains, which bind to a cell to induce the internalization of the LNP. For example, in one embodiment, the one or more internalization domains bind to a receptor found on a cell surface to induce receptor-mediated uptake of the LNP. In certain embodiments, the LNP is capable of binding a biomolecule in vivo, where the LNP-bound biomolecule can then be recognized by a cell-surface receptor to induce internalization. For example, in one embodiment, the LNP binds systemic ApoE, which leads to the uptake of the LNP and associated cargo.

Other exemplary LNPs and their manufacture are described in the art, for example in U.S. Patent Application Publication No. US20120276209, Semple et al., 2010, Nat Biotechnol., 28(2):172-176; Akinc et al., 2010, Mol Ther., 18(7): 1357-1364; Basha et al., 2011, Mol Ther, 19(12): 2186-2200; Leung et al., 2012, J Phys Chem C Nanomater Interfaces, 116(34): 18440-18450; Lee et al., 2012, Int J Cancer., 131(5): E781-90; Belliveau et al., 2012, Mol Ther nucleic Acids, 1: e37; Jayaraman et al., 2012, Angew Chem Int Ed Engl., 51(34): 8529-8533; Mui et al., 2013, Mol Ther Nucleic Acids. 2, e139; Maier et al., 2013, Mol Ther., 21(8): 1570-1578; and Tam et al., 2013, Nanomedicine, 9(5): 665-74, each of which are incorporated by reference in their entirety.

The following Reaction Schemes illustrate methods to make lipids of Formula (I), (II) or (III).

GENERAL REACTION SCHEME 1

Embodiments of the lipid of Formula (I) (e.g., compound A-5) can be prepared according to General Reaction Scheme 1 ("Method A"), wherein R is a saturated or unsaturated $C_1$-$C_{24}$ alkyl or saturated or unsaturated cycloalkyl, m is 0 or 1 and n is an integer from 1 to 24. Referring to General Reaction Scheme 1, compounds of structure A-1 can be purchased from commercial sources or prepared according to methods familiar to one of ordinary skill in the art. A mixture of A-1, A-2 and DMAP is treated with DCC to give the bromide A-3. A mixture of the bromide A-3, a base (e.g., N,N-diisopropylethylamine) and the N,N-dimethyldiamine A-4 is heated at a temperature and time sufficient to produce A-5 after any necessarily workup and or purification step.

GENERAL REACTION SCHEME 2

-continued

B-5

Different embodiments of the lipid of Formula (I) (e.g., compound C-7 or C9) can be prepared according to General Reaction Scheme 3 ("Method C"), wherein R is a saturated or unsaturated $C_1$-$C_{24}$ alkyl or saturated or unsaturated cycloalkyl, m is 0 or 1 and n is an integer from 1 to 24. Referring to General Reaction Scheme 3, compounds of structure C-1 can be purchased from commercial sources or prepared according to methods familiar to one of ordinary skill in the art.

Other embodiments of the compound of Formula (I) (e.g., compound B-5) can be prepared according to General Reaction Scheme 2 ("Method B"), wherein R is a saturated or unsaturated $C_1$-$C_{24}$ alkyl or saturated or unsaturated cycloalkyl, m is 0 or 1 and n is an integer from 1 to 24. As shown in General Reaction Scheme 2, compounds of structure B-1 can be purchased from commercial sources or prepared according to methods familiar to one of ordinary skill in the art. A solution of B-1 (1 equivalent) is treated with acid chloride B-2 (1 equivalent) and a base (e.g., triethylamine). The crude product is treated with an oxidizing agent (e.g., pyridinum chlorochromate) and intermediate product B-3 is recovered. A solution of crude B-3, an acid (e.g., acetic acid), and N,N-dimethylaminoamine B4 is then treated with a reducing agent (e.g., sodium triacetoxyborohydride) to obtain B-5 after any necessary work up and/or purification.

It should be noted that although starting materials A-1 and B-1 are depicted above as including only saturated methylene carbons, starting materials which include carbon-carbon double bonds may also be employed for preparation of compounds which include carbon-carbon double bonds.

GENERAL REACTION SCHEME 4

D-1

D-3

GENERAL REACTION SCHEME 3

C-1

C-3

C-5

C-6

C-8

C-7

C-9

-continued

D-5

D-7

Embodiments of the compound of Formula (II) (e.g., compounds D-5 and D-7) can be prepared according to General Reaction Scheme 4 ("Method D"), wherein $R^{1a}$, $R^{1b}$, $R^{2a}$, $R^{2b}$, $R^{3a}$, $R^{3b}$, $R^{4a}$, $R^{4b}$, $R^5$, $R^6$, $R^8$, $R^9$, $L^1$, $L^2$, $G^1$, $G^2$, $G^3$, a, b, c and d are as defined herein, and $R^{7'}$ represents $R^7$ or a $C_3$-$C_{19}$ alkyl. Referring to General Reaction Scheme 1, compounds of structure D-1 and D-2 can be purchased from commercial sources or prepared according to methods familiar to one of ordinary skill in the art. A solution of D-1 and D-2 is treated with a reducing agent (e.g., sodium triacetoxyborohydride) to obtain D-3 after any necessary work up. A solution of D-3 and a base (e.g. trimethylamine, DMAP) is treated with acyl chloride D-4 (or carboxylic acid and DCC) to obtain D-5 after any necessary work up and/or purification. D-5 can be reduced with LiAlH4 D-6 to give D-7 after any necessary work up and/or purification.

GENERAL REACTION SCHEME 5

E-1

E-3

E-5

Embodiments of the lipid of Formula (II) (e.g., compound E-5) can be prepared according to General Reaction Scheme 5 ("Method E"), wherein $R^{1a}$, $R^{1b}$, $R^{2a}$, $R^{2b}$, $R^{3a}$, $R^{3b}$, $R^{4a}$, $R^{4b}$, $R^5$, $R^6$, $R^7$, $R^8$, $R^9$, $L^1$, $L^2$, $G^3$, a, b, c and d are as defined herein. Referring to General Reaction Scheme 2, compounds of structure E-1 and E-2 can be purchased from commercial sources or prepared according to methods familiar to one of ordinary skill in the art. A mixture of E-1 (in excess), E-2 and a base (e.g., potassium carbonate) is heated to obtain E-3 after any necessary work up. A solution of E-3 and a base (e.g. trimethylamine, DMAP) is treated with acyl chloride E-4 (or carboxylic acid and DCC) to obtain E-5 after any necessary work up and/or purification.

GENERAL REACTION SCHEME 6

General Reaction Scheme 6 provides an exemplary method (Method F) for preparation of Lipids of Formula (III). $G^1$, $G^3$, $R^1$ and $R^3$ in General Reaction Scheme 6 are as defined herein for Formula (III), and G1' refers to a one-carbon shorter homologue of G1. Compounds of structure F-1 are purchased or prepared according to methods known in the art. Reaction of F-1 with diol F-2 under appropriate condensation conditions (e.g., DCC) yields ester/alcohol F-3, which can then be oxidized (e.g., PCC) to aldehyde F-4. Reaction of F-4 with amine F-5 under reductive amination conditions yields a lipid of Formula (III).

It should be noted that various alternative strategies for preparation of lipids of Formula (III) are available to those of ordinary skill in the art. For example, other lipids of Formula (III) wherein $L^1$ and $L^2$ are other than ester can be prepared according to analogous methods using the appropriate starting material. Further, General Reaction Scheme 6 depicts preparation of a lipids of Formula (III), wherein $G^1$ and $G^2$ are the same; however, this is not a required aspect of the invention and modifications to the above reaction scheme are possible to yield compounds wherein $G^1$ and $G^2$ are different.

It will be appreciated by those skilled in the art that in the process described herein the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (for example, t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)— R" (where R" is alkyl, aryl or arylalkyl), p-methoxybenzyl, trityl and the like. Suitable protecting groups for carboxylic acid include alkyl, aryl or arylalkyl esters. Protecting groups may be added or removed in accordance with standard techniques, which are known to one skilled in the art and as described herein. The use of protecting groups is described in detail in Green, T. W. and P. G. M. Wutz, *Protective Groups in Organic Synthesis* (1999), 3rd Ed., Wiley. As one of skill in the art would appreciate, the protecting group may also be a polymer resin such as a Wang resin, Rink resin or a 2-chlorotrityl-chloride resin.

Pharmaceutical Compositions

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the description of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as non-human primates, cattle, pigs, horses, sheep, cats, and dogs.

Pharmaceutical compositions that are useful in the methods of the invention may be prepared, packaged, or sold in formulations suitable for ophthalmic, oral, rectal, vaginal, parenteral, topical, pulmonary, intranasal, buccal, intravenous, intracerebroventricular, intradermal, intramuscular, or another route of administration. Other contemplated formulations include projected nanoparticles, liposomal preparations, resealed erythrocytes containing the active ingredient, and immunogenic-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient, which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents.

Controlled- or sustained-release formulations of a pharmaceutical composition of the invention may be made using conventional technology.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, intraocular, intravitreal, subcutaneous, intraperitoneal, intramuscular, intradermal, intrasternal injection, intratumoral, intravenous, intracerebroventricular and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, In certain embodiments, the formulation may comprise dry particles which comprise the active ingredient and which have a diameter in the range from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. In certain embodiments, such powders comprise particles wherein at least 98% of the particles by weight have a diameter greater than 0.5 nanometers and at least 95% of the particles by number have a diameter less than 7 nanometers. In certain embodiments, at least 95% of the particles by weight have a diameter greater than 1 nanometer and at least 90% of the particles by number have a diameter less than 6 nanometers. In certain embodiments, dry powder compositions include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (in certain instances having a particle size of the same order as particles comprising the active ingredient).

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations that are useful include those that comprise the active ingredient in microcrystalline form, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Remington's Pharmaceutical Sciences (1985, Genaro, ed., Mack Publishing Co., Easton, PA), which is incorporated herein by reference.

Treatment Methods

The present invention provides methods of inducing an adaptive immune response against SARS-CoV-2 in a subject comprising administering an effective amount of a composition comprising one or more isolated nucleic acids encoding one or more SARS-CoV-2 antigens.

In one embodiment, the method provides immunity in the subject to SARS-CoV-2, SARS-CoV-2 infection, or to a disease or disorder associated with SARS-CoV-2. The present invention thus provides a method of treating or preventing the infection, disease, or disorder associated with SARS-CoV-2. In one embodiment, the disease or disorder associated with SARS-CoV-2 is COVID-19 or a comorbidity of COVID-19.

In some embodiments, the invention is a method of administering to a subject a composition comprising at least one nucleoside-modified RNA encoding at least one SARS-CoV-2 antigen, In one embodiment, the composition is administered to a subject having an infection, disease, or disorder associated with SARS-CoV-2. In one embodiment, the composition is administered to a subject at risk for developing the infection, disease, or disorder associated with SARS-CoV-2. For example, the composition may be administered to a subject who is at risk for being in contact with a SARS-CoV-2. In one embodiment, the composition is administered to a subject who lives in, traveled to, or is expected to travel to a geographic region in which SARS-CoV-2 is prevalent. In one embodiment, the composition is administered to a subject who is in contact with or expected to be in contact with another person who lives in, traveled to, or is expected to travel to a geographic region in which SARS-CoV-2 is prevalent. In one embodiment, the composition is administered to a subject who has knowingly been exposed to SARS-CoV-2 through their occupation or contact.

In one embodiment, the method comprises administering a composition comprising one or more nucleoside-modified nucleic acid molecules encoding one or more SARS-CoV-2 antigens and one or more adjuvant. In one embodiment, the method comprises administering a composition comprising a first nucleoside-modified nucleic acid molecule encoding one or more SARS-CoV-2 antigens and a second nucleoside-modified nucleic acid molecule encoding one or more adjuvants. In one embodiment, the method comprises administering a first composition comprising one or more nucleoside-modified nucleic acid molecules encoding one or more SARS-CoV-2 antigens and administering a second composition comprising one or more nucleoside-modified nucleic acid molecules encoding one or more adjuvants.

In certain embodiments, the method comprises administering to subject a plurality of nucleoside-modified nucleic acid molecules encoding a plurality of SARS-CoV-2 antigens, adjuvants, or a combination thereof.

In certain embodiments, the method of the invention allows for sustained expression of the SARS-CoV-2 antigen or adjuvant, described herein, for at least several days following administration. In certain embodiments, the method of the invention allows for sustained expression of the SARS-CoV-2 antigen or adjuvant, described herein, for at least 2 weeks following administration. In certain embodiments, the method of the invention allows for sustained expression of the SARS-CoV-2 antigen or adjuvant, described herein, for at least 1 month following administration. However, the method, in certain embodiments, also provides for transient expression, as in certain embodiments, the nucleic acid is not integrated into the subject genome.

In certain embodiments, the method comprises administering nucleoside-modified RNA, which provides stable expression of the SARS-CoV-2 antigen or adjuvant described herein. In some embodiments, administration of nucleoside-modified RNA results in little to no innate immune response, while inducing an effective adaptive immune response.

In certain embodiments, the method provides sustained protection against SARS-CoV-2. For example, in certain embodiments, the method provides sustained protection against SARS-CoV-2 for more than 2 weeks. In certain embodiments, the method provides sustained protection against SARS-CoV-2 for 1 month or more. In certain embodiments, the method provides sustained protection against SARS-CoV-2 for 2 months or more. In certain embodiments, the method provides sustained protection against SARS-CoV-2 for 3 months or more. In certain embodiments, the method provides sustained protection against SARS-CoV-2 for 4 months or more. In certain embodiments, the method provides sustained protection against SARS-CoV-2 for 5 months or more. In certain embodiments, the method provides sustained protection against SARS-CoV-2 for 6 months or more. In certain embodiments, the method provides sustained protection against SARS-CoV-2 for 1 year or more.

In one embodiment, a single immunization of the composition induces a sustained protection against SARS-CoV-2 for 1 month or more, 2 months or more, 3 months or more, 4 months or more, 5 months or more, 6 months or more, or 1 year or more.

Administration of the compositions of the invention in a method of treatment can be achieved in a number of different ways, using methods known in the art. In one embodiment, the method of the invention comprises systemic administration of the subject, including for example enteral or parenteral administration. In certain embodiments, the method comprises intradermal delivery of the composition. In another embodiment, the method comprises intravenous delivery of the composition. In some embodiments, the method comprises intramuscular delivery of the composition. In one embodiment, the method comprises subcutaneous delivery of the composition. In one embodiment, the method comprises inhalation of the composition. In one embodiment, the method comprises intranasal delivery of the composition.

It will be appreciated that the composition of the invention may be administered to a subject either alone, or in conjunction with another agent.

The therapeutic and prophylactic methods of the invention thus encompass the use of pharmaceutical compositions encoding a SARS-CoV-2 antigen, adjuvant, or a combination thereof, described herein to practice the methods of the invention. The pharmaceutical compositions useful for practicing the invention may be administered to deliver a dose of from 1 ng/kg/day and 100 mg/kg/day. In one embodiment, the invention envisions administration of a dose, which results in a concentration of the compound of the present invention from 10 nM and 10 μM in a mammal.

Typically, dosages which may be administered in a method of the invention to a mammal, such as a human, range in amount from 0.01 μg to about 50 mg per kilogram of body weight of the mammal, while the precise dosage administered will vary depending upon any number of factors, including but not limited to, the type of mammal and type of disease state being treated, the age of the mammal and the route of administration. In certain embodiments, the dosage of the compound will vary from about 0.1 μg to about 10 mg per kilogram of body weight of the mammal. In certain embodiments, the dosage will vary from about 1 μg to about 1 mg per kilogram of body weight of the mammal.

The composition may be administered to a mammal as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the mammal, etc.

In certain embodiments, administration of an immunogenic composition or vaccine of the present invention may be performed by single administration or boosted by multiple administrations.

In one embodiment, the invention includes a method comprising administering one or more compositions encoding one or more SARS-CoV-2 antigens or adjuvants described herein. In certain embodiments, the method has an additive effect, wherein the overall effect of the administering the combination is approximately equal to the sum of the effects of administering each SARS-CoV-2 antigen or adjuvant. In other embodiments, the method has a synergistic effect, wherein the overall effect of administering the combination is greater than the sum of the effects of administering each SARS-CoV-2 antigen or adjuvant.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore are not to be construed as limiting in any way the remainder of the disclosure.

Example 1: A Single Immunization with
SARS-CoV-2 Nucleoside-Modified mRNA Vaccines
Elicits Protective Immune Responses in Mice In this study, the immunogenicity of two nucleoside-modified mRNA-LNP vaccines targeting the spike (S) glycoprotein of SARS-CoV-2 was studied: one encoding the full length S protein with deleted furin cleavage site and the other encoding the S protein receptor binding domain (RBD). Immune responses as well as protective efficacy after a single intramuscular (i.m.) injection were evaluated with the SARS-CoV-2 mRNA-LNP or control vaccines in BALB/c mice.

The experiments presented herein demonstrate that both the full-length Δfurin and RBD mRNA vaccines induced potent T cells, long-lived plasma and memory B cells, and the rapid generation of neutralizing antibodies that persisted at a high level until at least week 9 after immunization. Critically, neither vaccine elicited antibodies with ADE activity. Further, both mRNA-LNP vaccines induced highly protective immune responses in mice (>95% reduction in viral loads in the lungs, nasal swabs, and spleen in SARS-CoV-2 mRNA-vaccinated versus control animals). This high level of protection may significantly decrease morbidity and mortality caused by COVID-19.

The methods and materials employed in these experiments are now described.

mRNA-LNP Vaccine Production mRNA vaccines were designed based on the SARS-CoV-2 spike (S) protein sequence (Wuhan-Hu-1, GenBank: MN908947.3). Coding sequences of full length WT S protein, full length Δfurin S protein (RRAR furin cleavage site abolished), RBD and firefly luciferase (Luc) were codon-optimized, synthesized and cloned into the mRNA production plasmid as described (Freyn et al., 2020, Mol Ther, 28:1569-1584). mRNA production and LNP encapsulation was performed as described (Freyn et al., 2020, Mol Ther, 28:1569-1584).

Cell Culture

FreeStyle 293 (293F) cells (Gibco, #R79007) were cultured in Freestyle 293 Expression Medium (Gibco). The 293F cell line was tested for mycoplasma contamination after receipt from Life Technologies and before expansion and cryopreservation.

HEK 293T/17 cells (ATCC #CRL11268) were cultured in DMEM (Mediatech, #MT10-013-CM) containing 10% fetal calf serum (FCS). Vero E6 cells stably expressing TMPRSS2 were cultured in DMEM+10% FCS.

mRNA Transfection 293F cells were diluted to $1 \times 10^6$ cells/ml before transfection. 3 µg mRNA encoding full length WT and Δfurin S protein was transfected into 6 ml of cells. For soluble RBD, 30 ml of cells were transfected with 15 µg mRNA. TransIT-mRNA Transfection Kit (Mirus, #MIR2250) was used for mRNA transfection following the manufacturer's instructions. Transfected cells were cultured at 37° C. with 8% $CO_2$ and shaking at 130 rpm for 48 hours (for full length WT and Δfurin S protein) or 72 hours (for solubleRBD).

In Vitro Studies

Binding reactivity of anti-RBD chimeric mAb, D001 (Sino Biologicals, #40150-D001) and hACE2-Fc fusion protein to full length S protein constructs (WT and Δfurin) was measured by flow cytometry. Briefly, mRNA-transfected 293F cells were harvested 48 hours after transfection and were washed once with 1% bovine serum albumin (BSA) in phosphate buffered saline (PBS). Next, cells were incubated with 10 µg/ml D001 or hACE2-mFc in V-bottom 96-well plates for 30 min at 4° C. Cells were then incubated with goat anti-human IgG Fc secondary antibody, PE (Invitrogen, #12-4998-82) at final concentration of 2.5 µg/ml for 30 min at 4° C. in dark. Following this, dead cells were stained with LIVE/DEAD Fixable Aqua Dead Cell Stain Kit (Invitrogen, #L34966, used at 1:1000 in PBS) for 15 min at 4° C. in dark, then washed twice and resuspended with 1% BSA in PBS. Flow cytometric data were acquired on a LSRII with high-throughput system using FACSDIVA software (BD Biosciences).

T Cell Studies

In Vivo Antibody Labeling

To distinguish lung-infiltrating and vascular T cells, mice were injected intravenously under isoflurane anesthesia with 2 g of anti-CD45 Alexa Fluor 700 antibody (Biolegend #103128). After 5 minutes, mice were euthanized via cervical dislocation and organs were collected for analysis.

Lung and Spleen Isolation for Flow Cytometry

To isolate lung lymphocytes, the lung vasculature was first perfused with 5 ml 1% FBS in PBS by injecting into the cardiac right ventricle. Lungs were collected in gentleMACS C tubes containing 1% FBS in PBS on ice. Digest media was added to achieve a final concentration of 2.25 mg/ml sterile-filtered Collagenase D (Sigma #11088866001) and 0.15 mg/ml DNase I in 4 ml of 1% FBS in PBS. Lungs were disrupted using gentleMACS Dissociator program m_spleen_01.01, then incubated for 45 minutes at 37° C. with shaking. 10 ml of complete RPMI media (10% FBS, 2 mM L-glutamine, 50 µM 2-mercaptoethanol, and penicillin/streptomycin) was then added to each tube, followed by further homogenization using gentleMACS Dissociator program m_lung_02.01. Digested lungs were then passed through a 70 µm strainer, incubated in ACK lysis buffer to remove RBCs, then passed through a 40 µm strainer to obtain a single cell suspension. Spleens were collected in PBS and homogenized through a 70 µm cell strainer using the hard end of a syringe plunger. Splenocytes were incubated in ACK lysis buffer to remove red blood cells (RBCs), then passed through a 40 µm strainer to obtain a single cell suspension.

T Cell Activation Analysis

After preparing lung and spleen single cell suspensions, cells were immediately analyzed for activation markers. Cells were stained with Live/Dead Aqua (Thermo Fisher #L34957) in PBS, followed by Fc-receptor blockade with anti-CD16/CD32 (bioXcell #BE0307), and then stained for 30 minutes at 4° C. with the following antibody panel each at 1:100 in 0.1% BSA in PBS: anti-CD3 APC-Cy7 (BD #557596), anti-CD4 Pacific Blue (Biolegend #100531), anti-CD8 PerCP-Cy5.5 (BD #551162), anti-PD-1 APC (Biolegend #109112), anti-CD69 BV605 (Biolegend #104530), anti-CD44 BV785 (Biolegend #103059), anti-CD62L PE-Cy7 (Biolegend #104418). Samples were analyzed on the CytoFLEX LX flow cytometer (Beckman Coulter).

Intracellular Cytokine Staining

To measure antigen-specific T cells, 1 million cells per well of lung or spleen cells were stimulated with SARS-CoV-2 spike peptide pools (JPT PM-WCPV-S) in a U-bottom plate for at 37° C., 6% $CO_2$ with 2 µg/ml anti-CD28 (Tonbo #40-0281-M001) providing co-stimulation. Vial 1 (N-terminal) and vial 2 (C-terminal) of spike peptides were dissolved in DMSO at 666 µg/ml per peptide and used separately at a final concentration of 1.5 µg/ml. Stimulations proceeded for 1 hour before adding 5 µg/ml brefeldin A (Biolegend #420601), 2 M monensin (Biolegend #420701), and 5 µg/ml anti-CD107a Alexa Fluor 647 (Biolegend #121610) for 5 hours more. DMSO served as a negative control and the combination of 50 µg/ml phorbol 12-myristate 13-acetate and 1 µg/ml ionomycin served as a positive control. After a total of 6 hours, samples were kept <4° C. and stained with Live/Dead Aqua and anti-CD16/CD32 blockade as above, fixed and permeabilized using the Cytofix/Cytoperm kit (BD #554714), and stained intracellularly for 1 hour in 0.1% BSA in PBS with antibodies including (each at 2 µg/ml): anti-CD3 APC-Cy7 (BD #557596), anti-CD4 BV786 (BD #563727), anti-CD8 BUV395 (BD #563786), anti-IFN gamma Alexa Fluor 488

(Biolegend #505813), anti-TNF BV605 (Biolegend #506329), anti-IL-2 (Biolegend #503808), and anti-gran-zyme B Pacific Blue (Biolegend #515408). Samples were analyzed on the Aurora flow cytometer (Cytek).

B Cell Studies

Sample Processing

Spleens were mashed in complete Dulbecco's Modified Eagle's Medium [(DMEM, Corning #T10014CV) contain-ing 10% heat inactivated Fetal Bovine Serum (FBS, Corning #35-015), 1% Glutamax (Gibco, #35050-061) and 1% Peni-cillin/Streptomycin (Gibco, #5070063)] on ice and filtered through a 40 µm cell strainer. RBCs were lysed with ACK Lysing buffer (Lonza, #10-548E) for 5 minutes on ice and the reaction was stopped with ten times the volume PBS (Corning, #21-040-CV). Bone marrow (BM) was harvested from femurs and tibia from each mouse using a 23.5 g×¾" needle and syringe into FACS buffer and filtered through a 63 µm Nitex mesh. RBCs were lysed in ACT buffer for 5 minutes on ice. After RBC lysis, splenocytes and BM cells were resuspended in cold media and immediately used for cell counting, culture or staining.

Staining and Flow Cytometry

Single cell suspensions of murine splenocytes were incu-bated with anti-CD16/CD32 (BioXCell, #BE0307) in FACS buffer (PBS with 2% heat inactivated FBS) prior to staining with all surface anti-mouse antibodies, labeled recombinant proteins (probes) and viability dye for 30 min at 4° C. Recombinant SARS-CoV-2 Receptor Binding Domain (RBD) or Full length S proteins were independently conju-gated to both R-PE and Alexa Fluor 647 using Lightning-Link® R-Phycoerythrin (R-PE) (Expedeon, #336-0005) and Lightning-Link® Rapid Alexa Fluor 647 (Expedeon, #703-0010) kits according to the manufacturer's instructions. For immunophenotyping of antigen-specific memory B cells (MBC), splenocytes were stained with: anti-mouse CD19 BV605 (Biolegend, #115540), B220 AF700 (eBioScience, #56-0452-82), CD3 APC-Fire750 (Biolegend, #100248), Ter119 APC-Fire750 (Biolegend, #100248), CD38 PE-Cy7 (Biolegend, #100248), FAS BV510 (Biolegend, #100248), IgG1 eFluor450 (BD Bioscience, #562107), and IgG2a/2b BB700 (BD Bioscience, #745969) and IgM FITC (Jackson ImmunoResearch, #115-095-020) antibodies, together with RBD- or full length S-PE, RBD- or full length S AlexaFluor 647, and Fixable Viability Dye eFluor780 (eBioscience, #115-095-020). The excess of antibodies were washed away with FACS buffer and cells were fixed with 1% paraform-aldehyde (PFA) for 30 min at 4° C. prior to acquisition on a 5 laser Cytoflex LX (Beckman Coulter).

Alternatively, MBC were assessed without respect to isotype as follows: million splenocytes or bone marrow cells were prepared as above stained with fixable live dead aqua (Biolegend Zombie Aqua #423101) for 15 minutes at RT. Cells were then washed with FACS buffer and stained with the following dilutions of antibodies: B220-BUV496 (BD Bioscience, #612950), CD19-BUV661 (BD Biosciences, #612971), CD138-BUV737 (BD Biosciences, #564430), PD-L2-BV711 (BD Biosciences, #740818), CD4-PE-Cy5 (BD Biosciences, #553654), CD8a-PE-Cy5 (BD Biosci-ences, #553034), CD86-BV421 (Biolegend, #105031), IgA-biotin (Biolegend, #400703), CXCR4-PE-Dz594 (Bioleg-end, #146514), IgD-APC-Cy7 (Biolegend, #405716), GL7-AF488 (Biolegend, #144612), SA-BV650 (Biolegend, #405231), Ter-199-PE-Cy5 (eBioScience, #15-5921-82), F4/80-PE-Cy5 (eBioScience, #15-4801-82), CD73-PE-Cy7 (eBioScience, #25-0731-82), and CD38-AF700 (Invitrogen, #56-0381-82) in BD Brilliant Buffer (BD Biosciences #563794) for 15 minutes at 4° C. Cells were then washed and stained streptavidin BV650 for 10 minutes at 4° C. prior to wash and resuspension in FACS buffer. ~2 million events per sample were acquired on a BD Symphony A3 Lite.

All flow cytometry data were analyzed with FlowJo software (FlowJo LLC).

Full-Length S and RBD Protein Production

The RBD and full-length S proteins were produced in 293F cells, as described previously (Amanat et al., 2020, Nature Medicine. 26:1033-1036; Stadlbauer et al., 2020, Curr Protoc Microbiol 57, e100). Briefly, 600 million cells were transfected with 200 µg of purified DNA encoding codon-optimized RBD of SARS-CoV-2 using Expi-Fectamine 293 transfection kit (Gibco, #A14525). The manufacturer's protocol was followed and cells were harvest on day 3. Cells were spun at 4000 g for 10 minutes and sterile-filtered with a 0.22 µm filter. Supernatant was incu-bated with Ni-NTA resin (Qiagen cat #30230) for 2 hours. After 2 hours, this mixture was loaded onto columns and the protein was eluted using elution buffer with high amounts of imidazole. Protein was concentrated using 10 kDa Amicon centrifugal units (Millipore Sigma cat #UFC901024) and re-constituted in PBS. Concentration was measured using Bradford reagent (Bio-Rad cat #5000201) and a reducing sodium dodecyl sulphate-polyacrylamide gel electrophore-sis (SDS-PAGE) was run to check the integrity of the protein.

ELISPOT Assay

MultiScreenHTS IP Filter Plate, 0.45 µm (Millipore Sigma, #MSIPS4W10) were coated overnight at 4° C. with 2.5 µg/ml recombinant SARS-CoV-2 RBD or Full Spike proteins in bicarbonate buffer (35 mM $NaHCO_3$ and 15 mM $Na_2CO_3$). Plates were washed three times with PBS and blocked with complete DMEM for at least 1 hour at 37° C. Single cell suspensions of murine BM cells were diluted serially in complete DMEM with halving dilutions starting at $1×10^6$ cells. Following overnight incubation at 37° C. and 5% $CO_2$, plates were washed three times with 0.05% Tween-20 in PBS. Membranes were incubated with IgG-HRP (Jackson ImmunoResearch, cat #115-035-003) diluted in complete DMEM for 2 hours at room temperature. Follow-ing incubation with the detection antibody, plates were washed three times with 0.05% Tween-20 in PBS. Spots corresponding to antigen-specific antibody-secreting cells were developed using BD ELISPOT AEC Substrate Set (#551951) and counted using a CTL Immunospot analyzer. Isotype specific ELISPOT plates were coated and incubated with cells as above and then were washed 4× with 0.1% Tween-20 in PBS. Membranes were then incubated with 1:3000 isotype specific biotinylated antibody for 1 hour. Membranes were then washed 4× and incubated in 1:20,000 streptavidin-alkaline phosphatase for 30 minutes. Mem-branes were then washed 4× and incubated with 50 µL BCIP/NBT (Sigma, #B1911-100 mL) for ~10 minutes or until spots developed at which time reaction was quenched with 100 µl 1M sodium phosphate monobasic solution. Membranes were then dried and counted above.

Mouse Immunizations

BALB/c mice aged 8 weeks were purchased from Jackson Laboratory (T cell studies), Envigo (challenge studies) or Charles River Laboratories (all other studies). mRNA-LNPs were diluted in PBS and injected into the gastrocnemius muscle (40 µl injection volume) with a 3/10cc 29½G insulin syringe (BD Biosciences).

Blood Collection

Blood was collected from the orbital sinus under isoflu-rane anesthesia or the submandibular vein under manual restraint. Blood was centrifuged for 5 minutes at 13,000 rpm and the serum was stored at −20° C. and used for ELISA, virus neutralization assays, and ADE assays.

Enzyme Linked Immunosorbent Assay (ELISA)

Samples from Cell Transfections

Supernatant from 293F cells transfected with RBD-encoding mRNA was harvested 72 hours after transfection and concentrated 60× with Vivaspin 20 kDa molecular weight cut-off concentrator (GE Healthcare, #20-9323-60). The expression and binding of soluble RBD were measured by indirect ELISA. RBD samples were added to capture antibody D001 (2 µg/ml)-coated plates for one hour, followed by detection with serum from a SARS-CoV S protein-immunized guinea pig for 1 hour. Serum binding was detected via horseradish peroxidase-conjugated goat anti-guinea pig IgG (Fc) (Jackson ImmunoResearch, #106-035-008, used at 1:10000). Plates were developed with SureBlue Reserve TMB 1-Component Microwell Peroxidase Substrate (Seracare, #5120-0083). Absorbance at 450 nm were measured by a SpectraMax Plus 384 microplate reader (Molecular Devices) and log area under curve (log AUC) were calculated.

To test RBD sample binding to ACE2, plates were first coated with goat anti-human IgG (Fc) antibody (Sigma-Aldrich, #12136) (2 µg/ml), in order to capture the hACE2-mFc construct (5 µg/ml, one hour). Next, the RBD samples were incubated for one hour. The RBD was detected by a rabbit anti-RBD antibody R007 (Sino Biologicals, #40150-R007, used at 1:4000) followed by Goat Anti-Rabbit IgG H&L (HRP) (Abcam, #97080). The detection of RBD and development procedure were the same as described above.

Samples from Mouse Immunizations

Corning 96 Well Clear Polystyrene High Bind Stripwell™ Microplates were coated with 1 µg/ml purified RBD in PBS overnight at 4° C. The plates were blocked with 2% BSA in PBS for 2 hours and washed four times with wash buffer (0.05% Tween-20 in PBS). Mouse sera was diluted in blocking buffer and incubated for 2 hours at room temperature, followed by four washes. HRP-conjugated anti-mouse secondary antibody (Jackson Immunoresearch, #715-035-150) was diluted 1:10,000 in blocking buffer and incubated for 1.5 hours, followed by four washes. KPL TMB substrate was applied to the plate and the reaction was stopped with 2 N sulfuric acid. The absorbance was measured at 450 nm using a SpectraMax 190 microplate reader. RBD-specific IgG end-point dilution titer was defined as the highest dilution of serum to give an OD greater than the sum of the background OD plus 0.01 units. All samples were run in technical duplicates.

Pseudovirus Neutralization Assay

Production of VSV pseudotype with SARS-CoV-2 S: 293T cells plated 24 hours previously at $5 \times 10^6$ cells per 10 cm dish were transfected using calcium phosphate with 35 µg of pCG1 SARS-CoV-2 S delta18 expression plasmid encoding a codon optimized SARS-CoV S gene with an 18 residue truncation in the cytoplasmic tail (kindly provided by Stefan Pohlmann). Twelve hours post transfection the cells were fed with fresh media containing 5 mM sodium butyrate to increase expression of the transfected DNA. Thirty hours after transfection, the SARS-CoV-2 spike expressing cells were infected for 2-4 hours with VSV-G pseudotyped VSVAG-RFP at an MOI of ~1-3. After infection, the cells were washed twice with media to remove unbound virus. Media containing the VSVAG-RFP SARS-CoV-2 pseudotypes was harvested 28-30 hours after infection and clarified by centrifugation twice at 6000 g then aliquoted and stored at −80° C. until used for antibody neutralization analysis.

Antibody neutralization assay using VSVAG-RFP SARS-CoV-2: Vero E6 cells stably expressing TMPRSS2 were seeded in 100 µl at $2.5 \times 10^4$ cells/well in a 96 well collagen coated plate. The next day, 2-fold serially diluted serum samples were mixed with VSVAG-RFP SARS-CoV-2 pseudotype virus (50-200 focus forming units/well) and incubated for 1 hr at 37° C. Also included in this mixture to neutralize any potential VSV-G carryover virus was 8G5F11, a mouse anti-VSV Indiana G, at a concentration of 100 ng/ml (Absolute Antibody, #Ab01401-2.0). The antibody-virus mixture was then used to replace the media on VeroE6 TMPRSS2 cells. 20 hours post infection, the cells were washed and fixed with 4% paraformaldehyde before visualization on an S6 FluoroSpot Analyzer (CTL, Shaker Heights OH). Individual infected foci were enumerated and the values compared to control wells without antibody. The focus reduction neutralization titer 50% ($FRNT_{50}$) was measured as the greatest serum dilution at which focus count was reduced by at least 50% relative to control cells that were infected with pseudotype virus in the absence of mouse serum. $FRNT_{50}$ titers for each sample were measured in two technical replicates performed on separate days.

Microneutralization Assay

Neutralization assays with live SARS-CoV-2 (USA-WA1/2020; GenBank: MT020880) were performed in a biosafety level 3 (BSL3) facility with strict adherence to institutional regulations. Twenty thousand Vero.E6 cells per well were seeded in a 96-well cell culture plate one day before the neutralization assay (Amanat et al., 2020, Nature Medicine. 26:1033-1036). Mouse serum samples were heat-inactivated at 56° C. for 1 hour. Various dilutions of the serum samples in duplicates were prepared in 1× minimal essential medium (MEM) supplemented with fetal bovine serum (FBS) and each dilution was mixed with 600 $TCID_{50}$ of SARS-CoV-2 for 1 hour at room temperature. Cell culture medium from Vero.E6 cells was removed and each dilution was added to the 96-well plate. Cells were incubated with this serum-virus mixture for 1 hour at 37° C. After 1 hour, the serum-virus mixture was removed, and the same respective dilutions were added with an equal amount of 1×MEM supplemented with 2% FBS. Cells were incubated for 48 hours at 37° C. after which cells were fixed with 10% formaldehyde (Polysciences). Following fixation for 24 hours at 4° C., cells were stained with a SARS-CoV-1 nucleoprotein antibody (mouse 1C7). Further details have been described in Amanat et al. (Amanat et al., 2020, Nature Medicine. 26:1033-1036). Each plate had six controls wells that were not infected and six wells that were infected but had no serum. The background from uninfected control wells was averaged and subtracted from all the wells. Percent inhibition at each well was calculated by the following formula: 100−(((X−[average of "no virus" wells])/[average of "virus only" wells])*100) whereby 'X' is the read for each well. Non-linear regression curve fit analysis over the dilution curve was performed to calculate $IC_{50}$.

SARS-CoV-2 Pseudovirus (PV) and Zika Virus (ZIKV) Virus-Like Particle (VLP) Production SARS-CoV-2 PV was produced as previously described (Moore et al., 2004, J Virol 78, 10628-10635) with a minor modification. HEK293T cells were transfected by calcium-phosphate transfection method at a ratio of 5:5:1 with a plasmid encoding murine leukemia virus (MLV) gag/pol proteins, a retroviral vector pQCXIX expressing firefly luciferase, and a plasmid expressing the spike protein of SARS-CoV-2 (GenBank YP_009724390). Cells were washed 6 hours later, and the culture supernatant containing PV was harvested at 43 hours post transfection. ZIKV VLP was produced by transfecting HEK293T cells by the calcium transfection method with a ZIKV replicon (strain FSS13025, GenBank KU955593.1), whose expression is controlled by tetracycline, a plasmid encoding ZIKV capsid, prM, and E proteins (strain FSS13025, GenBank KU955593.1), and the pTet-On plasmid expressing a reverse Tet-responsive transcriptional activator (rtTA) at a ratio of 2:1:1. Cells were washed 6 hours later and replenished with fresh media containing 1 μg/ml Doxycycline. The VLP-containing culture supernatant was harvested 48 hours post transfection. ZIKV replicon was generated by replacing the region spanning 39th through 763rd amino acids of the polyprotein of a ZIKV molecular clone (Zhang et al., 2018, Viruses, 10:700) with Renilla luciferase with the 2A self-cleaving peptide fused at its C-terminus. This construct contains the tetracycline-responsive $P_{tight}$ promoter that derives ZIKV RNA transcription. The PV- and VLP-containing culture supernatants were cleared by 0.45 μm filtration and immediately frozen in aliquots at –80° C.

Antibody-Dependent Enhancement (ADE) Assay

The ability of SARS-CoV-2 immune sera to mediate ADE was measured using HEK293T cells or those stably expressing hACE2 transfected with pCMV-SPORT6-mFcγR1 (Dharmacon, #MMM1013-202708624). Mouse immune sera used for ADE assays were obtained 9 weeks post vaccination or from naive mice. Sera of ten mice per vaccine group were pooled in two groups (five per pool) and assessed separately in ADE assays but combined afterwards for data analysis. Efficient ZIKV ADE has previously been shown (Shim et al., 2019, mBio, 10:e00758-19), and thus used ZIKV VLP as a positive control in ADE assays. ZIKV immune sera were prepared by intraperitoneally injecting C57BL/6 mice with ZIKV (strain PB-81) and bled at 5 weeks post infection. The immune and naive sera samples, heat inactivated for 30 minutes at 56° C., were serially diluted in DMEM containing 10% heat-inactivated FBS. SARS-CoV-2 PV expressing firefly luciferase or ZIKV VLP expressing Renilla luciferase in 50 μl was preincubated for 1 hour at 37° C. with 50 μl of diluted plasma and added to cells plated on the 96 well plates. 24 hours later, infection levels were assessed using Luc-Pair Firefly Luciferase HS Assay Kit (Genocopia) for SARS2-CoV-2 PV and Luc-Pair Renilla Luciferase HS Assay Kit (Genocopia) for ZIKV VLP.

SARS-CoV-2 Challenge

Mice were inoculated with 50 μl of diluted virus stock (280 pfu/mouse) via the intranasal route (dropwise using a P200 pipettor) under ketamine/xylazine sedation. The challenge stock was generated at BIOQUAL in Vero E6 cells from a seed stock received from BEI Resources, cat #NR-52281. The stock has an RNA copy number of $6.7 \times 10^9$ copies/ml and its infectious titer is $5.6 \times 10^5$ PFU/ml in Vero E6 cells.

Viral Load Quantification (qRT-PCR)

The qRT-PCR assay utilizes primers and a probe specifically designed to amplify and bind to a conserved region of Nucleocapsid gene of Coronavirus. The signal is compared to a known standard curve and calculated to give copies per ml. For the qRT-PCR assay, viral RNA is first isolated from tissues. It is extracted with RNA-STAT 60 (Tel-test"B") mixed with chloroform, precipitated and resuspended in AVE Buffer (Qiagen 1020953).

To generate a control for the amplification reaction, RNA is isolated from the applicable SARS-CoV-2 virus stock using the same procedure. The amount of RNA is determined from an O.D. reading at 260, using the estimate that 1.0 OD at A260 equals 40 μg/ml of RNA. With the number of bases known and the average base of RNA weighing 340.5 g/mole, the number of copies is then calculated, and the control diluted accordingly. A final dilution of $10^8$ copies per 3 μl is then divided into single use aliquots of 10 μl. These are stored at –80° C. until needed. Several aliquots are chosen at random and compared to previous controls to verify consistency. For the master mix preparation, 2.5 ml of 2× buffer containing Taq-polymerase, obtained from the TaqMan RT-PCR kit (Bioline #BIO-78005), is added to a 15 ml tube. From the kit, 50 μl of the RT and 100 μl of RNAse inhibitor is also added. The primer pair at 2 μM concentration is then added in a volume of 1.5 ml. Lastly, 0.5 ml of water and 350 μl of the probe at a concentration of 2 μM are added and the tube vortexed. For the reactions, 45 μl of the master mix and 5 μl of the sample RNA are added to the wells of a 96-well plate. All samples are tested in triplicate. The plates are sealed with a plastic sheet.

For control curve preparation, samples of the control RNA are obtained from the –80° C. freezer. The control RNA is prepared to contain $10^6$ to $10^7$ copies per 3 μl. Eight (8) 10-fold serial dilutions of control RNA is prepared using RNAse-free water by adding 5 μl of the control to 45 μl of water and repeating this for 7 dilutions. This gives a standard curve with a range of 1 to $10^7$ copies/reaction. Duplicate samples of each dilution are prepared as described above. If the copy number exceeds the upper detection limit, the sample is diluted as needed. For amplification, the plate is placed in an Applied Biosystems 7500 Sequence detector and amplified using the following program: 48° C. for 30 minutes, 95° C. for 10 minutes followed by 40 cycles of 95° C. for 15 seconds, and 1 minute at 55° C. A printout of the results is maintained in the laboratory notebook. The number of copies of RNA per ml is calculated by extrapolation from the standard curve and multiplying by the reciprocal of 0.2 ml extraction volume. This gives a practical range of 50 to $5 \times 10^8$ RNA copies per mL for nasal washes, and for tissues the viral loads are given per gram.

List Primers/Probe Sequences:

```
2019-nCoV_N1-F:
                                    (SEQ ID NO: 10)
5'-GACCCCAAAATCAGCGAAAT-3'

2019-nCoV_N1-R:
                                    (SEQ ID NO: 11)
5'-TCTGGTTACTGCCAGTTGAATCTG-3'

2019-nCoV_N1-P:
                                    (SEQ ID NO: 12)
5'-FAM-ACCCCGCATTACGTTTGGTGGACC-BHQ1-3'
```

Statistical Analysis

GraphPad Prism was used to perform Kruskal-Wallis and Mann-Whitney tests for non-parametric data and one-way or two-way ANOVA corrected for multiple comparisons for parametric data to compare immune responses in vaccinated and control mice.

The results of the experiments are now described.

In Vitro Characterization of SARS-CoV-2 Nucleoside-Modified mRNA Constructs

Figures 1A, 1B:
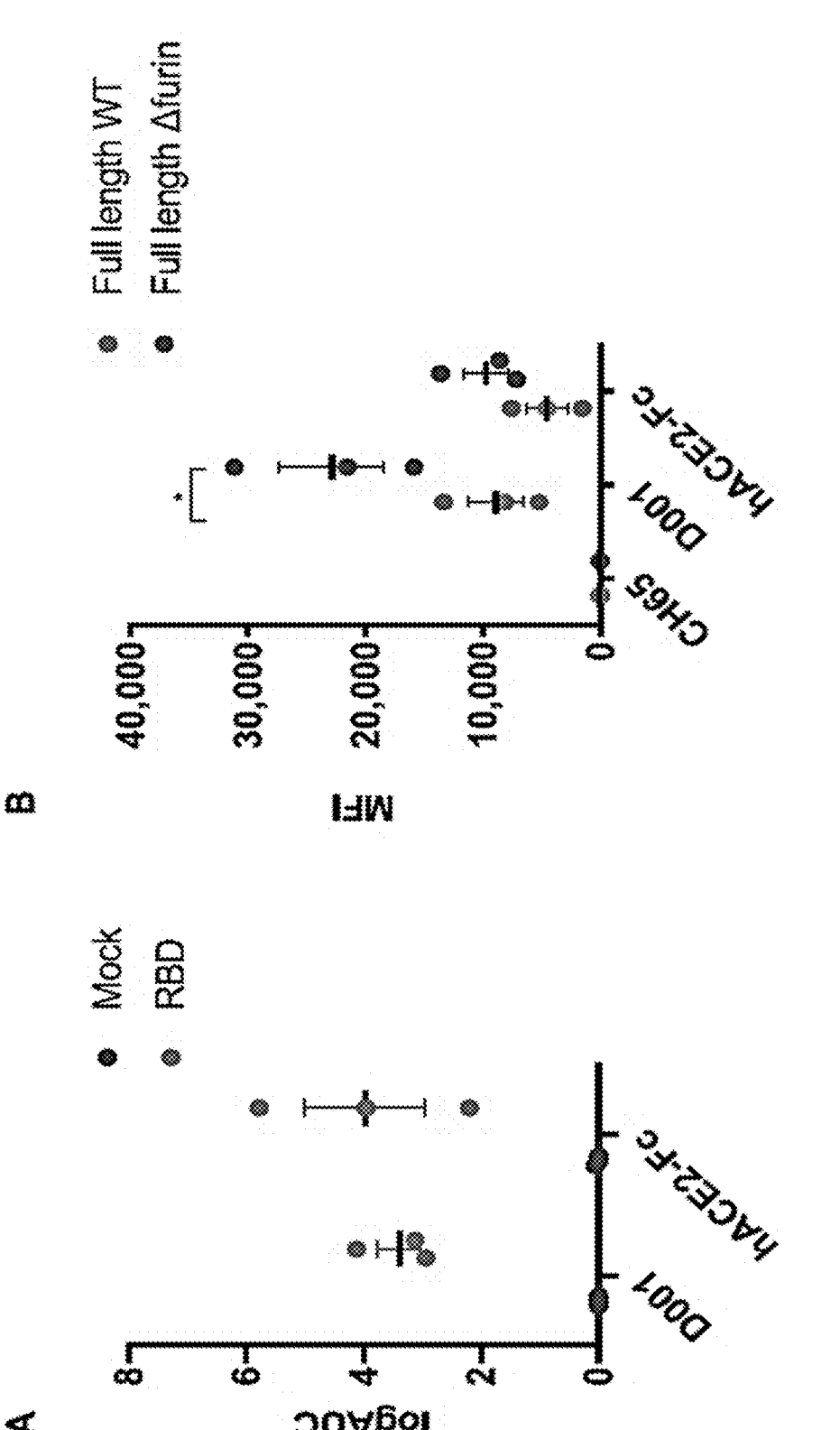
FIG. 1A and FIG. 1B depict exemplary experimental results demonstrating the in vitro characterization of SARS-CoV-2 nucleoside-modified mRNA constructs.

MRNAs encoding three potential SARS-CoV-2 vaccine antigens were designed and produced: full length S protein (wild type; WT), full length S protein with a deleted furin cleavage site (Δfurin), and a short construct encoding the soluble RBD of S protein. The Δfurin mutant was included as a potential way to stabilize the full length S and to maintain the covalent association of the S1 and S2 subunits (Kirchdoerfer et al., 2016, Nature, 531:118-121), while the RBD was investigated as it is a critical target of neutralizing antibodies against SARS-CoV-2. Protein expression from mRNAs was confirmed by in vitro cell transfection studies. RBD protein secretion was demonstrated by ELISA using supernatant from RBD mRNA-transfected 293F cells (FIG. 1A). As the full length WT and Δfurin S proteins contain the transmembrane domain, they were expressed on the surface of transfected 293F cells. Flow cytometry was used to assess binding of full length WT and Δfurin S proteins by an anti-RBD monoclonal antibody, D001, and a human ACE2-Fc (hACE2-Fc) fusion protein. Interestingly, the full length Δfurin S protein showed higher binding capacity to D001 and hACE2-Fc compared to its WT counterpart, indicating that it may be a better vaccine antigen, due either to higher expression or favorable antigenicity (FIG. 1B). Therefore, the full length Δfurin construct was selected to evaluate in immunization studies along with RBD.

SARS-CoV-2 mRNA Vaccines Induce Strong T Cell Responses in the Spleen and Lungs

Figures 4A, 4B:
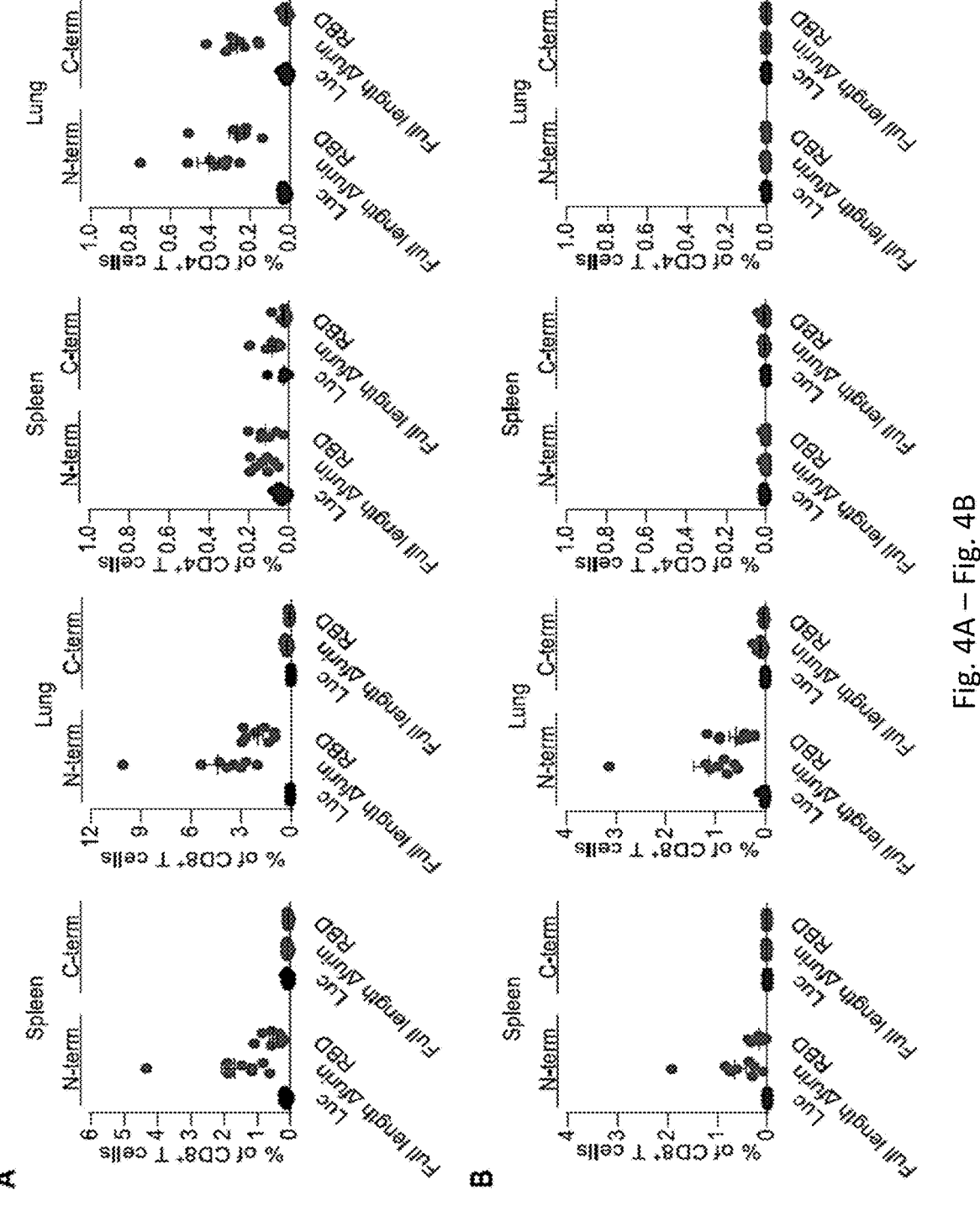
Figure 4C:
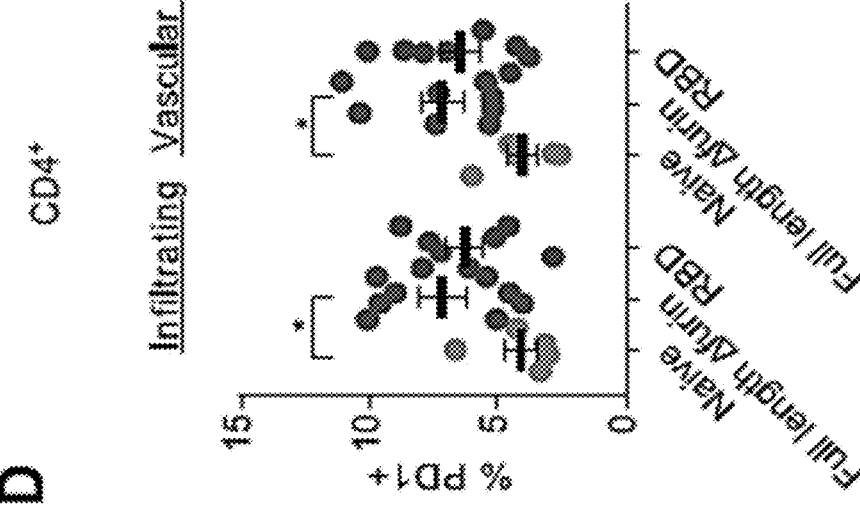
Figure 4D:
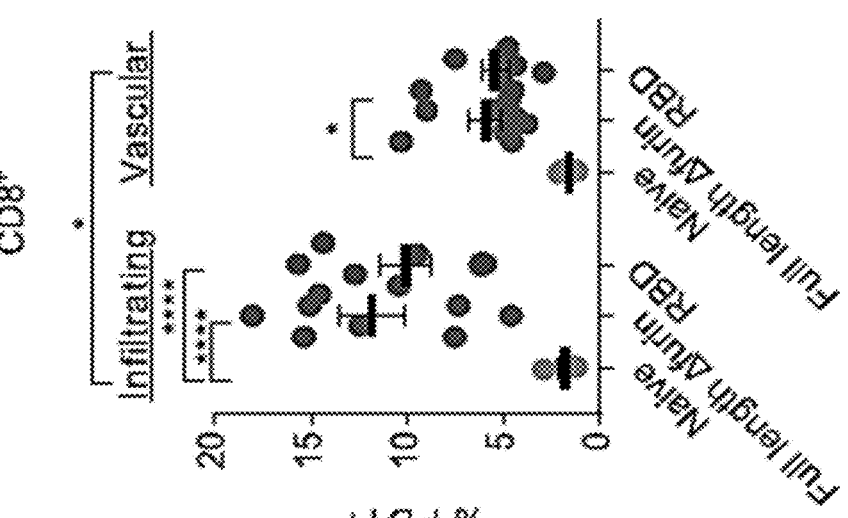

BALB/c mice were injected with a single i.m. dose of 30 μg of mRNA-LNPs encoding full length Δfurin, RBD, or firefly luciferase (Luc, negative control) mRNA-LNPs, and S protein-specific $CD4^+$ and $CD8^+$ T cell responses were evaluated after 10 days by intracellular cytokine staining (FIGS. 2-4). Both spike mRNA constructs elicited antigen-specific, polyfunctional $CD8^+$ (FIG. 2A) and $CD4^+$ (FIG. 2B) T cells expressing type 1 immune response cytokines (IFN-γ, TNF, and IL-2) as well as $CD8^+$ T cells with cytotoxic potential (granzyme $B^+$ $CD107a^+$) (FIG. 2C) in both the spleen and lungs. These responses were particularly robust in the lungs, especially for $CD8^+$ T cells. The vast majority of the $CD8^+$ T cell response in BALB/c mice was directed at epitopes in the N-terminal half of the S protein, while $CD4^+$ T cells recognized epitopes in both halves of the protein (FIG. 4A and FIG. 4B). As S protein-specific lung-infiltrating T cell responses may contribute to SARS-CoV-2 vaccine protection as seen with SARS-CoV-1 (Zhao et al., 2016, Immunity, 44:1379-1391), it was next examined whether vaccine-induced lung T cells were truly infiltrating into the lung parenchyma. Intravenous (i.v.) labeling was performed with a CD45-specific antibody in order to differentiate between vascular (i.v. label-positive) and tissue-infiltrating (i.v. label-negative) lung $CD4^+$ and $CD8^+$ T cells (FIG. 2D through FIG. 2G, FIG. 3C, and FIG. 2C through FIG. 2D)). SARS-CoV-2 mRNA-LNP vaccines elicited significant increases in activated ($CD69^+$ or PD-1$^+$) and antigen-experienced ($CD44^+CD62L^-$) $CD8^+$ and $CD4^+$ T cells that were tissue-infiltrating, with comparatively modest increases in the vasculature, suggesting that activated vaccine-induced T cells readily exit the vasculature and enter the lung parenchyma (FIG. 2D through FIG. 2G and FIG. 4C and FIG. 4D). Of note, in each of the above assays, the full length Δfurin vaccine induced greater T cell responses compared to the RBD vaccine. While not bound to any particular theory, this may be explained by the presence of additional T cell epitopes in the longer protein product produced by the full length Δfurin construct.

Figure 5A:
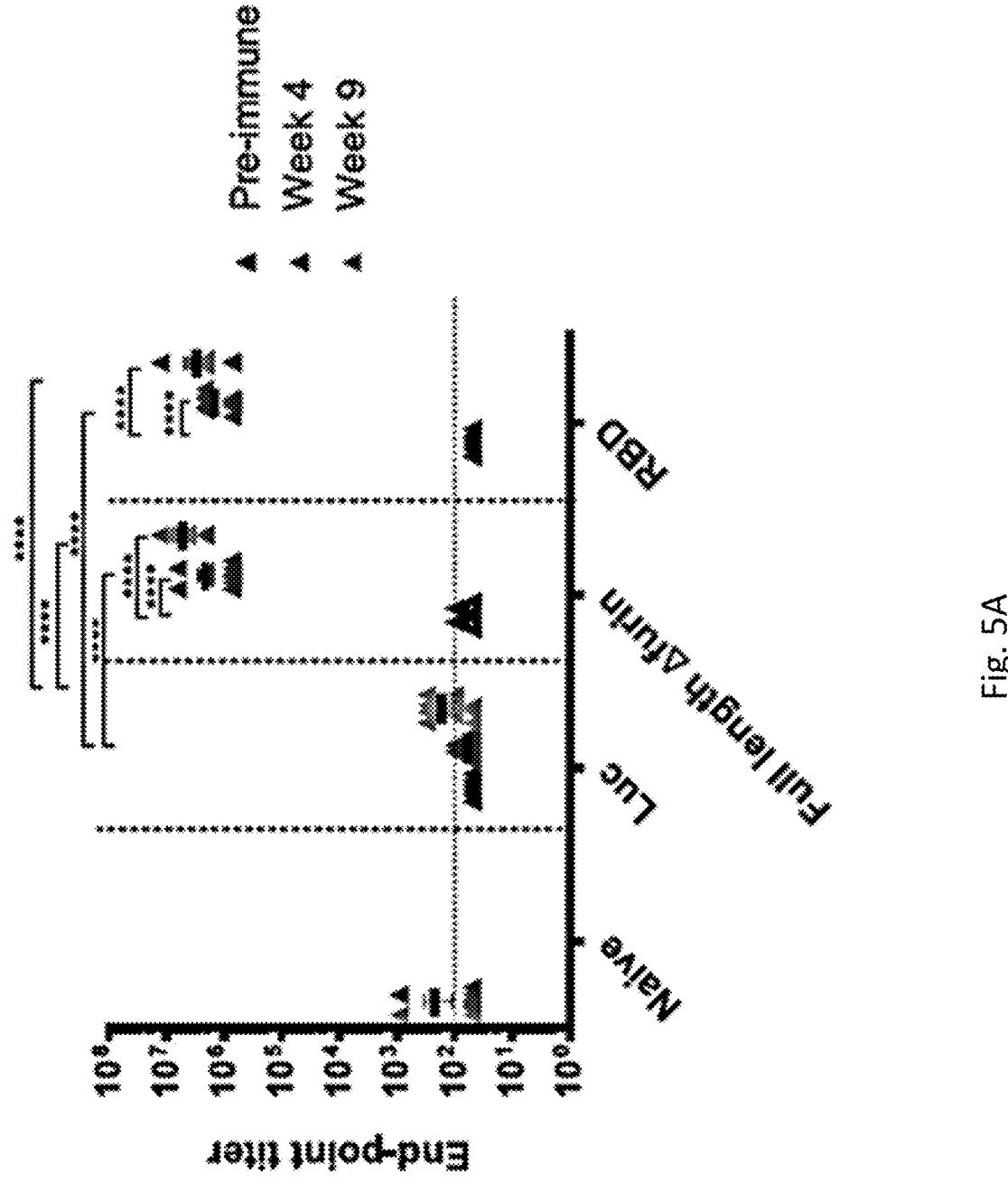
Figure 5B:
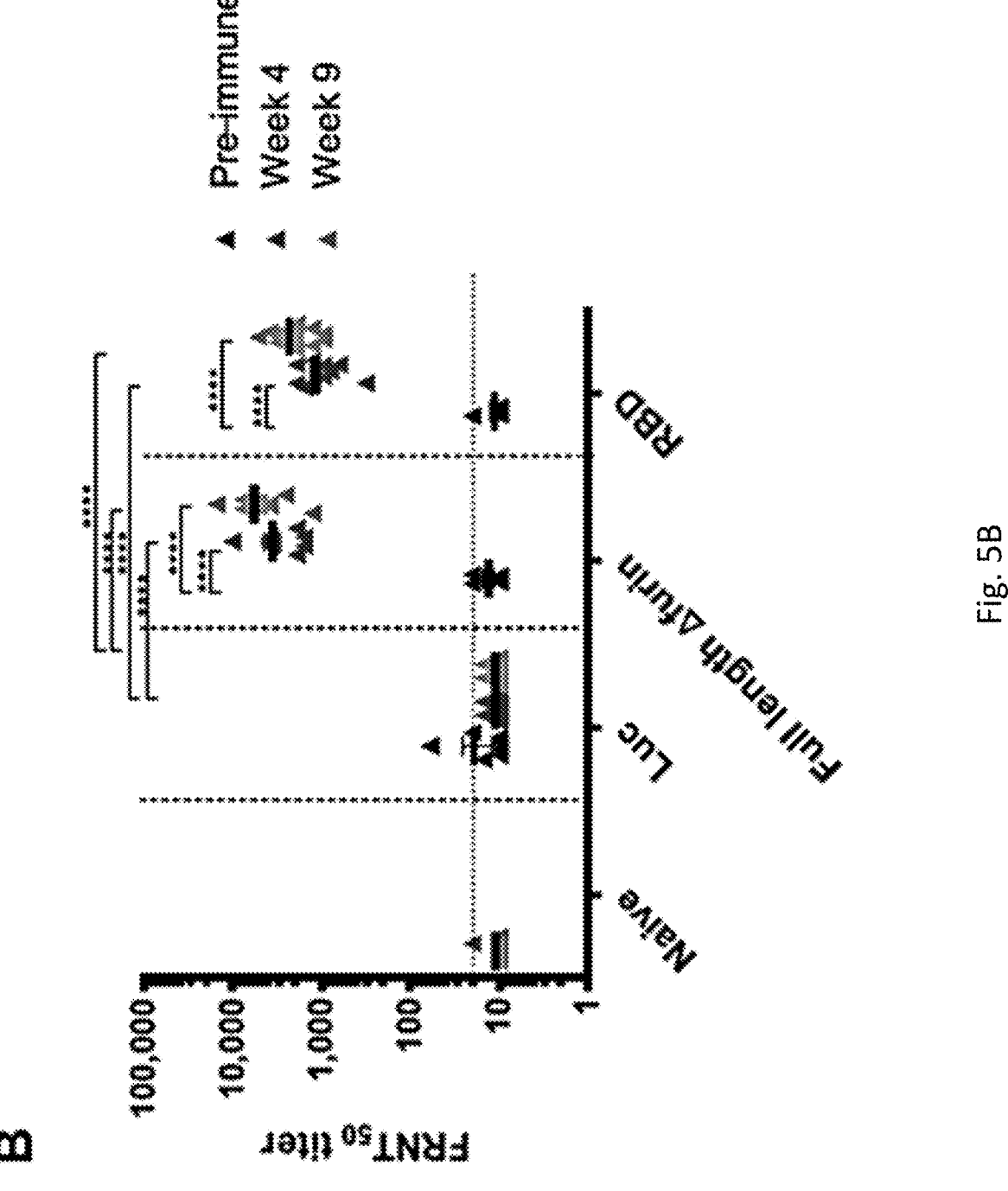
Figure 5C:
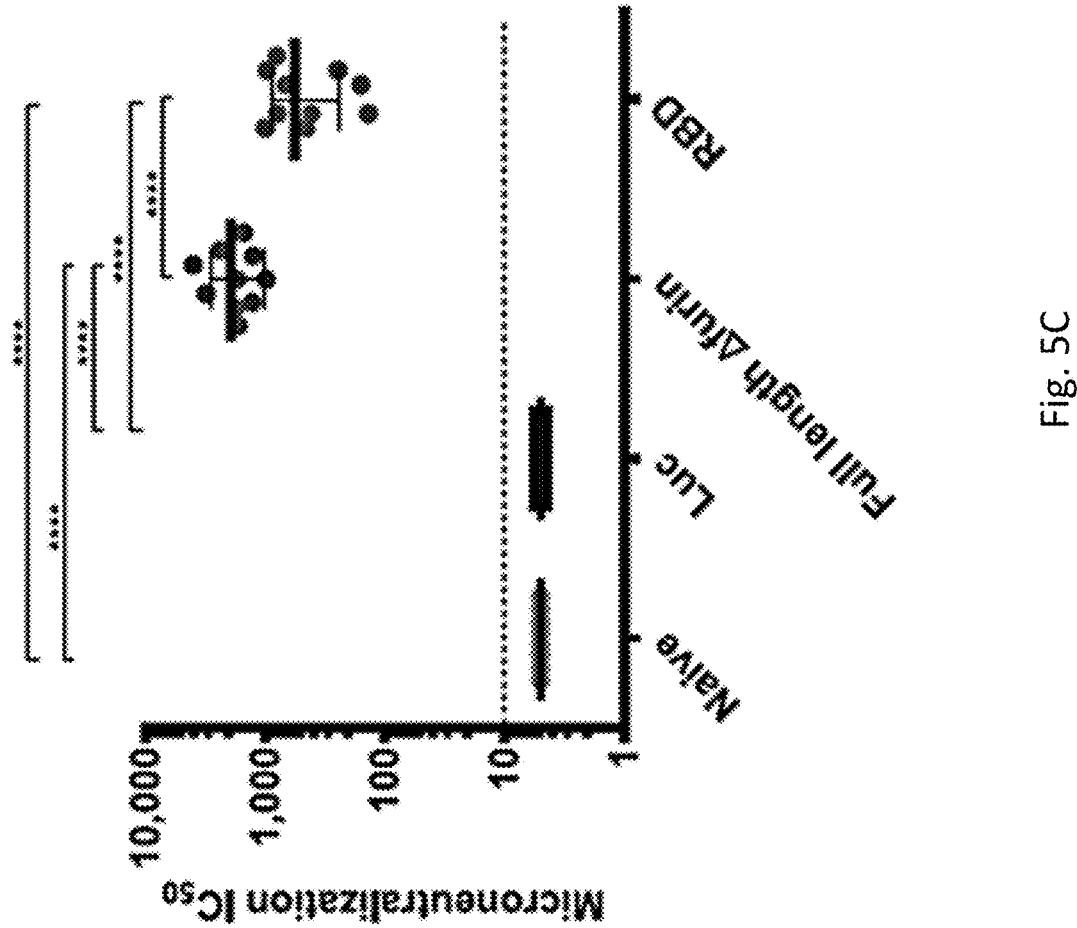

SARS-CoV-2 mRNA Vaccines Elicit Potent and Sustained Humoral Immune Responses with No ADE Activity Mice were immunized i.m. with a single dose of 30 μg of full length Δfurin, RBD, and Luc mRNA-LNPs and antibody responses were evaluated. Both SARS-CoV-2 vaccines induced high levels of S protein-specific IgG by four weeks post immunization, and IgG titers further increased by week 9 (FIG. 5A). Using a vesicular stomatitis virus (VSV)-based pseudovirus neutralization assay, it was demonstrated that nucleoside-modified SARS-CoV-2 mRNA-LNP vaccines induced high and sustained levels of neutralizing antibodies after administration of a single vaccine dose, with week 9 sera showing slightly higher neutralization activity than week 4 (FIG. 5B). Importantly, induction of antibodies with high neutralization titers was also demonstrated by microneutralization assay using live SARS-CoV-2 with week 9 post immunization samples (FIG. 5C). Both assays indicated that the full length Δfurin mRNA-LNPs generated slightly higher levels of neutralizing antibodies than the RBD vaccine at 9 weeks post immunization (FIG. 5B and FIG. 5C).

Figure 5D:
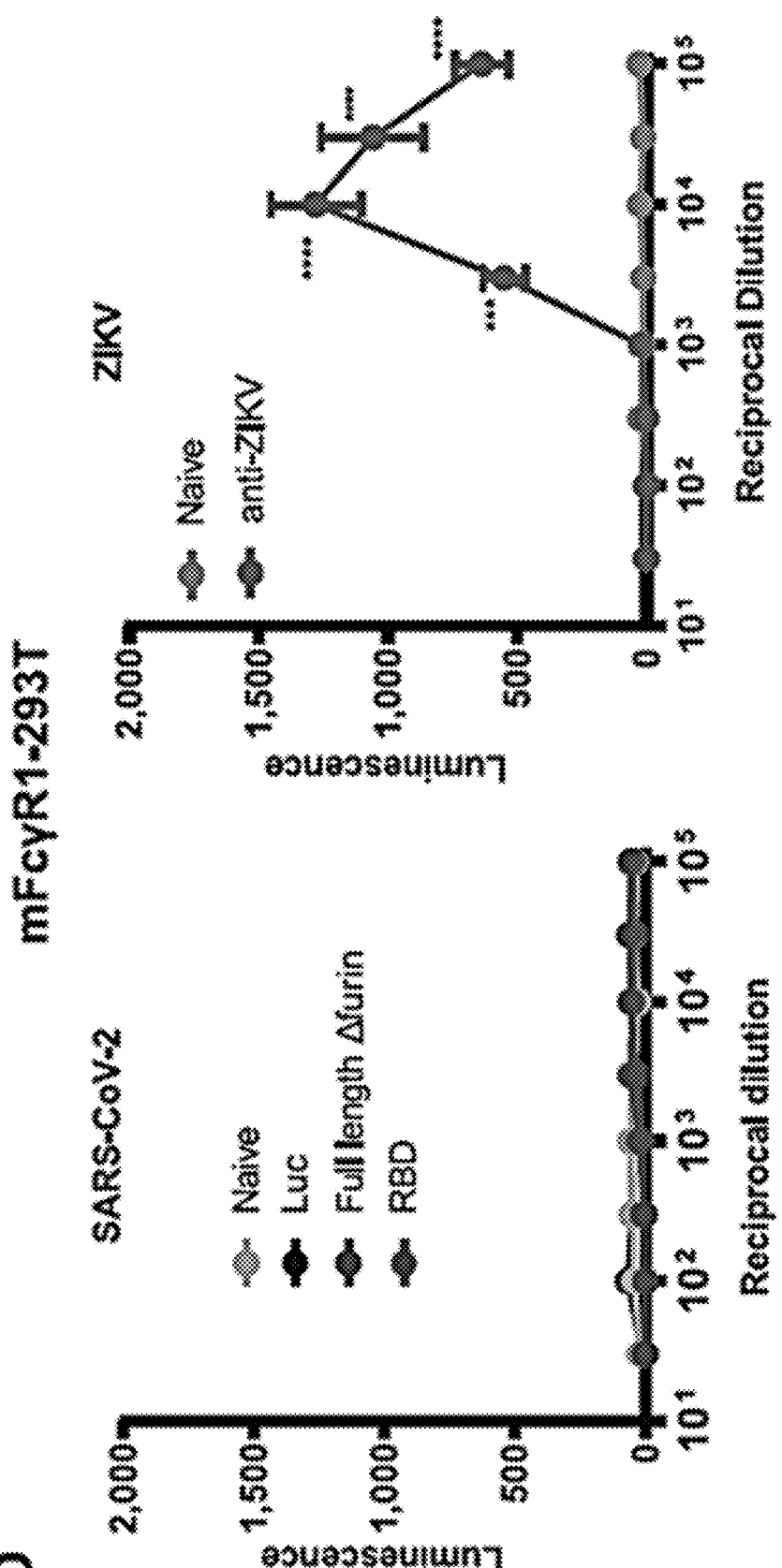

Antibody-dependent enhancement (ADE) of infection by virus-specific antibodies is a potential serious concern for several vaccines including those for Zika and dengue viruses and coronaviruses (Smatti et al., 2018, Front Microbiol, 9:2991). Thus, whether or not the SARS-CoV-2 mRNA vaccine-elicited antibodies induced ADE of infection in HEK293T cells expressing mouse FcγR1 (mFcγR1-293T cells) was investigated. It was demonstrated that none of the mouse immune sera mediated SARS-CoV-2 ADE, whereas robust Zika virus (ZIKV) ADE was observed with sera derived from ZIKV-infected mice (FIG. 5D). Although ADE assays are typically conducted in the absence of the bona-fide virus receptor, to examine whether viral receptor is necessary for efficient ADE, cells expressing hACE2 as well as mFcγR1 were used in ADE assays. SARS-CoV-2 pseudovirus infection of hACE2/mFcγR1-293T cells was efficiently neutralized as expected by sera derived from mice vaccinated with the full length Δfurin or RBD mRNAs at low dilutions (FIG. 6), and there was no enhanced infection observed at any serum dilution. As in themFcγR1-293T cells, ZIKV-immune mouse sera mediated robust ADE in the hACE2/mFcγR1-293T cells. These results demonstrate that neither the full-length Δfurin nor RBD mRNA-LNP vaccines generate ADE-mediating antibodies.

SARS-CoV-2 mRNA Vaccines Induce Strong Long-Lived Plasma and Memory B Cell Responses Most successful vaccine approaches rely on the generation of memory B cells (MBC) and long-lived plasma cells (LLPC)(Sallusto et al., 2010, Immunity, 33, 451-463). While MBCs can mount rapid recall responses upon a secondary exposure, LLPCs residing in the bone marrow contribute to protection from infection by a persistent production of antigen-specific antibodies. To examine the magnitude and quality of antigen-specific LLPC and MBC responses, mice were immunized i.m. with a single dose of 30 μg of full length Δfurin, RBD, or Luc mRNA-LNPs and sacrificed 9 weeks post vaccination (FIGS. 7-9). Splenic full length S protein and RBD-specific IgG1 (FIG. 7D, FIG. 7F and FIG. 4B) and IgG2a/b (FIG. 7E, FIG. 7G and FIG. 9B) expressing MBCs were identified by flow cytometry. Of note, a single immunization with the SARS-CoV-2 mRNA vaccines resulted in the generation of antigen-specific class-switched MBCs. A significant increase of full length S protein and RBD-specific IgM B cells (FIGS. 8-9) was also observed. To assess antigen-specific LLPC responses, bone marrow was collected from vaccinated mice, and the number of full length S protein and RBD-specific antibody secreting cells (ASC) was determined (FIG. 7H and FIG. 7I). Both SARS-CoV-2 mRNA vaccines induced high levels of antigen-specific ASCs after administration of a single vaccine dose. Various subsets of RBD-specific Ig-producing cells were further characterized by ELISPOT (FIG. 7J). ASCs primarily produce antigen-specific IgG1, IgG2a and IgG2b.

SARS-CoV-2 mRNA Vaccines Provide a High Level of Protection from Viral Replication To assess the protective efficacy of SARS-CoV-2 mRNA-LNP vaccines, BALB/c mice were immunized i.m. with a single dose of 30 μg of full length Δfurin, RBD, and Luc mRNA-LNPs and inoculated intranasally with live SARS-CoV-2 virus 4 weeks after vaccine administration. In line with the studies shown in FIG. 5, both SARS-CoV-2 mRNA-LNP vaccines rapidly induced high levels of antigen-specific IgG and neutralizing antibody titers (FIG. 10A and FIG. 10B). Neutralizing antibody titers were significantly higher at week 4 compared to week 2. Two days after challenge, animals were euthanized and viral RNA levels (positive-sense nucleocapsid) were determined in the nares (FIG. 10C), lungs (FIG. 10D), and spleen (FIG. 10E) by qRT-PCR. Significantly lower levels of viral RNA were observed in the SARS-CoV-2 mRNA-LNP-vaccinated animals compared to control Luc-immunized mice, with an overall average (full length Δfurin and RBD groups combined) of 99%, 95% and 98% reduction in the geometric means of the viral loads in the nasal swabs, lungs, and spleen, respectively (FIG. 10C through FIG. 10E). Complete elimination of virus in the spleen was observed in 2 out of 8 full length Δfurin and 5 out of 10 RBD-immunized mice (FIG. 10E). Importantly, 2 out of 8 full length Δfurin and 6 out of 10 RBD-immunized mice showed complete elimination of virus in the nares (FIG. 10C). These results demonstrate 95-99% lower viral titers in SARS-CoV-2 mRNA-vaccinated animals compared to control mice, which could be highly clinically significant.

ADDITIONAL REFERENCES

Alameh, M. G., Weissman, D., and Pardi, N. (2020). Messenger RNA-Based Vaccines Against Infectious Diseases. Curr Top Microbiol Immunol.

Gao, Q., Bao, L., Mao, H., Wang, L., Xu, K., Yang, M., Li, Y., Zhu, L., Wang, N., Lv, Z., et al. (2020). Rapid development of an inactivated vaccine candidate for SARS-CoV-2. Science.eabc1932

Pardi, N., Hogan, M. J., Naradikian, M. S., Parkhouse, K., Cain, D. W., Jones, L., Moody, M. A., Verkerke, H. P., Myles, A., Willis, E., et al. (2018a). Nucleoside-modified mRNA vaccines induce potent T follicular helper and germinal center B cell responses. J Exp Med 215, 1571-1588.

Pardi, N., Hogan, M. J., Pelc, R. S., Muramatsu, H., Andersen, H., DeMaso, C. R., Dowd, K. A., Sutherland, L. L., Scearce, R. M., Parks, R., et al. (2017). Zika virus protection by a single low-dose nucleoside-modified mRNA vaccination. Nature 543, 248-251.

Pardi, N., Parkhouse, K., Kirkpatrick, E., McMahon, M., Zost, S. J., Mui, B. L., Tam, Y. K., Kariko, K., Barbosa, C. J., Madden, T. D., et al. (2018b). Nucleoside-modified mRNA immunization elicits influenza virus hemagglutinin stalk-specific antibodies. Nat Commun 9, 3361.

Pardi, N., Tuyishime, S., Muramatsu, H., Kariko, K., Mui, B. L., Tam, Y. K., Madden, T. D., Hope, M. J., and Weissman, D. (2015). Expression kinetics of nucleoside-modified mRNA delivered in lipid nanoparticles to mice by various routes. J Control Release 217, 345-351.

Smith, T. R. F., Patel, A., Ramos, S., Elwood, D., Zhu, X., Yan, J., Gary, E. N., Walker, S. N., Schultheis, K., Purwar, M., et al. (2020). Immunogenicity of a DNA vaccine candidate for COVID-19. Nat Commun 11, 2601.

Yu, J., Tostanoski, L. H., Peter, L., Mercado, N. B., McMahan, K., Mahrokhian, S. H., Nkolola, J. P., Liu, J., Li, Z., Chandrashekar, A., et al. (2020). DNA vaccine protection against SARS-CoV-2 in rhesus macaques. Science eabc6284

Example 2: Potent Germinal Center-Derived B Cell Responses are Elicited by a Single-Dose SARS-CoV-2 mRNA Vaccine There are currently no existing vaccine or production process for coronaviruses. Several vaccines for SARS-CoV1 and MERS were developed and tested in animal models. These vaccines demonstrated that the S protein on the surface of the virus is an ideal vaccine candidate, and antibody binding the RDB efficiently neutralizes the virus. However, vaccination with live viruses might lead to complications (i.e. lung damage, eosinophil infiltration, etc.) and disease enhancement. Further, antibody (Ab) titers in people infected with SARS-CoV1 and MERS waned after 2-3 years. Thus there remains a need for vaccines that are safe and induce long-lasting protection.

The experiments described herein demonstrate that SARS-CoV-2 S protein-encoding mRNA-LNP vaccines have been developed (FIG. 11). There is a moderate induction of short-live plasma cells (PC) upon SARS-CoV-2 mRNA-LNP vaccination (FIG. 12). However, SARS-CoV-2 mRNA vaccines elicit potent antigen-specific germinal center (GC) B cell responses (FIG. 13 and FIG. 14) that wane by week 28 (FIG. 15). Further, there is strong generation of SARS-CoV-2 specific GC Tfh cells (FIG. 16 and FIG. 17). Elevated titers of neutralizing antibodies are stable at least until week 9 post single immunization. Further, there is potent bone marrow LLPC at week 9 post immunization.

Vaccination with the SARS-CoV-2 S protein-encoding mRNA-LNP vaccine resulted in high frequency/absolute numbers of RBD-specific MBC precursors in early GCs and class-switched MBC at week 9 post immunization (FIG. 18 and FIG. 19). Immune responses were biased toward a Th1 profile (FIG. 20 and FIG. 21). No in vitro ADE was observed (FIG. 5D).

Example 3: Sequences

```
Full-length WT S protein DNA
sequence (SEQ ID NO: 1):
ATGTTCGTGTTCCTGGTGCTGCTGCCCCTGGTGTC

CTCCCAGTGCGTGAACCTGACCACCCGCACCCAGC

TGCCCCCCGCCTACACCAACTCCTTCACCCGCGGC

GTGTACTACCCCGACAAGGTGTTCCGCTCCTCCGT

GCTGCACTCCACCCAGGACCTGTTCCTGCCCTTCT

TCTCCAACGTGACCTGGTTCCACGCCATCCACGTG

TCCGGCACCAACGGCACCAAGCGgTTCGACAACCC

CGTGCTGCCCTTCAACGACGGCGTGTACTTCGCCT

CCACCGAGAAGTCCAACATCATCCGCGGCTGGATC

TTCGGCACCACCCTGGACTCCAAGACCCAGTCCCT

GCTGATCGTGAACAACGCCACCAACGTGGTGATCA

AGGTGTGCGAGTTCCAGTTCTGCAACGACCCCTTC

CTGGGCGTGTACTACCACAAGAACAACAAGTCCTG
```

```
GATGGAGTCCGAGTTCCGCGTGTACTCCTCCGCCA

ACAACTGCACCTTCGAGTACGTGTCCCAGCCCTTC

CTGATGGACCTGGAGGGCAAGCAGGGCAACTTCAA

GAACCTGCGCGAGTTCGTGTTCAAGAACATCGACG

GCTACTTCAAGATCTACTCCAAGCACACCCCCATC

AACCTGGTGCGCGACCTGCCCCAGGGCTTCTCCGC

CCTGGAGCCCCTGGTGGACCTGCCCATCGGCATCA

ACATCACCCGCTTCCAGACCCTGCTGGCCCTGCAC

CGCTCCTACCTGACCCCCGGCGACTCCTCCTCCGG

CTGGACCGCCGGCGCCGCCGCCTACTACGTGGGCT

ACCTGCAGCCCCGCACCTTCCTGCTGAAGTACAAC

GAGAACGGCACCATCACCGACGCCGTGGACTGCGC

CCTGGACCCCCTGTCCGAGACCAAGTGCACCCTGA

AGTCCTTCACCGTGGAGAAGGGCATCTACCAGACC

TCCAACTTCCGCGTGCAGCCCACCGAGTCCATCGT

GCGCTTCCCCAACATCACCAACCTGTGCCCCTTCG

GCGAGGTGTTCAACGCCACCCGCTTCGCCTCCGTG

TACGCCTGGAACCGCAAGCGCATCTCCAACTGCGT

GGCCGACTACTCCGTGCTGTACAACTCCGCCTCCT

TCTCCACCTTCAAGTGCTACGGCGTGTCCCCCACC

AAGCTGAACGACCTGTGCTTCACCAACGTGTACGC

CGACTCCTTCGTGATCCGCGGCGACGAGGTGCGCC

AGATCGCCCCCGGCCAGACCGGCAAGATCGCCGAC

TACAACTACAAGCTGCCCGACGACTTCACCGGCTG

CGTGATCGCCTGGAACTCCAACAACCTGGACTCCA

AGGTGGGCGGCAACTACAACTACCTGTACCGCCTG

TTCCGCAAGTCCAACCTGAAGCCCTTCGAGCGCGA

CATCTCCACCGAGATCTACCAGGCCGGCTCCACCC

CCTGCAACGGCGTGGAGGGCTTCAACTGCTACTTC

CCCCTGCAGTCCTACGGCTTCCAGCCCACCAACGG

CGTGGGCTACCAGCCCTACCGCGTGGTGGTGCTGT

CCTTCGAGCTGCTGCACGCCCCCGCCACCGTGTGC

GGCCCCAAGAAGTCCACCAACCTGGTGAAGAACAA

GTGCGTGAACTTCAACTTCAACGGCCTGACCGGCA

CCGGCGTGCTGACCGAGTCCAACAAGAAGTTCCTG

CCCTTCCAGCAGTTCGGCCGCGACATCGCCGACAC

CACCGACGCCGTGCGCGACCCCCAGACCCTGGAGA

TCCTGGACATCACCCCCTGCTCCTTCGGCGGCGTG

TCCGTGATCACCCCCGGCACCAACACCTCCAACCA

GGTGGCCGTGCTGTACCAGGACGTGAACTGCACCG
```

```
AGGTGCCCGTGGCCATCCACGCCGACCAGCTGACC

CCCACCTGGCGCGTGTACTCCACCGGCTCCAACGT

GTTCCAGACCCGCGCCGGCTGCCTGATCGGCGCCG

AGCACGTGAACAACTCCTACGAGTGCGACATCCCC

ATCGGCGCCGGCATCTGCGCCTCCTACCAGACCCA

GACCAACTCCCCCCGCCGCGCCCGCTCCGTGGCCT

CCCAGTCCATCATCGCCTACACCATGTCCCTGGGC

GCCGAGAACTCCGTGGCCTACTCCAACAACTCCAT

CGCCATCCCCACCAACTTCACCATCTCCGTGACCA

CCGAGATCCTGCCCGTGTCCATGACCAAGACCTCC

GTGGACTGCACCATGTACATCTGCGGCGACTCCAC

CGAGTGCTCCAACCTGCTGCTGCAGTACGGCTCCT

TCTGCACCCAGCTGAACCGCGCCCTGACCGGCATC

GCCGTGGAGCAGGACAAGAACACCCAGGAGGTGTT

CGCCCAGGTGAAGCAGATCTACAAGACCCCCCCCA

TCAAGGACTTCGGCGGCTTCAACTTCTCCCAGATC

CTGCCCGACCCCTCCAAGCCCTCCAAGCGgTCCTT

CATCGAGGACCTGCTGTTCAACAAGGTGACCCTGG

CCGACGCCGGCTTCATCAAGCAGTACGGCGACTGC

CTGGGCGACATCGCCGCCCGCGACCTGATCTGCGC

CCAGAAGTTCAACGGCCTGACCGTGCTGCCCCCCC

TGCTGACCGACGAGATGATCGCCCAGTACACCTCC

GCCCTGCTGGCCGGCACCATCACCTCCGGCTGGAC

CTTCGGCGCCGGCGCCGCCCTGCAGATCCCCTTCG

CCATGCAGATGGCCTACCGCTTCAACGGCATCGGC

GTGACCCAGAACGTGCTGTACGAGAACCAGAAGCT

GATCGCCAACCAGTTCAACTCCGCCATCGGCAAGA

TCCAGGACTCCCTGTCCTCCACCGCCTCCGCCCTG

GGCAAGCTGCAGGACGTGGTGAACCAGAACGCCCA

GGCCCTGAACACCCTGGTGAAGCAGCTGTCCTCCA

ACTTCGGCGCCATCTCCTCCGTGCTGAACGACATC

CTGTCCCGCCTGGACAAGGTGGAGGCCGAGGTGCA

GATCGACCGCCTGATCACCGGCCGCCTGCAGTCCC

TGCAGACCTACGTGACCCAGCAGCTGATCCGCGCC

GCCGAGATCCGCGCCTCCGCCAACCTGGCCGCCAC

CAAGATGTCCGAGTGCGTGCTGGGCCAGTCCAAGC

GCGTGGACTTCTGCGGCAAGGGCTACCACCTGATG

TCCTTCCCCCAGTCCGCCCCCCACGGCGTGGTGTT

CCTGCACGTGACCTACGTGCCCGCCCAGGAGAAGA

ACTTCACCACCGCCCCCGCCATCTGCCACGACGGC

AAGGCCCACTTCCCCCGCGAGGGCGTGTTCGTGTC
```

-continued

CAACGGCACCCACTGGTTCGTGACCCAGCGCAACT

TCTACGAGCCCCAGATCATCACCACCGACAACACC

TTCGTGTCCGGCAACTGCGACGTGGTGATCGGCAT

CGTGAACAACACCGTGTACGACCCCCTGCAGCCCG

AGCTGGACTCCTTCAAGGAGGAGCTGGACAAGTAC

TTCAAGAACCACACCTCCCCCGACGTGGACCTGGG

CGACATCTCCGGCATCAACGCCTCCGTGGTGAACA

TCCAGAAGGAGATCGACCGCCTGAACGAGGTGGCC

AAGAACCTGAACGAGTCCCTGATCGACCTGCAGGA

GCTGGGCAAGTACGAGCAGTACATCAAGTGGCCCT

GGTACATCTGGCTGGGCTTCATCGCCGGCCTGATC

GCCATCGTGATGGTGACCATCATGCTGTGCTGCAT

GACCTCCTGCTGCTCCTGCCTGAAGGGCTGCTGCT

CCTGCGGCTCCTGCTGCAAGTTCGACGAGGACGAC

TCCGAGCCCGTGCTGAAGGGCGTGAAGCTGCACTA

CACCtaa

Full-length WT S protein mRNA-
coding DNA sequence(SEQ ID NO: 2):
aGcATAAAAGTCTCAACACAACATATACAAAACAA

ACGAATCTCAAGCAATCAAGCATTCTACTTCTATT

GCAGCAATTTAAATCATTTCTTTTAAAGCAAAAGC

AATTTTCTGAAAATTTTCACCATTTACGAACGATA

GCGCTATGTTCGTGTTCCTGGTGCTGCTGCCCCTG

GTGTCCTCCCAGTGCGTGAACCTGACCACCCGCAC

CCAGCTGCCCCCCGCCTACACCAACTCCTTCACCC

GCGGCGTGTACTACCCCGACAAGGTGTTCCGCTCC

TCCGTGCTGCACTCCACCCAGGACCTGTTCCTGCC

CTTCTTCTCCAACGTGACCTGGTTCCACGCCATCC

ACGTGTCCGGCACCAACGGCACCAAGCGgTTCGAC

AACCCCGTGCTGCCCTTCAACGACGGCGTGTACTT

CGCCTCCACCGAGAAGTCCAACATCATCCGCGGCT

GGATCTTCGGCACCACCCTGGACTCCAAGACCCAG

TCCCTGCTGATCGTGAACAACGCCACCAACGTGGT

GATCAAGGTGTGCGAGTTCCAGTTCTGCAACGACC

CCTTCCTGGGCGTGTACTACCACAAGAACAACAAG

TCCTGGATGGAGTCCGAGTTCCGCGTGTACTCCTC

CGCCAACAACTGCACCTTCGAGTACGTGTCCCAGC

CCTTCCTGATGGACCTGGAGGGCAAGCAGGGCAAC

TTCAAGAACCTGCGCGAGTTCGTGTTCAAGAACAT

CGACGGCTACTTCAAGATCTACTCCAAGCACACCC

CCATCAACCTGGTGCGCGACCTGCCCCAGGGCTTC

-continued

TCCGCCCTGGAGCCCCTGGTGGACCTGCCCATCGG

CATCAACATCACCCGCTTCCAGACCCTGCTGGCCC

TGCACCGCTCCTACCTGACCCCCGGCGACTCCTCC

TCCGGCTGGACCGCCGGCGCCGCCGCCTACTACGT

GGGCTACCTGCAGCCCCGCACCTTCCTGCTGAAGT

ACAACGAGAACGGCACCATCACCGACGCCGTGGAC

TGCGCCCTGGACCCCCTGTCCGAGACCAAGTGCAC

CCTGAAGTCCTTCACCGTGGGAGAAGGGCATCTACC

AGACCTCCAACTTCCGCGTGCAGCCCACCGAGTCC

ATCGTGCGCTTCCCCAACATCACCAACCTGTGCCC

CTTCGGCGAGGTGTTCAACGCCACCCGCTTCGCCT

CCGTGTACGCCTGGAACCGCAAGCGCATCTCCAAC

TGCGTGGCCGACTACTCCGTGCTGTACAACTCCGC

CTCCTTCTCCACCTTCAAGTGCTACGGCGTGTCCC

CCACCAAGCTGAACGACCTGTGCTTCACCAACGTG

TACGCCGACTCCTTCGTGATCCGCGGCGACGAGGT

GCGCCAGATCGCCCCCGGCCAGACCGGCAAGATCG

CCGACTACAACTACAAGCTGCCCGACGACTTCACC

GGCTGCGTGATCGCCTGGAACTCCAACAACCTGGA

CTCCAAGGTGGGCGGCAACTACAACTACCTGTACC

GCCTGTTCCGCAAGTCCAACCTGAAGCCCTTCGAG

CGCGACATCTCCACCGAGATCTACCAGGCCGGCTC

CACCCCCTGCAACGGCGTGGAGGGCTTCAACTGCT

ACTTCCCCCTGCAGTCCTACGGCTTCCAGCCCACC

AACGGCGTGGGCTACCAGCCCTACCGCGTGGTGGT

GCTGTCCTTCGAGCTGCTGCACGCCCCCGCCACCG

TGTGCGGCCCCAAGAAGTCCACCAACCTGGTGAAG

AACAAGTGCGTGAACTTCAACTTCAACGGCCTGAC

CGGCACCGGCGTGCTGACCGAGTCCAACAAGAAGT

TCCTGCCCTTCCAGCAGTTCGGCCGCGACATCGCC

GACACCACCGACGCCGTGCGCGACCCCCAGACCCT

GGAGATCCTGGACATCACCCCCTGCTCCTTCGGCG

GCGTGTCCGTGATCACCCCCGGCACCAACACCTCC

AACCAGGTGGCCGTGCTGTACCAGGACGTGAACTG

CACCGAGGTGCCCGTGGCCATCCACGCCGACCAGC

TGACCCCCACCTGGCGCGTGTACTCCACCGGCTCC

AACGTGTTCCAGACCCGCGCCGGCTGCCTGATCGG

CGCCGAGCACGTGAACAACTCCTACGAGTGCGACA

TCCCCATCGGCGCCGGCATCTGCGCCTCCTACCAG

ACCCAGACCAACTCCCCCCGCCGCGCCCGCTCCGT

GGCCTCCCAGTCCATCATCGCCTACACCATGTCCC

-continued

TGGGCGCCGAGAACTCCGTGGCCTACTCCAACAAC

TCCATCGCCATCCCCACCAACTTCACCATCTCCGT

GACCACCGAGATCCTGCCCGTGTCCATGACCAAGA

CCTCCGTGGACTGCACCATGTACATCTGCGGCGAC

TCCACCGAGTGCTCCAACCTGCTGCTGCAGTACGG

CTCCTTCTGCACCCAGCTGAACCGCGCCCTGACCG

GCATCGCCGTGGAGCAGGACAAGAACACCCAGGAG

GTGTTCGCCCAGGTGAAGCAGATCTACAAGACCCC

CCCCATCAAGGACTTCGGCGGCTTCAACTTCTCCC

AGATCCTGCCCGACCCCTCCAAGCCCTCCAAGCGg

TCCTTCATCGAGGACCTGCTGTTCAACAAGGTGAC

CCTGGCCGACGCCGGCTTCATCAAGCAGTACGGCG

ACTGCCTGGGCGACATCGCCGCCCGCGACCTGATC

TGCGCCCAGAAGTTCAACGGCCTGACCGTGCTGCC

CCCCCTGCTGACCGACGAGATGATCGCCCAGTACA

CCTCCGCCCTGCTGGCCGGCACCATCACCTCCGGC

TGGACCTTCGGCGCCGGCGCCGCCCTGCAGATCCC

CTTCGCCATGCAGATGGCCTACCGCTTCAACGGCA

TCGGCGTGACCCAGAACGTGCTGTACGAGAACCAG

AAGCTGATCGCCAACCAGTTCAACTCCGCCATCGG

CAAGATCCAGGACTCCCTGTCCTCCACCGCCTCCG

CCCTGGGCAAGCTGCAGGACGTGGTGAACCAGAAC

GCCCAGGCCCTGAACACCCTGGTGAAGCAGCTGTC

CTCCAACTTCGGCGCCATCTCCTCCGTGCTGAACG

ACATCCTGTCCCGCCTGGACAAGGTGGAGGCCGAG

GTGCAGATCGACCGCCTGATCACCGGCCGCCTGCA

GTCCCTGCAGACCTACGTGACCCAGCAGCTGATCC

GCGCCGCCGAGATCCGCGCCTCCGCCAACCTGGCC

GCCACCAAGATGTCCGAGTGCGTGCTGGGCCAGTC

CAAGCGCGTGGACTTCTGCGGCAAGGGCTACCACC

TGATGTCCTTCCCCCAGTCCGCCCCCCACGGCGTG

GTGTTCCTGCACGTGACCTACGTGCCCGCCCAGGA

GAAGAACTTCACCACCGCCCCCGCCATCTGCCACG

ACGGCAAGGCCCACTTCCCCCGCGAGGGCGTGTTC

GTGTCCAACGGCACCCACTGGTTCGTGACCCAGCG

CAACTTCTACGAGCCCCAGATCATCACCACCGACA

ACACCTTCGTGTCCGGCAACTGCGACGTGGTGATC

GGCATCGTGAACAACACCGTGTACGACCCCCTGCA

GCCCGAGTGGACTCCTTCAAGGAGGAGCTGGACA

AGTACTTCAAGAACCACACCTCCCCCGACGTGGAC

-continued

CTGGGCGACATCTCCGGCATCAACGCCTCCGTGGT

GAACATCCAGAAGGAGATCGACCGCCTGAACGAGG

TGGCCAAGAACCTGAACGAGTCCCTGATCGACCTG

CAGGAGCTGGGCAAGTACGAGCAGTACATCAAGTG

GCCCTGGTACATCTGGCTGGGCTTCATCGCCGGCC

TGATCGCCATCGTGATGGTGACCATCATGCTGTGC

TGCATGACCTCCTGCTGCTCCTGCCTGAAGGGCTG

CTGCTCCTGCGGCTCCTGCTGCAAGTTCGACGAGG

ACGACTCCGAGCCCGTGCTGAAGGGCGTGAAGCTG

CACTACACCtaaactagtAGTGACTGACTAGGATC

TGGTTACCACTAAACCAGCCTCAAGAACACCCGAA

TGGAGTCTCTAAGCTACATAATACCAACTTACACT

TACAAAATGTTGTCCCCCAAAATGTAGCCATTCGT

ATCTGCTCCTAATAAAAAGAAAGTTTCTTCACATT

CTAAAAAAAAAAAAAAAAAAAAAAAAAAAAAAAAAA

AAAAAAAAAAAAAAAAAAAAAAAAAAAAAAAAAAAA

AAAAAAAAAAAAAAAAAAAAAAAAAAAAAAAA

Full-length WT S protein AA
sequence (SEQ ID NO: 3):
MFVFLVLLPLVSSQCVNLTTRTQLPPAYTNSFTRG

VYYPDKVFRSSVLHSTQDLFLPFFSNVTWFHAIHV

SGTNGTKRFDNPVLPFNDGVYFASTEKSNIIRGWI

FGTTLDSKTQSLLIVNNATNVVIKVCEFQFCNDPF

LGVYYHKNNKSWMESEFRVYSSANNCTFEYVSQPF

LMDLEGKQGNFKNLREFVFKNIDGYFKIYSKHTPI

NLVRDLPQGFSALEPLVDLPIGINITRFQTLLALH

RSYLTPGDSSSGWTAGAAAYYVGYLQPRTFLLKYN

ENGTITDAVDCALDPLSETKCTLKSFTVEKGIYQT

SNFRVQPTESIVRFPNITNLCPFGEVFNATRFASV

YAWNRKRISNCVADYSVLYNSASFSTFKCYGVSPT

KLNDLCFTNVYADSFVIRGDEVRQIAPGQTGKIAD

YNYKLPDDFTGCVIAWNSNNLDSKVGGNYNYLYRL

FRKSNLKPFERDISTEIYQAGSTPCNGVEGFNCYF

PLQSYGFQPTNGVGYQPYRVVVLSFELLHAPATVC

GPKKSTNLVKNKCVNFNFNGLTGTGVLTESNKKFL

PFQQFGRDIADTTDAVRDPQTLEILDITPCSFGGV

SVITPGTNTSNQVAVLYQDVNCTEVPVAIHADQLT

PTWRVYSTGSNVFQTRAGCLIGAEHVNNSYECDIP

IGAGICASYQTQTNSPRRARSVASQSIIAYTMSLG

AENSVAYSNNSIAIPTNFTISVTTEILPVSMTKTS

VDCTMYICGDSTECSNLLLQYGSFCTQLNRALTGI

AVEQDKNTQEVFAQVKQIYKTPPIKDFGGFNFSQI

-continued

LPDPSKPSKRSFIEDLLFNKVTLADAGFIKQYGDC

LGDIAARDLICAQKFNGLTVLPPLLTDEMIAQYTS

ALLAGTITSGWTFGAGAALQIPFAMQMAYRFNGIG

VTQNVLYENQKLIANQFNSAIGKIQDSLSSTASAL

GKLQDVVNQNAQALNTLVKQLSSNFGAISSVLNDI

LSRLDKVEAEVQIDRLITGRLQSLQTYVTQQLIRA

AEIRASANLAATKMSECVLGQSKRVDFCGKGYHLM

SFPQSAPHGVVFLHVTYVPAQEKNFTTAPAICHDG

KAHFPREGVFVSNGTHWFVTQRNFYEPQUITTDNT

FVSGNCDVVIGIVNNTVYDPLQPELDSFKEELDKY

FKNHTSPDVDLGDISGINASVVNIQKEIDRLNEVA

KNLNESLIDLQELGKYEQYIKWPWYIWLGFIAGLI

AIVMVTIMLCCMTSCCSCLKGCCSCGSCCKFDEDD

SEPVLKGVKLHYT

Full-length S protein deleted furin
cleavage site DNA sequence
(SEQ ID NO: 4):
ATGTTCGTGTTCCTGGTGCTGCTGCCCCTGGTGTC

CTCCCAGTGCGTGAACCTGACCACCCGCACCCAGC

TGCCCCCCGCCTACACCAACTCCTTCACCCGCGGC

GTGTACTACCCCGACAAGGTGTTCCGCTCCTCCGT

GCTGCACTCCACCCAGGACCTGTTCCTGCCCTTCT

TCTCCAACGTGACCTGGTTCCACGCCATCCACGTG

TCCGGCACCAACGGCACCAAGCGgTTCGACAACCC

CGTGCTGCCCTTCAACGACGGCGTGTACTTCGCCT

CCACCGAGAAGTCCAACATCATCCGCGGCTGGATC

TTCGGCACCACCCTGGACTCCAAGACCCAGTCCCT

GCTGATCGTGAACAACGCCACCAACGTGGTGATCA

AGGTGTGCGAGTTCCAGTTCTGCAACGACCCCTTC

CTGGGCGTGTACTACCACAAGAACAACAAGTCCTG

GATGGAGTCCGAGTTCCGCGTGTACTCCTCCGCCA

ACAACTGCACCTTCGAGTACGTGTCCCAGCCCTTC

CTGATGGACCTGGAGGGCAAGCAGGGCAACTTCAA

GAACCTGCGCGAGTTCGTGTTCAAGAACATCGACG

GCTACTTCAAGATCTACTCCAAGCACACCCCCATC

AACCTGGTGCGCGACCTGCCCCAGGGCTTCTCCGC

CCTGGAGCCCCTGGTGGACCTGCCCATCGGCATCA

ACATCACCCGCTTCCAGACCCTGCTGGCCCTGCAC

CGCTCCTACCTGACCCCCGGCGACTCCTCCTCCGG

CTGGACCGCCGGCGCCGCCGCCTACTACGTGGGCT

ACCTGCAGCCCCGCACCTTCCTGCTGAAGTACAAC

GAGAACGGCACCATCACCGACGCCGTGGACTGCGC

-continued

CCTGGACCCCCTGTCCGAGACCAAGTGCACCCTGA

AGTCCTTCACCGTGGAGAAGGGCATCTACCAGACC

TCCAACTTCCGCGTGCAGCCCACCGAGTCCATCGT

GCGCTTCCCCAACATCACCAACCTGTGCCCCTTCG

GCGAGGTGTTCAACGCCACCCGCTTCGCCTCCGTG

TACGCCTGGAACCGCAAGCGCATCTCCAACTGCGT

GGCCGACTACTCCGTGCTGTACAACTCCGCCTCCT

TCTCCACCTTCAAGTGCTACGGCGTGTCCCCCACC

AAGCTGAACGACCTGTGCTTCACCAACGTGTACGC

CGACTCCTTCGTGATCCGCGGCGACGAGGTGCGCC

AGATCGCCCCCGGCCAGACCGGCAAGATCGCCGAC

TACAACTACAAGCTGCCCGACGACTTCACCGGCTG

CGTGATCGCCTGGAACTCCAACAACCTGGACTCCA

AGGTGGGCGGCAACTACAACTACCTGTACCGCCTG

TTCCGCAAGTCCAACCTGAAGCCCTTCGAGCGCGA

CATCTCCACCGAGATCTACCAGGCCGGCTCCACCC

CCTGCAACGGCGTGGAGGGCTTCAACTGCTACTTC

CCCCTGCAGTCCTACGGCTTCCAGCCCACCAACGG

CGTGGGCTACCAGCCCTACCGCGTGGTGGTGCTGT

CCTTCGAGCTGCTGCACGCCCCCGCCACCGTGTGC

GGCCCCAAGAAGTCCACCAACCTGGTGAAGAACAA

GTGCGTGAACTTCAACTTCAACGGCCTGACCGGCA

CCGGCGTGCTGACCGAGTCCAACAAGAAGTTCCTG

CCCTTCCAGCAGTTCGGCCGCGACATCGCCGACAC

CACCGACGCCGTGCGCGACCCCCAGACCCTGGAGA

TCCTGGACATCACCCCCTGCTCCTTCGGCGGCGTG

TCCGTGATCACCCCCGGCACCAACACCTCCAACCA

GGTGGCCGTGCTGTACCAGGACGTGAACTGCACCG

AGGTGCCCGTGGCCATCCACGCCGACCAGCTGACC

CCCACCTGGCGCGTGTACTCCACCGGCTCCAACGT

GTTCCAGACCCGCGCCGGCTGCCTGATCGGCGCCG

AGCACGTGAACAACTCCTACGAGTGCGACATCCCC

ATCGGCGCCGGCATCTGCGCCTCCTACCAGACCCA

GACCAACTCCCCCGCCTCCGTGGCCTCCCAGTCCA

TCATCGCCTACACCATGTCCCTGGGCGCCGAGAAC

TCCGTGGCCTACTCCAACAACTCCATCGCCATCCC

CACCAACTTCACCATCTCCGTGACCACCGAGATCC

TGCCCGTGTCCATGACCAAGACCTCCGTGGACTGC

ACCATGTACATCTGCGGCGACTCCACCGAGTGCTC

CAACCTGCTGCTGCAGTACGGCTCCTTCTGCACCC

-continued

```
AGCTGAACCGCGCCCTGACCGGCATCGCCGTGGAG

CAGGACAAGAACACCCAGGAGGTGTTCGCCCAGGT

GAAGCAGATCTACAAGACCCCCCCCATCAAGGACT

TCGGCGGCTTCAACTTCTCCCAGATCCTGCCCGAC

CCCTCCAAGCCCTCCAAGCGgTCCTTCATCGAGGA

CCTGCTGTTCAACAAGGTGACCCTGGCCGACGCCG

GCTTCATCAAGCAGTACGGCGACTGCCTGGGCGAC

ATCGCCGCCCGCGACCTGATCTGCGCCCAGAAGTT

CAACGGCCTGACCGTGCTGCCCCCCCTGCTGACCG

ACGAGATGATCGCCCAGTACACCTCCGCCCTGCTG

GCCGGCACCATCACCTCCGGCTGGACCTTCGGCGC

CGGCGCCGCCCTGCAGATCCCCTTCGCCATGCAGA

TGGCCTACCGCTTCAACGGCATCGGCGTGACCCAG

AACGTGCTGTACGAGAACCAGAAGCTGATCGCCAA

CCAGTTCAACTCCGCCATCGGCAAGATCCAGGACT

CCCTGTCCTCCACCGCCTCCGCCCTGGGCAAGCTG

CAGGACGTGGTGAACCAGAACGCCCAGGCCCTGAA

CACCCTGGTGAAGCAGCTGTCCTCCAACTTCGGCG

CCATCTCCTCCGTGCTGAACGACATCCTGTCCCGC

CTGGACAAGGTGGAGGCCGAGGTGCAGATCGACCG

CCTGATCACCGGCCGCCTGCAGTCCCTGCAGACCT

ACGTGACCCAGCAGCTGATCCGCGCCGCCGAGATC

CGCGCCTCCGCCAACCTGGCCGCCACCAAGATGTC

CGAGTGCGTGCTGGGCCAGTCCAAGCGCGTGGACT

TCTGCGGCAAGGGCTACCACCTGATGTCCTTCCCC

CAGTCCGCCCCCCACGGCGTGGTGTTCCTGCACGT

GACCTACGTGCCCGCCCAGGAGAAGAACTTCACCA

CCGCCCCCGCCATCTGCCACGACGGCAAGGCCCAC

TTCCCCCGCGAGGGCGTGTTCGTGTCCAACGGCAC

CCACTGGTTCGTGACCCAGCGCAACTTCTACGAGC

CCCAGATCATCACCACCGACAACACCTTCGTGTCC

GGCAACTGCGACGTGGTGATCGGCATCGTGAACAA

CACCGTGTACGACCCCCTGCAGCCCGAGCTGGACT

CCTTCAAGGAGGAGCTGGACAAGTACTTCAAGAAC

CACACCTCCCCCGACGTGGACCTGGGCGACATCTC

CGGCATCAACGCCTCCGTGGTGAACATCCAGAAGG

AGATCGACCGCCTGAACGAGGTGGCCAAGAACCTG

AACGAGTCCCTGATCGACCTGCAGGAGCTGGGCAA

GTACGAGCAGTACATCAAGTGGCCCTGGTACATCT

GGCTGGGCTTCATCGCCGGCCTGATCGCCATCGTG

ATGGTGACCATCATGCTGTGCTGCATGACCTCCTG
```

-continued

```
CTGCTCCTGCCTGAAGGGCTGCTGCTCCTGCGGCT

CCTGCTGCAAGTTCGACGAGGACGACTCCGAGCCC

GTGCTGAAGGGCGTGAAGCTGCACTACACCtaa
```

Full-length S protein deleted furin
cleavage site mRNA-coding DNA
sequence (SEQ ID NO: 5):

```
aGcATAAAAGTCTCAACACAACATATACAAAACAA

ACGAATCTCAAGCAATCAAGCATTCTACTTCTATT

GCAGCAATTTAAATCATTTCTTTTAAAGCAAAAGC

AATTTTCTGAAAATTTTCACCATTTACGAACGATA

GCGCTATGTTCGTGTTCCTGGTGCTGCTGCCCCTG

GTGTCCTCCCAGTGCGTGAACCTGACCACCCGCAC

CCAGCTGCCCCCCGCCTACACCAACTCCTTCACCC

GCGGCGTGTACTACCCCGACAAGGTGTTCCGCTCC

TCCGTGCTGCACTCCACCCAGGACCTGTTCCTGCC

CTTCTTCTCCAACGTGACCTGGTTCCACGCCATCC

ACGTGTCCGGCACCAACGGCACCAAGCGgTTCGAC

AACCCCGTGCTGCCCTTCAACGACGGCGTGTACTT

CGCCTCCACCGAGAAGTCCAACATCATCCGCGGCT

GGATCTTCGGCACCACCCTGGACTCCAAGACCCAG

TCCCTGCTGATCGTGAACAACGCCACCAACGTGGT

GATCAAGGTGTGCGAGTTCCAGTTCTGCAACGACC

CCTTCCTGGGCGTGTACTACCACAAGAACAACAAG

TCCTGGATGGAGTCCGAGTTCCGCGTGTACTCCTC

CGCCAACAACTGCACCTTCGAGTACGTGTCCCAGC

CCTTCCTGATGGACCTGGAGGGCAAGCAGGGCAAC

TTCAAGAACCTGCGCGAGTTCGTGTTCAAGAACAT

CGACGGCTACTTCAAGATCTACTCCAAGCACACCC

CCATCAACCTGGTGCGCGACCTGCCCCAGGGCTTC

TCCGCCCTGGAGCCCCTGGTGGACCTGCCCATCGG

CATCAACATCACCCGCTTCCAGACCCTGCTGGCCC

TGCACCGCTCCTACCTGACCCCCGGCGACTCCTCC

TCCGGCTGGACCGCCGGCGCCGCCGCCTACTACGT

GGGCTACCTGCAGCCCCGCACCTTCCTGCTGAAGT

ACAACGAGAACGGCACCATCACCGACGCCGTGGAC

TGCGCCCTGGACCCCCTGTCCGAGACCAAGTGCAC

CCTGAAGTCCTTCACCGTGGAGAAGGGCATCTACC

AGACCTCCAACTTCCGCGTGCAGCCCACCGAGTCC

ATCGTGCGCTTCCCCAACATCACCAACCTGTGCCC

CTTCGGCGAGGTGTTCAACGCCACCCGCTTCGCCT

CCGTGTACGCCTGGAACCGCAAGCGCATCTCCAAC

TGCGTGGCCGACTACTCCGTGCTGTACAACTCCGC
```

-continued

```
CTCCTTCTCCACCTTCAAGTGCTACGGCGTGTCCC

CCACCAAGCTGAACGACCTGTGCTTCACCAACGTG

TACGCCGACTCCTTCGTGATCCGCGGCGACGAGGT

GCGCCAGATCGCCCCCGGCCAGACCGGCAAGATCG

CCGACTACAACTACAAGCTGCCCGACGACTTCACC

GGCTGCGTGATCGCCTGGAACTCCAACAACCTGGA

CTCCAAGGTGGGCGGCAACTACAACTACCTGTACC

GCCTGTTCCGCAAGTCCAACCTGAAGCCCTTCGAG

CGCGACATCTCCACCGAGATCTACCAGGCCGGCTC

CACCCCCTGCAACGGCGTGGAGGGCTTCAACTGCT

ACTTCCCCCTGCAGTCCTACGGCTTCCAGCCCACC

AACGGCGTGGGCTACCAGCCCTACCGCGTGGTGGT

GCTGTCCTTCGAGCTGCTGCACGCCCCCGCCACCG

TGTGCGGCCCCAAGAAGTCCACCAACCTGGTGAAG

AACAAGTGCGTGAACTTCAACTTCAACGGCCTGAC

CGGCACCGGCGTGCTGACCGAGTCCAACAAGAAGT

TCCTGCCCTTCCAGCAGTTCGGCCGCGACATCGCC

GACACCACCGACGCCGTGCGCGACCCCCAGACCCT

GGAGATCCTGGACATCACCCCCTGCTCCTTCGGCG

GCGTGTCCGTGATCACCCCCGGCACCAACACCTCC

AACCAGGTGGCCGTGCTGTACCAGGACGTGAACTG

CACCGAGGTGCCCGTGGCCATCCACGCCGACCAGC

TGACCCCCACCTGGCGCGTGTACTCCACCGGCTCC

AACGTGTTCCAGACCCGCGCCGGCTGCCTGATCGG

CGCCGAGCACGTGAACAACTCCTACGAGTGCGACA

TCCCCATCGGCGCCGGCATCTGCGCCTCCTACCAG

ACCCAGACCAACTCCCCCGCCTCCGTGGCCTCCCA

GTCCATCATCGCCTACACCATGTCCCTGGGCGCCG

AGAACTCCGTGGCCTACTCCAACAACTCCATCGCC

ATCCCCACCAACTTCACCATCTCCGTGACCACCGA

GATCCTGCCCGTGTCCATGACCAAGACCTCCGTGG

ACTGCACCATGTACATCTGCGGCGACTCCACCGAG

TGCTCCAACCTGCTGCTGCAGTACGGCTCCTTCTG

CACCCAGCTGAACCGCGCCCTGACCGGCATCGCCG

TGGAGCAGGACAAGAACACCCAGGAGGTGTTCGCC

CAGGTGAAGCAGATCTACAAGACCCCCCCCATCAA

GGACTTCGGCGGCTTCAACTTCTCCCAGATCCTGC

CCGACCCCTCCAAGCCCTCCAAGCGgTCCTTCATC

GAGGACCTGCTGTTCAACAAGGTGACCCTGGCCGA

CGCCGGCTTCATCAAGCAGTACGGCGACTGCCTGG
```

-continued

```
GCGACATCGCCGCCCGCGACCTGATCTGCGCCCAG

AAGTTCAACGGCCTGACCGTGCTGCCCCCCCTGCT

GACCGACGAGATGATCGCCCAGTACACCTCCGCCC

TGCTGGCCGGCACCATCACCTCCGGCTGGACCTTC

GGCGCCGGCGCCGCCCTGCAGATCCCCTTCGCCAT

GCAGATGGCCTACCGCTTCAACGGCATCGGCGTGA

CCCAGAACGTGCTGTACGAGAACCAGAAGCTGATC

GCCAACCAGTTCAACTCCGCCATCGGCAAGATCCA

GGACTCCCTGTCCTCCACCGCCTCCGCCCTGGGCA

AGCTGCAGGACGTGGTGAACCAGAACGCCCAGGCC

CTGAACACCCTGGTGAAGCAGCTGTCCTCCAACTT

CGGCGCCATCTCCTCCGTGCTGAACGACATCCTGT

CCCGCCTGGACAAGGTGGAGGCCGAGGTGCAGATC

GACCGCCTGATCACCGGCCGCCTGCAGTCCCTGCA

GACCTACGTGACCCAGCAGCTGATCCGCGCCGCCG

AGATCCGCGCCTCCGCCAACCTGGCCGCCACCAAG

ATGTCCGAGTGCGTGCTGGGCCAGTCCAAGCGCGT

GGACTTCTGCGGCAAGGGCTACCACCTGATGTCCT

TCCCCCAGTCCGCCCCCCACGGCGTGGTGTTCCTG

CACGTGACCTACGTGCCCGCCCAGGAGAAGAACTT

CACCACCGCCCCCGCCATCTGCCACGACGGCAAGG

CCCACTTCCCCCGCGAGGGCGTGTTCGTGTCCAAC

GGCACCCACTGGTTCGTGACCCAGCGCAACTTCTA

CGAGCCCCAGATCATCACCACCGACAACACCTTCG

TGTCCGGCAACTGCGACGTGGTGATCGGCATCGTG

AACAACACCGTGTACGACCCCCTGCAGCCCGAGCT

GGACTCCTTCAAGGAGGAGCTGGACAAGTACTTCA

AGAACCACACCTCCCCCGACGTGGACCTGGGCGAC

ATCTCCGGCATCAACGCCTCCGTGGTGAACATCCA

GAAGGAGATCGACCGCCTGAACGAGGTGGCCAAGA

ACCTGAACGAGTCCCTGATCGACCTGCAGGAGCTG

GGCAAGTACGAGCAGTACATCAAGTGGCCCTGGTA

CATCTGGCTGGGCTTCATCGCCGGCCTGATCGCCA

TCGTGATGGTGACCATCATGCTGTGCTGCATGACC

TCCTGCTGCTCCTGCCTGAAGGGCTGCTGCTCCTG

CGGCTCCTGCTGCAAGTTCGACGAGGACGACTCCG

AGCCCGTGCTGAAGGGCGTGAAGCTGCACTACACC taaactagtAGTGACTGACTAGGATCTGGTTACCA

CTAAACCAGCCTCAAGAACACCCGAATGGAGTCTC

TAAGCTACATAATACCAACTTACACTTACAAAATG

TTGTCCCCCAAAATGTAGCCATTCGTATCTGCTCC
```

-continued

TAATAAAAAGAAAGTTTCTTCACATTCTAAAAAAA

AAAAAAAAAAAAAAAAAAAAAAAAAAAAAAAAAA

AAAAAAAAAAAAAAAAAAAAAAAAAAAAAAAAAA

AAAAAAAAAAAAAAAAAAAAAAAAA

Full-length S protein deleted furin
cleavage site AA sequence
(SEQ ID NO: 6):
MFVFLVLLPLVSSQCVNLTTRTQLPPAYTNSFTRG

VYYPDKVFRSSVLHSTQDLFLPFFSNVTWFHAIHV

SGTNGTKRFDNPVLPFNDGVYFASTEKSNIIRGWI

FGTTLDSKTQSLLIVNNATNVVIKVCEFQFCNDPF

LGVYYHKNNKSWMESEFRVYSSANNCTFEYVSQPF

LMDLEGKQGNFKNLREFVFKNIDGYFKIYSKHTPI

NLVRDLPQGFSALEPLVDLPIGINITRFQTLLALH

RSYLTPGDSSSGWTAGAAAYYVGYLQPRTFLLKYN

ENGTITDAVDCALDPLSETKCTLKSFTVEKGIYQT

SNFRVQPTESIVRFPNITNLCPFGEVFNATRFASV

YAWNRKRISNCVADYSVLYNSASFSTFKCYGVSPT

KLNDLCFTNVYADSFVIRGDEVRQIAPGQTGKIAD

YNYKLPDDFTGCVIAWNSNNLDSKVGGNYNYLYRL

FRKSNLKPFERDISTEIYQAGSTPCNGVEGFNCYF

PLQSYGFQPTNGVGYQPYRVVVLSFELLHAPATVC

GPKKSTNLVKNKCVNFNFNGLTGTGVLTESNKKFL

PFQQFGRDIADTTDAVRDPQTLEILDITPCSFGGV

SVITPGTNTSNQVAVLYQDVNCTEVPVAIHADQLT

PTWRVYSTGSNVFQTRAGCLIGAEHVNNSYECDIP

IGAGICASYQTQTNSPASVASQSIIAYTMSLGAEN

SVAYSNNSIAIPTNFTISVTTEILPVSMTKTSVDC

TMYICGDSTECSNLLLQYGSFCTQLNRALTGIAVE

QDKNTQEVFAQVKQIYKTPPIKDFGGFNFSQILPD

PSKPSKRSFIEDLLFNKVTLADAGFIKQYGDCLGD

IAARDLICAQKFNGLTVLPPLLTDEMIAQYTSALL

AGTITSGWTFGAGAALQIPFAMQMAYRFNGIGVTQ

NVLYENQKLIANQFNSAIGKIQDSLSSTASALGKL

QDVVNQNAQALNTLVKQLSSNFGAISSVLNDILSR

LDKVEAEVQIDRLITGRLQSLQTYVTQQLIRAAEI

RASANLAATKMSECVLGQSKRVDFCGKGYHLMSFP

QSAPHGVVFLHVTYVPAQEKNFTTAPAICHDGKAH

FPREGVFVSNGTHWFVTQRNFYEPQIITTDNTFVS

GNCDVVIGIVNNTVYDPLQPELDSFKEELDKYFKN

HTSPDVDLGDISGINASVVNIQKEIDRLNEVAKNL

NESLIDLQELGKYEQYIKWPWYIWLGFIAGLIAIV

-continued

MVTIMLCCMTSCCSCLKGCCSCGSCCKFDEDDSEP

VLKGVKLHYT

Soluble RBD of S protein DNA
sequence(SEQ ID NO: 7):
ATGTTCGTGTTCCTGGTGCTGCTGCCCCTGGTGTC

CTCCCAGCGCGTGCAGCCCACCGAGTCCATCGTGC

GCTTCCCCAACATCACCAACCTGTGCCCCTTCGGC

GAGGTGTTCAACGCCACCCGCTTCGCCTCCGTGTA

CGCCTGGAACCGCAAGCGCATCTCCAACTGCGTGG

CCGACTACTCCGTGCTGTACAACTCCGCCTCCTTC

TCCACCTTCAAGTGCTACGGCGTGTCCCCCACCAA

GCTGAACGACCTGTGCTTCACCAACGTGTACGCCG

ACTCCTTCGTGATCCGCGGCGACGAGGTGCGCCAG

ATCGCCCCCGGCCAGACCGGCAAGATCGCCGACTA

CAACTACAAGCTGCCCGACGACTTCACCGGCTGCG

TGATCGCCTGGAACTCCAACAACCTGGACTCCAAG

GTGGGCGGCAACTACAACTACCTGTACCGCCTGTT

CCGCAAGTCCAACCTGAAGCCCTTCGAGCGCGACA

TCTCCACCGAGATCTACCAGGCCGGCTCCACCCCC

TGCAACGGCGTGGAGGGCTTCAACTGCTACTTCCC

CCTGCAGTCCTACGGCTTCCAGCCCACCAACGGCG

TGGGCTACCAGCCCTACCGCGTGGTGGTGCTGTCC

TTCGAGCTGCTGCACGCCCCCGCCACCGTGTGCGG

CCCCAAGAAGTCCACCAACCTGGTGAAGAACAAGT

GCGTGAACTTCtaa

Soluble RBD of S protein mRNA-
coding DNA sequence (SEQ ID NO: 8):
aGcATAAAAGTCTCAACACAACATATACAAACAA

ACGAATCTCAAGCAATCAAGCATTCTACTTCTATT

GCAGCAATTTAAATCATTTCTTTTAAAGCAAAAGC

AATTTTCTGAAAATTTTCACCATTTACGAACGATA

GCGCTATGTTCGTGTTCCTGGTGCTGCTGCCCCTG

GTGTCCTCCCAGCGCGTGCAGCCCACCGAGTCCAT

CGTGCGCTTCCCCAACATCACCAACCTGTGCCCCT

TCGGCGAGGTGTTCAACGCCACCCGCTTCGCCTCC

GTGTACGCCTGGAACCGCAAGCGCATCTCCAACTG

CGTGGCCGACTACTCCGTGCTGTACAACTCCGCCT

CCTTCTCCACCTTCAAGTGCTACGGCGTGTCCCCC

ACCAAGCTGAACGACCTGTGCTTCACCAACGTGTA

CGCCGACTCCTTCGTGATCCGCGGCGACGAGGTGC

GCCAGATCGCCCCCGGCCAGACCGGCAAGATCGCC

GACTACAACTACAAGCTGCCCGACGACTTCACCGG

-continued

```
CTGCGTGATCGCCTGGAACTCCAACAACCTGGACT

CCAAGGTGGGCGGCAACTACAACTACCTGTACCGC

CTGTTCCGCAAGTCCAACCTGAAGCCCTTCGAGCG

CGACATCTCCACCGAGATCTACCAGGCCGGCTCCA

CCCCCTGCAACGGCGTGGAGGGCTTCAACTGCTAC

TTCCCCCTGCAGTCCTACGGCTTCCAGCCCACCAA

CGGCGTGGGCTACCAGCCCTACCGCGTGGTGGTGC

TGTCCTTCGAGCTGCTGCACGCCCCCGCCACCGTG

TGCGGCCCCAAGAAGTCCACCAACCTGGTGAAGAA

CAAGTGCGTGAACTTCtaaactagtAGTGACTGAC

TAGGATCTGGTTACCACTAAACCAGCCTCAAGAAC

ACCCGAATGGAGTCTCTAAGCTACATAATACCAAC

TTACACTTACAAAATGTTGTCCCCCAAAATGTAGC

CATTCGTATCTGCTCCTAATAAAAAGAAAGTTTCT

TCACATTCTAAAAAAAAAAAAAAAAAAAAAAAAAA

AAAAAAAAAAAAAAAAAAAAAAAAAAAAAAAAAAA
```

-continued

```
AAAAAAAAAAAAAAAAAAAAAAAAAAAAAAAAAAAA

AAAAA
```

Soluble RBD of S protein AA
sequence (SEQ ID NO: 9):
MFVFLVLLPLVSSQRVQPTESIVRFPNITNLCPFG

EVFNATRFASVYAWNRKRISNCVADYSVLYNSASF

STFKCYGVSPTKLNDLCFTNVYADSFVIRGDEVRQ

IAPGQTGKIADYNYKLPDDFTGCVIAWNSNNLDSK

VGGNYNYLYRLFRKSNLKPFERDISTEIYQAGSTP

CNGVEGFNCYFPLQSYGFQPTNGVGYQPYRVVVLS

FELLHAPATVCGPKKSTNLVKNKCVNF

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A composition for inducing an immune response against severe acute respiratory syndrome coronavirus 2 (SARS-CoV-2) in a subject, the composition comprising at least one isolated nucleoside-modified mRNA encoding at least one SARS-CoV-2 antigen, wherein the at least one nucleoside modified mRNA comprises a nucleotide sequence transcribed from a nucleotide sequence selected from the group consisting of SEQ ID NO: 1, SEQ ID NO: 2, SEQ ID NO: 4, SEQ ID NO: 5, SEQ ID NO: 7 and SEQ ID NO: 8.

2. The composition of claim 1, wherein the at least one isolated nucleoside-modified mRNA comprises pseudouridine or 1-methyl-pseudouridine.

3. The composition of claim 1, wherein the at least one isolated nucleoside-modified mRNA is a purified nucleoside-modified mRNA.

4. The composition of claim 1, wherein the composition further comprises an adjuvant.

5. The composition of claim 1, further comprising a lipid nanoparticle (LNP), wherein the at least one nucleoside-modified mRNA is encapsulated within the LNP.

6. The composition of claim 1, wherein the composition is a vaccine.

7. A method of inducing an adaptive immune response against severe acute respiratory syndrome coronavirus 2 (SARS-CoV-2) in a subject comprising administering to the subject an effective amount of the composition of claim 1.

8. The method of claim 7, wherein the at least one isolated nucleoside-modified mRNA comprises pseudouridine or 1-methyl-pseudouridine.

9. The method of claim 7, wherein the at least one isolated nucleoside-modified RNA is a purified nucleoside-modified mRNA.

10. The method of claim 7, wherein the method further comprises administering to the subject an effective amount of an adjuvant.

11. The method of claim 7, wherein the composition further comprises a lipid nanoparticle (LNP), wherein the at least one nucleoside modified mRNA is encapsulated within the LNP.

12. The method of claim 7, wherein the composition is administered by a delivery route selected from the group consisting of intradermal, subcutaneous, inhalation, intranasal, and intramuscular.

* * * * *

SEQUENCE LISTING

```
<160> NUMBER OF SEQ ID NOS: 12

<210> SEQ ID NO 1
<211> LENGTH: 3822
<212> TYPE: DNA
<213> ORGANISM: Artificial Sequence
<220> FEATURE:
<223> OTHER INFORMATION: Chemically Synthesized, Full-length WT S
      protein DNA sequence

<400> SEQUENCE: 1
atgttcgtgt tcctggtgct gctgcccctg gtgtcctccc agtgcgtgaa cctgaccacc      60
cgcacccagc tgcccccgc ctacaccaac tccttcaccc gcggcgtgta ctaccccgac     120
aaggtgttcc gctcctccgt gctgcactcc acccaggacc tgttcctgcc cttcttctcc     180
aacgtgacct ggttccacgc catccacgtg tccggcacca acggcaccaa gcggttcgac     240 aacccgtgc tgcccttcaa cgacggcgtg tacttcgcct ccaccgagaa gtccaacatc     300
atccgcggct ggatcttcgg caccaccctg gactccaaga cccagtccct gctgatcgtg     360
aacaacgcca ccaacgtggt gatcaaggtg tgcgagttcc agttctgcaa cgaccccttc     420
ctgggcgtgt actaccacaa gaacaacaag tcctggatgg agtccgagtt ccgcgtgtac     480
tcctccgcca caactgcac cttcgagtac gtgtcccagc ccttcctgat ggacctggag     540
ggcaagcagg gcaacttcaa gaacctgcgc gagttcgtgt tcaagaacat cgacggctac     600
ttcaagatct actccaagca caccccatc aacctggtgc gcgacctgcc ccagggcttc     660 tccgcctgg agccctggt ggacctgccc atcggcatca acatcacccg cttccagacc     720
ctgctggccc tgcaccgctc ctacctgacc cccggcgact cctcctccgg ctggaccgcc     780
ggcgccgccg cctactacgt gggctacctg cagccccgca ccttcctgct gaagtacaac     840
gagaacggca ccatcaccga cgccgtggac tgcgcccctgg acccctgtc cgagaccaag     900 tgcaccctga agtccttcac cgtggagaag ggcatctacc agacctccaa cttccgcgtg     960
```

```
cagcccaccg agtccatcgt gcgcttcccc aacatcacca acctgtgccc cttcggcgag    1020
gtgttcaacg ccacccgctt cgcctccgtg tacgcctgga accgcaagcg catctccaac    1080
tgcgtggccg actactccgt gctgtacaac tccgcctcct tctccacctt caagtgctac    1140
ggcgtgtccc ccaccaagct gaacgacctg tgcttcacca acgtgtacgc cgactccttc    1200
gtgatccgcg gcgacgaggt gcgccagatc gcccccggcc agaccggcaa gatcgccgac    1260
tacaactaca agctgcccga cgacttcacc ggctgcgtga tcgcctggaa ctccaacaac    1320
ctggactcca aggtgggcgg caactacaac tacctgtacc gcctgttccg caagtccaac    1380
ctgaagccct tcgagcgcga catctccacc gagatctacc aggccggctc cacccccctgc    1440 aacggcgtgg agggcttcaa ctgctacttc cccctgcagt cctacggctt ccagcccacc    1500
aacggcgtgg gctaccagcc ctaccgcgtg gtggtgctgt ccttcgagct gctgcacgcc    1560
cccgccaccg tgtgcggccc caagaagtcc accaacctgg tgaagaacaa gtgcgtgaac    1620
ttcaacttca acggcctgac cggcaccggc gtgctgaccg agtccaacaa gaagttcctg    1680
cccttccagc agttcggccg cgacatcgcc gacaccaccg acgccgtgcg cgacccccag    1740
accctggaga tcctggacat cacccccctgc tccttcggcg gcgtgtccgt gatcacccccc    1800 ggcaccaaca cctccaacca ggtggccgtg ctgtaccagg acgtgaactg caccgaggtg    1860
cccgtggcca tccacgccga ccagctgacc cccacctggc gcgtgtactc caccggctcc    1920
aacgtgttcc agacccgcgc cggctgcctg atcggcgccg agcacgtgaa caactcctac    1980
gagtgcgaca tccccatcgg cgccggcatc tgcgcctcct accagaccca gaccaactcc    2040
ccccgccgcg cccgctccgt ggcctcccag tccatcatcg cctacaccat gtccctgggc    2100
gccgagaact ccgtggccta ctccaacaac tccatcgcca tccccaccaa cttcaccatc    2160
tccgtgacca ccgagatcct gcccgtgtcc atgaccaaga cctccgtgga ctgcaccatg    2220
tacatctgcg gcgactccac cgagtgctcc aacctgctgc tgcagtacgg ctccttctgc    2280
acccagctga accgcgccct gaccggcatc gccgtggagc aggacaagaa cacccaggag    2340
gtgttcgccc aggtgaagca gatctacaag accccccccca tcaaggactt cggcggcttc    2400
aacttctccc agatcctgcc cgaccccctcc aagccctcca gcggtccttt catcgaggac    2460
ctgctgttca acaaggtgac cctggccgac gccggcttca tcaagcagta cggcgactgc    2520
ctgggcgaca tcgccgcccg cgacctgatc tgcgcccaga gttcaacgg cctgaccgtg    2580 ctgcccccccc tgctgaccga cgagatgatc gcccagtaca cctccgccct gctggccggc    2640
accatcaccc tccggctggac cttcggcgcc ggcgccgccc tgcagatccc cttcgccatg    2700
cagatggcct accgcttcaa cggcatcggc gtgacccaga acgtgctgta cgagaaccag    2760
aagctgatcg ccaaccagtt caactccgcc atcggcaaga tccaggactc cctgtcctcc    2820
accgcctccg ccctgggcaa gctgcaggac gtggtgaacc agaacgccca ggccctgaac    2880
accctggtga gcagctgtc ctccaacttc ggcgccatct cctccgtgct gaacgacatc    2940
ctgtcccgcc tggacaaggt ggaggccgag gtgcagatcg accgcctgat caccggccgc    3000
ctgcagtccc tgcagaccta cgtgacccag cagctgatcc gcgccgccga gatccgcgcc    3060
tccgccaacc tggccgccac caagatgtcc gagtgcgtgc tgggccagtc caagcgcgtg    3120
gacttctgcg gcaagggcta ccacctgatg tccttccccc agtccgcccc ccacggcgtg    3180
gtgttcctgc acgtgaccta cgtgcccgcc caggagaaga acttcaccac cgcccccgcc    3240
atctgccacg acggcaaggc ccacttcccc cgcgagggcg tgttcgtgtc caacggcacc    3300
```

-continued

```
cactggttcg tgacccagcg caacttctac gagccccaga tcatcaccac cgacaacacc      3360
ttcgtgtccg gcaactgcga cgtggtgatc ggcatcgtga acaacaccgt gtacgacccc      3420
ctgcagcccg agctggactc cttcaaggag gagctggaca agtacttcaa gaaccacacc      3480
tcccccgacg tggacctggg cgacatctcc ggcatcaacg cctccgtggt gaacatccag      3540
aaggagatcg accgcctgaa cgaggtggcc aagaacctga cgagtccct gatcgacctg      3600 caggagctgg gcaagtacga gcagtacatc aagtggccct ggtacatctg gctgggcttc      3660
atcgccggcc tgatcgccat cgtgatggtg accatcatgc tgtgctgcat gacctcctgc      3720
tgctcctgcc tgaagggctg ctgctcctgc ggctcctgct gcaagttcga cgaggacgac      3780
tccgagcccg tgctgaaggg cgtgaagctg cactacacct aa                        3822
```

<210> SEQ ID NO 2
<211> LENGTH: 4233
<212> TYPE: DNA
<213> ORGANISM: Artificial Sequence
<220> FEATURE:
<223> OTHER INFORMATION: Chemically Synthesized, Full-length WT S
     protein mRNA-coding DNA sequence <400> SEQUENCE: 2

```
agcataaaag tctcaacaca acatatacaa aacaaacgaa tctcaagcaa tcaagcattc       60
tacttctatt gcagcaattt aaatcatttc ttttaaagca aaagcaattt tctgaaaatt      120
ttcaccattt acgaacgata gcgctatgtt cgtgttcctg gtgctgctgc ccctggtgtc      180
ctcccagtgc gtgaacctga ccacccgcac ccagctgccc cccgcctaca ccaactcctt      240 caccccgcggc gtgtactacc ccgacaaggt gttccgctcc tccgtgctgc actccaccca      300
ggacctgttc ctgcccttct tctccaacgt gacctggttc cacgccatcc acgtgtccgg      360
caccaacggc accaagcggt tcgacaaccc cgtgctgccc ttcaacgacg gcgtgtactt      420
cgcctccacc gagaagtcca acatcatccg cggctggatc ttcggcacca ccctggactc      480
caagacccag tccctgctga tcgtgaacaa cgccaccaac gtggtgatca aggtgtgcga      540
gttccagttc tgcaacgacc ccttcctggg cgtgtactac cacaagaaca caagtcctg      600 gatggagtcc gagttccgcg tgtactcctc cgccaacaac tgcaccttcg agtacgtgtc      660
ccagcccttc ctgatggacc tggagggcaa gcagggcaac ttcaagaacc tgcgcgagtt      720
cgtgttcaag aacatcgacg gctacttcaa gatctactcc aagcacaccc ccatcaacct      780
ggtgcgcgac ctgccccagg gcttctccgc cctggagccc ctggtggacc tgcccatcgg      840
catcaacatc acccgcttcc agaccctgct ggccctgcac cgctcctacc tgacccccgg      900
cgactcctcc tccggctgga ccgccggcgc cgccgcctac tacgtgggct acctgcagcc      960
ccgcaccttc ctgctgaagt acaacgagaa cggcaccatc accgacgccg tggactcgc      1020 cctggacccc ctgtccgaga ccaagtgcac cctgaagtcc ttcaccgtgg agaagggcat     1080
ctaccagacc tccaacttcc gcgtgcagcc caccgagtcc atcgtgcgct tccccaacat     1140
caccaacctg tgcccttcg gcgaggtgtt caacgccacc cgcttcgcct ccgtgtacgc     1200
ctggaaccgc aagcgcatct ccaactgcgt ggccgactac tccgtgctgt acaactccgc     1260
ctccttctcc accttcaagt gctacggcgt gtcccccacc aagctgaacg acctgtgctt     1320
caccaacgtg tacgccgact ccttcgtgat ccgcggcgac gaggtgcgcc agatcgcccc     1380
cggccagacc ggcaagatcg ccgactacaa ctacaagctg cccgacgact tcaccggctg     1440
cgtgatcgcc tggaactcca caacctgga ctccaaggtg ggcggcaact acaactacct     1500
```

-continued

```
gtaccgcctg ttccgcaagt ccaacctgaa gcccttcgag cgcgacatct ccaccgagat    1560
ctaccaggcc ggctccaccc cctgcaacgg cgtggagggc ttcaactgct acttccccct    1620
gcagtcctac ggcttccagc ccaccaacgg cgtgggctac cagccctacc gcgtggtggt    1680
gctgtccttc gagctgctgc acgccccgc caccgtgtgc ggcccaaga agtccaccaa    1740 cctggtgaag aacaagtgcg tgaacttcaa cttcaacggc ctgaccggca ccggcgtgct    1800
gaccgagtcc aacaagaagt cctgcccctt ccagcagttc ggccgcgaca tcgccgacac    1860
caccgacgcc gtgcgcgacc cccagaccct ggagatcctg gacatcaccc cctgctcctt    1920
cggcggcgtg tccgtgatca cccccggcac caacacctcc aaccaggtgg ccgtgctgta    1980
ccaggacgtg aactgcaccg aggtgcccgt ggccatccac gccgaccagc tgaccccac    2040 ctggcgcgtg tactccaccg gctccaacgt gttccagacc cgcgccggct gcctgatcgg    2100
cgccgagcac gtgaacaact cctacgagtg cgacatcccc atcggcgccg gcatctgcgc    2160
ctcctaccag acccgacca actcccccg ccgcgcccgc tccgtggcct cccagtccat    2220
catcgcctac accatgtccc tgggcgccga gaactccgtg gcctactcca acaactccat    2280
cgccatcccc accaacttca ccatctccgt gaccaccgag atcctgcccg tgtccatgac    2340
caagacctcc gtggactgca ccatgtacat ctgcggcgac tccaccgagt gctccaacct    2400
gctgctgcag tacggctcct tctgcaccca gctgaaccgc gccctgaccg gcatcgccgt    2460
ggagcaggac aagaacaccc aggaggtgtt cgcccaggtg aagcagatct acaagacccc    2520
ccccatcaag gacttcggcg gcttcaactt ctcccagatc ctgcccgacc cctccaagcc    2580
ctccaagcgg tccttcatcg aggacctgct gttcaacaag gtgaccctgg ccgacgccgg    2640
cttcatcaag cagtacggcg actgcctggg cgacatcgcc gcccgcgacc tgatctgcgc    2700
ccagaagttc aacggcctga ccgtgctgcc ccccctgctg accgacgaga tgatcgccca    2760
gtacacctcc gccctgctgg ccggcaccat cacctccggc tggaccttcg gcgccggcgc    2820
cgccctgcag atccccttcg ccatgcagat ggcctaccgc ttcaacggca tcggcgtgac    2880
ccagaacgtg ctgtacgaga accagaagct gatcgccaac cagttcaact ccgccatcgg    2940
caagatccag gactccctgt cctccaccgc ctccgccctg ggcaagctgc aggacgtggt    3000
gaaccagaac gcccaggccc tgaacaccct ggtgaagcag ctgtcctcca acttcggcgc    3060
catctcctcc gtgctgaacg acatcctgtc ccgcctggac aaggtggagg ccgaggtgca    3120
gatcgaccgc ctgatcaccg gccgcctgca gtccctgcag acctacgtga cccagcagct    3180
gatccgcgcc gccgagatcc gcgcctccgc caacctggcc gccaccaaga tgtccgagtg    3240
cgtgctgggc cagtccaagc gcgtggactt ctgcggcaag ggctaccacc tgatgtcctt    3300 ccccccagtcc gcccccccacg cgcgtggtgtt cctgcacgtg acctacgtgc cgcccaggga    3360
gaagaacttc accaccgccc ccgccatctg ccacgacggc aaggcccact cccccgcga    3420 gggcgtgttc gtgtccaacg gcacccactg gttcgtgacc cagcgcaact ctacgagcc    3480 ccagatcatc accaccgaca caccttcgt gtccggcaac tgcgacgtgg tgatcggcat    3540
cgtgaacaac accgtgtacg accccctgca gcccgagctg gactccttca aggaggagct    3600
ggacaagtac ttcaagaacc acacctcccc cgacgtggac ctgggcgaca tctccggcat    3660
caacgcctcc gtggtgaaca tccagaagga gatcgaccgc ctgaacgagg tggccaagaa    3720
cctgaacgag tccctgatcg acctgcagga gctgggcaag tacgagcagt acatcaagtg    3780
gccctggtac atctggctgg gcttcatcgc cggcctgatc gccatcgtga tggtgaccat    3840
catgctgtgc tgcatgacct cctgctgctc ctgcctgaag ggctgctgct cctgcggctc    3900
```

-continued

```
ctgctgcaag ttcgacgagg acgactccga gcccgtgctg aagggcgtga agctgcacta    3960
cacctaaact agtagtgact gactaggatc tggttaccac taaaccagcc tcaagaacac    4020
ccgaatggag tctctaagct acataatacc aacttacact tacaaaatgt tgtcccccaa    4080
aatgtagcca ttcgtatctg ctcctaataa aaagaaagtt tcttcacatt ctaaaaaaaa    4140
aaaaaaaaaa aaaaaaaaaa aaaaaaaaaa aaaaaaaaaa aaaaaaaaaa aaaaaaaaaa    4200
aaaaaaaaaa aaaaaaaaaa aaaaaaaaaa aaa                                 4233
```

```
<210> SEQ ID NO 3
<211> LENGTH: 1273
<212> TYPE: PRT
<213> ORGANISM: Artificial Sequence
<220> FEATURE:
<223> OTHER INFORMATION: Chemically Synthesized, Full-length WT S
      protein AA sequence

<400> SEQUENCE: 3

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
            115                 120                 125

Lys Val Cys Glu Phe Gln Phe Cys Asn Asp Pro Phe Leu Gly Val Tyr
        130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
            195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
```

-continued

```
       290              295              300

Ser Phe Thr Val Glu Lys Gly Ile Tyr Gln Thr Ser Asn Phe Arg Val
305              310              315              320

Gln Pro Thr Glu Ser Ile Val Arg Phe Pro Asn Ile Thr Asn Leu Cys
                 325              330              335

Pro Phe Gly Glu Val Phe Asn Ala Thr Arg Phe Ala Ser Val Tyr Ala
                 340              345              350

Trp Asn Arg Lys Arg Ile Ser Asn Cys Val Ala Asp Tyr Ser Val Leu
             355              360              365

Tyr Asn Ser Ala Ser Phe Ser Thr Phe Lys Cys Tyr Gly Val Ser Pro
        370              375              380

Thr Lys Leu Asn Asp Leu Cys Phe Thr Asn Val Tyr Ala Asp Ser Phe
385              390              395              400

Val Ile Arg Gly Asp Glu Val Arg Gln Ile Ala Pro Gly Gln Thr Gly
                 405              410              415

Lys Ile Ala Asp Tyr Asn Tyr Lys Leu Pro Asp Asp Phe Thr Gly Cys
             420              425              430

Val Ile Ala Trp Asn Ser Asn Asn Leu Asp Ser Lys Val Gly Gly Asn
             435              440              445

Tyr Asn Tyr Leu Tyr Arg Leu Phe Arg Lys Ser Asn Leu Lys Pro Phe
        450              455              460

Glu Arg Asp Ile Ser Thr Glu Ile Tyr Gln Ala Gly Ser Thr Pro Cys
465              470              475              480

Asn Gly Val Glu Gly Phe Asn Cys Tyr Phe Pro Leu Gln Ser Tyr Gly
                 485              490              495

Phe Gln Pro Thr Asn Gly Val Gly Tyr Gln Pro Tyr Arg Val Val Val
                 500              505              510

Leu Ser Phe Glu Leu Leu His Ala Pro Ala Thr Val Cys Gly Pro Lys
                 515              520              525

Lys Ser Thr Asn Leu Val Lys Asn Lys Cys Val Asn Phe Asn Phe Asn
        530              535              540

Gly Leu Thr Gly Thr Gly Val Leu Thr Glu Ser Asn Lys Lys Phe Leu
545              550              555              560

Pro Phe Gln Gln Phe Gly Arg Asp Ile Ala Asp Thr Thr Asp Ala Val
                 565              570              575

Arg Asp Pro Gln Thr Leu Glu Ile Leu Asp Ile Thr Pro Cys Ser Phe
                 580              585              590

Gly Gly Val Ser Val Ile Thr Pro Gly Thr Asn Thr Ser Asn Gln Val
                 595              600              605

Ala Val Leu Tyr Gln Asp Val Asn Cys Thr Glu Val Pro Val Ala Ile
        610              615              620

His Ala Asp Gln Leu Thr Pro Thr Trp Arg Val Tyr Ser Thr Gly Ser
625              630              635              640

Asn Val Phe Gln Thr Arg Ala Gly Cys Leu Ile Gly Ala Glu His Val
                 645              650              655

Asn Asn Ser Tyr Glu Cys Asp Ile Pro Ile Gly Ala Gly Ile Cys Ala
             660              665              670

Ser Tyr Gln Thr Gln Thr Asn Ser Pro Arg Arg Ala Arg Ser Val Ala
        675              680              685

Ser Gln Ser Ile Ile Ala Tyr Thr Met Ser Leu Gly Ala Glu Asn Ser
        690              695              700

Val Ala Tyr Ser Asn Asn Ser Ile Ala Ile Pro Thr Asn Phe Thr Ile
705              710              715              720
```

-continued

```
Ser Val Thr Thr Glu Ile Leu Pro Val Ser Met Thr Lys Thr Ser Val
            725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
            755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
            805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
            835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
            885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
            915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
            965                 970                 975

Leu Asn Asp Ile Leu Ser Arg Leu Asp Lys Val Glu Ala Glu Val Gln
            980                 985                 990

Ile Asp Arg Leu Ile Thr Gly Arg  Leu Gln Ser Leu Gln  Thr Tyr Val
            995                 1000                1005

Thr Gln  Gln Leu Ile Arg Ala  Ala Glu Ile Arg Ala  Ser Ala Asn
    1010                1015                1020

Leu Ala  Ala Thr Lys Met Ser  Glu Cys Val Leu Gly  Gln Ser Lys
    1025                1030                1035

Arg Val  Asp Phe Cys Gly Lys  Gly Tyr His Leu Met  Ser Phe Pro
    1040                1045                1050

Gln Ser  Ala Pro His Gly Val  Val Phe Leu His Val  Thr Tyr Val
    1055                1060                1065

Pro Ala  Gln Glu Lys Asn Phe  Thr Thr Ala Pro Ala  Ile Cys His
    1070                1075                1080

Asp Gly  Lys Ala His Phe Pro  Arg Glu Gly Val Phe  Val Ser Asn
    1085                1090                1095

Gly Thr  His Trp Phe Val Thr  Gln Arg Asn Phe Tyr  Glu Pro Gln
    1100                1105                1110

Ile Ile  Thr Thr Asp Asn Thr  Phe Val Ser Gly Asn  Cys Asp Val
    1115                1120                1125
```

Val Ile  Gly Ile Val Asn Asn  Thr Val Tyr Asp Pro  Leu Gln Pro
    1130              1135              1140

Glu Leu  Asp Ser Phe Lys Glu  Glu Leu Asp Lys Tyr  Phe Lys Asn
    1145              1150              1155

His Thr  Ser Pro Asp Val Asp  Leu Gly Asp Ile Ser  Gly Ile Asn
    1160              1165              1170

Ala Ser  Val Val Asn Ile Gln  Lys Glu Ile Asp Arg  Leu Asn Glu
    1175              1180              1185

Val Ala  Lys Asn Leu Asn Glu  Ser Leu Ile Asp Leu  Gln Glu Leu
    1190              1195              1200

Gly Lys  Tyr Glu Gln Tyr Ile  Lys Trp Pro Trp Tyr  Ile Trp Leu
    1205              1210              1215

Gly Phe  Ile Ala Gly Leu Ile  Ala Ile Val Met Val  Thr Ile Met
    1220              1225              1230

Leu Cys  Cys Met Thr Ser Cys  Cys Ser Cys Leu Lys  Gly Cys Cys
    1235              1240              1245

Ser Cys  Gly Ser Cys Cys Lys  Phe Asp Glu Asp Asp  Ser Glu Pro
    1250              1255              1260

Val Leu  Lys Gly Val Lys Leu  His Tyr Thr
    1265              1270

<210> SEQ ID NO 4
<211> LENGTH: 3813
<212> TYPE: DNA
<213> ORGANISM: Artificial Sequence
<220> FEATURE:
<223> OTHER INFORMATION: Chemically Synthesized, Full-length S protein
      deleted furin cleavage site DNA sequence

<400> SEQUENCE: 4
atgttcgtgt tcctggtgct gctgcccctg gtgtcctccc agtgcgtgaa cctgaccacc      60
cgcacccagc tgccccccgc ctacaccaac tccttcaccc gcggcgtgta ctaccccgac     120
aaggtgttcc gctcctccgt gctgcactcc acccaggacc tgttcctgcc cttcttctcc     180
aacgtgacct ggttccacgc catccacgtg tccggcacca acggcaccaa gcggttcgac     240
aaccccgtgc tgcccttcaa cgacggcgtg tacttcgcct ccaccgagaa gtccaacatc     300
atccgcggct ggatcttcgg caccaccctg gactccaaga cccagtccct gctgatcgtg     360
aacaacgcca ccaacgtggt gatcaaggtg tgcgagttcc agttctgcaa cgacccccttc    420 ctgggcgtgt actaccacaa gaacaacaag tcctggatgg agtccgagtt ccgcgtgtac     480
tcctccgcca caactgcac cttcgagtac gtgtcccagc ccttcctgat ggacctggag      540
ggcaagcagg gcaacttcaa gaacctgcgc gagttcgtgt tcaagaacat cgacggctac     600
ttcaagatct actccaagca cacccccatc aacctggtgc gcgacctgcc ccagggcttc     660
tccgccctgg agcccctggt ggacctgccc atcggcatca acatcacccg cttccagacc     720
ctgctggccc tgcaccgctc ctacctgacc cccggcgact cctcctccgg ctggaccgcc     780
ggcgccgccg cctactacgt gggctacctg cagccccgca ccttcctgct gaagtacaac     840
gagaacggca ccatcaccga cgccgtggac tgcgccctgg accccctgtc cgagaccaag     900
tgcaccctga agtccttcac cgtggagaag ggcatctacc agacctccaa cttccgcgtg     960
cagcccaccg agtccatcgt gcgcttcccc aacatcacca acctgtgccc cttcggcgag    1020
gtgttcaacg ccaccgcttt cgcctccgtg tacgcctgga accgcaagcg catctccaac    1080
tgcgtggccg actactccgt gctgtacaac tccgcctcct ctccaccttt caagtgctac    1140

-continued

```
ggcgtgtccc ccaccaagct gaacgacctg tgcttcacca acgtgtacgc cgactccttc   1200
gtgatccgcg gcgacgaggt cgcgccagatc gccccggcc agaccggcaa gatcgccgac   1260
tacaactaca agctgcccga cgacttcacc ggctgcgtga tcgcctggaa ctccaacaac   1320
ctggactcca aggtgggcgg caactacaac tacctgtacc gcctgttccg caagtccaac   1380
ctgaagccct tcgagcgcga catctccacc gagatctacc aggccggctc cacccccctgc   1440 aacggcgtgg agggcttcaa ctgctacttc ccctgcagt cctacggctt ccagcccacc   1500
aacggcgtgg gctaccagcc ctaccgcgtg gtggtgctgt ccttcgagct gctgcacgcc   1560
cccgccaccg tgtgcggccc caagaagtcc accaacctgg tgaagaacaa gtgcgtgaac   1620
ttcaacttca acggcctgac cggcaccggc gtgctgaccg agtccaacaa gaagttcctg   1680
cccttccagc agttcggccg cgacatcgcc gacaccaccg acgccgtgcg cgaccccag   1740 accctggaga tcctggacat cacccccctgc tccttcggcg gcgtgtccgt gatcaccccc   1800
ggcaccaaca cctccaacca ggtggccgtg ctgtaccagg acgtgaactg caccgaggtg   1860
cccgtggcca tccacgccga ccagctgacc cccacctggc gcgtgtactc caccggctcc   1920
aacgtgttcc agacccgcgc cggctgcctg atcggcgccg agcacgtgaa caactcctac   1980
gagtgcgaca tccccatcgg cgccggcatc tgcgcctcct accagaccca gaccaactcc   2040
cccgcctccg tggcctccca gtccatcatc gcctacacca tgtccctggg cgccgagaac   2100
tccgtggcct actccaacaa ctccatcgcc atccccacca acttcaccat ctccgtgacc   2160
accgagatcc tgcccgtgtc catgaccaag acctccgtgg actgcaccat gtacatctgc   2220
ggcgactcca ccgagtgctc caacctgctg ctgcagtacg gctccttctg cacccagctg   2280
aaccgcgccc tgaccggcat cgccgtggag caggacaaga acacccagga ggtgttcgcc   2340
caggtgaagc agatctacaa gacccccccc atcaaggact tcggcggctt caacttctcc   2400
cagatcctgc ccgacccctc caagccctcc aagcggtcct tcatcgagga cctgctgttc   2460
aacaaggtga ccctggccga cgccggcttc atcaagcagt acggcgactg cctgggcgac   2520
atcgccgccc gcgacctgat ctgcgcccag aagttcaacg gcctgaccgt gctgcccccc   2580
ctgctgaccg acgagatgat cgcccagtac acctccgccc tgctggccgg caccatcacc   2640
tccggctgga ccttcggcgc cggcgccgcc ctgcagatcc ccttcgccat gcagatggcc   2700
taccgcttca acggcatcgg cgtgacccag aacgtgctgt acgagaacca gaagctgatc   2760
gccaaccagt tcaactccgc catcggcaag atccaggact ccctgtcctc caccgcctcc   2820
gccctgggca gctgcaggga cgtggtgaac cagaacgccc aggccctgaa caccctggtg   2880
aagcagctgt cctccaactt cggcgccatc tcctccgtgc tgaacgacat cctgtcccgc   2940
ctggacaagg tggaggccga ggtgcagatc gaccgcctga tcaccggccg cctgcagtcc   3000
ctgcagacct acgtgaccca gcagctgatc cgcgccgccg agatccgcgc ctccgccaac   3060
ctggccgcca ccaagatgtc cgagtgcgtg ctgggccagt ccaagcgcgt ggacttctgc   3120
ggcaagggct accacctgat gtccttcccc cagtccgccc ccacggcgt ggtgttcctg   3180 cacgtgacct acgtgcccgc ccaggagaag aacttcacca ccgccccgc catctgccac   3240 gacggcaagg cccacttccc ccgcgagggc gtgttcgtgt ccaacggcac ccactggttc   3300
gtgacccagc gcaacttcta cgagcccag atcatcacca ccgacaacac cttcgtgtcc   3360
ggcaactgcg acgtggtgat cggcatcgtg aacaacaccg tgtacgaccc cctgcagccc   3420
gagctggact ccttcaagga ggagctggac aagtacttca agaaccacac ctccccccgac   3480 gtggacctgg cgacatctc cggcatcaac gcctccgtgg tgaacatcca gaaggagatc   3540
```

```
gaccgcctga acgaggtggc caagaacctg aacgagtccc tgatcgacct gcaggagctg      3600
ggcaagtacg agcagtacat caagtggccc tggtacatct ggctgggctt catcgccggc      3660
ctgatcgcca tcgtgatggt gaccatcatg ctgtgctgca tgacctcctg ctgctcctgc      3720
ctgaagggct gctgctcctg cggctcctgc tgcaagttcg acgaggacga ctccgagccc      3780
gtgctgaagg gcgtgaagct gcactacacc taa                                   3813
```

<210> SEQ ID NO 5
<211> LENGTH: 4224
<212> TYPE: DNA
<213> ORGANISM: Artificial Sequence
<220> FEATURE:
<223> OTHER INFORMATION: Chemically Synthesized, Full-length S protein
      deleted furin cleavage site mRNA-coding DNA sequence

<400> SEQUENCE: 5

```
agcataaaag tctcaacaca acatatacaa aacaaacgaa tctcaagcaa tcaagcattc        60
tacttctatt gcagcaattt aaatcatttc ttttaaagca aaagcaattt tctgaaaatt       120
ttcaccattt acgaacgata gcgctatgtt cgtgttcctg gtgctgctgc ccctggtgtc       180
ctcccagtgc gtgaacctga ccacccgcac ccagctgccc cccgcctaca ccaactcctt       240 caccccgcggc gtgtactacc ccgacaaggt gttccgctcc tccgtgctgc actccacccca     300 ggacctgttc ctgcccttct tctccaacgt gacctggttc cacgccatcc acgtgtccgg       360
caccaacggc accaagcggt tcgacaaccc cgtgctgccc ttcaacgacg gcgtgtactt       420
cgcctccacc gagaagtcca acatcatccg cggctggatc ttcggcacca ccctggactc       480
caagacccag tccctgctga tcgtgaacaa cgccaccaac gtggtgatca aggtgtgcga       540
gttccagttc tgcaacgacc ccttcctggg cgtgtactac cacaagaaca acaagtcctg       600
gatggagtcc gagttccgcg tgtactcctc cgccaacaac tgcaccttcg agtacgtgtc       660
ccagcccttc ctgatggacc tggagggcaa gcagggcaac ttcaagaacc tgcgcgagtt       720
cgtgttcaag aacatcgacg gctacttcaa gatctactcc aagcacaccc ccatcaacct       780
ggtgcgcgac ctgccccagg gcttctccgc cctggagccc ctggtggacc tgcccatcgg       840
catcaacatc acccgcttcc agaccctgct ggccctgcac cgctcctacc tgaccccccgg      900 cgactcctcc tccggctgga ccgccggcgc cgccgcctac tacgtgggct acctgcagcc       960
ccgcaccttc ctgctgaagt acaacgagaa cggcaccatc accgacgccg tggactgcgc      1020
cctggacccc ctgtccgaga ccaagtgcac cctgaagtcc ttcaccgtgg agaagggcat      1080
ctaccagacc tccaacttcc gcgtgcagcc caccgagtcc atcgtgcgct tccccaacat      1140
caccaacctg tgcccctttcg gcgaggtgtt caacgccacc cgcttcgcct ccgtgtacgc      1200
ctggaaccgc aagcgcatct ccaactgcgt ggccgactac tccgtgctgt acaactccgc      1260
ctccttctcc accttcaagt gctacggcgt gtccccaccc aagctgaacg acctgtgctt      1320
caccaacgtg tacgccgact ccttcgtgat ccgcggcgac gaggtgcgcc agatcgcccc      1380
cggccagacc ggcaagatcg ccgactacaa ctacaagctg cccgacgact tcaccggctg      1440
cgtgatcgcc tggaactcca caaacctgga ctccaaggtg ggcggcaact acaactacct      1500
gtaccgcctg ttccgcaagt ccaacctgaa gcccttcgag cgcgacatct ccaccgagat      1560
ctaccaggcc ggctcacacc cctgcaacgg cgtggagggc ttcaactgct acttccccct      1620
gcagtcctac ggcttccagc ccaccaacgg cgtgggctac cagccctacc gcgtggtggt      1680
gctgtccttc gagctgctgc acgcccccgc caccgtgtgc ggccccaaga gtccaccaa      1740
```

-continued

```
cctggtgaag aacaagtgcg tgaacttcaa cttcaacggc ctgaccggca ccggcgtgct   1800
gaccgagtcc aacaagaagt tcctgccctt ccagcagttc ggccgcgaca tcgccgacac   1860
caccgacgcc gtgcgcgacc cccagaccct ggagatcctg gacatcaccc cctgctcctt   1920
cggcggcgtg tccgtgatca cccccggcac caacacctcc aaccaggtgg ccgtgctgta   1980
ccaggacgtg aactgcaccg aggtgcccgt ggccatccac gccgaccagc tgaccccac   2040 ctggcgcgtg tactccaccg gctccaacgt gttccagacc cgcgccggct gcctgatcgg   2100
cgccgagcac gtgaacaact cctacgagtg cgacatcccc atcggcgccg gcatctgcgc   2160
ctcctaccag acccagacca actcccccgc ctccgtggcc tcccagtcca tcatcgccta   2220
caccatgtcc ctgggcgccg agaactccgt ggcctactcc aacaactcca tcgccatccc   2280
caccaacttc accatctccg tgaccaccga gatcctgccc gtgtccatga ccaagacctc   2340
cgtggactgc accatgtaca tctgcggcga ctccaccgag tgctccaacc tgctgctgca   2400
gtacggctcc ttctgcaccc agctgaaccg cgccctgacc ggcatcgccg tggagcagga   2460
caagaacacc caggaggtgt tcgcccaggt gaagcagatc tacaagaccc cccccatcaa   2520
ggacttcggc ggcttcaact tctcccccgat cctgcccgac ccctccaagc cctccaagcg   2580
gtccttcatc gaggacctgc tgttcaacaa ggtgaccctg gccgacgccg gcttcatcaa   2640
gcagtacggc gactgcctgg gcgacatcgc cgcccgcgac ctgatctgcg cccagaagtt   2700
caacggcctg accgtgctgc ccccctgct gaccgacgag atgatcgccc agtacacctc   2760
cgccctgctg gccggcacca tcacctccgg ctggaccttc ggcgccggcg ccgccctgca   2820 gatcccttc gccatgcaga tggcctaccg cttcaacggc atcggcgtga cccagaacgt   2880
gctgtacgag aaccagaagc tgatcgccaa ccagttcaac tccgccatcg gcaagatcca   2940
ggactccctg tcctccaccg cctccgccct gggcaagctg caggacgtgg tgaaccagaa   3000
cgcccaggcc ctgaacaccc tggtgaagca gctgtcctcc aacttcggcg ccatctcctc   3060
cgtgctgaac gacatcctgt cccgcctgga caaggtggag gccgaggtgc agatcgaccg   3120
cctgatcacc ggccgcctgc agtccctgca gacctacgtg acccagcagc tgatccgcgc   3180
cgccgagatc cgcgcctccg ccaacctggc cgccaccaag atgtccgagt gcgtgctggg   3240
ccagtccaag cgcgtggact ctgcggcaa gggctaccac ctgatgtcct tcccccagtc   3300 cgcccccac ggcgtggtgt tcctgcacgt gacctacgtg cccgcccagg agaagaactt   3360
caccaccgcc cccgccatct gccacgacgg caaggcccac ttcccccgcg agggcgtgtt   3420
cgtgtccaac ggcacccact ggttcgtgac ccagcgcaac ttctacgagc cccagatcat   3480
caccaccgac aacaccttcg tgtccggcaa ctgcgacgtg gtgatcggca tcgtgaacaa   3540
caccgtgtac gacccctgc agcccgagct ggactccttc aaggaggagc tggacaagta   3600
cttcaagaac cacacctccc ccgacgtgga cctgggcgac atctccggca tcaacgcctc   3660
cgtggtgaac atccagaagg agatcgaccg cctgaacgag gtggccaaga acctgaacga   3720
gtccctgatc gacctgcagg agctgggcaa gtacgagcag tacatcaagt ggccctggta   3780
catctggctg ggcttcatcg ccggcctgat cgccatcgtg atggtgacca tcatgctgtg   3840
ctgcatgacc tcctgctgct cctgcctgaa gggctgctgc tcctgcggct cctgctgcaa   3900
gttcgacgag gacgactccg agccgtgct gaagggcgtg aagctgcact acacctaaac   3960
tagtagtgac tgactaggat ctggttacca ctaaaccagc ctcaagaaca cccgaatgga   4020
gtctctaagc tacataatac caacttacac ttacaaaatg ttgtccccca aaatgtagcc   4080
```

-continued

```
attcgtatct gctcctaata aaagaaagt ttcttcacat tctaaaaaaa aaaaaaaaaa      4140
aaaaaaaaaa aaaaaaaaaa aaaaaaaaaa aaaaaaaaaa aaaaaaaaaa aaaaaaaaaa      4200
aaaaaaaaaa aaaaaaaaaa aaaa                                            4224
```

```
<210> SEQ ID NO 6
<211> LENGTH: 1270
<212> TYPE: PRT
<213> ORGANISM: Artificial Sequence
<220> FEATURE:
<223> OTHER INFORMATION: Chemically Synthesized, Full-length S protein
      deleted furin cleavage site AA sequence

<400> SEQUENCE: 6

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
            115                 120                 125

Lys Val Cys Glu Phe Gln Phe Cys Asn Asp Pro Phe Leu Gly Val Tyr
        130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
            195                 200                 205

Pro Ile Asn Leu Val Arg Asp Leu Pro Gln Gly Phe Ser Ala Leu Glu
        210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
            275                 280                 285

Val Asp Cys Ala Leu Asp Pro Leu Ser Glu Thr Lys Cys Thr Leu Lys
        290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335
```

-continued

```
Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
            355                 360                 365

Tyr Asn Ser Ala Ser Phe Ser Thr Phe Lys Cys Tyr Gly Val Ser Pro
            370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
                420                 425                 430

Val Ile Ala Trp Asn Ser Asn Asn Leu Asp Ser Lys Val Gly Gly Asn
            435                 440                 445

Tyr Asn Tyr Leu Tyr Arg Leu Phe Arg Lys Ser Asn Leu Lys Pro Phe
            450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
                500                 505                 510

Leu Ser Phe Glu Leu Leu His Ala Pro Ala Thr Val Cys Gly Pro Lys
            515                 520                 525

Lys Ser Thr Asn Leu Val Lys Asn Lys Cys Val Asn Phe Asn Phe Asn
            530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
                580                 585                 590

Gly Gly Val Ser Val Ile Thr Pro Gly Thr Asn Thr Ser Asn Gln Val
                595                 600                 605

Ala Val Leu Tyr Gln Asp Val Asn Cys Thr Glu Val Pro Val Ala Ile
            610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Ala Ser Val Ala Ser Gln Ser
            675                 680                 685

Ile Ile Ala Tyr Thr Met Ser Leu Gly Ala Glu Asn Ser Val Ala Tyr
            690                 695                 700

Ser Asn Asn Ser Ile Ala Ile Pro Thr Asn Phe Thr Ile Ser Val Thr
705                 710                 715                 720

Thr Glu Ile Leu Pro Val Ser Met Thr Lys Thr Ser Val Asp Cys Thr
                725                 730                 735

Met Tyr Ile Cys Gly Asp Ser Thr Glu Cys Ser Asn Leu Leu Leu Gln
            740                 745                 750
```

```
Tyr Gly Ser Phe Cys Thr Gln Leu Asn Arg Ala Leu Thr Gly Ile Ala
        755                 760                 765

Val Glu Gln Asp Lys Asn Thr Gln Glu Val Phe Ala Gln Val Lys Gln
        770                 775                 780

Ile Tyr Lys Thr Pro Pro Ile Lys Asp Phe Gly Gly Phe Asn Phe Ser
785                 790                 795                 800

Gln Ile Leu Pro Asp Pro Ser Lys Pro Ser Lys Arg Ser Phe Ile Glu
                805                 810                 815

Asp Leu Leu Phe Asn Lys Val Thr Leu Ala Asp Ala Gly Phe Ile Lys
                820                 825                 830

Gln Tyr Gly Asp Cys Leu Gly Asp Ile Ala Ala Arg Asp Leu Ile Cys
        835                 840                 845

Ala Gln Lys Phe Asn Gly Leu Thr Val Leu Pro Pro Leu Leu Thr Asp
        850                 855                 860

Glu Met Ile Ala Gln Tyr Thr Ser Ala Leu Leu Ala Gly Thr Ile Thr
865                 870                 875                 880

Ser Gly Trp Thr Phe Gly Ala Gly Ala Ala Leu Gln Ile Pro Phe Ala
                885                 890                 895

Met Gln Met Ala Tyr Arg Phe Asn Gly Ile Gly Val Thr Gln Asn Val
        900                 905                 910

Leu Tyr Glu Asn Gln Lys Leu Ile Ala Asn Gln Phe Asn Ser Ala Ile
        915                 920                 925

Gly Lys Ile Gln Asp Ser Leu Ser Ser Thr Ala Ser Ala Leu Gly Lys
        930                 935                 940

Leu Gln Asp Val Val Asn Gln Asn Ala Gln Ala Leu Asn Thr Leu Val
945                 950                 955                 960

Lys Gln Leu Ser Ser Asn Phe Gly Ala Ile Ser Ser Val Leu Asn Asp
                965                 970                 975

Ile Leu Ser Arg Leu Asp Lys Val Glu Ala Glu Val Gln Ile Asp Arg
                980                 985                 990

Leu Ile Thr Gly Arg Leu Gln Ser  Leu Gln Thr Tyr Val  Thr Gln Gln
        995                 1000                1005

Leu Ile  Arg Ala Ala Glu Ile  Arg Ala Ser Ala Asn  Leu Ala Ala
        1010                1015                1020

Thr Lys  Met Ser Glu Cys Val  Leu Gly Gln Ser Lys  Arg Val Asp
        1025                1030                1035

Phe Cys  Gly Lys Gly Tyr His  Leu Met Ser Phe Pro  Gln Ser Ala
        1040                1045                1050

Pro His  Gly Val Val Phe Leu  His Val Thr Tyr Val  Pro Ala Gln
        1055                1060                1065

Glu Lys  Asn Phe Thr Thr Ala  Pro Ala Ile Cys His  Asp Gly Lys
        1070                1075                1080

Ala His  Phe Pro Arg Glu Gly  Val Phe Val Ser Asn  Gly Thr His
        1085                1090                1095

Trp Phe  Val Thr Gln Arg Asn  Phe Tyr Glu Pro Gln  Ile Ile Thr
        1100                1105                1110

Thr Asp  Asn Thr Phe Val Ser  Gly Asn Cys Asp Val  Val Ile Gly
        1115                1120                1125

Ile Val  Asn Asn Thr Val Tyr  Asp Pro Leu Gln Pro  Glu Leu Asp
        1130                1135                1140

Ser Phe  Lys Glu Glu Leu Asp  Lys Tyr Phe Lys Asn  His Thr Ser
        1145                1150                1155

Pro Asp  Val Asp Leu Gly Asp  Ile Ser Gly Ile Asn  Ala Ser Val
```

-continued

```
        1160            1165            1170

Val Asn Ile Gln Lys Glu Ile Asp Arg Leu Asn Glu  Val Ala Lys
    1175            1180            1185

Asn Leu Asn Glu Ser Leu Ile Asp Leu Gln Glu Leu  Gly Lys Tyr
    1190            1195            1200

Glu Gln Tyr Ile Lys Trp Pro Trp Tyr Ile Trp Leu  Gly Phe Ile
    1205            1210            1215

Ala Gly Leu Ile Ala Ile Val Met Val Thr Ile Met  Leu Cys Cys
    1220            1225            1230

Met Thr Ser Cys Cys Ser Cys Leu Lys Gly Cys Cys  Ser Cys Gly
    1235            1240            1245

Ser Cys Cys Lys Phe Asp Glu Asp Asp Ser Glu Pro  Val Leu Lys
    1250            1255            1260

Gly Val Lys Leu His Tyr Thr
    1265            1270
```

```
<210> SEQ ID NO 7
<211> LENGTH: 714
<212> TYPE: DNA
<213> ORGANISM: Artificial Sequence
<220> FEATURE:
<223> OTHER INFORMATION: Chemically Synthesized, Soluble RBD of S
      protein DNA sequence

<400> SEQUENCE: 7
atgttcgtgt tcctggtgct gctgcccctg gtgtcctccc agcgcgtgca gcccaccgag     60
tccatcgtgc gcttccccaa catcaccaac ctgtgcccct cggcgaggt gttcaacgcc    120 acccgcttcg cctccgtgta cgcctggaac cgcaagcgca tctccaactg cgtggccgac    180
tactccgtgc tgtacaactc cgcctccttc tccaccttca agtgctacgg cgtgtccccc    240
accaagctga cgacctgtg cttcaccaac gtgtacgccg actccttcgt gatccgcggc    300
gacgaggtgc gccagatcgc ccccggccag accggcaaga tcgccgacta caactacaag    360
ctgcccgacg acttcaccgg ctgcgtgatc gcctggaact ccaacaacct ggactccaag    420
gtgggcggca actacaacta cctgtaccgc ctgttccgca gtccaacct gaagcccttc    480 gagcgcgaca tctccaccga gatctaccag gccggctcca cccctgcaa cggcgtggag    540 ggcttcaact gctacttccc cctgcagtcc tacggcttcc agcccaccaa cggcgtgggc    600
taccagccct accgcgtggt ggtgctgtcc ttcgagctgc tgcacgcccc cgccaccgtg    660
tgcggcccca gaagtccac caacctggtg aagaacaagt gcgtgaactt ctaa           714
```

```
<210> SEQ ID NO 8
<211> LENGTH: 1125
<212> TYPE: DNA
<213> ORGANISM: Artificial Sequence
<220> FEATURE:
<223> OTHER INFORMATION: Chemically Synthesized, Soluble RBD of S
      protein mRNA-coding DNA sequence

<400> SEQUENCE: 8
agcataaaag tctcaacaca acatatacaa aacaaacgaa tctcaagcaa tcaagcattc     60
tacttctatt gcagcaattt aaatcatttc ttttaaagca aaagcaattt ctgaaaatt    120 ttcaccattt acgaacgata gcgctatgtt cgtgttcctg gtgctgctgc ccctggtgtc    180 ctccagcgc gtgcagccca ccgagtccat cgtgcgcttc cccaacatca ccaacctgtg    240 cccccttcggc gaggtgttca cgccacccg cttcgcctcc gtgtacgcct ggaaccgcaa    300
```

-continued

```
gcgcatctcc aactgcgtgg ccgactactc cgtgctgtac aactccgcct ccttctccac        360
cttcaagtgc tacggcgtgt cccccaccaa gctgaacgac ctgtgcttca ccaacgtgta        420
cgccgactcc ttcgtgatcc gcggcgacga ggtgcgccag atcgccccg gccagaccgg         480 caagatcgcc gactacaact acaagctgcc cgacgacttc accggctgcg tgatcgcctg        540
gaactccaac aacctggact ccaaggtggg cggcaactac aactacctgt accgcctgtt        600
ccgcaagtcc aacctgaagc ccttcgagcg cgacatctcc accgagatct accaggccgg        660
ctccaccccc tgcaacggcg tggagggctt caactgctac ttcccctgc agtcctacgg         720 cttccagccc accaacggcg tgggctacca gccctaccgc gtggtggtgc tgtccttcga        780
gctgctgcac gcccccgcca ccgtgtgcgg ccccaagaag tccaccaacc tggtgaagaa        840
caagtgcgtg aacttctaaa ctagtagtga ctgactagga tctggttacc actaaaccag        900
cctcaagaac acccgaatgg agtctctaag ctacataata ccaacttaca cttacaaaat        960
gttgtccccc aaaatgtagc cattcgtatc tgctcctaat aaaaagaaag tttcttcaca       1020
ttctaaaaaa aaaaaaaaaa aaaaaaaaaa aaaaaaaaaa aaaaaaaaaa aaaaaaaaaa       1080
aaaaaaaaaa aaaaaaaaaa aaaaaaaaaa aaaaaaaaaa aaaaa                       1125
```

<210> SEQ ID NO 9
<211> LENGTH: 237
<212> TYPE: PRT
<213> ORGANISM: Artificial Sequence
<220> FEATURE:
<223> OTHER INFORMATION: Chemically Synthesized, Soluble RBD of S
      protein AA sequence

<400> SEQUENCE: 9

```
Met Phe Val Phe Leu Val Leu Leu Pro Leu Val Ser Ser Gln Arg Val
1               5                   10                  15

Gln Pro Thr Glu Ser Ile Val Arg Phe Pro Asn Ile Thr Asn Leu Cys
            20                  25                  30

Pro Phe Gly Glu Val Phe Asn Ala Thr Arg Phe Ala Ser Val Tyr Ala
        35                  40                  45

Trp Asn Arg Lys Arg Ile Ser Asn Cys Val Ala Asp Tyr Ser Val Leu
    50                  55                  60

Tyr Asn Ser Ala Ser Phe Ser Thr Phe Lys Cys Tyr Gly Val Ser Pro
65                  70                  75                  80

Thr Lys Leu Asn Asp Leu Cys Phe Thr Asn Val Tyr Ala Asp Ser Phe
                85                  90                  95

Val Ile Arg Gly Asp Glu Val Arg Gln Ile Ala Pro Gly Gln Thr Gly
            100                 105                 110

Lys Ile Ala Asp Tyr Asn Tyr Lys Leu Pro Asp Asp Phe Thr Gly Cys
        115                 120                 125

Val Ile Ala Trp Asn Ser Asn Asn Leu Asp Ser Lys Val Gly Gly Asn
    130                 135                 140

Tyr Asn Tyr Leu Tyr Arg Leu Phe Arg Lys Ser Asn Leu Lys Pro Phe
145                 150                 155                 160

Glu Arg Asp Ile Ser Thr Glu Ile Tyr Gln Ala Gly Ser Thr Pro Cys
                165                 170                 175

Asn Gly Val Glu Gly Phe Asn Cys Tyr Phe Pro Leu Gln Ser Tyr Gly
            180                 185                 190

Phe Gln Pro Thr Asn Gly Val Gly Tyr Gln Pro Tyr Arg Val Val Val
        195                 200                 205

Leu Ser Phe Glu Leu Leu His Ala Pro Ala Thr Val Cys Gly Pro Lys
```

-continued

```
        210              215              220
Lys Ser Thr Asn Leu Val Lys Asn Lys Cys Val Asn Phe
225                       230                  235

<210> SEQ ID NO 10
<211> LENGTH: 20
<212> TYPE: DNA
<213> ORGANISM: Artificial Sequence
<220> FEATURE:
<223> OTHER INFORMATION: Chemically Synthesized, 2019-nCoV N1-Forward
      Primer

<400> SEQUENCE: 10
gaccccaaaa tcagcgaaat                                              20

<210> SEQ ID NO 11
<211> LENGTH: 24
<212> TYPE: DNA
<213> ORGANISM: Artificial Sequence
<220> FEATURE:
<223> OTHER INFORMATION: Chemically Synthesized, 2019-nCoV N1-Reverse
      Primer

<400> SEQUENCE: 11
tctggttact gccagttgaa tctg                                        24

<210> SEQ ID NO 12
<211> LENGTH: 24
<212> TYPE: DNA
<213> ORGANISM: Artificial Sequence
<220> FEATURE:
<223> OTHER INFORMATION: Chemically Synthesized, 2019-nCoV N1-Probe

<400> SEQUENCE: 12
accccgcatt acgtttggtg gacc                                        24
```